(12) United States Patent
Fischer et al.

(10) Patent No.: US 6,939,888 B2
(45) Date of Patent: Sep. 6, 2005

(54) 1-H-3-ARYLPIRROLIDINE-2,4-DIONE DERIVATIVES

(75) Inventors: Reiner Fischer, Monheim (DE); Thomas Bretschneider, Lohmar (DE); Bernd-Wieland Krüger, Bergisch Gladbach (DE); Michael Ruther, Monheim (DE); Christoph Erdelen, Leichlingen (DE); Ulrike Wachendorff-Neumann, Neuwied (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/189,236

(22) Filed: Jul. 3, 2002

(65) Prior Publication Data

US 2004/0019061 A1 Jan. 29, 2004

Related U.S. Application Data

(62) Division of application No. 08/967,254, filed on Nov. 5, 1997, now Pat. No. 6,472,419, which is a continuation of application No. 08/676,363, filed as application No. PCT/EP95/00150 on Jan. 16, 1995, now abandoned.

(30) Foreign Application Priority Data

Jan. 28, 1994 (DE) ....................................... P 44 02 531
Jul. 20, 1994 (DE) ....................................... P 44 25 617

(51) Int. Cl.[7] ......................... A01N 43/38; C07D 209/96
(52) U.S. Cl. ........................................ 514/409; 548/408
(58) Field of Search ................................. 514/409, 408; 548/408

(56) References Cited

U.S. PATENT DOCUMENTS 5,258,527 A 11/1993 Krauskopf et al.
5,462,913 A * 10/1995 Fischer et al. .............. 504/138
5,567,671 A 10/1996 Fischer et al.
5,589,469 A 12/1996 Fischer, II et al.

FOREIGN PATENT DOCUMENTS

| | | | |
|---|---|---|---|
| DE | 43 26 909 | A | 5/1994 |
| EP | 0 456 063 | A | 11/1991 |
| EP | 0 521 334 | A | 1/1993 |
| EP | 0 613 885 | A | 7/1994 |

* cited by examiner

*Primary Examiner*—Patricia L. Morris
(74) *Attorney, Agent, or Firm*—Norris McLaughlin & Marcus PA

(57) ABSTRACT

The invention concerns 1-H-3-arylpyrrolidine-2,4-dione derivatives of formula (I), (I)

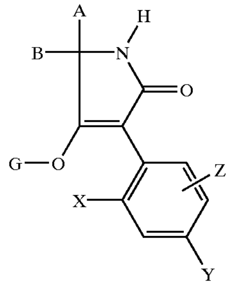

in which A, B, G, X, Y and Z are as defined in the description, methods of preparing them and intermediates used in their preparation. The compounds of formula (I) are suitable for use as pest-control agents.

8 Claims, No Drawings

1-H-3-ARYLPIRROLIDINE-2,4-DIONE DERIVATIVES

This application is a divisional application of U.S. Ser. No. 08/987,254, filed an 5 Nov. 1997, now U.S. Pat. No. 6,472,419, granted on 29 Oct. 2002, which in turn was a continuation of U.S. Ser. No. 08/616,363, filed on 22 Jul. 1996, now abandoned, which was a 371 application of PCT/EP95/00150, filed on 16 Jan. 1995.

The invention relates to new 1-H-3-aryl-pyrrolidine-2,4-dione derivatives, to a plurality of processes for their preparation, and to their use as pesticides, in particular as insecticides and acaricides.

3-Acyl-pyrrolidine-2,4-diones have previously been described as having pharmaceutical properties (S. Suzuki et al. Chem. Pharm. Bull. 15 1120 (1967)). Moreover, N-phenylpyrrolidine-2,4-diones have been synthesized by R. Schmierer and H. Mildenberger (Liebigs Ann. Chem. 1985 1095). A biological activity of these compounds has not been described.

EP-A 0 262 399 and GB-A 2 266 888 disclose compounds of a similar structure (3-aryl-pyrrolidine-2,4-diones), but nothing has been disclosed about them having a herbicidal, insecticidal or acaricidal activity. Known, and having a herbicidal, insecticidal or acaricidal activity, are unsubstituted bicyclic 3-aryl-pyrrolidine-2,4-dione derivatives (EP-A 355 599 and EP 415 211) and substituted monocyclic 3-aryl-pyrrolidine-2,4-dione derivatives (EP-A 377 893 and EP 442 077).

Substances which are furthermore known are polycyclic 3-aryl-pyrrolidine-2,4-dione derivatives (EP 442 073) and 1-H-3-aryl-pyrrolidine-dione derivatives (EP 456 063 and EP 521 334).

New substituted 1-H-3-aryl-pyrrolidine-2,4-dione derivatives have now been found, of the formula (I)

(I)

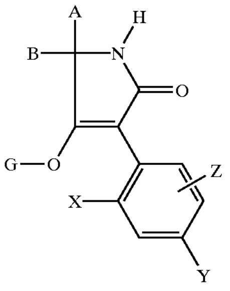

in which

A represents hydrogen, or represents alkyl, alkenyl, alkoxyalkyl, polyalkoxyalkyl or alkylthioalkyl, in each case optionally substituted by halogen, or represents cycloalkyl which is optionally interrupted by at least one hetero atom, or represents aryl, arylalkyl or hetaryl, in each case optionally substituted by halogen, alkyl, halogenoalkyl, alkoxy or nitro, B represents hydrogen, alkyl or alkoxyalkyl, or A and B together with the carbon atom to which they are bonded represent a saturated or unsaturated, unsubstituted or substituted cycle which is optionally interrupted by at least one hetero atom, X represents halogen or alkoxy, Y represents hydrogen, halogen or alkoxy, Z represents hydrogen, halogen or alkoxy, G represents hydrogen (a) or the groups (b)

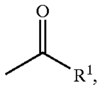

(c)

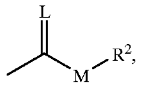

(d)

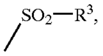

(e)

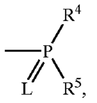

(f)

E or (g)

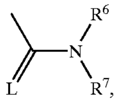

E represents a metal ion equivalent or an ammonium ion,

L and M in each case represent oxygen or sulfur, $R^1$ represents alkyl, alkenyl, alkoxyalkyl, alkylthioalkyl, polyalkoxyalkyl or cycloalkyl which can be interrupted by hetero atoms, in each case optionally substituted by halogen, or represents optionally substituted phenyl or in each case optionally substituted phenylalkyl, hetaryl, phenoxyalkyl or hetaryloxyalkyl, $R^2$ represents alkyl, alkenyl, alkoxyalkyl or polyalkoxyalkyl, in each case optionally substituted by halogen, or represents in each case optionally substituted cycloalkyl, phenyl or benzyl, $R^3$, $R^4$ and $R^5$ independently of one another represent alkyl, alkoxy, alkylamino, dialkylamino, alkylthio, alkenylthio or cycloalkylthio, in each case optionally substituted by halogen, or represent in each case optionally substituted phenyl, phenoxy or phenylthio, $R^6$ and $R^7$ independently of one another represent hydrogen, or represent alkyl, cycloalkyl, alkenyl, alkoxy or alkoxyalkyl, in each case optionally substituted by halogen, or represent optionally substituted phenyl, or represent optionally substituted benzyl, or together with the N atom to which they are bonded represent a cycle which is optionally interrupted by oxygen or sulfur, with the proviso that X and Y or X and Z do not simultaneously represent halogen.

Taking into account the various meanings (a), (b), (c), (d), (e) (f) and (g) of group G of the general formula (I), the following main structures (Ia) to (Ig) result:

(Ia)

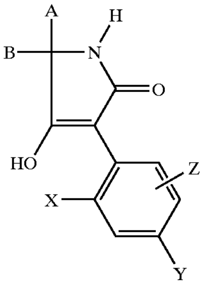

(Ib)

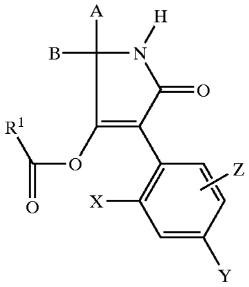

(Ic)

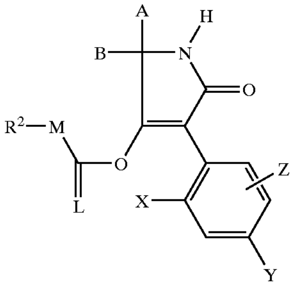

(Id)

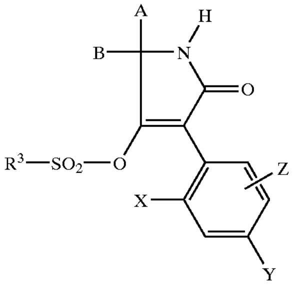

(Ie)

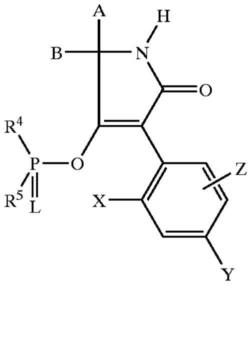

-continued (If)

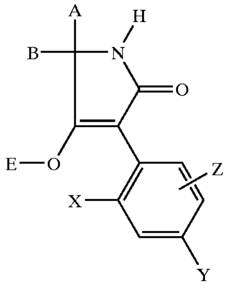

(Ig)

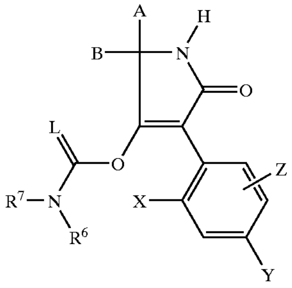

in which

A, B, E, L, M, X, Y, Z, $R^1$, $R^2$, $R^3$, $R^4$, $R^5$, $R^6$ and $R^7$ have the abovementioned meanings.

Because of one or more chiral centers, the compounds of the formulae (Ia)–(Ig) are generally obtained in the form of a mixture of stereoisomers which, if appropriate, can be separated in the customary manner. They can be used in the form of their diastereomer mixtures as well as in the form of the pure diastereomers or enantiomers. For simplicity's sake, the following text will always mention compounds of the formulae (Ia) to (Ig), even though this is to be understood as meaning the pure compounds as well as the mixtures comprising various proportions of isomeric, enantiomeric and stereomeric compounds.

Furthermore, it has been found that the new substituted 1-H-3-aryl-pyrrolidine-2,4-dione derivatives of the formula (I) are obtained by one of the processes described below:

(A) 1-H-3-aryl-pyrrolidine-2,4-diones or their enols of the formula (Ia)

(Ia)

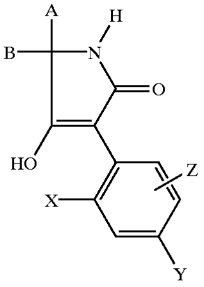

in which

A, B, X, Y and Z have the abovementioned meanings, are obtained when

α) N-acylamino acid esters of the formula (II)

(II)

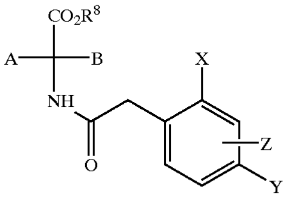

in which

A, B, X, Y and Z have the abovementioned meanings, and $R^8$ represents alkyl are subjected to an intramolecular condensation reaction in the presence of a diluent and in the presence of a base; or β) 1-H-3-aryl-pyrrolidine-2,4-diones or their enols of the formula (Ia-a)

(Ia-a)

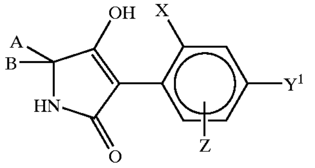

in which

A, B, X and Z have the abovementioned meanings, and $Y^1$ represents —$OR^8$, where $R^8$ represents alkyl, are obtained when N-acylamino acid esters of the formula (IIa)

(IIa)

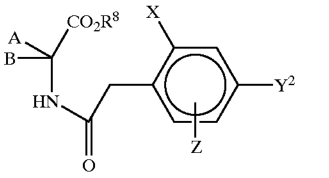

in which

A, B, X and Z have the abovementioned meanings, $Y^2$ represents fluorine and $R^8$ represents alkyl, preferably $C_1$–$C_8$-alkyl, are subjected to an intramolecular condensation reaction in the presence of a diluent and in the presence of a base; or (B) compounds of the formula (Ib)

(Ib)

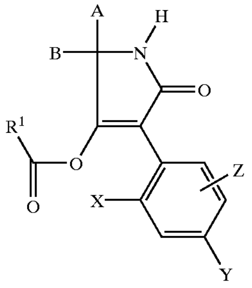

in which

A, B, X, Y, Z and $R^1$ have the abovementioned meanings, are obtained when compounds of the formula (Ia), (Ia)

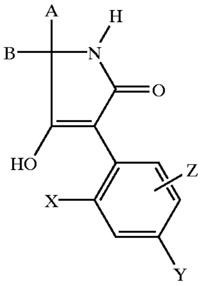

in which

A, B, X, Y and Z have the abovementioned meanings, are reacted

α) with acid halides of the general formula (III)

(III)

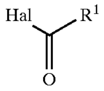

in which $R^1$ has the abovementioned meaning and

Hal represents halogen, in particular chlorine or bromine, if appropriate in the presence of a diluent and if appropriate in the presence of an acid-binding agent, or β) with carboxylic anhydrides of the general formula (IV)

$$R^1—CO—O—CO—R^1 \qquad (IV)$$

in which $R^1$ has the abovementioned meaning, if appropriate in the presence of a diluent and if appropriate in the presence of an acid-binding agent; or (C) compounds of the formula (Ic-a)

(Ic-a)

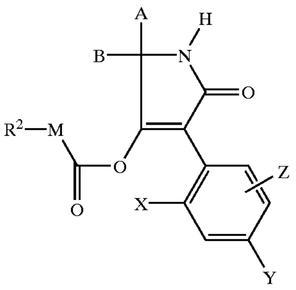

in which

A, B, X, Y, Z and $R^2$ have the abovementioned meanings, and

M represents oxygen or sulfur are obtained when compounds of the formula (Ia)

(Ia)

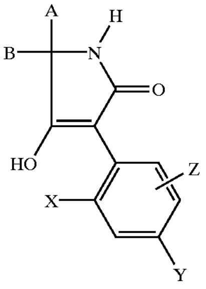

in which

A, B, X, Y and Z have the abovementioned meanings, are reacted with chloroformic esters or chloroformic thioesters of the general formula (V)

$R^2$—M—CO—Cl (V)

in which $R^2$ and M have the abovementioned meanings, if appropriate in the presence of a diluent and if appropriate in the presence of an acid-binding agent; or (D) compounds of the formula (Ic-b)

(Ic-b)

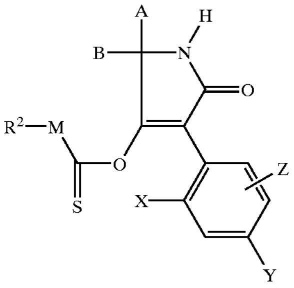

in which

A, B, $R^2$, X, Y and Z have the abovementioned meanings and

M represents oxygen or sulfur are obtained when compounds of the formula (Ia)

(Ia)

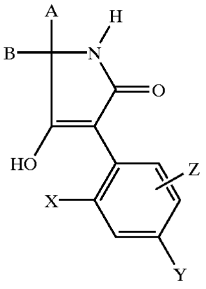

in which

A, B, X, Y and Z have the abovementioned meanings are reacted

α) with chloromonothioformic esters or chlorodithioformic esters of the general formula (VI)

(VI)

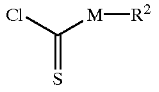

in which

M and $R^2$ have the abovementioned meanings, if appropriate in the presence of a diluent and if appropriate in the presence of an acid-binding agent, or β) with carbon disulfide and then with alkyl halides of the general formula (VII)

$R^2$—Hal (VII)

in which $R^2$ has the abovementioned meaning and

Hal represents chlorine, bromine or iodine; or (E) compounds of the formula (Id)

(Id)

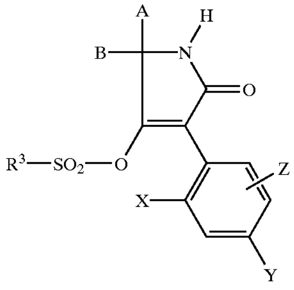

in which

A, B, X, Y, Z and $R^3$ have the abovementioned meanings are obtained when compounds of the formula (Ia)

(Ia)

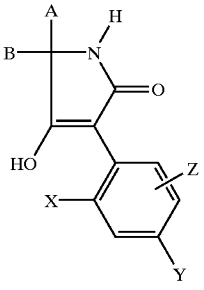

in which

A, B, X, Y and Z have the abovementioned meanings are reacted with sulfonyl chlorides of the general formula (VIII)

$R^3$—$SO_2$—Cl (VIII)

in which $R^3$ has the abovementioned meaning, if appropriate in the presence of a diluent and if appropriate in the presence of an acid-binding agent, or (F) 1-H-3-aryl-pyrrolidine-2,4-diones of the formula (Ie)

(Ie)

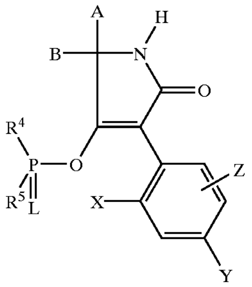

in which

A, B, L, X, Y, Z, $R^4$ and $R^5$ have the abovementioned meanings are obtained when 1-H-3-aryl-pyrrolidine-2,4-diones of the formula (Ia) or their enols (Ia)

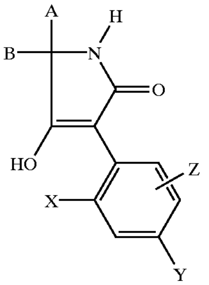

in which

A, B, X, Y and Z have the abovementioned meanings are reacted with phosphorus compounds of the general formula (IX)

(IX)

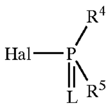

in which

L, $R^4$ $R^5$ have the abovementioned meanings and

Hal represents halogen, in particular chlorine or bromine;

or (G) compounds of the formula (If)

(I-f)

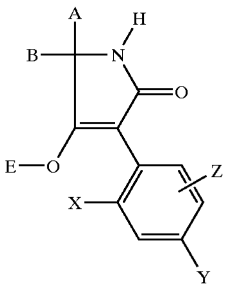

in which

A, B, X, Y and Z have the abovementioned meanings and

E represents a metal ion equivalent or an ammonium ion are obtained when compounds of the formula (Ia)

(Ia)

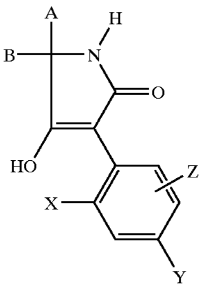

in which

A, B, X, Y and Z have the abovementioned meanings are reacted with metal compounds or amines of the general formulae (X) and (XI)

$Me(OR^9)_t$ (X)

(XI)

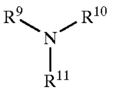

in which

Me represents mono- or divalent metal ions, t represents the number 1 or 2 and $R^9$, $R^{10}$ and $R^{11}$ independently of one another represent hydrogen and/or alkyl, if appropriate in the presence of a diluent.

(H) Furthermore, it has been found that compounds of the formula (Ig)

(Ig)

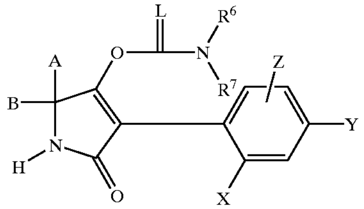

in which

A, B, L, X, Y, X, $R^6$ and $R^7$ have the abovementioned meanings are obtained when compounds of the formula (Ia)

(Ia)

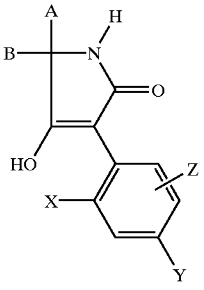

in which

A, B, X, Y and Z have the abovementioned meanings are reacted

α) with isocyanates or isothiocyanates of the general formula (XII)

$R^6$—N═C═L (XII)

in which $R^6$ has the abovementioned meaning, if appropriate in the presence of a diluent and if appropriate in the presence of a catalyst, or β) with carbamoyl chlorides or thiocarbamoyl chlorides of the general formula (XIII)

(XIII)

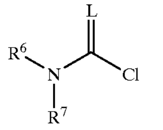

in which

L, $R^6$ and $R^7$ have the abovementioned meanings, if appropriate in the presence of a diluent and if appropriate in the presence of an acid-binding agent.

Furthermore, it has been found that the new 1-H-3-arylpyrrolidine-2,4-dione derivatives of the formula (I) are distinguished by outstanding insecticidal and acaricidal activities. Furthermore, compounds of the formula (I) have herbicidal and fungicidal secondary effects.

The following applies to the general formulae of the present application:

A preferably represents hydrogen, or represents $C_1$–$C_{12}$-alkyl, $C_3$–$C_8$-alkenyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_6$-alkyl or cycloalkyl having 3 to 8 ring atoms which can optionally be interrupted by oxygen and/or sulfur, in each case optionally substituted by halogen, or represents aryl, hetaryl or aryl-$C_1$–$C_6$-alkyl, in each case optionally substituted by halogen, $C_1$–$C_6$-alkyl, $C_1$–$C_6$-halogenoalkyl, $C_1$–$C_6$-alkoxy, and/or nitro.

B preferably represents hydrogen, or represents $C_1$–$C_{12}$-alkyl or $C_1$–$C_8$-alkoxyalkyl, or A, B and the carbon atom to which they are bonded preferably represent a saturated or unsaturated $C_3$–$C_{10}$-spirocycle which is optionally monosubstituted or polysubstituted by alkyl, cycloalkyl, halogenoalkyl, alkoxy, thioalkyl, halogen or phenyl and optionally interrupted by oxygen or sulfur, or A, B and the carbon atom to which they are bonded preferably represent a $C_3$–$C_6$-spirocycle which is substituted by an alkylenediyl group which is optionally interrupted by one or two oxygen and/or sulfur atoms or substituted by an alkylenedioxy or by an alkylenedithioyl group and this alkylenediyl, alkylenedioxy or alkylenedithioyl group together with the carbon atom to which it is bonded forms a further five- to eight-membered spirocycle, or A, B and the carbon atom to which they are bonded preferably represent a $C_3$–$C_8$-spirocycle in which two substituents together represent a saturated or unsaturated five- or six-membered cycle which is optionally substituted by alkyl, alkoxy or halogen and which can be interrupted by oxygen or sulfur.

A particularly preferably represents hydrogen, or represents $C_1$–$C_{10}$-alkyl, $C_3$–$C_6$-alkenyl, $C_1$–$C_8$-alkoxy-$C_2$–$C_6$-alkyl, $C_1$–$C_6$-polyalkoxy-$C_2$–$C_6$-alkyl, $C_1$–$C_8$-alkylthio-$C_2$–$C_6$-alkyl or cycloalkyl having 3 to 7 ring atoms which can be interrupted by 1 to 2 oxygen and/or sulfur atoms, in each case optionally substituted by halogen, or represents phenyl, thienyl, pyridyl, imidazolyl, pyrazolyl, triazolyl, indolyl, thiazolyl or phenyl-$C_1$–$C_4$-alkyl, in each case optionally substituted by halogen, $C_1$–$C_4$-alkyl, $C_1$–$C_4$-halogenoalkyl, $C_1$–$C_4$-alkoxy and/or nitro.

B particularly preferably represents hydrogen, $C_1$–$C_{10}$-alkyl or $C_1$–$C_6$-alkoxyalkyl, or A, B and the carbon atom to which they are bonded particularly preferably represent a saturated or unsaturated $C_3$–$C_9$-spirocycle which is optionally monosubstituted or polysubstituted by $C_1$–$C_6$-alkyl, $C_3$–$C_8$-cycloalkyl, $C_1$–$C_3$-halogenoalkyl, $C_1$–$C_6$-alkoxy, $C_1$–$C_6$-thioalkyl, fluorine, chlorine or phenyl and which is optionally interrupted by oxygen or sulfur, or A, B and the carbon atom to which they are bonded particularly preferably represent a $C_3$–$C_6$-spirocycle which is substituted by an alkylenediyl group which is optionally interrupted by one or two oxygen or sulfur atoms or substituted by an alkylenedioxy or by an alkylenedithiol group, and this alkylenediyl, alkylenedioxy or alkylenedithiol group together with the carbon atom to which it is bonded forms a further five- to seven-membered spirocycle, or A, B and the carbon atom to which they are bonded particularly preferably represent a $C_3$–$C_6$-spirocycle in which two adjacent substituents together represent a saturated or unsaturated five- or six-membered cycle which is substituted by $C_1$–$C_3$-alkyl, $C_1$–$C_3$-alkoxy, fluorine, chlorine or bromine and which can be interrupted by oxygen or sulfur.

A very particularly preferably represents hydrogen, or represents $C_1$–$C_8$-alkyl, $C_3$–$C_4$-alkenyl, $C_1$–$C_6$-alkoxy-$C_2$–$C_4$-alkyl, $C_1$–$C_4$-polyalkoxy-$C_2$–$C_4$-alkyl, $C_1$–$C_6$-alkylthio-$C_2$–$C_4$-alkyl or cycloalkyl having 3 to 6 ring atoms which can be interrupted by 1 to 2 oxygen and/or sulfur atoms, in each case optionally substituted by halogen, or represents phenyl, thienyl, pyridyl, imidazolyl, pyrazolyl, triazolyl, indolyl, thiazolyl or phenyl-$C_1$–$C_3$-alkyl, in each case optionally substituted by fluorine, chlorine, bromine, methyl, ethyl, propyl, iso-propyl, methoxy, ethoxy, trifluoromethyl and/or nitro.

B very particularly preferably represents hydrogen, $C_1$–$C_8$-alkyl or $C_1$–$C_4$-alkoxyalkyl, or A, B and the carbon atom to which they are bonded very particularly preferably represent a saturated or unsaturated $C_3$–$C_8$-spirocycle which is optionally monosubstituted or polysubstituted by methyl, ethyl, propyl, isopropyl, butyl, iso-butyl, sec-butyl, tert-butyl, cyclohexyl, trifluoromethyl, methoxy, ethoxy, propoxy, iso-propoxy, butoxy, iso-butoxy, sec-butoxy, tert-butoxy, methylthio, ethylthio, fluorine, chlorine or phenyl and optionally interrupted by oxygen or sulfur, or A, B and the carbon atom to which they are bonded very particularly preferably represent a $C_3$–$C_6$-spirocycle which is substituted by an alkylenediyl group which is optionally interrupted by an oxygen or sulfur atom or by an alkylenedioxy group, and this alkylenediyl or alkylenedioxy group together with the carbon atom to which it is bonded forms a further five- to seven-membered spirocycle, or A, B and the carbon atom to which they are bonded very particularly preferably represent a $C_3$–$C_6$-spirocycle in which two substituents together represent a saturated or unsaturated five- or six-membered cycle which can be interrupted by oxygen or sulfur.

X preferably represents halogen or $C_1$–$C_6$-alkoxy.

X particularly preferably reresents halogen or $C_1$–$C_4$-alkoxy.

X very particularly preferably represents fluorine, chlorine, bromine, methoxy, ethoxy, propoxy or isopropoxy.

Y preferably represents hydrogen, halogen or $C_1$–$C_6$-alkoxy.

Y particularly preferably represents hydrogen, halogen or $C_1$–$C_4$-alkoxy.

Y very particularly preferably represents hydrogen, fluorine, chlorine, bromine, methoxy, ethoxy, propoxy or isopropoxy.

Z preferably represents hydrogen, halogen or $C_1$–$C_6$-alkoxy.

Z particularly preferably represents hydrogen, halogen or $C_1$–$C_4$-alkoxy.

Z very particularly preferably represents hydrogen, fluorine, chlorine, bromine, methoxy, ethoxy, propoxy or isopropoxy.

In each case, X and Y or X and Z do not simultaneously represent halogen.

G preferably represents hydrogen (a) or the groups (b)

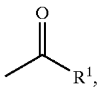

(c)

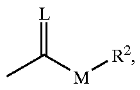

(d)

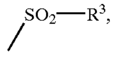

(e)

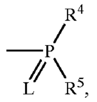

(f)

E or (g)

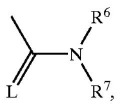

in which

E represents a metal ion equivalent or an ammonium ion and

L and M in each case represent oxygen or sulfur.

$R^1$ preferably represents $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, $C_1$–$C_8$-polyalkoxy-$C_2$–$C_8$-alkyl or cycloalkyl having 3 to 8 ring atoms which can be interrupted by oxygen and/or sulfur atoms, in each case optionally substituted by halogen, phenyl which is optionally substituted by halogen, nitro, $C_1$–$C_6$-alkyl, $C_1$–$C_6$-alkoxy, $C_1$–$C_6$-halogenoalkyl, $C_1$–$C_6$-halogenoalkoxy, $C_1$–$C_6$-alkylthio or $C_1$–$C_6$-alkylsulfonyl, phenyl-$C_1$–$C_6$-alkyl which is optionally substituted by halogen, $C_1$–$C_6$-alkyl, $C_1$–$C_6$-alkoxy, $C_1$–$C_6$-halogenoalkyl or $C_1$–$C_6$-halogenoalkoxy, hetaryl which is optionally substituted by halogen and/or $C_1$–$C_6$-alkyl, phenoxy-$C_1$–$C_6$-alkyl which is optionally substituted by halogen and/or $C_1$–$C_6$-alkyl, hetaryloxy-$C_1$–$C_6$-alkyl which is optionally substituted by halogen, amino and/or $C_1$–$C_6$-alkyl.

$R^2$ preferably represents $C_1$–$C_{20}$-alkyl, $C_3$–$C_{20}$-alkenyl, $C_1$–$C_8$-alkoxy-$C_2$–$C_8$-alkyl or $C_1$–$C_8$-polyalkoxy-$C_2$–$C_8$-alkyl, in each case optionally substituted by halogen, $C_3$–$C_8$-cycloalkyl which is optionally substituted by halogen, $C_1$–$C_4$-alkyl and/or $C_1$–$C_4$-alkoxy, or phenyl or benzyl, in each case optionally substituted by halogen, nitro, $C_1$–$C_6$-alkyl, $C_1$–$C_4$-alkoxy and/or $C_1$–$C_6$-halogenoalkyl, $R^3{}_1$, $R^4$ and $R^5$ independently of one another preferably represent $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_3$–$C_6$-alkenylthio or $C_3$–$C_7$-cycloalkylthio, in each case optionally substituted by halogen, or represent phenyl, phenoxy or phenylthio, in each case optionally substituted by halogen, nitro, cyano, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkyl or $C_1$–$C_4$-halogenoalkyl, $R^6$ and $R^7$ independently of one another preferably represent hydrogen, $C_1$–$C_8$-alkyl, $C_3$–$C_8$-cycloalkyl, $C_1$–$C_8$-alkoxy, $C_3$–$C_8$-alkenyl or $C_1$–$C_8$-alkoxy-$C_2$–$C_8$-alkyl, in each case optionally substituted by halogen, or represent phenyl which is optionally substituted by halogen, $C_1$–$C_8$-halogenoalkyl, $C_1$–$C_8$-alkyl and/or $C_1$–$C_8$-alkoxy, or represent benzyl which is optionally substituted by halogen, $C_1$–$C_8$-alkyl, $C_1$–$C_8$-halogenoalkyl and/or $C_1$–$C_8$-alkoxy, or together with the N atom to which they are bonded represent a $C_3$–$C_6$-alkylene ring which is optionally interrupted by oxygen or sulfur.

G particularly preferably represents hydrogen (a) or the groups (b)

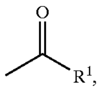

(c)

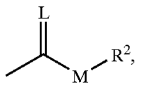

(d)

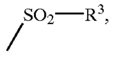

(e)

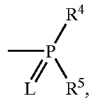

(f)

E or (g)

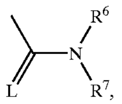

in which

E represents a metal ion equivalent or an ammonium ion,

L and M in each case represent oxygen or sulfur, $R^1$ particularly preferably represents $C_1$–$C_{16}$-alkyl, $C_2$–$C_{16}$-alkenyl, $C_1$–$C_6$-alkoxy-$C_1$–$C_6$-alkyl, $C_1$–$C_6$-alkylthio-$C_1$–$C_6$-alkyl, $C_1$–$C_6$-polyalkoxy-$C_2$–$C_6$-alkyl or cycloalkyl having 3 to 7 ring atoms which can be interrupted by 1 or 2 oxygen and/or sulfur atoms, in each case optionally substituted by halogen, phenyl which is optionally substituted by halogen, nitro, $C_1$–$C_4$-alkyl, $C_1$–$C_4$-alkoxy, $C_1$–$C_3$-halogenoalkyl, $C_1$–$C_3$-halogenoalkoxy, $C_1$–$C_4$-alkylthio and/or $C_1$–$C_4$-alkylsulfonyl, phenyl-$C_1$–$C_4$-alkyl which is optionally substituted by halogen, $C_1$–$C_4$-alkyl, $C_1$–$C_4$-alkoxy, $C_1$–$C_3$-halogenoalkyl or $C_1$–$C_3$-halogenoalkoxy, thienyl, furanyl, pyridyl, pyrimidyl, thiazolyl or pyrazolyl, in each case optionally substituted by fluorine, chlorine, bromine and/or $C_1$–$C_4$-alkyl, phenoxy-$C_1$–$C_5$-alkyl which is optionally substituted by fluorine, chlorine, bromine and/or $C_1$–$C_4$-alkyl, or pyridyloxy-$C_1$–$C_5$-alkyl, pyrimidyloxy-$C_1$–$C_5$-alkyl or thiazolyloxy-$C_1$–$C_5$-alkyl, in each case optionally substituted by fluorine, chlorine, bromine, amino and/or $C_1$–$C_4$-alkyl.

$R^2$ particularly preferably represents $C_1$–$C_{16}$-alkyl, $C_3$–$C_{16}$-alkenyl, $C_1$–$C_6$-alkoxy-$C_2$–$C_6$-alkyl or $C_1$–$C_6$-polyalkoxy-$C_2$–$C_6$-alkyl, in each case optionally substituted by halogen, $C_3$–$C_7$-cycloalkyl which is optionally substituted by halogen, $C_1$–$C_3$-alkyl and/or $C_1$–$C_3$-alkoxy, or phenyl or benzyl, in each case optionally substituted by halogen, nitro, $C_1$–$C_4$-alkyl, $C_1$–$C_3$-alkoxy and/or $C_1$–$C_3$-halogenoalkyl.

$R^3$, $R^4$ and $R^5$ independently of one another particularly preferably represent $C_1$–$C_6$-alkyl, $C_1$–$C_6$-alkoxy, $C_1$–$C_6$-alkylamino, Di-($C_1$–$C_6$)-alkylamino, $C_1$–$C_6$-alkylthio, $C_3$–$C_4$-alkenylthio or $C_3$–$C_6$-cycloalkylthio, in each case optionally substituted by halogen, or phenyl, phenoxy or phenylthio, in each case optionally substituted by fluorine, chlorine, bromine, nitro, cyano, $C_1$–$C_3$-alkoxy, $C_1$–$C_3$-halogenoalkoxy, $C_1$–$C_3$-alkylthio, $C_1$–$C_3$-halogenoalkylthio, $C_1$–$C_3$-alkyl or $C_1$–$C_3$-halogenoalkyl.

$R^6$ and $R^7$ independently of one another particularly preferably represent hydrogen, or $C_1$–$C_6$-alkyl, $C_3$–$C_6$-cycloalkyl, $C_1$–$C_6$-alkoxy, $C_3$–$C_6$-alkenyl or $C_1$–$C_6$-alkoxy-$C_2$–$C_6$-alkyl, in each case optionally substituted by halogen, or phenyl which is optionally substituted by halogen, $C_1$–$C_5$-halogenoalkyl, $C_1$–$C_5$-alkyl and/or $C_1$–$C_5$-alkoxy, or benzyl which is optionally substituted by halogen, $C_1$–$C_5$-alkyl, $C_1$–$C_5$-halogenoalkyl, and/or $C_1$–$C_5$-alkoxy, or together with the N atom to which they are bonded a $C_3$–$C_6$-alkylene ring which is optionally interrupted by oxygen or sulfur.

G very particularly preferably represents hydrogen (a) or the groups (b)

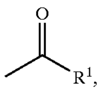

(c)

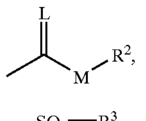

(d)

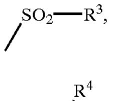

(e)

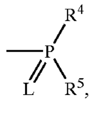

(f)

E or

-continued (g)

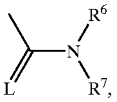

in which

E represents a metal ion equivalent or an ammonium ion and

L and M in each case represent oxygen or sulfur.

$R^1$ very particularly preferably represents $C_1$–$C_{14}$-alkyl, $C_2$–$C_{14}$-alkenyl, $C_1$–$C_4$-alkoxy-$C_1$–$C_6$-alkyl, $C_1$–$C_4$-alkylthio-$C_1$–$C_6$-alkyl, $C_1$–$C_4$-polyalkoxy-$C_2$–$C_4$-alkyl or cycloalkyl having 3 to 6 ring atoms which can be interrupted by 1 to 2 oxygen and/or sulfur atoms, in each case optionally substituted by fluorine and/or chlorine, phenyl which is optionally substituted by fluorine, chlorine, bromine, methyl, ethyl, propyl, i-propyl, methoxy, ethoxy, trifluoromethyl, trifluoromethoxy, methylthio, ethylthio, methylsulfonyl, ethylsulfonyl and/or nitro, phenyl-$C_1$–$C_3$-alkyl which is optionally substituted by fluorine, chlorine, bromine, methyl, ethyl, propyl, i-propyl, methoxy, ethoxy, trifluoromethyl and/or trifluoromethoxy, thienyl, furanyl, pyridyl, pyrimidyl, thiazolyl or pyrazolyl, in each case optionally substituted by fluorine, chlorine, bromine, methyl and/or ethyl, phenoxy-$C_1$–$C_4$-alkyl which is optionally substituted by fluorine, chlorine, methyl and/or ethyl, or pyridyloxy-$C_1$–$C_4$-alkyl, pyrimidyloxy-$C_1$–$C_4$-alkyl or thiazolyloxy-$C_1$–$C_4$-alkyl, in each case optionally substituted by fluorine, chlorine, amino, methyl and/or ethyl.

$R^2$ very particularly preferably represents $C_1$–$C_{14}$-alkyl, $C_3$–$C_{14}$-alkenyl, $C_1$–$C_4$-alkoxy-$C_2$–$C_6$-alkyl or $C_1$–$C_4$-polyalkoxy-$C_2$–$C_6$-alkyl, in each case optionally substituted by fluorine and/or chlorine, $C_3$–$C_6$-cycloalkyl which is optionally substituted by fluorine, chlorine, methyl, ethyl, propyl, iso-propyl and/or methoxy, or phenyl or benzyl, in each case optionally substituted by fluorine, chlorine, nitro, methyl, ethyl propyl, i-propyl, methoxy, ethoxy and/or trifluoromethyl.

$R^3$, $R^4$ and $R^5$ very particularly preferably independently of one another represent $C_1$–$C_4$-alkyl, $C_1$–$C_4$-alkoxy, $C_1$–$C_4$-alkylamino, di-($C_1$–$C_4$)-alkylamino or $C_1$–$C_4$-alkylthio, in each case optionally substituted by fluorine and/or chlorine, or phenyl, phenoxy or phenylthio, in each case optionally substituted by fluorine, chlorine, bromine, nitro, cyano, $C_1$–$C_2$-alkoxy, $C_1$–$C_2$-fluoroalkoxy, $C_1$–$C_2$-alkylthio, $C_1$–$C_2$-fluoroalkylthio and/or $C_1$–$C_3$-alkyl.

$R^6$ and $R^7$ very particularly preferably independently of one another represent hydrogen, or $C_1$–$C_4$-alkyl, $C_3$–$C_6$-cycloalkyl, $C_1$–$C_4$-alkoxy, $C_3$–$C_4$-alkenyl or $C_1$–$C_4$-alkoxy-$C_2$–$C_4$-alkyl, in each case optionally substituted by fluorine, chlorine and/or bromine, or phenyl which is optionally substituted by fluorine, chlorine, bromine, $C_1$–$C_4$-halogenoalkyl, $C_1$–$C_4$-alkyl and/or $C_1$–$C_4$-alkoxy, or benzyl which is optionally substituted by fluorine, chlorine, bromine, $C_1$–$C_4$-alkyl, $C_1$–$C_4$-halogenoalkyl, and/or $C_1$–$C_4$-alkoxy, or together with the N atom to which they are bonded a $C_3$–$C_6$-alkylene ring which is optionally interrupted by oxygen or sulfur.

Unless otherwise specified, alkyl radicals, also in connection with hetero atoms such as, for example, in alkoxy, are in each case straight-chain or branched as far as this is possible.

The general definitions of radicals or illustrations, or the preferred ranges of the definitions of radicals or illustrations, which have been mentioned above can be combined with each other as desired, that is to say that combinations between the specific ranges and preferred ranges are also possible. They apply to the end product and, analogously, to the precursors and intermediates.

Preferred according to the invention are those compounds of the general formula (I) which show a combination of the meanings given above as being preferred (which are preferable).

Particularly preferred according to the invention are those compounds of the general formula (I) which show a combination of the meanings given above as being particularly preferred.

Very particularly preferred according to the invention are those compounds of the general formula (I) which show a combination of the meanings given above as being very particularly preferred.

The following compounds of the formula (Ia) may be mentioned individually in addition to the compounds mentioned in the preparation examples:

TABLE 1

(Ia)

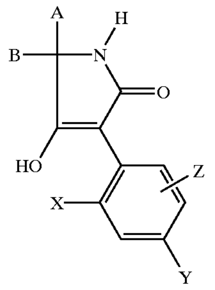

| X | Y | Z | A | B |
|---|---|---|---|---|
| Cl | $OCH_3$ | H | $CH_3$ | H |
| Cl | $OCH_3$ | H | $C_2H_5$ | H |
| Cl | $OCH_3$ | H | $C_3H_7$ | H |
| Cl | $OCH_3$ | H | i-$C_3H_7$ | H |
| Cl | $OCH_3$ | H | $C_4H_9$ | H |
| Cl | $OCH_3$ | H | i-$C_4H_9$ | H |
| Cl | $OCH_3$ | H | s-$C_4H_9$ | H |
| Cl | $OCH_3$ | H | t-$C_4H_9$ | H |
| Cl | $OCH_3$ | H | $CH_3$ | $CH_3$ |
| Cl | $OCH_3$ | H | $C_2H_5$ | $CH_3$ |
| Cl | $OCH_3$ | H | $C_3H_7$ | $CH_3$ |
| Cl | $OCH_3$ | H | i-$C_3H_7$ | $CH_3$ |
| Cl | $OCH_3$ | H | $C_4H_9$ | $CH_3$ |
| Cl | $OCH_3$ | H | i-$C_4H_9$ | $CH_3$ |
| Cl | $OCH_3$ | H | s-$C_4H_9$ | $CH_3$ |
| Cl | $OCH_3$ | H | t-$C_4H_9$ | $CH_3$ |
| Cl | $OCH_3$ | H | $C_2H_5$ | $C_2H_5$ |
| Cl | $OCH_3$ | H | $C_3H_7$ | $C_3H_7$ |
| Cl | $OCH_3$ | H | 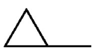 | $CH_3$ |
| Cl | $OCH_3$ | H | 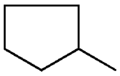 | $CH_3$ |
| Cl | $OCH_3$ | H | 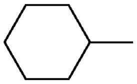 | $CH_3$ |
| Cl | H | 6-$OCH_3$ | $CH_3$ | H |
| Cl | H | 6-$OCH_3$ | $C_2H_5$ | H |

TABLE 1-continued (Ia)

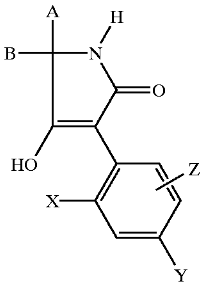

| X | Y | Z | A | B |
|---|---|---|---|---|
| Cl | H | 6-$OCH_3$ | $C_3H_7$ | H |
| Cl | H | 6-$OCH_3$ | i-$C_3H_7$ | H |
| Cl | H | 6-$OCH_3$ | $C_4H_9$ | H |
| Cl | H | 6-$OCH_3$ | i-$C_4H_9$ | H |
| Cl | H | 6-$OCH_3$ | s-$C_4H_9$ | H |
| Cl | H | 6-$OCH_3$ | t-$C_4H_9$ | H |
| Cl | H | 6-$OCH_3$ | $CH_3$ | $CH_3$ |
| Cl | H | 6-$OCH_3$ | $C_2H_5$ | $CH_3$ |
| Cl | H | 6-$OCH_3$ | $C_3H_7$ | $CH_3$ |
| Cl | H | 6-$OCH_3$ | i-$C_3H_7$ | $CH_3$ |
| Cl | H | 6-$OCH_3$ | $C_4H_9$ | $CH_3$ |
| Cl | H | 6-$OCH_3$ | i-$C_4H_9$ | $CH_3$ |
| Cl | H | 6-$OCH_3$ | s-$C_4H_9$ | $CH_3$ |
| Cl | H | 6-$OCH_3$ | t-$C_4H_9$ | $CH_3$ |
| Cl | H | 6-$OCH_3$ | $C_2H_5$ | $C_2H_5$ |
| Cl | H | 6-$OCH_3$ | $C_3H_7$ | $C_3H_7$ |
| Cl | H | 6-$OCH_3$ | 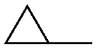 | $CH_3$ |
| Cl | H | 6-$OCH_3$ | 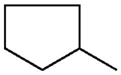 | $CH_3$ |
| Cl | H | 6-$OCH_3$ | 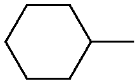 | $CH_3$ |
| $OCH_3$ | Cl | H | $CH_3$ | H |
| $OCH_3$ | Cl | H | $C_2H_5$ | H |
| $OCH_3$ | Cl | H | $C_3H_7$ | H |
| $OCH_3$ | Cl | H | i-$C_3H_7$ | H |
| $OCH_3$ | Cl | H | $C_4H_9$ | H |
| $OCH_3$ | Cl | H | i-$C_4H_9$ | H |
| $OCH_3$ | Cl | H | s-$C_4H_9$ | H |
| $OCH_3$ | Cl | H | t-$C_4H_9$ | H |
| $OCH_3$ | Cl | H | $CH_3$ | $CH_3$ |
| $OCH_3$ | Cl | H | $C_2H_5$ | $CH_3$ |
| $OCH_3$ | Cl | H | $C_3H_7$ | $CH_3$ |
| $OCH_3$ | Cl | H | i-$C_3H_7$ | $CH_3$ |
| $OCH_3$ | Cl | H | $C_4H_9$ | $CH_3$ |
| $OCH_3$ | Cl | H | i-$C_4H_9$ | $CH_3$ |
| $OCH_3$ | Cl | H | s-$C_4H_9$ | $CH_3$ |
| $OCH_3$ | Cl | H | t-$C_4H_9$ | $CH_3$ |
| $OCH_3$ | Cl | H | $C_2H_5$ | $C_2H_5$ |
| $OCH_3$ | Cl | H | $C_3H_7$ | $C_3H_7$ |
| $OCH_3$ | Cl | H | 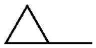 | $CH_3$ |
| $OCH_3$ | Cl | H | 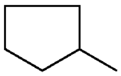 | $CH_3$ |
| $OCH_3$ | Cl | H | 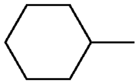 | $CH_3$ |

TABLE 1-continued (Ia)

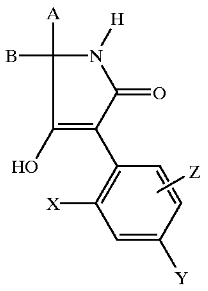

| X | Y | Z | A | B |
|---|---|---|---|---|
| Cl | $OCH_3$ | H | | $-(CH_2)_2-$ |
| Cl | $OCH_3$ | H | | $-(CH_2)_4-$ |
| Cl | $OCH_3$ | H | | $-(CH_2)_5-$ |
| Cl | $OCH_3$ | H | | $-(CH_2)_6-$ |
| Cl | $OCH_3$ | H | | $-(CH_2)_7-$ |
| Cl | $OCH_3$ | H | | $-(CH_2)_2-O-(CH_2)_2-$ |
| Cl | $OCH_3$ | H | | $-(CH_2)_2-S-(CH_2)_2-$ |
| Cl | $OCH_3$ | H | | $-CH_2-CHCH_3-(CH_2)_3-$ |
| Cl | $OCH_3$ | H | | $-(CH_2)_2-CHCH_3-(CH_2)_2-$ |
| Cl | $OCH_3$ | H | | $-(CH_2)_2-CHC_2H_5-(CH_2)_2-$ |
| Cl | $OCH_3$ | H | | $-(CH_2)_2-CHC_3H_7-(CH_2)_2-$ |
| Cl | $OCH_3$ | H | | $-(CH_2)_2-CHi\text{-}C_3H_7-(CH_2)_2-$ |
| Cl | $OCH_3$ | H | | $-(CH_2)_2-CHOCH_3-(CH_2)_2-$ |
| Cl | $OCH_3$ | H | | $-(CH_2)_2-CHOC_2H_5-(CH_2)_2-$ |
| Cl | $OCH_3$ | H | | $-(CH_2)_2-CHOC_3H_7-(CH_2)_2-$ |
| Cl | $OCH_3$ | H | | $-(CH_2)_2-CHi\text{-}OC_3H_7-(CH_2)_2-$ |
| Cl | $OCH_3$ | H | | $-(CH_2)_2-C(CH_3)_2-(CH_2)_2-$ |
| Cl | $OCH_3$ | H | | $-CH_2-(CHCH_3)_2-(CH_2)_2-$ |
| Cl | $OCH_3$ | H | | 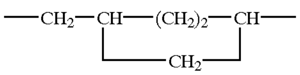 |
| Cl | $OCH_3$ | H | | 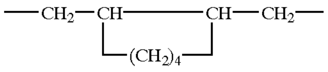 |
| Cl | $OCH_3$ | H | | 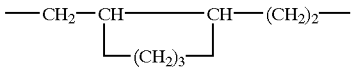 |
| Cl | H | $6\text{-}OCH_3$ | | $-(CH_2)_2-$ |
| Cl | H | $6\text{-}OCH_3$ | | $-(CH_2)_4-$ |
| Cl | H | $6\text{-}OCH_3$ | | $-(CH_2)_5-$ |
| Cl | H | $6\text{-}OCH_3$ | | $-(CH_2)_6-$ |
| Cl | H | $6\text{-}OCH_3$ | | $-(CH_2)_7-$ |
| Cl | H | $6\text{-}OCH_3$ | | $-(CH_2)_2-O-(CH_2)_2-$ |
| Cl | H | $6\text{-}OCH_3$ | | $-(CH_2)_2-S-(CH_2)_2-$ |
| Cl | H | $6\text{-}OCH_3$ | | $-CH_2-CHCH_3-(CH_2)_3-$ |
| Cl | H | $6\text{-}OCH_3$ | | $-(CH_2)_2-CHCH_3-(CH_2)_2-$ |
| Cl | H | $6\text{-}OCH_3$ | | $-(CH_2)_2-CHC_2H_5-(CH_2)_2-$ |
| Cl | H | $6\text{-}OCH_3$ | | $-(CH_2)_2-CHC_3H_7-(CH_2)_2-$ |
| Cl | H | $6\text{-}OCH_3$ | | $-(CH_2)_2-CHi\text{-}C_3H_7-(CH_2)_2-$ |
| Cl | H | $6\text{-}OCH_3$ | | $-(CH_2)_2-CHOCH_3-(CH_2)_2-$ |
| Cl | H | $6\text{-}OCH_3$ | | $-(CH_2)_2-CHOC_2H_5-(CH_2)_2-$ |
| Cl | H | $6\text{-}OCH_3$ | | $-(CH_2)_2-CHOC_3H_7-(CH_2)_2-$ |
| Cl | H | $6\text{-}OCH_3$ | | $-(CH_2)_2-CHi\text{-}OC_3H_7-(CH_2)_2-$ |
| Cl | H | $6\text{-}OCH_3$ | | $-(CH_2)_2-C(CH_3)_2-(CH_2)_2-$ |
| Cl | H | $6\text{-}OCH_3$ | | $-CH_2-(CHCH_2)_2-(CH_2)_2-$ |

TABLE 1-continued (Ia)

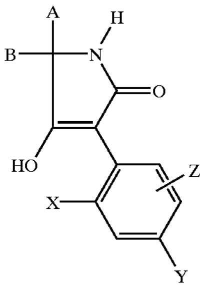

| X | Y | Z | A | B |
|---|---|---|---|---|
| Cl | H | $6\text{-}OCH_3$ | | 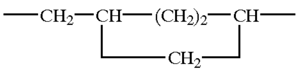 |
| Cl | H | $6\text{-}OCH_3$ | | 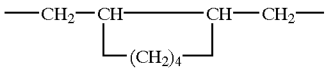 |
| Cl | H | $6\text{-}OCH_3$ | | 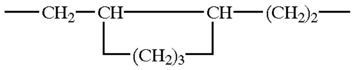 |
| $OCH_3$ | Cl | H | | $-(CH_2)_2-$ |
| $OCH_3$ | Cl | H | | $-(CH_2)_4-$ |
| $OCH_3$ | Cl | H | | $-(CH_2)_5-$ |
| $OCH_3$ | Cl | H | | $-(CH_2)_6-$ |
| $OCH_3$ | Cl | H | | $-(CH_2)_7-$ |
| $OCH_3$ | Cl | H | | $-(CH_2)_2-O-(CH_2)_2-$ |
| $OCH_3$ | Cl | H | | $-(CH_2)_2-S-(CH_2)_2-$ |
| $OCH_3$ | Cl | H | | $-CH_2-CHCH_3-(CH_2)_3-$ |
| $OCH_3$ | Cl | H | | $-(CH_2)_2-CHCH_3-(CH_2)_2-$ |
| $OCH_3$ | Cl | H | | $-(CH_2)_2-CHC_2H_5-(CH_2)_2-$ |
| $OCH_3$ | Cl | H | | $-(CH_2)_2-CHC_3H_7-(CH_2)_2-$ |
| $OCH_3$ | Cl | H | | $-(CH_2)_2-CHi\text{-}C_3H_7-(CH_2)_2-$ |
| $OCH_3$ | Cl | H | | $-(CH_2)_2-CHOCH_3-(CH_2)_2-$ |
| $OCH_3$ | Cl | H | | $-(CH_2)_2-CHOC_2H_5-(CH_2)_2-$ |
| $OCH_3$ | Cl | H | | $-(CH_2)_2-CHOC_3H_7-(CH_2)_2-$ |
| $OCH_3$ | Cl | H | | $-(CH_2)_2-CHi\text{-}OC_3H_7-(CH_2)_2-$ |
| $OCH_3$ | Cl | H | | $-(CH_2)_2-C(CH_3)_2-(CH_2)_2-$ |
| $OCH_3$ | Cl | H | | $-CH_2-(CHCH_3)_2-(CH_2)_2-$ |
| $OCH_3$ | Cl | H | | 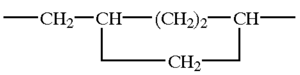 |
| $OCH_3$ | Cl | H | | 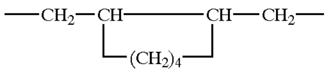 |
| $OCH_3$ | Cl | H | | 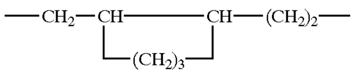 |

The following compounds of the formula (Ib) may be mentioned individually in addition to the compounds mentioned in the preparation examples:

TABLE 2

(Ib)

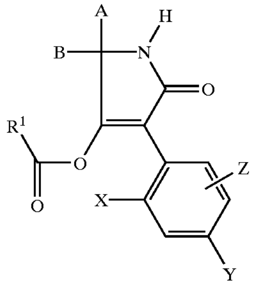

| X | Y | Z | A | B | $R^1$ |
|---|---|---|---|---|---|
| Cl | $OCH_3$ | H | $CH_3$ | H | $CH_3$ |
| Cl | $OCH_3$ | H | $C_2H_5$ | H | $CH_3$ |
| Cl | $OCH_3$ | H | $C_3H_7$ | H | $CH_3$ |
| Cl | $OCH_3$ | H | i-$C_3H_7$ | H | $CH_3$ |
| Cl | $OCH_3$ | H | $C_4H_9$ | H | $CH_3$ |
| Cl | $OCH_3$ | H | i-$C_4H_9$ | H | $CH_3$ |
| Cl | $OCH_3$ | H | s-$C_4H_9$ | H | $CH_3$ |
| Cl | $OCH_3$ | H | t-$C_4H_9$ | H | $CH_3$ |
| Cl | $OCH_3$ | H | $CH_3$ | $CH_3$ | $CH_3$ |
| Cl | $OCH_3$ | H | $C_2H_5$ | $CH_3$ | $CH_3$ |
| Cl | $OCH_3$ | H | $C_3H_7$ | $CH_3$ | $CH_3$ |
| Cl | $OCH_3$ | H | i-$C_3H_7$ | $CH_3$ | $CH_3$ |
| Cl | $OCH_3$ | H | $C_4H_9$ | $CH_3$ | $CH_3$ |
| Cl | $OCH_3$ | H | i-$C_4H_9$ | $CH_3$ | $CH_3$ |
| Cl | $OCH_3$ | H | s-$C_4H_9$ | $CH_3$ | $CH_3$ |
| Cl | $OCH_3$ | H | t-$C_4H_9$ | $CH_3$ | $CH_3$ |
| Cl | $OCH_3$ | H | $C_2H_5$ | $C_2H_5$ | $CH_3$ |
| Cl | $OCH_3$ | H | $C_3H_7$ | $C_3H_7$ | $CH_3$ |
| Cl | $OCH_3$ | H | 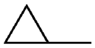 | $CH_3$ | $CH_3$ |
| Cl | $OCH_3$ | H | 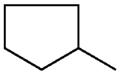 | $CH_3$ | $CH_3$ |
| Cl | $OCH_3$ | H | 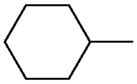 | $CH_3$ | $CH_3$ |
| Cl | H | 6-$OCH_3$ | $CH_3$ | H | $CH_3$ |
| Cl | H | 6-$OCH_3$ | $C_2H_5$ | H | $CH_3$ |
| Cl | H | 6-$OCH_3$ | $C_3H_7$ | H | $CH_3$ |
| Cl | H | 6-$OCH_3$ | i-$C_3H_7$ | H | $CH_3$ |
| Cl | H | 6-$OCH_3$ | $C_4H_9$ | H | $CH_3$ |
| Cl | H | 6-$OCH_3$ | i-$C_4H_9$ | H | $CH_3$ |
| Cl | H | 6-$OCH_3$ | s-$C_4H_9$ | H | $CH_3$ |
| Cl | H | 6-$OCH_3$ | t-$C_4H_9$ | H | $CH_3$ |
| Cl | H | 6-$OCH_3$ | $CH_3$ | $CH_3$ | $CH_3$ |
| Cl | H | 6-$OCH_3$ | $C_2H_5$ | $CH_3$ | $CH_3$ |
| Cl | H | 6-$OCH_3$ | $C_3H_7$ | $CH_3$ | $CH_3$ |
| Cl | H | 6-$OCH_3$ | i-$C_3H_7$ | $CH_3$ | $CH_3$ |
| Cl | H | 6-$OCH_3$ | $C_4H_9$ | $CH_3$ | $CH_3$ |
| Cl | H | 6-$OCH_3$ | i-$C_4H_9$ | $CH_3$ | $CH_3$ |
| Cl | H | 6-$OCH_3$ | s-$C_4H_9$ | $CH_3$ | $CH_3$ |
| Cl | H | 6-$OCH_3$ | t-$C_4H_9$ | $CH_3$ | $CH_3$ |
| Cl | H | 6-$OCH_3$ | $C_2H_5$ | $C_2H_5$ | $CH_3$ |
| Cl | H | 6-$OCH_3$ | $C_3H_7$ | $C_3H_7$ | $CH_3$ |
| Cl | H | 6-$OCH_3$ | 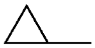 | $CH_3$ | $CH_3$ |
| Cl | H | 6-$OCH_3$ | 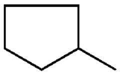 | $CH_3$ | $CH_3$ |

TABLE 2-continued (Ib)

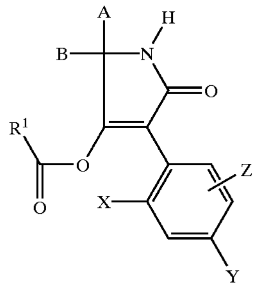

| X | Y | Z | A | B | $R^1$ |
|---|---|---|---|---|---|
| Cl | H | 6-$OCH_3$ | 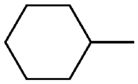 | $CH_3$ | $CH_3$ |
| $OCH_3$ | Cl | H | $CH_3$ | H | $CH_3$ |
| $OCH_3$ | Cl | H | $C_2H_5$ | H | $CH_3$ |
| $OCH_3$ | Cl | H | $C_3H_7$ | H | $CH_3$ |
| $OCH_3$ | Cl | H | i-$C_3H_7$ | H | $CH_3$ |
| $OCH_3$ | Cl | H | $C_4H_9$ | H | $CH_3$ |
| $OCH_3$ | Cl | H | i-$C_4H_9$ | H | $CH_3$ |
| $OCH_3$ | Cl | H | s-$C_4H_9$ | H | $CH_3$ |
| $OCH_3$ | Cl | H | t-$C_4H_9$ | H | $CH_3$ |
| $OCH_3$ | Cl | H | $CH_3$ | $CH_3$ | $CH_3$ |
| $OCH_3$ | Cl | H | $C_2H_5$ | $CH_3$ | $CH_3$ |
| $OCH_3$ | Cl | H | $C_3H_7$ | $CH_3$ | $CH_3$ |
| $OCH_3$ | Cl | H | i-$C_3H_7$ | $CH_3$ | $CH_3$ |
| $OCH_3$ | Cl | H | $C_4H_9$ | $CH_3$ | $CH_3$ |
| $OCH_3$ | Cl | H | i-$C_4H_9$ | $CH_3$ | $CH_3$ |
| $OCH_3$ | Cl | H | s-$C_4H_9$ | $CH_3$ | $CH_3$ |
| $OCH_3$ | Cl | H | t-$C_4H_9$ | $CH_3$ | $CH_3$ |
| $OCH_3$ | Cl | H | $C_2H_5$ | $C_2H_5$ | $CH_3$ |
| $OCH_3$ | Cl | H | $C_3H_7$ | $C_3H_7$ | $CH_3$ |
| $OCH_3$ | Cl | H | 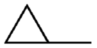 | $CH_3$ | $CH_3$ |
| $OCH_3$ | Cl | H | 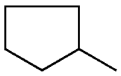 | $CH_3$ | $CH_3$ |
| $OCH_3$ | Cl | H | 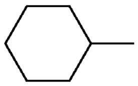 | $CH_3$ | $CH_3$ |
| Cl | $OCH_3$ | H | $-(CH_2)_2-$ | | $CH_3$ |
| Cl | $OCH_3$ | H | $-(CH_2)_4-$ | | $CH_3$ |
| Cl | $OCH_3$ | H | $-(CH_2)_5-$ | | $CH_3$ |
| Cl | $OCH_3$ | H | $-(CH_2)_6-$ | | $CH_3$ |
| Cl | $OCH_3$ | H | $-(CH_2)_7-$ | | $CH_3$ |
| Cl | $OCH_3$ | H | $-(CH_2)_2-O-(CH_2)_2-$ | | $CH_3$ |
| Cl | $OCH_3$ | H | $-(CH_2)_2-S-(CH_2)_2-$ | | $CH_3$ |
| Cl | $OCH_3$ | H | $-CH_2-CHCH_3-(CH_2)_3-$ | | $CH_3$ |
| Cl | $OCH_3$ | H | $-(CH_2)_2-CHCH_3-(CH_2)_2-$ | | $CH_3$ |
| Cl | $OCH_3$ | H | $-(CH_2)_2-CHC_2H_5-(CH_2)_2-$ | | $CH_3$ |
| Cl | $OCH_3$ | H | $-(CH_2)_2-CHC_3H_7-(CH_2)_2$ | | $CH_3$ |
| Cl | $OCH_3$ | H | $-(CH_2)_2-$CHi-$C_3H_7-(CH_2)_2-$ | | $CH_3$ |
| Cl | $OCH_3$ | H | $-(CH_2)_2-CHOCH_3-(CH_2)_2-$ | | $CH_3$ |
| Cl | $OCH_3$ | H | $-(CH_2)_2-CHOC_2H_5-(CH_2)_2-$ | | $CH_3$ |
| Cl | $OCH_3$ | H | $-(CH_2)_2-CHOC_3H_7-(CH_2)_2-$ | | $CH_3$ |
| Cl | $OCH_3$ | H | $-(CH_2)_2-$CHi-$OC_3H_7-(CH_2)_2-$ | | $CH_3$ |
| Cl | $OCH_3$ | H | $-(CH_2)_2-C(CH_3)_2-(CH_2)_2-$ | | $CH_3$ |
| Cl | $OCH_3$ | H | $-CH_2-(CHCH_3)_2-(CH_2)_2-$ | | $CH_3$ |
| Cl | $OCH_3$ | H | 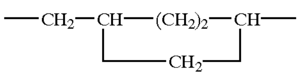 | | $CH_3$ |

TABLE 2-continued (Ib)

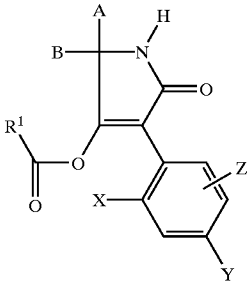

| X | Y | Z | A | B | $R^1$ |
|---|---|---|---|---|---|
| Cl | $OCH_3$ | H | 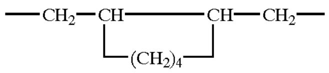 | | $CH_3$ |
| Cl | $OCH_3$ | H | 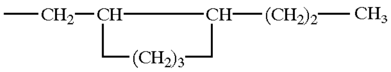 | | |
| Cl | H | 6-$OCH_3$ | $—(CH_2)_2—$ | | $CH_3$ |
| Cl | H | 6-$OCH_3$ | $—(CH_2)_4—$ | | $CH_3$ |
| Cl | H | 6-$OCH_3$ | $—(CH_2)_5—$ | | $CH_3$ |
| Cl | H | 6-$OCH_3$ | $—(CH_2)_6—$ | | $CH_3$ |
| Cl | H | 6-$OCH_3$ | $—(CH_2)_7—$ | | $CH_3$ |
| Cl | H | 6-$OCH_3$ | $—(CH_2)_2—O—(CH_2)_2—$ | | $CH_3$ |
| Cl | H | 6-$OCH_3$ | $—(CH_2)_2—S—(CH_2)_2—$ | | $CH_3$ |
| Cl | H | 6-$OCH_3$ | $—CH_2—CHCH_3—(CH_2)_3$ | | $CH_3$ |
| Cl | H | 6-$OCH_3$ | $—(CH_2)_2—CHCH_3—(CH_2)_2—$ | | $CH_3$ |
| Cl | H | 6-$OCH_3$ | $—(CH_2)_2—CHC_2H_5—(CH_2)_2—$ | | $CH_3$ |
| Cl | H | 6-$OCH_3$ | $—(CH_2)_2—CHC_3H_7—(CH_2)_2—$ | | $CH_3$ |
| Cl | H | 6-$OCH_3$ | $—(CH_2)_2—CHi\text{-}C_3H_7—(CH_2)_2—$ | | $CH_3$ |
| Cl | H | 6-$OCH_3$ | $—(CH_2)_2—CHOCH_3—(CH_2)_2—$ | | $CH_3$ |
| Cl | H | 6-$OCH_3$ | $—(CH_2)_2—CHOC_2H_5—(CH_2)_2—$ | | $CH_3$ |
| Cl | H | 6-$OCH_3$ | $—(CH_2)_2—CHOC_3H_7—(CH_2)_2—$ | | $CH_3$ |
| Cl | H | 6-$OCH_3$ | $—(CH_2)_2—CHi\text{-}OC_3H_7—(CH_2)_2—$ | | $CH_3$ |
| Cl | H | 6-$OCH_3$ | $—(CH_2)_2—C(CH_3)_2—(CH_2)_2—$ | | $CH_3$ |
| Cl | H | 6-$OCH_3$ | $—CH_2—(CHCH_3)_2—(CH_2)_2—$ | | $CH_3$ |
| Cl | H | 6-$OCH_3$ | 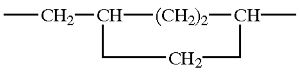 | | $CH_3$ |
| Cl | H | 6-$OCH_3$ | 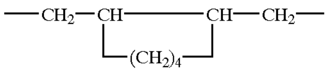 | | $CH_3$ |
| Cl | H | 6-$OCH_3$ | 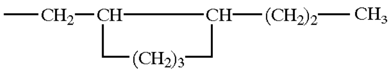 | | |
| $OCH_3$ | Cl | H | $—(CH_2)_2—$ | | $CH_3$ |
| $OCH_3$ | Cl | H | $—(CH_2)_4—$ | | $CH_3$ |
| $OCH_3$ | Cl | H | $—(CH_2)_5—$ | | $CH_3$ |
| $OCH_3$ | Cl | H | $—(CH_2)_6—$ | | $CH_3$ |
| $OCH_3$ | Cl | H | $—(CH_2)_7—$ | | $CH_3$ |
| $OCH_3$ | Cl | H | $—(CH_2)_2—O—(CH_2)_2—$ | | $CH_3$ |
| $OCH_3$ | Cl | H | $—(CH_2)_2—S—(CH_2)_2—$ | | $CH_3$ |
| $OCH_3$ | Cl | H | $—CH_2—CHCH_3—(CH_2)_3—$ | | $CH_3$ |
| $OCH_3$ | Cl | H | $—(CH_2)_2—CHCH_3—(CH_2)_2—$ | | $CH_3$ |
| $OCH_3$ | Cl | H | $—(CH_2)_2—CHC_2H_5—(CH_2)_2—$ | | $CH_3$ |
| $OCH_3$ | Cl | H | $—(CH_2)_2—CHC_3H_7—(CH_2)_2—$ | | $CH_3$ |
| $OCH_3$ | Cl | H | $—(CH_2)_2—CHi\text{-}C_3H_7—(CH_2)_2—$ | | $CH_3$ |
| $OCH_3$ | Cl | H | $—(CH_2)_2—CHOCH_3—(CH_2)_2—$ | | $CH_3$ |
| $OCH_3$ | Cl | H | $—(CH_2)_2—CHOC_2H_5—(CH_2)_2—$ | | $CH_3$ |
| $OCH_3$ | Cl | H | $—(CH_2)_2—CHOC_3H_7—(CH_2)_2—$ | | $CH_3$ |
| $OCH_3$ | Cl | H | $—(CH_2)_2—CHi\text{-}OC_3H_7—(CH_2)_2—$ | | $CH_3$ |
| $OCH_3$ | Cl | H | $—(CH_2)_2—C(CH_3)_2—(CH_2)_2—$ | | $CH_3$ |
| $OCH_3$ | Cl | H | $—CH_2—(CHCH_3)_2—(CH_2)_2—$ | | $CH_3$ |

TABLE 2-continued (Ib)

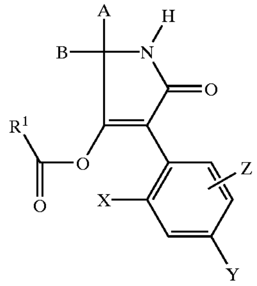

| X | Y | Z | A | B | $R^1$ |
|---|---|---|---|---|---|
| $OCH_3$ | Cl | H | 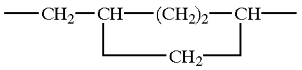 | | $CH_3$ |
| $OCH_3$ | Cl | H | 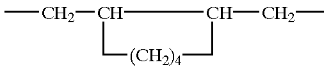 | | $CH_3$ |
| $OCH_3$ | Cl | H | 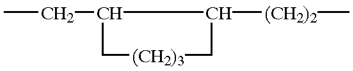 | | $CH_3$ |
| Cl | $OCH_3$ | H | $CH_3$ | H | i-$C_3H_7$ |
| Cl | $OCH_3$ | H | $C_2H_5$ | H | i-$C_3H_7$ |
| Cl | $OCH_3$ | H | $C_3H_7$ | H | i-$C_3H_7$ |
| Cl | $OCH_3$ | H | i-$C_3H_7$ | H | i-$C_3H_7$ |
| Cl | $OCH_3$ | H | $C_4H_9$ | H | i-$C_3H_7$ |
| Cl | $OCH_3$ | H | i-$C_4H_9$ | H | i-$C_3H_7$ |
| Cl | $OCH_3$ | H | s-$C_4H_9$ | H | i-$C_3H_7$ |
| Cl | $OCH_3$ | H | t-$C_4H_9$ | H | i-$C_3H_7$ |
| Cl | $OCH_3$ | H | $CH_3$ | $CH_3$ | i-$C_3H_7$ |
| Cl | $OCH_3$ | H | $C_2H_5$ | $CH_3$ | i-$C_3H_7$ |
| Cl | $OCH_3$ | H | $C_3H_7$ | $CH_3$ | i-$C_3H$ |
| Cl | $OCH_3$ | H | i-$C_3H_7$ | $CH_3$ | i-$C_3H_7$ |
| Cl | $OCH_3$ | H | $C_4H_9$ | $CH_3$ | i-$C_3H_7$ |
| Cl | $OCH_3$ | H | i-$C_4H_9$ | $CH_3$ | i-$C_3H_7$ |
| Cl | $OCH_3$ | H | s-$C_4H_9$ | $CH_3$ | i-$C_3H_7$ |
| Cl | $OCH_3$ | H | t-$C_4H_9$ | $CH_3$ | i-$C_3H_7$ |
| Cl | $OCH_3$ | H | $C_2H_5$ | $C_2H_5$ | i-$C_3H_7$ |
| Cl | $OCH_3$ | H | $C_3H_7$ | $C_3H_7$ | i-$C_3H_7$ |
| Cl | $OCH_3$ | H | 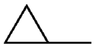 | $CH_3$ | i-$C_3H_7$ |
| Cl | $OCH_3$ | H | 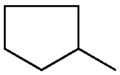 | $CH_3$ | i-$C_3H_7$ |
| Cl | $OCH_3$ | H | 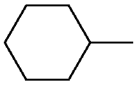 | $CH_3$ | i-$C_3H_7$ |
| Cl | H | 6-$OCH_3$ | $CH_3$ | H | i-$C_3H_7$ |
| Cl | H | 6-$OCH_3$ | $C_2H_5$ | H | i-$C_3H_7$ |
| Cl | H | 6-$OCH_3$ | $C_3H_7$ | H | i-$C_3H_7$ |
| Cl | H | 6-$OCH_3$ | i-$C_3H_7$ | H | i-$C_3H_7$ |
| Cl | H | 6-$OCH_3$ | $C_4H_9$ | H | i-$C_3H_7$ |
| Cl | H | 6-$OCH_3$ | i-$C_4H_9$ | H | i-$C_3H_7$ |
| Cl | H | 6-$OCH_3$ | s-$C_4H_9$ | H | i-$C_3H_7$ |
| Cl | H | 6-$OCH_3$ | t-$C_4H_9$ | H | i-$C_3H_7$ |
| Cl | H | 6-$OCH_3$ | $CH_3$ | $CH_3$ | i-$C_3H_7$ |
| Cl | H | 6-$OCH_3$ | $C_2H_5$ | $CH_3$ | i-$C_3H_7$ |
| Cl | H | 6-$OCH_3$ | $C_3H_7$ | $CH_3$ | i-$C_3H_7$ |
| Cl | H | 6-$OCH_3$ | i-$C_3H_7$ | $CH_3$ | i-$C_3H_7$ |
| Cl | H | 6-$OCH_3$ | $C_4H_9$ | $CH_3$ | i-$C_3H_7$ |
| Cl | H | 6-$OCH_3$ | i-$C_4H_9$ | $CH_3$ | i-$C_3H_7$ |
| Cl | H | 6-$OCH_3$ | s-$C_4H_9$ | $CH_3$ | i-$C_3H_7$ |
| Cl | H | 6-$OCH_3$ | t-$C_4H_9$ | $CH_3$ | i-$C_3H_7$ |

TABLE 2-continued (Ib)

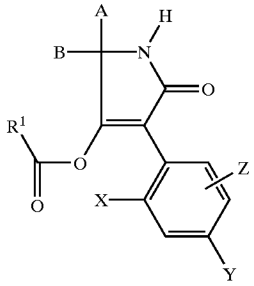

| X | Y | Z | A | B | $R^1$ |
| --- | --- | --- | --- | --- | --- |
| Cl | H | 6-$OCH_3$ | $C_2H_5$ | $C_2H_5$ | i-$C_3H_7$ |
| Cl | H | 6-$OCH_3$ | $C_3H_7$ | $C_3H_7$ | i-$C_3H_7$ |
| Cl | H | 6-$OCH_3$ | 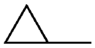 | $CH_3$ | i-$C_3H_7$ |
| Cl | H | 6-$OCH_3$ | 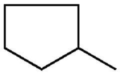 | $CH_3$ | i-$C_3H_7$ |
| Cl | H | 6-$OCH_3$ | 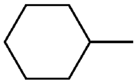 | $CH_3$ | i-$C_3H_7$ |
| $OCH_3$ | Cl | H | $CH_3$ | H | i-$C_3H_7$ |
| $OCH_3$ | Cl | H | $C_2H_5$ | H | i-$C_3H_7$ |
| $OCH_3$ | Cl | H | $C_3H_7$ | H | i-$C_3H_7$ |
| $OCH_3$ | Cl | H | i-$C_3H_7$ | H | i-$C_3H_7$ |
| $OCH_3$ | Cl | H | $C_4H_9$ | H | i-$C_3H_7$ |
| $OCH_3$ | Cl | H | i-$C_4H_9$ | H | i-$C_3H_7$ |
| $OCH_3$ | Cl | H | s-$C_4H_9$ | H | i-$C_3H_7$ |
| $OCH_3$ | Cl | H | t-$C_4H_9$ | H | i-$C_3H_7$ |
| $OCH_3$ | Cl | H | $CH_3$ | $CH_3$ | i-$C_3H_7$ |
| $OCH_3$ | Cl | H | $C_2H_5$ | $CH_3$ | i-$C_3H_7$ |
| $OCH_3$ | Cl | H | $C_3H_7$ | $CH_3$ | i-$C_3H_7$ |
| $OCH_3$ | Cl | H | i-$C_3H_7$ | $CH_3$ | i-$C_3H_7$ |
| $OCH_3$ | Cl | H | $C_4H_9$ | $CH_3$ | i-$C_3H_7$ |
| $OCH_3$ | Cl | H | i-$C_4H_9$ | $CH_3$ | i-$C_3H_7$ |
| $OCH_3$ | Cl | H | s-$C_4H_9$ | $CH_3$ | i-$C_3H_7$ |
| $OCH_3$ | Cl | H | t-$C_4H_9$ | $CH_3$ | i-$C_3H_7$ |
| $OCH_3$ | Cl | H | $C_2H_5$ | $C_2H_5$ | i-$C_3H_7$ |
| $OCH_3$ | Cl | H | $C_3H_7$ | $C_3H_7$ | i-$C_3H_7$ |
| $OCH_3$ | Cl | H | 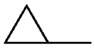 | $CH_3$ | i-$C_3H_7$ |
| $OCH_3$ | Cl | H | 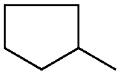 | $CH_3$ | i-$C_3H_7$ |
| $OCH_3$ | Cl | H | 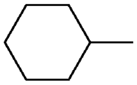 | $CH_3$ | i-$C_3H_7$ |
| Cl | $OCH_3$ | H | $-(CH_2)_2-$ | | i-$C_3H_7$ |
| Cl | $OCH_3$ | H | $-(CH_2)_4-$ | | i-$C_3H_7$ |
| Cl | $OCH_3$ | H | $-(CH_3)_5-$ | | i-$C_3H_7$ |
| Cl | $OCH_3$ | H | $-(CH_2)_6-$ | | i-$C_3H_7$ |
| Cl | $OCH_3$ | H | $-(CH_2)_7-$ | | i-$C_3H_7$ |
| Cl | $OCH_3$ | H | $-(CH_2)_2-O-(CH_2)_2-$ | | i-$C_3H_7$ |
| Cl | $OCH_3$ | H | $-(CH_2)_2-S-(CH_2)_2-$ | | i-$C_3H_7$ |
| Cl | $OCH_3$ | H | $-CH_2-CHCH_3-(CH_2)_3-$ | | i-$C_3H_7$ |
| Cl | $OCH_3$ | H | $-(CH_2)_2-CHCH_3-(CH_2)_2-$ | | i-$C_3H_7$ |
| Cl | $OCH_3$ | H | $-(CH_2)_2-CHC_2H_5-(CH_2)_2-$ | | i-$C_3H_7$ |
| Cl | $OCH_3$ | H | $-(CH_2)_2-CHC_3H_7-(CH_2)_2-$ | | i-$C_3H_7$ |
| Cl | $OCH_3$ | H | $-(CH_2)_2-CHi\text{-}C_3H_7-(CH_2)_2-$ | | i-$C_3H_7$ |
| Cl | $OCH_3$ | H | $-(CH_2)_2-CHOCH_3-(CH_2)_2-$ | | i-$C_3H_7$ |

TABLE 2-continued (Ib)

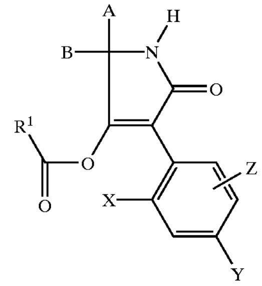

| X | Y | Z | A | B | $R^1$ |
|---|---|---|---|---|---|
| Cl | $OCH_3$ | H | | $-(CH_2)_2-CHOC_2H_5-(CH_2)_2-$ | i-$C_3H_7$ |
| Cl | $OCH_3$ | H | | $-(CH_2)_2-CHOC_3H_7-(CH_2)_2-$ | i-$C_3H_7$ |
| Cl | $OCH_3$ | H | | $-(CH_2)_2-CHi\text{-}OC_3H_7-(CH_2)_2-$ | i-$C_3H_7$ |
| Cl | $OCH_3$ | H | | $-(CH_2)_2-C(CH_3)_2-(CH_2)_2-$ | i-$C_3H_7$ |
| Cl | $OCH_3$ | H | | $-CH_2-(CHCH_3)_2-(CH_2)_2-$ | i-$C_3H_7$ |
| Cl | $OCH_3$ | H | | 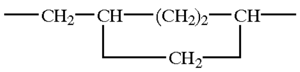 | i-$C_3H_7$ |
| Cl | $OCH_3$ | H | | 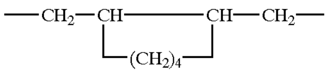 | i-$C_3H_7$ |
| Cl | $OCH_3$ | H | | 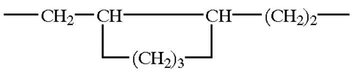 | i-$C_3H_7$ |
| Cl | H | 6-$OCH_3$ | | $-(CH_2)_2-$ | i-$C_3H_7$ |
| Cl | H | 6-$OCH_3$ | | $-(CH_2)_4-$ | i-$C_3H_7$ |
| Cl | H | 6-$OCH_3$ | | $-(CH_2)_5-$ | i-$C_3H_7$ |
| Cl | H | 6-$OCH_3$ | | $-(CH_2)_6-$ | i-$C_3H_7$ |
| Cl | H | 6-$OCH_3$ | | $-(CH_2)_7-$ | i-$C_3H_7$ |
| Cl | H | 6-$OCH_3$ | | $-(CH_2)_2-O-(CH_2)_2-$ | i-$C_3H_7$ |
| Cl | H | 6-$OCH_3$ | | $-(CH_2)_2-S-(CH_2)_2-$ | i-$C_37_7$ |
| Cl | H | 6-$OCH_3$ | | $-CH_2-CHCH_3-(CH_2)_3-$ | i-$C_3H_7$ |
| Cl | H | 6-$OCH_3$ | | $-(CH_2)_2-CHCH_3-(CH_2)_2-$ | i-$C_3H_7$ |
| Cl | H | 6-$OCH_3$ | | $-(CH_2)_2-CHC_2H_5-(CH_2)_2-$ | i-$C_3H_7$ |
| Cl | H | 6-$OCH_3$ | | $-(CH_2)_2-CHC_3H_7-(CH_2)_2-$ | i-$C_3H_7$ |
| Cl | H | 6-$OCH_3$ | | $-(CH_2)_2-CHi\text{-}C_3H_7-(CH_2)_2-$ | i-$C_3H_7$ |
| Cl | H | 6-$OCH_3$ | | $-(CH_2)_2-CHOCH_3-(CH_2)_2-$ | i-$C_3H_7$ |
| Cl | H | 6-$OCH_3$ | | $-(CH_2)_2-CHOC_2H_5-(CH_2)_2-$ | i-$C_3H_7$ |
| Cl | H | 6-$OCH_3$ | | $-(CH_2)_2-CHOC_3H_7-(CH_2)_2-$ | i-$C_3H_7$ |
| Cl | H | 6-$OCH_3$ | | $-(CH_2)_2-CHi\text{-}OC_3H_7-(CH_2)_2-$ | i-$C_3H_7$ |
| Cl | H | 6-$OCH_3$ | | $-(CH_2)_2-C(CH_3)_2-(CH_2)_2-$ | i-$C_3H_7$ |
| Cl | H | 6-$OCH_3$ | | $-CH_2-(CHCH_3)_2-(CH_2)_2-$ | i-$C_3H_7$ |
| Cl | H | 6-$OCH_3$ | | 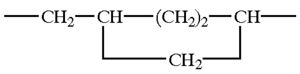 | i-$C_3H_7$ |
| Cl | H | 6-$OCH_3$ | | 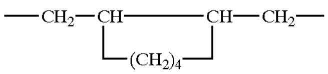 | i-$C_3H_7$ |
| Cl | H | 6-$OCH_3$ | | 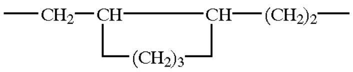 | i-$C_3H_7$ |
| $OCH_3$ | Cl | H | | $-(CH_2)_2-$ | i-$C_3H_7$ |
| $OCH_3$ | Cl | H | | $-(CH_2)_4-$ | i-$C_3H_7$ |
| $OCH_3$ | Cl | H | | $-(CH_2)_5-$ | i-$C_3H_7$ |
| $OCH_3$ | Cl | H | | $-(CH_2)_6-$ | i-$C_3H_7$ |
| $OCH_3$ | Cl | H | | $-(CH_2)_7-$ | i-$C_3H_7$ |
| $OCH_3$ | Cl | H | | $-(CH_2)_2-O-(CH_2)_2-$ | i-$C_3H_7$ |
| $OCH_3$ | Cl | H | | $-(CH_2)_2-S-(CH_2)_2-$ | i-$C_3H_7$ |
| $OCH_3$ | Cl | H | | $-CH_2-CHCH_3-(CH_2)_3-$ | i-$C_3H_7$ |
| $OCH_3$ | Cl | H | | $-(CH_2)_2-CHCH_3-(CH_2)_2-$ | i-$C_3H_7$ |
| $OCH_3$ | Cl | H | | $-(CH_2)_2-CHC_2H_5-(CH_2)_2-$ | i-$C_3H_7$ |
| $OCH_3$ | Cl | H | | $-(CH_2)_2-CHC_3H_7-(CH_2)_2-$ | i-$C_3H_7$ |

TABLE 2-continued (Ib)

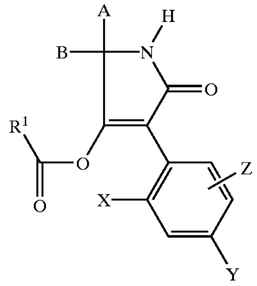

| X | Y | Z | A | B | $R^1$ |
|---|---|---|---|---|---|
| $OCH_3$ | Cl | H | $-(CH_2)_2-CHi\text{-}C_3H_7-(CH_2)_2-$ | | $i\text{-}C_3H_7$ |
| $OCH_3$ | Cl | H | $-(CH_2)_2-CHOCH_3-(CH_2)_2-$ | | $i\text{-}C_3H_7$ |
| $OCH_3$ | Cl | H | $-(CH_2)_2-CHOC_2H_5-(CH_2)_2-$ | | $i\text{-}C_3H_7$ |
| $OCH_3$ | Cl | H | $-(CH_2)_2-CHOC_3H_7-(CH_2)_2-$ | | $i\text{-}C_3H_7$ |
| $OCH_3$ | Cl | H | $-(CH_2)_2-CHi\text{-}OC_3H_7-(CH_2)_2-$ | | $i\text{-}C_3H_7$ |
| $OCH_3$ | Cl | H | $-(CH_2)_2-C(CH_3)_2-(CH_2)_2-$ | | $i\text{-}C_3H_7$ |
| $OCH_3$ | Cl | H | $-CH_2-(CHCH_3)_2-(CH_2)_2-$ | | $i\text{-}C_3H_7$ |
| $OCH_3$ | Cl | H | 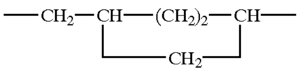 | | $i\text{-}C_3H_7$ |
| $OCH_3$ | Cl | H | 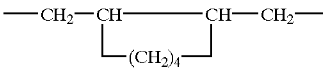 | | $i\text{-}C_3H_7$ |
| $OCH_3$ | Cl | H | 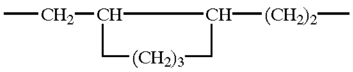 | | $i\text{-}C_3H_7$ |
| Cl | $OCH_3$ | H | $CH_3$ | H | $t\text{-}C_4H_9$ |
| Cl | $OCH_3$ | H | $C_2H_5$ | H | $t\text{-}C_4H_9$ |
| Cl | $OCH_3$ | H | $C_3H_7$ | H | $t\text{-}C_4H_9$ |
| Cl | $OCH_3$ | H | $i\text{-}C_3H_7$ | H | $t\text{-}C_4H_9$ |
| Cl | $OCH_3$ | H | $C_4H_9$ | H | $t\text{-}C_4H_9$ |
| Cl | $OCH_3$ | H | $i\text{-}C_4H_9$ | H | $t\text{-}C_4H_9$ |
| Cl | $OCH_3$ | H | $s\text{-}C_4H_9$ | H | $t\text{-}C_4H_9$ |
| Cl | $OCH_3$ | H | $t\text{-}C_4H_9$ | H | $t\text{-}C_4H_9$ |
| Cl | $OCH_3$ | H | $CH_3$ | $CH_3$ | $t\text{-}C_4H_9$ |
| Cl | $OCH_3$ | H | $C_2H_5$ | $CH_3$ | $t\text{-}C_4H_9$ |
| Cl | $OCH_3$ | H | $C_3H_7$ | $CH_3$ | $t\text{-}C_4H_9$ |
| Cl | $OCH_3$ | H | $i\text{-}C_3H_7$ | $CH_3$ | $t\text{-}C_4H_9$ |
| Cl | $OCH_3$ | H | $C_4H_9$ | $CH_3$ | $t\text{-}C_4H_9$ |
| Cl | $OCH_3$ | H | $i\text{-}C_4H_9$ | $CH_3$ | $t\text{-}C_4H_9$ |
| Cl | $OCH_3$ | H | $s\text{-}C_4H_9$ | $CH_3$ | $t\text{-}C_4H_9$ |
| Cl | $OCH_3$ | H | $t\text{-}C_4H_9$ | $CH_3$ | $t\text{-}C_4H_9$ |
| Cl | $OCH_3$ | H | $C_2H_5$ | $C_2H_5$ | $t\text{-}C_4H_9$ |
| Cl | $OCH_3$ | H | $C_3H_7$ | $C_3H_7$ | $t\text{-}C_4H_9$ |
| Cl | $OCH_3$ | H | 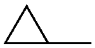 | $CH_3$ | $t\text{-}C_4H_9$ |
| Cl | $OCH_3$ | H | 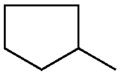 | $CH_3$ | $t\text{-}C_4H_9$ |
| Cl | $OCH_3$ | H | 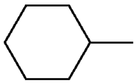 | $CH_3$ | $t\text{-}C_4H_9$ |
| Cl | H | $6\text{-}OCH_3$ | $CH_3$ | H | $t\text{-}C_4H_9$ |
| Cl | H | $6\text{-}OCH_3$ | $C_2H_5$ | H | $t\text{-}C_4H_9$ |
| Cl | H | $6\text{-}OCH_3$ | $C_3H_7$ | H | $t\text{-}C_4H_9$ |
| Cl | H | $6\text{-}OCH_3$ | $i\text{-}C_3H_7$ | H | $t\text{-}C_4H_9$ |
| Cl | H | $6\text{-}OCH_3$ | $C_4H_9$ | H | $t\text{-}C_4H_9$ |
| Cl | H | $6\text{-}OCH_3$ | $i\text{-}C_4H_9$ | H | $t\text{-}C_4H_9$ |
| Cl | H | $6\text{-}OCH_3$ | $s\text{-}C_4H_9$ | H | $t\text{-}C_4H_9$ |
| Cl | H | $6\text{-}OCH_3$ | $t\text{-}C_4H_9$ | H | $t\text{-}C_4H_9$ |

TABLE 2-continued (Ib)

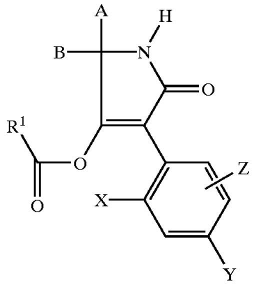

| X | Y | Z | A | B | $R^1$ |
|---|---|---|---|---|---|
| Cl | H | 6-$OCH_3$ | $CH_3$ | $CH_3$ | t-$C_4H_9$ |
| Cl | H | 6-$OCH_3$ | $C_2H_5$ | $CH_3$ | t-$C_4H_9$ |
| Cl | H | 6-$OCH_3$ | $C_3H_7$ | $CH_3$ | t-$C_4H_9$ |
| Cl | H | 6-$OCH_3$ | i-$C_3H_7$ | $CH_3$ | t-$C_4H_9$ |
| Cl | H | 6-$OCH_3$ | $C_4H_9$ | $CH_3$ | t-$C_4H_9$ |
| Cl | H | 6-$OCH_3$ | i-$C_4H_9$ | $CH_3$ | t-$C_4H_9$ |
| Cl | H | 6-$OCH_3$ | s-$C_4H_9$ | $CH_3$ | t-$C_4H_9$ |
| Cl | H | 6-$OCH_3$ | t-$C_4H_9$ | $CH_3$ | t-$C_4H_9$ |
| Cl | H | 6-$OCH_3$ | $C_2H_5$ | $C_2H_5$ | t-$C_4H_9$ |
| Cl | H | 6-$OCH_3$ | $C_3H_7$ | $C_3H_7$ | t-$C_4H_9$ |
| Cl | H | 6-$OCH_3$ | 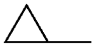 | $CH_3$ | t-$C_4H_9$ |
| Cl | H | 6-$OCH_3$ | 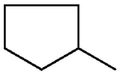 | $CH_3$ | t-$C_4H_9$ |
| Cl | H | 6-$OCH_3$ | 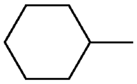 | $CH_3$ | t-$C_4H_9$ |
| $OCH_3$ | Cl | H | $CH_3$ | H | t-$C_4H_9$ |
| $OCH_3$ | Cl | H | $C_2H_5$ | H | t-$C_4H_9$ |
| $OCH_3$ | Cl | H | $C_3H_7$ | H | t-$C_4H_9$ |
| $OCH_3$ | Cl | H | i-$C_3H_7$ | H | t-$C_4H_9$ |
| $OCH_3$ | Cl | H | $C_4H_9$ | H | t-$C_4H_9$ |
| $OCH_3$ | Cl | H | i-$C_4H_9$ | H | t-$C_4H_9$ |
| $OCH_3$ | Cl | H | s-$C_4H_9$ | H | t-$C_4H_9$ |
| $OCH_3$ | Cl | H | t-$C_4H_9$ | H | t-$C_4H_9$ |
| $OCH_3$ | Cl | H | $CH_3$ | $CH_3$ | t-$C_4H_9$ |
| $OCH_3$ | Cl | H | $C_2H_5$ | $CH_3$ | t-$C_4H_9$ |
| $OCH_3$ | Cl | H | $C_3H_7$ | $CH_3$ | t-$C_4H_9$ |
| $OCH_3$ | Cl | H | i-$C_3H_7$ | $CH_3$ | t-$C_4H_9$ |
| $OCH_3$ | Cl | H | $C_4H_9$ | $CH_3$ | t-$C_4H_9$ |
| $OCH_3$ | Cl | H | i-$C_4H_9$ | $CH_3$ | t-$C_4H_9$ |
| $OCH_3$ | Cl | H | s-$C_4H_9$ | $CH_3$ | t-$C_4H_9$ |
| $OCH_3$ | Cl | H | t-$C_4H_9$ | $CH_3$ | t-$C_4H_9$ |
| $OCH_3$ | Cl | H | $C_2H_5$ | $C_2H_5$ | t-$C_4H_9$ |
| $OCH_3$ | Cl | H | $C_3H_7$ | $C_3H_7$ | t-$C_4H_9$ |
| $OCH_3$ | Cl | H | 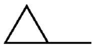 | $CH_3$ | t-$C_4H_9$ |
| $OCH_3$ | Cl | H | 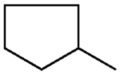 | $CH_3$ | t-$C_4H_9$ |
| $OCH_3$ | Cl | H | 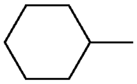 | $CH_3$ | t-$C_4H_9$ |
| Cl | $OCH_3$ | H | $-(CH_2)_2-$ | | t-$C_4H_9$ |
| Cl | $OCH_3$ | H | $-(CH_2)_4-$ | | t-$C_4H_9$ |
| Cl | $OCH_3$ | H | $-(CH_2)_5-$ | | t-$C_4H_9$ |
| Cl | $OCH_3$ | H | $-(CH_2)_6-$ | | t-$C_4H_9$ |
| Cl | $OCH_3$ | H | $-(CH_2)_7-$ | | t-$C_4H_9$ |

TABLE 2-continued (Ib)

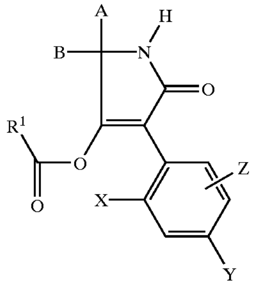

| X | Y | Z | A | B | $R^1$ |
|---|---|---|---|---|---|
| Cl | $OCH_3$ | H | | $—(CH_2)_2—O—(CH_2)_2—$ | $t-C_4H_9$ |
| Cl | $OCH_3$ | H | | $—(CH_2)_2—S—(CH_2)_2—$ | $t-C_4H_9$ |
| Cl | $OCH_3$ | H | | $—CH_2—CHCH_3—(CH_2)_3—$ | $t-C_4H_9$ |
| Cl | $OCH_3$ | H | | $—(CH_2)_2—CHCH_3—(CH_2)_2—$ | $t-C_4H_9$ |
| Cl | $OCH_3$ | H | | $—(CH_2)_2—CHC_2H_5—(CH_2)_2—$ | $t-C_4H_9$ |
| Cl | $OCH_3$ | H | | $—(CH_2)_2—CHC_3H_7—(CH_2)_2—$ | $t-C_4H_9$ |
| Cl | $OCH_3$ | H | | $—(CH_2)_2—CHi-C_3H_7—(CH_2)_2—$ | $t-C_4H_9$ |
| Cl | $OCH_3$ | H | | $—(CH_2)_2—CHOCH_3—(CH_2)_2—$ | $t-C_4H_9$ |
| Cl | $OCH_3$ | H | | $—(CH_2)_2—CHOC_2H_5—(CH_2)_2—$ | $t-C_4H_9$ |
| Cl | $OCH_3$ | H | | $—(CH_2)_2—CHOC_3H_7—(CH_2)_2—$ | $t-C_4H_9$ |
| Cl | $OCH_3$ | H | | $—(CH_2)_2—CHi-OC_3H_7—(CH_2)_2—$ | $t-C_4H_9$ |
| Cl | $OCH_3$ | H | | $—(CH_2)_2—C(CH_3)_2—(CH_2)_2—$ | $t-C_4H_9$ |
| Cl | $OCH_3$ | H | | $—CH_2—(CHCH_3)_2—(CH_2)_2—$ | $t-C_4H_9$ |
| Cl | $OCH_3$ | H | | 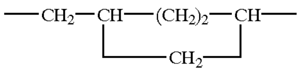 | $t-C_4H_9$ |
| Cl | $OCH_3$ | H | | 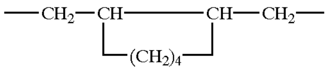 | $t-C_4H_9$ |
| Cl | $OCH_3$ | H | | 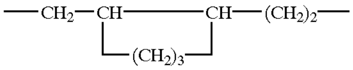 | $t-C_4H_9$ |
| Cl | H | $6-OCH_3$ | | $—(CH_2)_2—$ | $t-C_4H_9$ |
| Cl | H | $6-OCH_3$ | | $—(CH_2)_4—$ | $t-C_4H_9$ |
| Cl | H | $6-OCH_3$ | | $—(CH_2)_5—$ | $t-C_4H_9$ |
| Cl | H | $6-OCH_3$ | | $—(CH_2)_6—$ | $t-C_4H_9$ |
| Cl | H | $6-OCH_3$ | | $—(CH_2)_7—$ | $t-C_4H_9$ |
| Cl | H | $6-OCH_3$ | | $—(CH_2)_2—O—(CH_2)_2—$ | $t-C_4H_9$ |
| Cl | H | $6-OCH_3$ | | $—(CH_2)_2—S—(CH_2)_2—$ | $t-C_4H_9$ |
| Cl | H | $6-OCH_3$ | | $—CH_2—CHCH_3—(CH_2)_3—$ | $t-C_4H_9$ |
| Cl | H | $6-OCH_3$ | | $—(CH_2)_2—CHCH_3—(CH_2)_2—$ | $t-C_4H_9$ |
| Cl | H | $6-OCH_3$ | | $—(CH_2)_2—CHC_2H_5—(CH_2)_2—$ | $t-C_4H_9$ |
| Cl | H | $6-OCH_3$ | | $—(CH_2)_2—CHC_3H_7—(CH_2)_2—$ | $t-C_4H_9$ |
| Cl | H | $6-OCH_3$ | | $—(CH_2)_2—CHi—C_3H_7—(CH_2)_2—$ | $t-C_4H_9$ |
| Cl | H | $6-OCH_3$ | | $—(CH_2)_2—CHOCH_3—(CH_2)_2—$ | $t-C_4H_9$ |
| Cl | H | $6-OCH_3$ | | $—(CH_2)_2—CHOC_2H_5—(CH_2)_2—$ | $t-C_4H_9$ |
| Cl | H | $6-OCH_3$ | | $—(CH_2)_2—CHOC_3H_7—(CH_2)_2—$ | $t-C_4H_9$ |
| Cl | H | $6-OCH_3$ | | $—(CH_2)_2—CHi-OC_3H_7—(CH_2)_2—$ | $t-C_4H_9$ |
| Cl | H | $6-OCH_3$ | | $—(CH_2)_2—C(CH_3)_2—(CH_2)_2—$ | $t-C_4H_9$ |
| Cl | H | $6-OCH_3$ | | $—CH_2—(CHCH_3)_2—(CH_2)_2—$ | $t-C_4H_9$ |
| Cl | H | $6-OCH_3$ | | 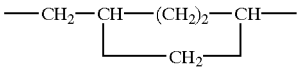 | $t-C_4H_9$ |
| Cl | H | $6-OCH_3$ | | 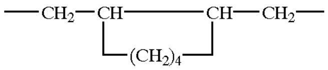 | $t-C_4H_9$ |
| Cl | H | $6-OCH_3$ | | 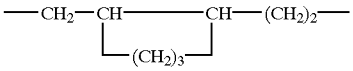 | $t-C_4H_9$ |
| $OCH_3$ | Cl | H | | $—(CH_2)_2—$ | $t-C_4H_9$ |
| $OCH_3$ | Cl | H | | $—(CH_2)_4—$ | $t-C_4H_9$ |
| $OCH_3$ | Cl | H | | $—(CH_2)_5—$ | $t-C_4H_9$ |

TABLE 2-continued (Ib)

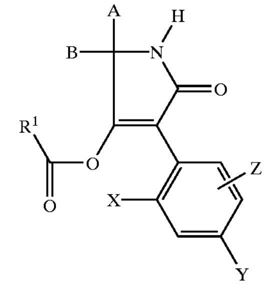

| X | Y | Z | A | B | $R^1$ |
|---|---|---|---|---|---|
| $OCH_3$ | Cl | H | $—(CH_2)_6—$ | | $t\text{-}C_4H_9$ |
| $OCH_3$ | Cl | H | $—(CH_2)_7—$ | | $t\text{-}C_4H_9$ |
| $OCH_3$ | Cl | H | $—(CH_2)_2—O—(CH_2)_2—$ | | $t\text{-}C_4H_9$ |
| $OCH_3$ | Cl | H | $—(CH_2)_2—S—(CH_2)_2—$ | | $t\text{-}C_4H_9$ |
| $OCH_3$ | Cl | H | $—CH_2—CHCH_3—(CH_2)_2—$ | | $t\text{-}C_4H_9$ |
| $OCH_3$ | Cl | H | $—(CH_2)_2—CHCH_3—(CH_2)_2—$ | | $t\text{-}C_4H_9$ |
| $OCH_3$ | Cl | H | $—(CH_2)_2—CHC_2H_5—(CH_2)_2—$ | | $t\text{-}C_4H_9$ |
| $OCH_3$ | Cl | H | $—(CH_2)_2—CHC_3H_7—(CH_2)_2—$ | | $t\text{-}C_4H_9$ |
| $OCH_3$ | Cl | H | $—(CH_2)_2—CHi\text{-}C_3H_7—(CH_2)_2—$ | | $t\text{-}C_4H_9$ |
| $OCH_3$ | Cl | H | $—(CH_2)_2—CHOCH_3—(CH_2)_2—$ | | $t\text{-}C_4H_9$ |
| $OCH_3$ | Cl | H | $—(CH_2)_2—CHOC_2H_5—(CH_2)_2—$ | | $t\text{-}C_4H_9$ |
| $OCH_3$ | Cl | H | $—(CH_2)_2—CHOC_3H_7—(CH_2)_2—$ | | $t\text{-}C_4H_9$ |
| $OCH_3$ | Cl | H | $—(CH_2)_2—CHi\text{-}OC_3H_7—(CH_2)_2—$ | | $t\text{-}C_4H_9$ |
| $OCH_3$ | Cl | H | $—(CH_2)_2—C(CH_3)_2—(CH_2)_2—$ | | $t\text{-}C_4H_9$ |
| $OCH_3$ | Cl | H | $—CH_2—(CHCH_3)_2—(CH_2)_2—$ | | $t\text{-}C_4H_9$ |
| $OCH_3$ | Cl | H | 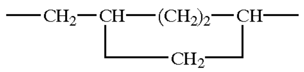 | | $t\text{-}C_4H_9$ |
| $OCH_3$ | Cl | H | 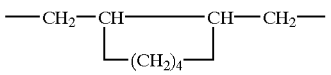 | | $t\text{-}C_4H_9$ |
| $OCH_3$ | Cl | H | 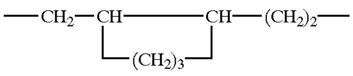 | | $t\text{-}C_4H_9$ |

The following compounds of the for a (Ic) may be mentioned individually in addition to the compound a mentioned in the preparation examples:

TABLE 3

(Ic)

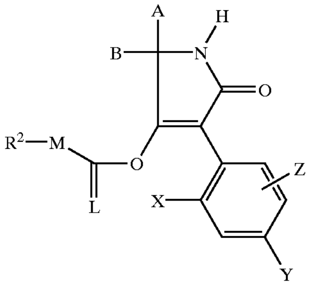

| X | Y | Z | A | B | L | M | $R^2$ |
|---|---|---|---|---|---|---|---|
| Cl | $OCH_3$ | H | $CH_3$ | H | O | O | $C_2H_5$ |
| Cl | $OCH_3$ | H | $C_2H_5$ | H | O | O | $C_2H_5$ |
| Cl | $OCH_3$ | H | $C_3H_7$ | H | O | O | $C_2H_5$ |
| Cl | $OCH_3$ | H | $i\text{-}C_3H_7$ | H | O | O | $C_2H_5$ |
| Cl | $OCH_3$ | H | $C_4H_9$ | H | O | O | $C_2H_5$ |
| Cl | $OCH_3$ | H | $i\text{-}C_4H_9$ | H | O | O | $C_2H_5$ |

TABLE 3-continued (Ic)

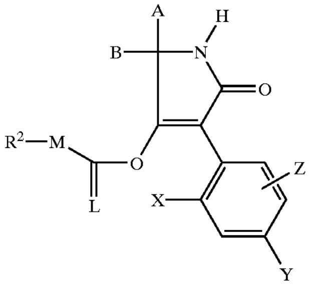

| X | Y | Z | A | B | L | M | $R^2$ |
|---|---|---|---|---|---|---|---|
| Cl | $OCH_3$ | H | s-$C_4H_9$ | H | O | O | $C_2H_5$ |
| Cl | $OCH_3$ | H | t-$C_4H_9$ | H | O | O | $C_2H_5$ |
| Cl | $OCH_3$ | H | $CH_3$ | $CH_3$ | O | O | $C_2H_5$ |
| Cl | $OCH_3$ | H | $C_2H_5$ | $CH_3$ | O | O | $C_2H_5$ |
| Cl | $OCH_3$ | H | $C_3H_7$ | $CH_3$ | O | O | $C_2H_5$ |
| Cl | $OCH_3$ | H | i-$C_3H_7$ | $CH_3$ | O | O | $C_2H_5$ |
| Cl | $OCH_3$ | H | $C_4H_9$ | $CH_3$ | O | O | $C_2H_5$ |
| Cl | $OCH_3$ | H | i-$C_4H_9$ | $CH_3$ | O | O | $C_2H_5$ |
| Cl | $OCH_3$ | H | s-$C_4H_9$ | $CH_3$ | O | O | $C_2H_5$ |
| Cl | $OCH_3$ | H | t-$C_4H_9$ | $CH_3$ | O | O | $C_2H_5$ |
| Cl | $OCH_3$ | H | $C_2H_5$ | $C_2H_5$ | O | O | $C_2H_5$ |
| Cl | $OCH_3$ | H | $C_3H_7$ | $C_3H_7$ | O | O | $C_2H_5$ |
| Cl | $OCH_3$ | H | 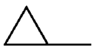 | $CH_3$ | O | O | $C_2H_5$ |
| Cl | $OCH_3$ | H | 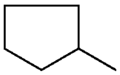 | $CH_3$ | O | O | $C_2H_5$ |
| Cl | $OCH_3$ | H | 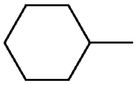 | $CH_3$ | O | O | $C_2H_5$ |
| Cl | H | 6-$OCH_3$ | $CH_3$ | H | O | O | $C_2H_5$ |
| Cl | H | 6-$OCH_3$ | $C_2H_5$ | H | O | O | $C_2H_5$ |
| Cl | H | 6-$OCH_3$ | $C_3H_7$ | H | O | O | $C_2H_5$ |
| Cl | H | 6-$OCH_3$ | i-$C_3H_7$ | H | O | O | $C_2H_5$ |
| Cl | H | 6-$OCH_3$ | $C_4H_9$ | H | O | O | $C_2H_5$ |
| Cl | H | 6-$OCH_3$ | i-$C_4H_9$ | H | O | O | $C_2H_5$ |
| Cl | H | 6-$OCH_3$ | s-$C_4H_9$ | H | O | O | $C_2H_5$ |
| Cl | H | 6-$OCH_3$ | t-$C_4H_9$ | H | O | O | $C_2H_5$ |
| Cl | H | 6-$OCH_3$ | $CH_3$ | $CH_3$ | O | O | $C_2H_5$ |
| Cl | H | 6-$OCH_3$ | $C_2H_5$ | $CH_3$ | O | O | $C_2H_5$ |
| Cl | H | 6-$OCH_3$ | $C_3H_7$ | $CH_3$ | O | O | $C_2H_5$ |
| Cl | H | 6-$OCH_3$ | i-$C_3H_7$ | $CH_3$ | O | O | $C_2H_5$ |
| Cl | H | 6-$OCH_3$ | $C_4H_9$ | $CH_3$ | O | O | $C_2H_5$ |
| Cl | H | 6-$OCH_3$ | i-$C_4H_9$ | $CH_3$ | O | O | $C_2H_5$ |
| Cl | H | 6-$OCH_3$ | s-$C_4H_9$ | $CH_3$ | O | O | $C_2H_5$ |
| Cl | H | 6-$OCH_3$ | t-$C_4H_9$ | $CH_3$ | O | O | $C_2H_5$ |
| Cl | H | 6-$OCH_3$ | $C_2H_5$ | $C_2H_5$ | O | O | $C_2H_5$ |
| Cl | H | 6-$OCH_3$ | $C_3H_7$ | $C_3H_7$ | O | O | $C_2H_5$ |
| Cl | H | 6-$OCH_3$ | 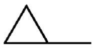 | $CH_3$ | O | O | $C_2H_5$ |
| Cl | H | 6-$OCH_3$ | 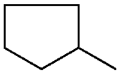 | $CH_3$ | O | O | $C_2H_5$ |
| Cl | H | 6-$OCH_3$ | 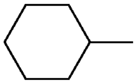 | $CH_3$ | O | O | $C_2H_5$ |
| $OCH_3$ | Cl | H | $CH_3$ | H | O | O | $C_2H_5$ |
| $OCH_3$ | Cl | H | $C_2H_5$ | H | O | O | $C_2H_5$ |
| $OCH_3$ | Cl | H | $C_3H_7$ | H | O | O | $C_2H_5$ |

TABLE 3-continued (Ic)

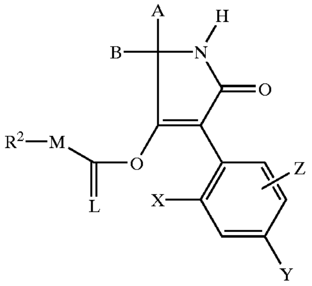

| X | Y | Z | A | B | L | M | $R^2$ |
|---|---|---|---|---|---|---|---|
| $OCH_3$ | Cl | H | i-$C_3H_7$ | H | O | O | $C_2H_5$ |
| $OCH_3$ | Cl | H | $C_4H_9$ | H | O | O | $C_2H_5$ |
| $OCH_3$ | Cl | H | i-$C_4H_9$ | H | O | O | $C_2H_5$ |
| $OCH_3$ | Cl | H | s-$C_4H_9$ | H | O | O | $C_2H_5$ |
| $OCH_3$ | Cl | H | t-$C_4H_9$ | H | O | O | $C_2H_5$ |
| $OCH_3$ | Cl | H | $CH_3$ | $CH_3$ | O | O | $C_2H_5$ |
| $OCH_3$ | Cl | H | $C_2H_5$ | $CH_3$ | O | O | $C_2H_5$ |
| $OCH_3$ | Cl | H | $C_3H_7$ | $CH_3$ | O | O | $C_2H_5$ |
| $OCH_3$ | Cl | H | i-$C_3H_7$ | $CH_3$ | O | O | $C_2H_5$ |
| $OCH_3$ | Cl | H | $C_4H_9$ | $CH_3$ | O | O | $C_2H_5$ |
| $OCH_3$ | Cl | H | i-$C_4H_9$ | $CH_3$ | O | O | $C_2H_5$ |
| $OCH_3$ | Cl | H | s-$C_4H_9$ | $CH_3$ | O | O | $C_2H_5$ |
| $OCH_3$ | Cl | H | t-$C_4H_9$ | $CH_3$ | O | O | $C_2H_5$ |
| $OCH_3$ | Cl | H | $C_2H_5$ | $C_2H_5$ | O | O | $C_2H_5$ |
| $OCH_3$ | Cl | H | $C_3H_7$ | $C_3H_7$ | O | O | $C_2H_5$ |
| $OCH_3$ | Cl | H | 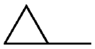 | $CH_3$ | O | O | $C_2H_5$ |
| $OCH_3$ | Cl | H | 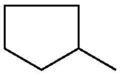 | $CH_3$ | O | O | $C_2H_5$ |
| $OCH_3$ | Cl | H | 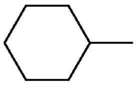 | $CH_3$ | O | O | $C_2H_5$ |
| Cl | $OCH_3$ | H | $—(CH_2)_2—$ | | O | O | $C_2H_5$ |
| Cl | $OCH_3$ | H | $—(CH_2)_4—$ | | O | O | $C_2H_5$ |
| Cl | $OCH_3$ | H | $—(CH_2)_5—$ | | O | O | $C_2H_5$ |
| Cl | $OCH_3$ | H | $—(CH_2)_6—$ | | O | O | $C_2H_5$ |
| Cl | $OCH_3$ | H | $—(CH_2)_7—$ | | O | O | $C_2H_5$ |
| Cl | $OCH_3$ | H | $—(CH_2)_2—O—(CH_2)_2—$ | | O | O | $C_2H_5$ |
| Cl | $OCH_3$ | H | $—(CH_2)_2—S—(CH_2)_2—$ | | O | O | $C_2H_5$ |
| Cl | $OCH_3$ | H | $—CH_2—CHCH_3—(CH_2)_3—$ | | O | O | $C_2H_5$ |
| Cl | $OCH_3$ | H | $—(CH_2)_2—CHCH_3—(CH_2)_2—$ | | O | O | $C_2H_5$ |
| Cl | $OCH_3$ | H | $—(CH_2)_2—CHC_2H_5—(CH_2)_2—$ | | O | O | $C_2H_5$ |
| Cl | $OCH_3$ | H | $—(CH_2)_2—CHC_3H_7—(CH_2)_2—$ | | O | O | $C_2H_5$ |
| Cl | $OCH_3$ | H | $—(CH_2)_2—CHi—C_3H_7—(CH_2)_2—$ | | O | O | $C_2H_5$ |
| Cl | $OCH_3$ | H | $—(CH_2)_2—CHOCH_3—(CH_2)_2—$ | | O | O | $C_2H_5$ |
| Cl | $OCH_3$ | H | $—(CH_2)_2—CHOC_2H_5—(CH_2)_2—$ | | O | O | $C_2H_5$ |
| Cl | $OCH_3$ | H | $—(CH_2)_2—CHOC_3H_7—(CH_2)_2—$ | | O | O | $C_2H_5$ |
| Cl | $OCH_3$ | H | $—(CH_2)_2—CHi—OC_3H_7—(CH_2)_2—$ | | O | O | $C_2H_5$ |
| Cl | $OCH_3$ | H | $—(CH_2)_2—C(CH_3)_2—(CH_2)_2—$ | | O | O | $C_2H_5$ |
| Cl | $OCH_3$ | H | $—CH_2—(CHCH_3)_2—(CH_2)_2—$ | | O | O | $C_2H_5$ |
| Cl | $OCH_3$ | H | 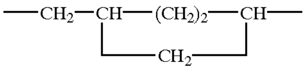 | | O | O | $C_2H_5$ |
| Cl | $OCH_3$ | H | 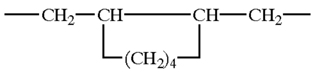 | | O | O | $C_2H_5$ |
| Cl | $OCH_3$ | H | 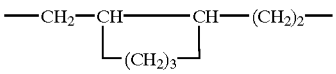 | | O | O | $C_2H_5$ |

TABLE 3-continued (Ic)

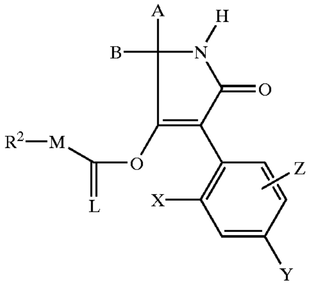

| X | Y | Z | A | B | L | M | $R^2$ |
|---|---|---|---|---|---|---|---|
| Cl | H | 6-$OCH_3$ | | $-(CH_2)_2-$ | O | O | $C_2H_5$ |
| Cl | H | 6-$OCH_3$ | | $-(CH_2)_4-$ | O | O | $C_2H_5$ |
| Cl | H | 6-$OCH_3$ | | $-(CH_2)_5-$ | O | O | $C_2H_5$ |
| Cl | H | 6-$OCH_3$ | | $-(CH_2)_6-$ | O | O | $C_2H_5$ |
| Cl | H | 6-$OCH_3$ | | $-(CH_2)_7-$ | O | O | $C_2H_5$ |
| Cl | H | 6-$OCH_3$ | | $-(CH_2)_2-O-(CH_2)_2-$ | O | O | $C_2H_5$ |
| Cl | H | 6-$OCH_3$ | | $-(CH_2)_2-S-(CH_2)_2-$ | O | O | $C_2H_5$ |
| Cl | H | 6-$OCH_3$ | | $-CH_2-CHCH_3-(CH_2)_3-$ | O | O | $C_2H_5$ |
| Cl | H | 6-$OCH_3$ | | $-(CH_2)_2-CHCH_3-(CH_2)_2-$ | O | O | $C_2H_5$ |
| Cl | H | 6-$OCH_3$ | | $-(CH_2)_2-CHC_2H_5-(CH_2)_2-$ | O | O | $C_2H_5$ |
| Cl | H | 6-$OCH_3$ | | $-(CH_2)_2-CHC_3H_7-(CH_2)_2-$ | O | O | $C_2H_5$ |
| Cl | H | 6-$OCH_3$ | | $-(CH_2)_2-CHi-C_3H_7-(CH_2)_2-$ | O | O | $C_2H_5$ |
| Cl | H | 6-$OCH_3$ | | $-(CH_2)_2-CHOCH_3-(CH_2)_2-$ | O | O | $C_2H_5$ |
| Cl | H | 6-$OCH_3$ | | $-(CH_2)_2-CHOC_2H_5-(CH_2)_2-$ | O | O | $C_2H_5$ |
| Cl | H | 6-$OCH_3$ | | $-(CH_2)_2-CHOC_3H_7-(CH_2)_2-$ | O | O | $C_2H_5$ |
| Cl | H | 6-$OCH_3$ | | $-(CH_2)_2-CHi-OC_3H_7-(CH_2)_2-$ | O | O | $C_2H_5$ |
| Cl | H | 6-$OCH_3$ | | $-(CH_2)_2-C(CH_3)_2-(CH_2)_2-$ | O | O | $C_2H_5$ |
| Cl | H | 6-$OCH_3$ | | $-CH_2-(CHCH_3)_2-(CH_2)_2-$ | O | O | $C_2H_5$ |
| Cl | H | 6-$OCH_3$ | | 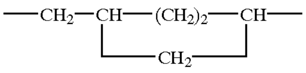 | O | O | $C_2H_5$ |
| Cl | H | 6-$OCH_3$ | | 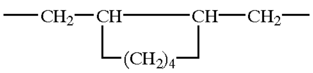 | O | O | $C_2H_5$ |
| Cl | H | 6-$OCH_3$ | | 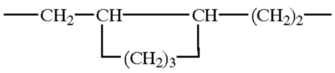 | O | O | $C_2H_5$ |
| $OCH_3$ | Cl | H | | $-(CH_2)_2-$ | O | O | $C_2H_5$ |
| $OCH_3$ | Cl | H | | $-(CH_2)_4-$ | O | O | $C_2H_5$ |
| $OCH_3$ | Cl | H | | $-(CH_2)_5-$ | O | O | $C_2H_5$ |
| $OCH_3$ | Cl | H | | $-(CH_2)_6-$ | O | O | $C_2H_5$ |
| $OCH_3$ | Cl | H | | $-(CH_2)_7-$ | O | O | $C_2H_5$ |
| $OCH_3$ | Cl | H | | $-(CH_2)_2-O-(CH_2)_2-$ | O | O | $C_2H_5$ |
| $OCH_3$ | Cl | H | | $-(CH_2)_2-S-(CH_2)_2-$ | O | O | $C_2H_5$ |
| $OCH_3$ | Cl | H | | $-CH_2-CHCH_3-(CH_2)_3-$ | O | O | $C_2H_5$ |
| $OCH_3$ | Cl | H | | $-(CH_2)_2-CHCH_3-(CH_2)_2-$ | O | O | $C_2H_5$ |
| $OCH_3$ | Cl | H | | $-(CH_2)_2-CHC_2H_5-(CH_2)_2-$ | O | O | $C_2H_5$ |
| $OCH_3$ | Cl | H | | $-(CH_2)_2-CHC_3H_7-(CH_2)_2-$ | O | O | $C_2H_5$ |
| $OCH_3$ | Cl | H | | $-(CH_2)_2-CHi-C_3H_7-(CH_2)_2-$ | O | O | $C_2H_5$ |
| $OCH_3$ | Cl | H | | $-(CH_2)_2-CHOCH_3-(CH_2)_2-$ | O | O | $C_2H_5$ |
| $OCH_3$ | Cl | H | | $-(CH_2)_2-CHOC_2H_5-(CH_2)_2-$ | O | O | $C_2H_5$ |
| $OCH_3$ | Cl | H | | $-(CH_2)_2-CHOC_3H_7-(CH_2)_2-$ | O | O | $C_2H_5$ |
| $OCH_3$ | Cl | H | | $-(CH_2)_2-CHi-OC_3H_7-(CH_2)_2-$ | O | O | $C_2H_5$ |
| $OCH_3$ | Cl | H | | $-(CH_2)_2-C(CH_3)_2-(CH_2)_2-$ | O | O | $C_2H_5$ |
| $OCH_3$ | Cl | H | | $-CH_2-(CHCH_3)_2-(CH_2)_2-$ | O | O | $C_2H_5$ |
| $OCH_3$ | Cl | H | | 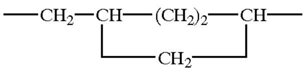 | O | O | $C_2H_5$ |
| $OCH_3$ | Cl | H | | 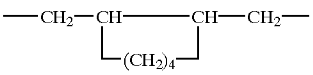 | O | O | $C_2H_5$ |

TABLE 3-continued (Ic)

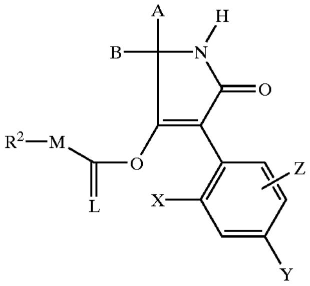

| X | Y | Z | A | B | L | M | $R^2$ |
|---|---|---|---|---|---|---|---|
| $OCH_3$ | Cl | H | 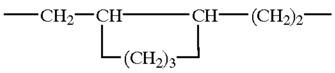 | | O | O | $C_2H_5$ |
| Cl | $OCH_3$ | H | $CH_3$ | H | O | O | i-$C_3H_7$ |
| Cl | $OCH_3$ | H | $C_2H_5$ | H | O | O | i-$C_3H_7$ |
| Cl | $OCH_3$ | H | $C_3H_7$ | H | O | O | i-$C_3H_7$ |
| Cl | $OCH_3$ | H | i-$C_3H_7$ | H | O | O | i-$C_3H_7$ |
| Cl | $OCH_3$ | H | $C_4H_9$ | H | O | O | i-$C_3H_7$ |
| Cl | $OCH_3$ | H | i-$C_4H_9$ | H | O | O | i-$C_3H_7$ |
| Cl | $OCH_3$ | H | s-$C_4H_9$ | H | O | O | i-$C_3H_7$ |
| Cl | $OCH_3$ | H | t-$C_4H_9$ | H | O | O | i-$C_3H_7$ |
| Cl | $OCH_3$ | H | $CH_3$ | $CH_3$ | O | O | i-$C_3H_7$ |
| Cl | $OCH_3$ | H | $C_2H_5$ | $CH_3$ | O | O | i-$C_3H_7$ |
| Cl | $OCH_3$ | H | $C_3H_7$ | $CH_3$ | O | O | i-$C_3H_7$ |
| Cl | $OCH_3$ | H | i-$C_3H_7$ | $CH_3$ | O | O | i-$C_3H_7$ |
| Cl | $OCH_3$ | H | $C_4H_9$ | $CH_3$ | O | O | i-$C_3H_7$ |
| Cl | $OCH_3$ | H | i-$C_4H_9$ | $CH_3$ | O | O | i-$C_3H_7$ |
| Cl | $OCH_3$ | H | s-$C_4H_9$ | $CH_3$ | O | O | i-$C_3H_7$ |
| Cl | $OCH_3$ | H | t-$C_4H_9$ | $CH_3$ | O | O | i-$C_3H_7$ |
| Cl | $OCH_3$ | H | $C_2H_5$ | $C_2H_5$ | O | O | i-$C_3H_7$ |
| Cl | $OCH_3$ | H | $C_3H_7$ | $C_3H_7$ | O | O | i-$C_3H_7$ |
| Cl | $OCH_3$ | H | 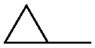 | $CH_3$ | O | O | i-$C_3H_7$ |
| Cl | $OCH_3$ | H | 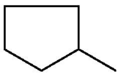 | $CH_3$ | O | O | i-$C_3H_7$ |
| Cl | $OCH_3$ | H | 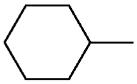 | $CH_3$ | O | O | i-$C_3H_7$ |
| Cl | H | 6-$OCH_3$ | $CH_3$ | H | O | O | i-$C_3H_7$ |
| Cl | H | 6-$OCH_3$ | $C_2H_5$ | H | O | O | i-$C_3H_7$ |
| Cl | H | 6-$OCH_3$ | $C_3H_7$ | H | O | O | i-$C_3H_7$ |
| Cl | H | 6-$OCH_3$ | i-$C_3H_7$ | H | O | O | i-$C_3H_7$ |
| Cl | H | 6-$OCH_3$ | $C_4H_9$ | H | O | O | i-$C_3H_7$ |
| Cl | H | 6-$OCH_3$ | i-$C_4H_9$ | H | O | O | i-$C_3H_7$ |
| Cl | H | 6-$OCH_3$ | s-$C_4H_9$ | H | O | O | i-$C_3H_7$ |
| Cl | H | 6-$OCH_3$ | t-$C_4H_9$ | H | O | O | i-$C_3H_7$ |
| Cl | H | 6-$OCH_3$ | $CH_3$ | $CH_3$ | O | O | i-$C_3H_7$ |
| Cl | H | 6-$OCH_3$ | $C_2H_5$ | $CH_3$ | O | O | i-$C_3H_7$ |
| Cl | H | 6-$OCH_3$ | $C_3H_7$ | $CH_3$ | O | O | i-$C_3H_7$ |
| Cl | H | 6-$OCH_3$ | i-$C_3H_7$ | $CH_3$ | O | O | i-$C_3H_7$ |
| Cl | H | 6-$OCH_3$ | $C_4H_9$ | $CH_3$ | O | O | i-$C_3H_7$ |
| Cl | H | 6-$OCH_3$ | i-$C_4H_9$ | $CH_3$ | O | O | i-$C_3H_7$ |
| Cl | H | 6-$OCH_3$ | s-$C_4H_9$ | $CH_3$ | O | O | i-$C_3H_7$ |
| Cl | H | 6-$OCH_3$ | t-$C_4H_9$ | $CH_3$ | O | O | i-$C_3H_7$ |
| Cl | H | 6-$OCH_3$ | $C_2H_5$ | $C_2H_5$ | O | O | i-$C_3H_7$ |
| Cl | H | 6-$OCH_3$ | $C_3H_7$ | $C_3H_7$ | O | O | i-$C_3H_7$ |
| Cl | H | 6-$OCH_3$ | 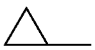 | $CH_3$ | O | O | i-$C_3H_7$ |

TABLE 3-continued (Ic)

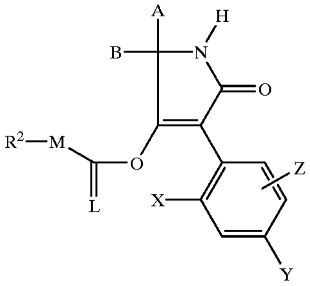

| X | Y | Z | A | B | L | M | $R^2$ |
|---|---|---|---|---|---|---|---|
| Cl | H | 6-$OCH_3$ | 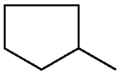 | $CH_3$ | O | O | i-$C_3H_7$ |
| Cl | H | 6-$OCH_3$ | 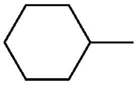 | $CH_3$ | O | O | i-$C_3H_7$ |
| $OCH_3$ | Cl | H | $CH_3$ | H | O | O | i-$C_3H_7$ |
| $OCH_3$ | Cl | H | $C_2H_5$ | H | O | O | i-$C_3H_7$ |
| $OCH_3$ | Cl | H | $C_3H_7$ | H | O | O | i-$C_3H_7$ |
| $OCH_3$ | Cl | H | i-$C_3H_7$ | H | O | O | i-$C_3H_7$ |
| $OCH_3$ | Cl | H | $C_4H_9$ | H | O | O | i-$C_3H_7$ |
| $OCH_3$ | Cl | H | i-$C_4H_9$ | H | O | O | i-$C_3H_7$ |
| $OCH_3$ | Cl | H | s-$C_4H_9$ | H | O | O | i-$C_3H_7$ |
| $OCH_3$ | Cl | H | t-$C_4H_9$ | H | O | O | i-$C_3H_7$ |
| $OCH_3$ | Cl | H | $CH_3$ | $CH_3$ | O | O | i-$C_3H_7$ |
| $OCH_3$ | Cl | H | $C_2H_5$ | $CH_3$ | O | O | i-$C_3H_7$ |
| $OCH_3$ | Cl | H | $C_3H_7$ | $CH_3$ | O | O | i-$C_3H_7$ |
| $OCH_3$ | Cl | H | i-$C_3H_7$ | $CH_3$ | O | O | i-$C_3H_7$ |
| $OCH_3$ | Cl | H | $C_4H_9$ | $CH_3$ | O | O | i-$C_3H_7$ |
| $OCH_3$ | Cl | H | i-$C_4H_9$ | $CH_3$ | O | O | i-$C_3H_7$ |
| $OCH_3$ | Cl | H | s-$C_4H_9$ | $CH_3$ | O | O | i-$C_3H_7$ |
| $OCH_3$ | Cl | H | t-$C_4H_9$ | $CH_3$ | O | O | i-$C_3H_7$ |
| $OCH_3$ | Cl | H | $C_2H_5$ | $C_2H_5$ | O | O | i-$C_3H_7$ |
| $OCH_3$ | Cl | H | $C_3H_7$ | $C_3H_7$ | O | O | i-$C_3H_7$ |
| $OCH_3$ | Cl | H | 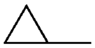 | $CH_3$ | O | O | i-$C_3H_7$ |
| $OCH_3$ | Cl | H | 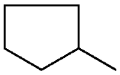 | $CH_3$ | O | O | i-$C_3H_7$ |
| $OCH_3$ | Cl | H | 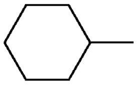 | $CH_3$ | O | O | i-$C_3H_7$ |
| Cl | $OCH_3$ | H | $—(CH_2)_2—$ | | O | O | i-$C_3H_7$ |
| Cl | $OCH_3$ | H | $—(CH_2)_4—$ | | O | O | i-$C_3H_7$ |
| Cl | $OCH_3$ | H | $—(CH_2)_5—$ | | O | O | i-$C_3H_7$ |
| Cl | $OCH_3$ | H | $—(CH_2)_6—$ | | O | O | i-$C_3H_7$ |
| Cl | $OCH_3$ | H | $—(CH_2)_7—$ | | O | O | i-$C_3H_7$ |
| Cl | $OCH_3$ | H | $—(CH_2)_2—O—(CH_2)_2—$ | | O | O | i-$C_3H_7$ |
| Cl | $OCH_3$ | H | $—(CH_2)_2—S—(CH_2)_2—$ | | O | O | i-$C_3H_7$ |
| Cl | $OCH_3$ | H | $—CH_2—CHCH_3—(CH_2)_3—$ | | O | O | i-$C_3H_7$ |
| Cl | $OCH_3$ | H | $—(CH_2)_2—CHCH_3—(CH_2)_2—$ | | O | O | i-$C_3H_7$ |
| Cl | $OCH_3$ | H | $—(CH_2)_2—CHC_2H_5—(CH_2)_2—$ | | O | O | i-$C_3H_7$ |
| Cl | $OCH_3$ | H | $—(CH_2)_2—CHC_3H_7—(CH_2)_2—$ | | O | O | i-$C_3H_7$ |
| Cl | $OCH_3$ | H | $—(CH_2)_2—CHi—C_3H_7—(CH_2)_2—$ | | O | O | i-$C_3H_7$ |
| Cl | $OCH_3$ | H | $—(CH_2)_2—CHOCH_3—(CH_2)_2—$ | | O | O | i-$C_3H_7$ |
| Cl | $OCH_3$ | H | $—(CH_2)_2—CHOC_2H_5—(CH_2)_2—$ | | O | O | i-$C_3H_7$ |
| Cl | $OCH_3$ | H | $—(CH_2)_2—CHOC_3H_7—(CH_2)_2—$ | | O | O | i-$C_3H_7$ |
| Cl | $OCH_3$ | H | $—(CH_2)_2—CHi—OC_3H_7—(CH_2)_2—$ | | O | O | i-$C_3H_7$ |
| Cl | $OCH_3$ | H | $—(CH_2)_2—C(CH_3)_2—(CH_2)_2—$ | | O | O | i-$C_3H_7$ |
| Cl | $OCH_3$ | H | $—CH_2—(CHCH_3)_2—(CH_2)_2—$ | | O | O | i-$C_3H_7$ |

TABLE 3-continued (Ic)

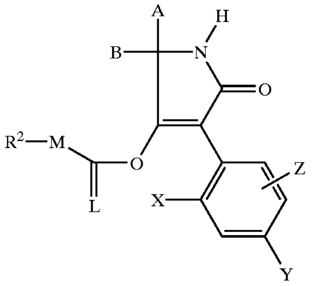

| X | Y | Z | A | B | L | M | $R^2$ |
|---|---|---|---|---|---|---|---|
| Cl | $OCH_3$ | H | | 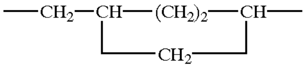 | O | O | i-$C_3H_7$ |
| Cl | $OCH_3$ | H | | 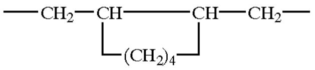 | O | O | i-$C_3H_7$ |
| Cl | $OCH_3$ | H | | 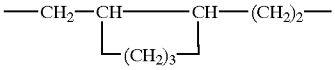 | O | O | i-$C_3H_7$ |
| Cl | H | 6-$OCH_3$ | | $-(CH_2)_2-$ | O | O | i-$C_3H_7$ |
| Cl | H | 6-$OCH_3$ | | $-(CH_2)_4-$ | O | O | i-$C_3H_7$ |
| Cl | H | 6-$OCH_3$ | | $-(CH_2)_5-$ | O | O | i-$C_3H_7$ |
| Cl | H | 6-$OCH_3$ | | $-(CH_2)_6-$ | O | O | i-$C_3H_7$ |
| Cl | H | 6-$OCH_3$ | | $-(CH_2)_7-$ | O | O | i-$C_3H_7$ |
| Cl | H | 6-$OCH_3$ | | $-(CH_2)_2-O-(CH_2)_2-$ | O | O | i-$C_3H_7$ |
| Cl | H | 6-$OCH_3$ | | $-(CH_2)_2-S-(CH_2)_2-$ | O | O | i-$C_3H_7$ |
| Cl | H | 6-$OCH_3$ | | $-CH_2-CHCH_3-(CH_2)_3-$ | O | O | i-$C_3H_7$ |
| Cl | H | 6-$OCH_3$ | | $-(CH_2)_2-CHCH_3-(CH_2)_2-$ | O | O | i-$C_3H_7$ |
| Cl | H | 6-$OCH_3$ | | $-(CH_2)_2-CHC_2H_5-(CH_2)_2-$ | O | O | i-$C_3H_7$ |
| Cl | H | 6-$OCH_3$ | | $-(CH_2)_2-CHC_3H_7-(CH_2)_2-$ | O | O | i-$C_3H_7$ |
| Cl | H | 6-$OCH_3$ | | $-(CH_2)_2-CHi-C_3H_7-(CH_2)_2-$ | O | O | i-$C_3H_7$ |
| Cl | H | 6-$OCH_3$ | | $-(CH_2)_2-CHOCH_3-(CH_2)_2-$ | O | O | i-$C_3H_7$ |
| Cl | H | 6-$OCH_3$ | | $-(CH_2)_2-CHOC_2H_5-(CH_2)_2-$ | O | O | i-$C_3H_7$ |
| Cl | H | 6-$OCH_3$ | | $-(CH_2)_2-CHOC_3H_7-(CH_2)_2-$ | O | O | i-$C_3H_7$ |
| Cl | H | 6-$OCH_3$ | | $-(CH_2)_2-CHi-OC_3H_7-(CH_2)_2-$ | O | O | i-$C_3H_7$ |
| Cl | H | 6-$OCH_3$ | | $-(CH_2)_2-C(CH_3)_2-(CH_2)_2-$ | O | O | i-$C_3H_7$ |
| Cl | H | 6-$OCH_3$ | | $-CH_2-(CHCH_3)_2-(CH_2)_2-$ | O | O | i-$C_3H_7$ |
| Cl | H | 6-$OCH_3$ | | 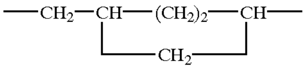 | O | O | i-$C_3H_7$ |
| Cl | H | 6-$OCH_3$ | | 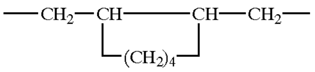 | O | O | i-$C_3H_7$ |
| Cl | H | 6-$OCH_3$ | | 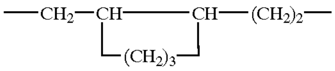 | O | O | i-$C_3H_7$ |
| $OCH_3$ | Cl | H | | $-(CH_2)_2-$ | O | O | i-$C_3H_7$ |
| $OCH_3$ | Cl | H | | $-(CH_2)_4-$ | O | O | i-$C_3H_7$ |
| $OCH_3$ | Cl | H | | $-(CH_2)_5-$ | O | O | i-$C_3H_7$ |
| $OCH_3$ | Cl | H | | $-(CH_2)_6-$ | O | O | i-$C_3H_7$ |
| $OCH_3$ | Cl | H | | $-(CH_2)_7-$ | O | O | i-$C_3H_7$ |
| $OCH_3$ | Cl | H | | $-(CH_2)_2-O-(CH_2)_2-$ | O | O | i-$C_3H_7$ |
| $OCH_3$ | Cl | H | | $-(CH_2)_2-S-(CH_2)_2-$ | O | O | i-$C_3H_7$ |
| $OCH_3$ | Cl | H | | $-CH_2-CHCH_3-(CH_2)_3-$ | O | O | i-$C_3H_7$ |
| $OCH_3$ | Cl | H | | $-(CH_2)_2-CHCH_3-(CH_2)_2-$ | O | O | i-$C_3H_7$ |
| $OCH_3$ | Cl | H | | $-(CH_2)_2-CHC_2H_5-(CH_2)_2-$ | O | O | i-$C_3H_7$ |
| $OCH_3$ | Cl | H | | $-(CH_2)_2-CHC_3H_7-(CH_2)_2-$ | O | O | i-$C_3H_7$ |
| $OCH_3$ | Cl | H | | $-(CH_2)_2-CHi-C_3H_7-(CH_2)_2-$ | O | O | i-$C_3H_7$ |
| $OCH_3$ | Cl | H | | $-(CH_2)_2-CHOCH_3-(CH_2)_2-$ | O | O | i-$C_3H_7$ |
| $OCH_3$ | Cl | H | | $-(CH_2)_2-CHOC_2H_5-(CH_2)_2-$ | O | O | i-$C_3H_7$ |
| $OCH_3$ | Cl | H | | $-(CH_2)_2-CHOC_3H_7-(CH_2)_2-$ | O | O | i-$C_3H_7$ |
| $OCH_3$ | Cl | H | | $-(CH_2)_2-CHi-OC_3H_7-(CH_2)_2-$ | O | O | i-$C_3H_7$ |
| $OCH_3$ | Cl | H | | $-(CH_2)_2-C(CH_3)_2-(CH_2)_2-$ | O | O | i-$C_3H_7$ |

TABLE 3-continued (Ic)

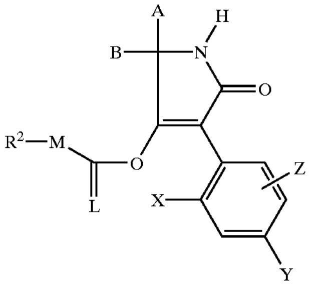

| X | Y | Z | A | B | L | M | $R^2$ |
|---|---|---|---|---|---|---|---|
| $OCH_3$ | Cl | H | $—CH_2—(CHCH_3)_2—(CH_2)_2—$ | | O | O | i-$C_3H_7$ |
| $OCH_3$ | Cl | H | 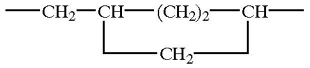 | | O | O | i-$C_3H_7$ |
| $OCH_3$ | Cl | H | 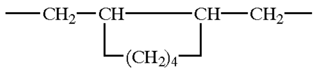 | | O | O | i-$C_3H_7$ |
| $OCH_3$ | Cl | H | 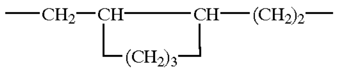 | | O | O | i-$C_3H_7$ |
| Cl | $OCH_3$ | H | $CH_3$ | H | O | S | i-$C_3H_7$ |
| Cl | $OCH_3$ | H | $C_2H_5$ | H | O | S | i-$C_3H_7$ |
| Cl | $OCH_3$ | H | $C_3H_7$ | H | O | S | i-$C_3H_7$ |
| Cl | $OCH_3$ | H | i-$C_3H_7$ | H | O | S | i-$C_3H_7$ |
| Cl | $OCH_3$ | H | $C_4H_9$ | H | O | S | i-$C_3H_7$ |
| Cl | $OCH_3$ | H | i-$C_4H_9$ | H | O | S | i-$C_3H_7$ |
| Cl | $OCH_3$ | H | s-$C_4H_9$ | H | O | S | i-$C_3H_7$ |
| Cl | $OCH_3$ | H | t-$C_4H_9$ | H | O | S | i-$C_3H_7$ |
| Cl | $OCH_3$ | H | $CH_3$ | $CH_3$ | O | S | i-$C_3H_7$ |
| Cl | $OCH_3$ | H | $C_2H_5$ | $CH_3$ | O | S | i-$C_3H_7$ |
| Cl | $OCH_3$ | H | $C_3H_7$ | $CH_3$ | O | S | i-$C_3H_7$ |
| Cl | $OCH_3$ | H | i-$C_3H_7$ | $CH_3$ | O | S | i-$C_3H_7$ |
| Cl | $OCH_3$ | H | $C_4H_9$ | $CH_3$ | O | S | i-$C_3H_7$ |
| Cl | $OCH_3$ | H | i-$C_4H_9$ | $CH_3$ | O | S | i-$C_3H_7$ |
| Cl | $OCH_3$ | H | s-$C_4H_9$ | $CH_3$ | O | S | i-$C_3H_7$ |
| Cl | $OCH_3$ | H | t-$C_4H_9$ | $CH_3$ | O | S | i-$C_3H_7$ |
| Cl | $OCH_3$ | H | $C_2H_5$ | $C_2H_5$ | O | S | i-$C_3H_7$ |
| Cl | $OCH_3$ | H | $C_3H_7$ | $C_3H_7$ | O | S | i-$C_3H_7$ |
| Cl | $OCH_3$ | H | 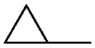 | $CH_3$ | O | S | i-$C_3H_7$ |
| Cl | $OCH_3$ | H | 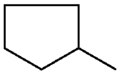 | $CH_3$ | O | S | i-$C_3H_7$ |
| Cl | $OCH_3$ | H | 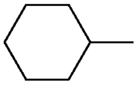 | $CH_3$ | O | S | i-$C_3H_7$ |
| Cl | H | 6-$OCH_3$ | $CH_3$ | H | O | S | i-$C_3H_7$ |
| Cl | H | 6-$OCH_3$ | $C_2H_5$ | H | O | S | i-$C_3H_7$ |
| Cl | H | 6-$OCH_3$ | $C_3H_7$ | H | O | S | i-$C_3H_7$ |
| Cl | H | 6-$OCH_3$ | i-$C_3H_7$ | H | O | S | i-$C_3H_7$ |
| Cl | H | 6-$OCH_3$ | $C_4H_9$ | H | O | S | i-$C_3H_7$ |
| Cl | H | 6-$OCH_3$ | i-$C_4H_9$ | H | O | S | i-$C_3H_7$ |
| Cl | H | 6-$OCH_3$ | s-$C_4H_9$ | H | O | S | i-$C_3H_7$ |
| Cl | H | 6-$OCH_3$ | t-$C_4H_9$ | H | O | S | i-$C_3H_7$ |
| Cl | H | 6-$OCH_3$ | $CH_3$ | $CH_3$ | O | S | i-$C_3H_7$ |
| Cl | H | 6-$OCH_3$ | $C_2H_5$ | $CH_3$ | O | S | i-$C_3H_7$ |
| Cl | H | 6-$OCH_3$ | $C_3H_7$ | $CH_3$ | O | S | i-$C_3H_7$ |
| Cl | H | 6-$OCH_3$ | i-$C_3H_7$ | $CH_3$ | O | S | i-$C_3H_7$ |
| Cl | H | 6-$OCH_3$ | $C_4H_9$ | $CH_3$ | O | S | i-$C_3H_7$ |
| Cl | H | 6-$OCH_3$ | i-$C_4H_9$ | $CH_3$ | O | S | i-$C_3H_7$ |

TABLE 3-continued (Ic)

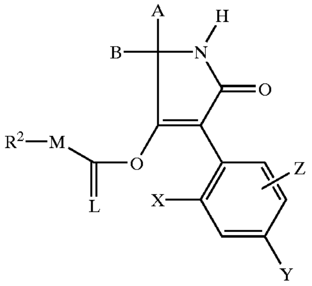

| X | Y | Z | A | B | L | M | $R^2$ |
|---|---|---|---|---|---|---|---|
| Cl | H | 6-$OCH_3$ | s-$C_4H_9$ | $CH_3$ | O | S | i-$C_3H_7$ |
| Cl | H | 6-$OCH_3$ | t-$C_4H_9$ | $CH_3$ | O | S | i-$C_3H_7$ |
| Cl | H | 6-$OCH_3$ | $C_2H_5$ | $C_2H_5$ | O | S | i-$C_3H_7$ |
| Cl | H | 6-$OCH_3$ | $C_3H_7$ | $C_3H_7$ | O | S | i-$C_3H_7$ |
| Cl | H | 6-$OCH_3$ | 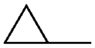 | $CH_3$ | O | S | i-$C_3H_7$ |
| Cl | H | 6-$OCH_3$ | 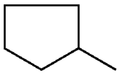 | $CH_3$ | O | S | i-$C_3H_7$ |
| Cl | H | 6-$OCH_3$ | 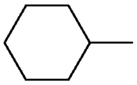 | $CH_3$ | O | S | i-$C_3H_7$ |
| $OCH_3$ | Cl | H | $CH_3$ | H | O | S | i-$C_3H_7$ |
| $OCH_3$ | Cl | H | $C_2H_5$ | H | O | S | i-$C_3H_7$ |
| $OCH_3$ | Cl | H | $C_3H_7$ | H | O | S | i-$C_3H_7$ |
| $OCH_3$ | Cl | H | i-$C_3H_7$ | H | O | S | i-$C_3H_7$ |
| $OCH_3$ | Cl | H | $C_4H_9$ | H | O | S | i-$C_3H_7$ |
| $OCH_3$ | Cl | H | i-$C_4H_9$ | H | O | S | i-$C_3H_7$ |
| $OCH_3$ | Cl | H | s-$C_4H_9$ | H | O | S | i-$C_3H_7$ |
| $OCH_3$ | Cl | H | t-$C_4H_9$ | H | O | S | i-$C_3H_7$ |
| $OCH_3$ | Cl | H | $CH_3$ | $CH_3$ | O | S | i-$C_3H_7$ |
| $OCH_3$ | Cl | H | $C_2H_5$ | $CH_3$ | O | S | i-$C_3H_7$ |
| $OCH_3$ | Cl | H | $C_3H_7$ | $CH_3$ | O | S | i-$C_3H_7$ |
| $OCH_3$ | Cl | H | i-$C_3H_7$ | $CH_3$ | O | S | i-$C_3H_7$ |
| $OCH_3$ | Cl | H | $C_4H_9$ | $CH_3$ | O | S | i-$C_3H_7$ |
| $OCH_3$ | Cl | H | i-$C_4H_9$ | $CH_3$ | O | S | i-$C_3H_7$ |
| $OCH_3$ | Cl | H | s-$C_4H_9$ | $CH_3$ | O | S | i-$C_3H_7$ |
| $OCH_3$ | Cl | H | t-$C_4H_9$ | $CH_3$ | O | S | i-$C_3H_7$ |
| $OCH_3$ | Cl | H | $C_2H_5$ | $C_2H_5$ | O | S | i-$C_3H_7$ |
| $OCH_3$ | Cl | H | $C_3H_7$ | $C_3H_7$ | O | S | i-$C_3H_7$ |
| $OCH_3$ | Cl | H | 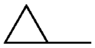 | $CH_3$ | O | S | i-$C_3H_7$ |
| $OCH_3$ | Cl | H | 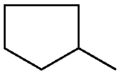 | $CH_3$ | O | S | i-$C_3H_7$ |
| $OCH_3$ | Cl | H | 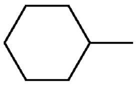 | $CH_3$ | O | S | i-$C_3H_7$ |
| Cl | $OCH_3$ | H | $-(CH_2)_2-$ | | O | S | i-$C_3H_7$ |
| Cl | $OCH_3$ | H | $-(CH_2)_4-$ | | O | S | i-$C_3H_7$ |
| Cl | $OCH_3$ | H | $-(CH_2)_5-$ | | O | S | i-$C_3H_7$ |
| Cl | $OCH_3$ | H | $-(CH_2)_6-$ | | O | S | i-$C_3H_7$ |
| Cl | $OCH_3$ | H | $-(CH_2)_7-$ | | O | S | i-$C_3H_7$ |
| Cl | $OCH_3$ | H | $-(CH_2)_2-O-(CH_2)_2-$ | | O | S | i-$C_3H_7$ |
| Cl | $OCH_3$ | H | $-(CH_2)_2-S-(CH_2)_2-$ | | O | S | i-$C_3H_7$ |
| Cl | $OCH_3$ | H | $-CH_2-CHCH_3-(CH_2)_3-$ | | O | S | i-$C_3H_7$ |
| Cl | $OCH_3$ | H | $-(CH_2)_2-CHCH_3-(CH_2)_2-$ | | O | S | i-$C_3H_7$ |
| Cl | $OCH_3$ | H | $-(CH_2)_2-CHC_2H_5-(CH_2)_2-$ | | O | S | i-$C_3H_7$ |
| Cl | $OCH_3$ | H | $-(CH_2)_2-CHC_3H_7-(CH_2)_2-$ | | O | S | i-$C_3H_7$ |

TABLE 3-continued (Ic)

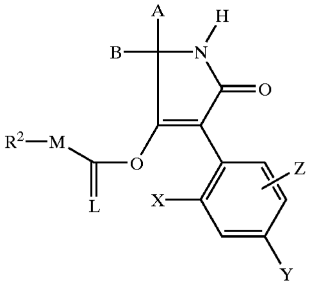

| X | Y | Z | A | B | L | M | $R^2$ |
|---|---|---|---|---|---|---|---|
| Cl | $OCH_3$ | H | | $—(CH_2)_2—CHi—C_3H_7—(CH_2)_2—$ | O | S | $i\text{-}C_3H_7$ |
| Cl | $OCH_3$ | H | | $—(CH_2)_2—CHOCH_3—(CH_2)_2—$ | O | S | $i\text{-}C_3H_7$ |
| Cl | $OCH_3$ | H | | $—(CH_2)_2—CHOC_2H_5—(CH_2)_2—$ | O | S | $i\text{-}C_3H_7$ |
| Cl | $OCH_3$ | H | | $—(CH_2)_2—CHOC_3H_7—(CH_2)_2—$ | O | S | $i\text{-}C_3H_7$ |
| Cl | $OCH_3$ | H | | $—(CH_2)_2—CHi—OC_3H_7—(CH_2)_2—$ | O | S | $i\text{-}C_3H_7$ |
| Cl | $OCH_3$ | H | | $—(CH_2)_2—C(CH_3)_2—(CH_2)_2—$ | O | S | $i\text{-}C_3H_7$ |
| Cl | $OCH_3$ | H | | $—CH_2—(CHCH_3)_2—(CH_2)_2—$ | O | S | $i\text{-}C_3H_7$ |
| Cl | $OCH_3$ | H | | 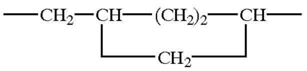 | O | S | $i\text{-}C_3H_7$ |
| Cl | $OCH_3$ | H | | 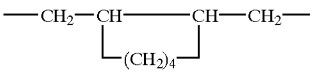 | O | S | $i\text{-}C_3H_7$ |
| Cl | $OCH_3$ | H | | 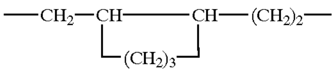 | O | S | $i\text{-}C_3H_7$ |
| Cl | H | $6\text{-}OCH_3$ | | $—(CH_2)_2—$ | O | S | $i\text{-}C_3H_7$ |
| Cl | H | $6\text{-}OCH_3$ | | $—(CH_2)_4—$ | O | S | $i\text{-}C_3H_7$ |
| Cl | H | $6\text{-}OCH_3$ | | $—(CH_2)_5—$ | O | S | $i\text{-}C_3H_7$ |
| Cl | H | $6\text{-}OCH_3$ | | $—(CH_2)_6—$ | O | S | $i\text{-}C_3H_7$ |
| Cl | H | $6\text{-}OCH_3$ | | $—(CH_2)_7—$ | O | S | $i\text{-}C_3H_7$ |
| Cl | H | $6\text{-}OCH_3$ | | $—(CH_2)_2—O—(CH_2)_2—$ | O | S | $i\text{-}C_3H_7$ |
| Cl | H | $6\text{-}OCH_3$ | | $—(CH_2)_2—S—(CH_2)_2—$ | O | S | $i\text{-}C_3H_7$ |
| Cl | H | $6\text{-}OCH_3$ | | $—CH_2—CHCH_3—(CH_2)_3—$ | O | S | $i\text{-}C_3H_7$ |
| Cl | H | $6\text{-}OCH_3$ | | $—(CH_2)_2—CHCH_3—(CH_2)_2—$ | O | S | $i\text{-}C_3H_7$ |
| Cl | H | $6\text{-}OCH_3$ | | $—(CH_2)_2—CHC_2H_5—(CH_2)_2—$ | O | S | $i\text{-}C_3H_7$ |
| Cl | H | $6\text{-}OCH_3$ | | $—(CH_2)_2—CHC_3H_7—(CH_2)_2—$ | O | S | $i\text{-}C_3H_7$ |
| Cl | H | $6\text{-}OCH_3$ | | $—(CH_2)_2—CHi—C_3H_7—(CH_2)_2—$ | O | S | $i\text{-}C_3H_7$ |
| Cl | H | $6\text{-}OCH_3$ | | $—(CH_2)_2—CHOCH_3—(CH_2)_2—$ | O | S | $i\text{-}C_3H_7$ |
| Cl | H | $6\text{-}OCH_3$ | | $—(CH_2)_2—CHOC_2H_5—(CH_2)_2—$ | O | S | $i\text{-}C_3H_7$ |
| Cl | H | $6\text{-}OCH_3$ | | $—(CH_2)_2—CHOC_3H_7—(CH_2)_2—$ | O | S | $i\text{-}C_3H_7$ |
| Cl | H | $6\text{-}OCH_3$ | | $—(CH_2)_2—CHi—OC_3H_7—(CH_2)_2—$ | O | S | $i\text{-}C_3H_7$ |
| Cl | H | $6\text{-}OCH_3$ | | $—(CH_2)_2—C(CH_3)_2—(CH_2)_2—$ | O | S | $i\text{-}C_3H_7$ |
| Cl | H | $6\text{-}OCH_3$ | | $—CH_2—(CHCH_3)_2—(CH_2)_2—$ | O | S | $i\text{-}C_3H_7$ |
| Cl | H | $6\text{-}OCH_3$ | | 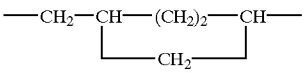 | O | S | $i\text{-}C_3H_7$ |
| Cl | H | $6\text{-}OCH_3$ | | 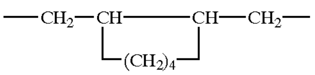 | O | S | $i\text{-}C_3H_7$ |
| Cl | H | $6\text{-}OCH_3$ | | 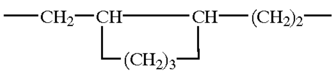 | O | S | $i\text{-}C_3H_7$ |
| $OCH_3$ | Cl | H | | $—(CH_2)_2—$ | O | S | $i\text{-}C_3H_7$ |
| $OCH_3$ | Cl | H | | $—(CH_2)_4—$ | O | S | $i\text{-}C_3H_7$ |
| $OCH_3$ | Cl | H | | $—(CH_2)_5—$ | O | S | $i\text{-}C_3H_7$ |
| $OCH_3$ | Cl | H | | $—(CH_2)_6—$ | O | S | $i\text{-}C_3H_7$ |
| $OCH_3$ | Cl | H | | $—(CH_2)_7—$ | O | S | $i\text{-}C_3H_7$ |
| $OCH_3$ | Cl | H | | $—(CH_2)_2—O—(CH_2)_2—$ | O | S | $i\text{-}C_3H_7$ |
| $OCH_3$ | Cl | H | | $—(CH_2)_2—S—(CH_2)_2—$ | O | S | $i\text{-}C_3H_7$ |
| $OCH_3$ | Cl | H | | $—CH_2—CHCH_3—(CH_2)_3—$ | O | S | $i\text{-}C_3H_7$ |
| $OCH_3$ | Cl | H | | $—(CH_2)_2—CHCH_3—(CH_2)_2—$ | O | S | $i\text{-}C_3H_7$ |

TABLE 3-continued (Ic)

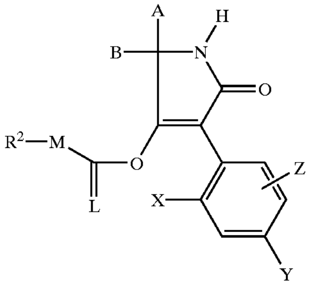

| X | Y | Z | A | B | L | M | $R^2$ |
|---|---|---|---|---|---|---|---|
| $OCH_3$ | Cl | H | $—(CH_2)_2—CHC_2H_5—(CH_2)_2—$ | | O | S | i-$C_3H_7$ |
| $OCH_3$ | Cl | H | $—(CH_2)_2—CHC_3H_7—(CH_2)_2—$ | | O | S | i-$C_3H_7$ |
| $OCH_3$ | Cl | H | $—(CH_2)_2—CHi—C_3H_7—(CH_2)_2—$ | | O | S | i-$C_3H_7$ |
| $OCH_3$ | Cl | H | $—(CH_2)_2—CHOCH_3—(CH_2)_2—$ | | O | S | i-$C_3H_7$ |
| $OCH_3$ | Cl | H | $—(CH_2)_2—CHOC_2H_5—(CH_2)_2—$ | | O | S | i-$C_3H_7$ |
| $OCH_3$ | Cl | H | $—(CH_2)_2—CHOC_3H_7—(CH_2)_2—$ | | O | S | i-$C_3H_7$ |
| $OCH_3$ | Cl | H | $—(CH_2)_2—CHi—OC_3H_7—(CH_2)_2—$ | | O | S | i-$C_3H_7$ |
| $OCH_3$ | Cl | H | $—(CH_2)_2—C(CH_3)_2—(CH_2)_2—$ | | O | S | i-$C_3H_7$ |
| $OCH_3$ | Cl | H | $—CH_2—(CHCH_3)_2—(CH_2)_2—$ | | O | S | i-$C_3H_7$ |
| $OCH_3$ | Cl | H | 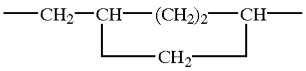 | | O | S | i-$C_3H_7$ |
| $OCH_3$ | Cl | H | 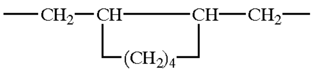 | | O | S | i-$C_3H_7$ |
| $OCH_3$ | Cl | H | 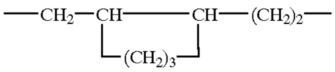 | | O | S | i-$C_3H_7$ |
| Cl | $OCH_3$ | H | $CH_3$ | H | O | O | s-$C_4H_9$ |
| Cl | $OCH_3$ | H | $C_2H_5$ | H | O | O | s-$C_4H_9$ |
| Cl | $OCH_3$ | H | $C_3H_7$ | H | O | O | s-$C_4H_9$ |
| Cl | $OCH_3$ | H | s-$C_4H_9$ | H | O | O | s-$C_4H_9$ |
| Cl | $OCH_3$ | H | $C_4H_9$ | H | O | O | s-$C_4H_9$ |
| Cl | $OCH_3$ | H | i-$C_4H_9$ | H | O | O | s-$C_4H_9$ |
| Cl | $OCH_3$ | H | s-$C_4H_9$ | H | O | O | s-$C_4H_9$ |
| Cl | $OCH_3$ | H | t-$C_4H_9$ | H | O | O | s-$C_4H_9$ |
| Cl | $OCH_3$ | H | $CH_3$ | $CH_3$ | O | O | s-$C_4H_9$ |
| Cl | $OCH_3$ | H | $C_2H_5$ | $CH_3$ | O | O | s-$C_4H_9$ |
| Cl | $OCH_3$ | H | $C_3H_7$ | $CH_3$ | O | O | s-$C_4H_9$ |
| Cl | $OCH_3$ | H | s-$C_4H_9$ | $CH_3$ | O | O | s-$C_4H_9$ |
| Cl | $OCH_3$ | H | $C_4H_9$ | $CH_3$ | O | O | s-$C_4H_9$ |
| Cl | $OCH_3$ | H | i-$C_4H_9$ | $CH_3$ | O | O | s-$C_4H_9$ |
| Cl | $OCH_3$ | H | s-$C_4H_9$ | $CH_3$ | O | O | s-$C_4H_9$ |
| Cl | $OCH_3$ | H | t-$C_4H_9$ | $CH_3$ | O | O | s-$C_4H_9$ |
| Cl | $OCH_3$ | H | $C_2H_5$ | $C_2H_5$ | O | O | s-$C_4H_9$ |
| Cl | $OCH_3$ | H | $C_3H_7$ | $C_3H_7$ | O | O | s-$C_4H_9$ |
| Cl | $OCH_3$ | H | 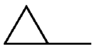 | $CH_3$ | O | O | s-$C_4H_9$ |
| Cl | $OCH_3$ | H | 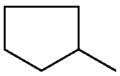 | $CH_3$ | O | O | s-$C_4H_9$ |
| Cl | $OCH_3$ | H | 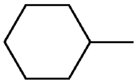 | $CH_3$ | O | O | s-$C_4H_9$ |
| Cl | H | 6-$OCH_3$ | $CH_3$ | H | O | O | s-$C_4H_9$ |
| Cl | H | 6-$OCH_3$ | $C_2H_5$ | H | O | O | s-$C_4H_9$ |
| Cl | H | 6-$OCH_3$ | $C_3H_7$ | H | O | O | s-$C_4H_9$ |
| Cl | H | 6-$OCH_3$ | s-$C_4H_9$ | H | O | O | s-$C_4H_9$ |
| Cl | H | 6-$OCH_3$ | $C_4H_9$ | H | O | O | s-$C_4H_9$ |
| Cl | H | 6-$OCH_3$ | i-$C_4H_9$ | H | O | O | s-$C_4H_9$ |

TABLE 3-continued (Ic)

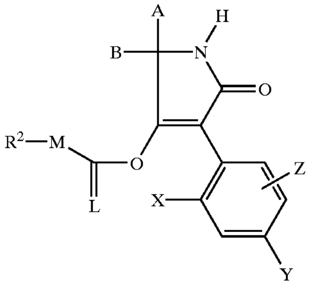

| X | Y | Z | A | B | L | M | $R^2$ |
|---|---|---|---|---|---|---|---|
| Cl | H | 6-$OCH_3$ | s-$C_4H_9$ | H | O | O | s-$C_4H_9$ |
| Cl | H | 6-$OCH_3$ | t-$C_4H_9$ | H | O | O | s-$C_4H_9$ |
| Cl | H | 6-$OCH_3$ | $CH_3$ | $CH_3$ | O | O | s-$C_4H_9$ |
| Cl | H | 6-$OCH_3$ | $C_2H_5$ | $CH_3$ | O | O | s-$C_4H_9$ |
| Cl | H | 6-$OCH_3$ | $C_3H_7$ | $CH_3$ | O | O | s-$C_4H_9$ |
| Cl | H | 6-$OCH_3$ | s-$C_4H_9$ | $CH_3$ | O | O | s-$C_4H_9$ |
| Cl | H | 6-$OCH_3$ | $C_4H_9$ | $CH_3$ | O | O | s-$C_4H_9$ |
| Cl | H | 6-$OCH_3$ | i-$C_4H_9$ | $CH_3$ | O | O | s-$C_4H_9$ |
| Cl | H | 6-$OCH_3$ | s-$C_4H_9$ | $CH_3$ | O | O | s-$C_4H_9$ |
| Cl | H | 6-$OCH_3$ | t-$C_4H_9$ | $CH_3$ | O | O | s-$C_4H_9$ |
| Cl | H | 6-$OCH_3$ | $C_2H_5$ | $C_2H_5$ | O | O | s-$C_4H_9$ |
| Cl | H | 6-$OCH_3$ | $C_3H_7$ | $C_3H_7$ | O | O | s-$C_4H_9$ |
| Cl | H | 6-$OCH_3$ | 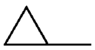 | $CH_3$ | O | O | s-$C_4H_9$ |
| Cl | H | 6-$OCH_3$ | 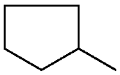 | $CH_3$ | O | O | s-$C_4H_9$ |
| Cl | H | 6-$OCH_3$ | 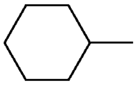 | $CH_3$ | O | O | s-$C_4H_9$ |
| $OCH_3$ | Cl | H | $CH_3$ | H | O | O | s-$C_4H_9$ |
| $OCH_3$ | Cl | H | $C_2H_5$ | H | O | O | s-$C_4H_9$ |
| $OCH_3$ | Cl | H | $C_3H_7$ | H | O | O | s-$C_4H_9$ |
| $OCH_3$ | Cl | H | s-$C_4H_9$ | H | O | O | s-$C_4H_9$ |
| $OCH_3$ | Cl | H | $C_4H_9$ | H | O | O | s-$C_4H_9$ |
| $OCH_3$ | Cl | H | i-$C_4H_9$ | H | O | O | s-$C_4H_9$ |
| $OCH_3$ | Cl | H | s-$C_4H_9$ | H | O | O | s-$C_4H_9$ |
| $OCH_3$ | Cl | H | t-$C_4H_9$ | H | O | O | s-$C_4H_9$ |
| $OCH_3$ | Cl | H | $CH_3$ | $CH_3$ | O | O | s-$C_4H_9$ |
| $OCH_3$ | Cl | H | $C_2H_5$ | $CH_3$ | O | O | s-$C_4H_9$ |
| $OCH_3$ | Cl | H | $C_3H_7$ | $CH_3$ | O | O | s-$C_4H_9$ |
| $OCH_3$ | Cl | H | s-$C_4H_9$ | $CH_3$ | O | O | s-$C_4H_9$ |
| $OCH_3$ | Cl | H | $C_4H_9$ | $CH_3$ | O | O | s-$C_4H_9$ |
| $OCH_3$ | Cl | H | i-$C_4H_9$ | $CH_3$ | O | O | s-$C_4H_9$ |
| $OCH_3$ | Cl | H | s-$C_4H_9$ | $CH_3$ | O | O | s-$C_4H_9$ |
| $OCH_3$ | Cl | H | t-$C_4H_9$ | $CH_3$ | O | O | s-$C_4H_9$ |
| $OCH_3$ | Cl | H | $C_2H_5$ | $C_2H_5$ | O | O | s-$C_4H_9$ |
| $OCH_3$ | Cl | H | $C_3H_7$ | $C_3H_7$ | O | O | s-$C_4H_9$ |
| $OCH_3$ | Cl | H | 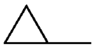 | $CH_3$ | O | O | s-$C_4H_9$ |
| $OCH_3$ | Cl | H | 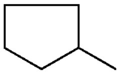 | $CH_3$ | O | O | s-$C_4H_9$ |
| $OCH_3$ | Cl | H | 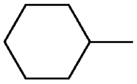 | $CH_3$ | O | O | s-$C_4H_9$ |
| Cl | $OCH_3$ | H | | $-(CH_2)_2-$ | O | O | s-$C_4H_9$ |
| Cl | $OCH_3$ | H | | $-(CH_2)_4-$ | O | O | s-$C_4H_9$ |
| Cl | $OCH_3$ | H | | $-(CH_2)_5-$ | O | O | s-$C_4H_9$ |

TABLE 3-continued (Ic)

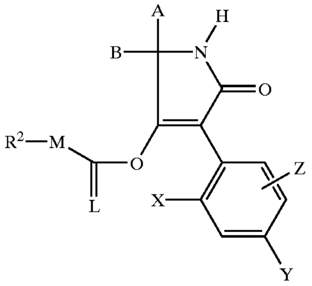

| X | Y | Z | A | B | L | M | $R^2$ |
|---|---|---|---|---|---|---|---|
| Cl | $OCH_3$ | H | | $-(CH_2)_6-$ | O | O | s-$C_4H_9$ |
| Cl | $OCH_3$ | H | | $-(CH_2)_7-$ | O | O | s-$C_4H_9$ |
| Cl | $OCH_3$ | H | | $-(CH_2)_2-O-(CH_2)_2-$ | O | O | s-$C_4H_9$ |
| Cl | $OCH_3$ | H | | $-(CH_2)_2-S-(CH_2)_2-$ | O | O | s-$C_4H_9$ |
| Cl | $OCH_3$ | H | | $-CH_2-CHCH_3-(CH_2)_3-$ | O | O | s-$C_4H_9$ |
| Cl | $OCH_3$ | H | | $-(CH_2)_2-CHCH_3-(CH_2)_2-$ | O | O | s-$C_4H_9$ |
| Cl | $OCH_3$ | H | | $-(CH_2)_2-CHC_2H_5-(CH_2)_2-$ | O | O | s-$C_4H_9$ |
| Cl | $OCH_3$ | H | | $-(CH_2)_2-CHC_3H_7-(CH_2)_2-$ | O | O | s-$C_4H_9$ |
| Cl | $OCH_3$ | H | | $-(CH_2)_2-CHi-C_3H_7-(CH_2)_2-$ | O | O | s-$C_4H_9$ |
| Cl | $OCH_3$ | H | | $-(CH_2)_2-CHOCH_3-(CH_2)_2-$ | O | O | s-$C_4H_9$ |
| Cl | $OCH_3$ | H | | $-(CH_2)_2-CHOC_2H_5-(CH_2)_2-$ | O | O | s-$C_4H_9$ |
| Cl | $OCH_3$ | H | | $-(CH_2)_2-CHOC_3H_7-(CH_2)_2-$ | O | O | s-$C_4H_9$ |
| Cl | $OCH_3$ | H | | $-(CH_2)_2-CHi-OC_3H_7-(CH_2)_2-$ | O | O | s-$C_4H_9$ |
| Cl | $OCH_3$ | H | | $-(CH_2)_2-C(CH_3)_2-(CH_2)_2-$ | O | O | s-$C_4H_9$ |
| Cl | $OCH_3$ | H | | $-CH_2-(CHCH_3)_2-(CH_2)_2-$ | O | O | s-$C_4H_9$ |
| Cl | $OCH_3$ | H | | 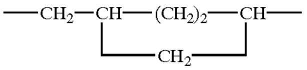 | O | O | s-$C_4H_9$ |
| Cl | $OCH_3$ | H | | 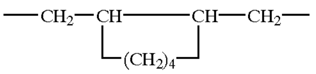 | O | O | s-$C_4H_9$ |
| Cl | $OCH_3$ | H | | 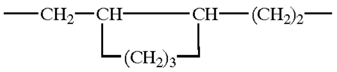 | O | O | s-$C_4H_9$ |
| Cl | H | 6-$OCH_3$ | | $-(CH_2)_2-$ | O | O | s-$C_4H_9$ |
| Cl | H | 6-$OCH_3$ | | $-(CH_2)_4-$ | O | O | s-$C_4H_9$ |
| Cl | H | 6-$OCH_3$ | | $-(CH_2)_5-$ | O | O | s-$C_4H_9$ |
| Cl | H | 6-$OCH_3$ | | $-(CH_2)_6-$ | O | O | s-$C_4H_9$ |
| Cl | H | 6-$OCH_3$ | | $-(CH_2)_7-$ | O | O | s-$C_4H_9$ |
| Cl | H | 6-$OCH_3$ | | $-(CH_2)_2-O-(CH_2)_2-$ | O | O | s-$C_4H_9$ |
| Cl | H | 6-$OCH_3$ | | $-(CH_2)_2-S-(CH_2)_2-$ | O | O | s-$C_4H_9$ |
| Cl | H | 6-$OCH_3$ | | $-CH_2-CHCH_3-(CH_2)_3-$ | O | O | s-$C_4H_9$ |
| Cl | H | 6-$OCH_3$ | | $-(CH_2)_2-CHCH_3-(CH_2)_2-$ | O | O | s-$C_4H_9$ |
| Cl | H | 6-$OCH_3$ | | $-(CH_2)_2-CHC_2H_5-(CH_2)_2-$ | O | O | s-$C_4H_9$ |
| Cl | H | 6-$OCH_3$ | | $-(CH_2)_2-CHC_3H_7-(CH_2)_2-$ | O | O | s-$C_4H_9$ |
| Cl | H | 6-$OCH_3$ | | $-(CH_2)_2-CHi-C_3H_7-(CH_2)_2-$ | O | O | s-$C_4H_9$ |
| Cl | H | 6-$OCH_3$ | | $-(CH_2)_2-CHOCH_3-(CH_2)_2-$ | O | O | s-$C_4H_9$ |
| Cl | H | 6-$OCH_3$ | | $-(CH_2)_2-CHOC_2H_5-(CH_2)_2-$ | O | O | s-$C_4H_9$ |
| Cl | H | 6-$OCH_3$ | | $-(CH_2)_2-CHOC_3H_7-(CH_2)_2-$ | O | O | s-$C_4H_9$ |
| Cl | H | 6-$OCH_3$ | | $-(CH_2)_2-CHi-OC_3H_7-(CH_2)_2-$ | O | O | s-$C_4H_9$ |
| Cl | H | 6-$OCH_3$ | | $-(CH_2)_2-C(CH_3)_2-(CH_2)_2-$ | O | O | s-$C_4H_9$ |
| Cl | H | 6-$OCH_3$ | | $-CH_2-(CHCH_3)_2-(CH_2)_2-$ | O | O | s-$C_4H_9$ |
| Cl | H | 6-$OCH_3$ | | 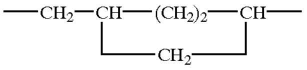 | O | O | s-$C_4H_9$ |
| Cl | H | 6-$OCH_3$ | | 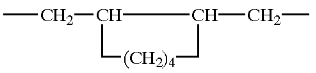 | O | O | s-$C_4H_9$ |
| Cl | H | 6-$OCH_3$ | | 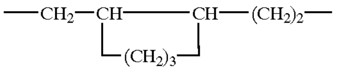 | O | O | s-$C_4H_9$ |
| $OCH_3$ | Cl | H | | $-(CH_2)_2-$ | O | O | s-$C_4H_9$ |

TABLE 3-continued (Ic)

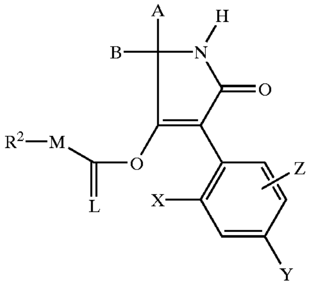

| X | Y | Z | A | B | L | M | $R^2$ |
|---|---|---|---|---|---|---|---|
| $OCH_3$ | Cl | H | | $-(CH_2)_4-$ | O | O | s-$C_4H_9$ |
| $OCH_3$ | Cl | H | | $-(CH_2)_5-$ | O | O | s-$C_4H_9$ |
| $OCH_3$ | Cl | H | | $-(CH_2)_6-$ | O | O | s-$C_4H_9$ |
| $OCH_3$ | Cl | H | | $-(CH_2)_7-$ | O | O | s-$C_4H_9$ |
| $OCH_3$ | Cl | H | | $-(CH_2)_2-O-(CH_2)_2-$ | O | O | s-$C_4H_9$ |
| $OCH_3$ | Cl | H | | $-(CH_2)_2-S-(CH_2)_2-$ | O | O | s-$C_4H_9$ |
| $OCH_3$ | Cl | H | | $-CH_2-CHCH_3-(CH_2)_3-$ | O | O | s-$C_4H_9$ |
| $OCH_3$ | Cl | H | | $-(CH_2)_2-CHCH_3-(CH_2)_2-$ | O | O | s-$C_4H_9$ |
| $OCH_3$ | Cl | H | | $-(CH_2)_2-CHC_2H_5-(CH_2)_2-$ | O | O | s-$C_4H_9$ |
| $OCH_3$ | Cl | H | | $-(CH_2)_2-CHC_3H_7-(CH_2)_2-$ | O | O | s-$C_4H_9$ |
| $OCH_3$ | Cl | H | | $-(CH_2)_2-CHi-C_3H_7-(CH_2)_2-$ | O | O | s-$C_4H_9$ |
| $OCH_3$ | Cl | H | | $-(CH_2)_2-CHOCH_3-(CH_2)_2-$ | O | O | s-$C_4H_9$ |
| $OCH_3$ | Cl | H | | $-(CH_2)_2-CHOC_2H_5-(CH_2)_2-$ | O | O | s-$C_4H_9$ |
| $OCH_3$ | Cl | H | | $-(CH_2)_2-CHOC_3H_7-(CH_2)_2-$ | O | O | s-$C_4H_9$ |
| $OCH_3$ | Cl | H | | $-(CH_2)_2-CHi-OC_3H_7-(CH_2)_2-$ | O | O | s-$C_4H_9$ |
| $OCH_3$ | Cl | H | | $-(CH_2)_2-C(CH_3)_2-(CH_2)_2-$ | O | O | s-$C_4H_9$ |
| $OCH_3$ | Cl | H | | $-CH_2-(CHCH_3)_2-(CH_2)_2-$ | O | O | s-$C_4H_9$ |
| $OCH_3$ | Cl | H | | 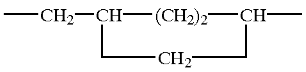 | O | O | s-$C_4H_9$ |
| $OCH_3$ | Cl | H | | 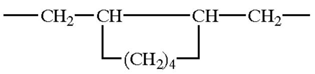 | O | O | s-$C_4H_9$ |
| $OCH_3$ | Cl | H | | 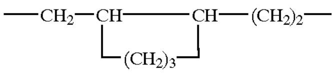 | O | O | s-$C_4H_9$ |

The following compound of the formula (Id) may be mentioned individually in addition to the compounds mentioned in the preparation examples:

TABLE 4

(Id)

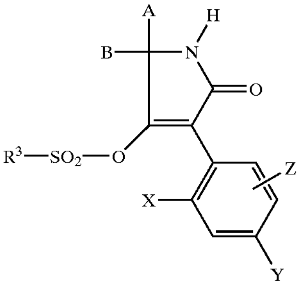

| | Y | Z | A | B | $R^3$ |
|---|---|---|---|---|---|
| Cl | $OCH_3$ | H | $CH_3$ | H | $CH_3$ |
| Cl | $OCH_3$ | H | $C_2H_5$ | H | $CH_3$ |
| Cl | $OCH_3$ | H | $C_3H_7$ | H | $CH_3$ |
| Cl | $OCH_3$ | H | i-$C_3H_7$ | H | $CH_3$ |

TABLE 4-continued (Id)

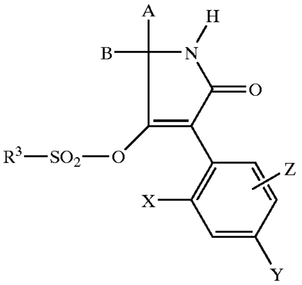

| | Y | Z | A | B | $R^3$ |
|---|---|---|---|---|---|
| Cl | $OCH_3$ | H | $C_4H_9$ | H | $CH_3$ |
| Cl | $OCH_3$ | H | i-$C_4H_9$ | H | $CH_3$ |
| Cl | $OCH_3$ | H | s-$C_4H_9$ | H | $CH_3$ |
| Cl | $OCH_3$ | H | t-$C_4H_9$ | H | $CH_3$ |
| Cl | $OCH_3$ | H | $CH_3$ | $CH_3$ | $CH_3$ |
| Cl | $OCH_3$ | H | $C_2H_5$ | $CH_3$ | $CH_3$ |
| Cl | $OCH_3$ | H | $C_3H_7$ | $CH_3$ | $CH_3$ |

TABLE 4-continued (Id)

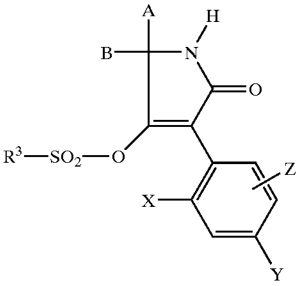

| | Y | Z | A | B | $R^3$ |
|---|---|---|---|---|---|
| Cl | $OCH_3$ | H | i-$C_3H_7$ | $CH_3$ | $CH_3$ |
| Cl | $OCH_3$ | H | $C_4H_9$ | $CH_3$ | $CH_3$ |
| Cl | $OCH_3$ | H | i-$C_4H_9$ | $CH_3$ | $CH_3$ |
| Cl | $OCH_3$ | H | s-$C_4H_9$ | $CH_3$ | $CH_3$ |
| Cl | $OCH_3$ | H | t-$C_4H_9$ | $CH_3$ | $CH_3$ |
| Cl | $OCH_3$ | H | $C_2H_5$ | $C_2H_5$ | $CH_3$ |
| Cl | $OCH_3$ | H | $C_3H_7$ | $C_3H_7$ | $CH_3$ |
| Cl | $OCH_3$ | H | 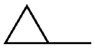 | $CH_3$ | $CH_3$ |
| Cl | $OCH_3$ | H | 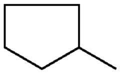 | $CH_3$ | $CH_3$ |
| Cl | $OCH_3$ | H | 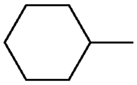 | $CH_3$ | $CH_3$ |
| Cl | H | 6-$OCH_3$ | $CH_3$ | H | $CH_3$ |
| Cl | H | 6-$OCH_3$ | $C_2H_5$ | H | $CH_3$ |
| Cl | H | 6-$OCH_3$ | $C_3H_7$ | H | $CH_3$ |
| Cl | H | 6-$OCH_3$ | i-$C_3H_7$ | H | $CH_3$ |
| Cl | H | 6-$OCH_3$ | $C_4H_9$ | H | $CH_3$ |
| Cl | H | 6-$OCH_3$ | i-$C_4H_9$ | H | $CH_3$ |
| Cl | H | 6-$OCH_3$ | s-$C_4H_9$ | H | $CH_3$ |
| Cl | H | 6-$OCH_3$ | t-$C_4H_9$ | H | $CH_3$ |
| Cl | H | 6-$OCH_3$ | $CH_3$ | $CH_3$ | $CH_3$ |
| Cl | H | 6-$OCH_3$ | $C_2H_5$ | $CH_3$ | $CH_3$ |
| Cl | H | 6-$OCH_3$ | $C_3H_7$ | $CH_3$ | $CH_3$ |
| Cl | H | 6-$OCH_3$ | i-$C_3H_7$ | $CH_3$ | $CH_3$ |
| Cl | H | 6-$OCH_3$ | $C_4H_9$ | $CH_3$ | $CH_3$ |
| Cl | H | 6-$OCH_3$ | i-$C_4H_9$ | $CH_3$ | $CH_3$ |
| Cl | H | 6-$OCH_3$ | s-$C_4H_9$ | $CH_3$ | $CH_3$ |
| Cl | H | 6-$OCH_3$ | t-$C_4H_9$ | $CH_3$ | $CH_3$ |
| Cl | H | 6-$OCH_3$ | $C_2H_5$ | $C_2H_5$ | $CH_3$ |
| Cl | H | 6-$OCH_3$ | $C_3H_7$ | $C_3H_7$ | $CH_3$ |
| Cl | H | 6-$OCH_3$ | 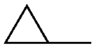 | $CH_3$ | $CH_3$ |
| Cl | H | 6-$OCH_3$ | 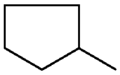 | $CH_3$ | $CH_3$ |
| Cl | H | 6-$OCH_3$ | 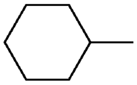 | $CH_3$ | $CH_3$ |
| $OCH_3$ | Cl | H | $CH_3$ | H | $CH_3$ |
| $OCH_3$ | Cl | H | $C_2H_5$ | H | $CH_3$ |
| $OCH_3$ | Cl | H | $C_3H_7$ | H | $CH_3$ |
| $OCH_3$ | Cl | H | i-$C_3H_7$ | H | $CH_3$ |
| $OCH_3$ | Cl | H | $C_4H_9$ | H | $CH_3$ |
| $OCH_3$ | Cl | H | i-$C_4H_9$ | H | $CH_3$ |
| $OCH_3$ | Cl | H | s-$C_4H_9$ | H | $CH_3$ |
| $OCH_3$ | Cl | H | t-$C_4H_9$ | H | $CH_3$ |
| $OCH_3$ | Cl | H | $CH_3$ | $CH_3$ | $CH_3$ |

TABLE 4-continued (Id)

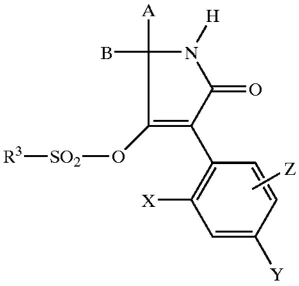

| | Y | Z | A | B | $R^3$ |
|---|---|---|---|---|---|
| $OCH_3$ | Cl | H | $C_2H_5$ | $CH_3$ | $CH_3$ |
| $OCH_3$ | Cl | H | $C_3H_7$ | $CH_3$ | $CH_3$ |
| $OCH_3$ | Cl | H | i-$C_3H_7$ | $CH_3$ | $CH_3$ |
| $OCH_3$ | Cl | H | $C_4H_9$ | $CH_3$ | $CH_3$ |
| $OCH_3$ | Cl | H | i-$C_4H_9$ | $CH_3$ | $CH_3$ |
| $OCH_3$ | Cl | H | s-$C_4H_9$ | $CH_3$ | $CH_3$ |
| $OCH_3$ | Cl | H | t-$C_4H_9$ | $CH_3$ | $CH_3$ |
| $OCH_3$ | Cl | H | $C_2H_5$ | $C_2H_5$ | $CH_3$ |
| $OCH_3$ | Cl | H | $C_3H_7$ | $C_3H_7$ | $CH_3$ |
| $OCH_3$ | Cl | H | 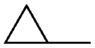 | $CH_3$ | $CH_3$ |
| $OCH_3$ | Cl | H | 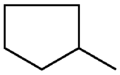 | $CH_3$ | $CH_3$ |
| $OCH_3$ | Cl | H | 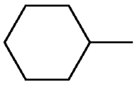 | $CH_3$ | $CH_3$ |
| Cl | $OCH_3$ | H | $-(CH_2)_2-$ | | $CH_3$ |
| Cl | $OCH_3$ | H | $-(CH_2)_4-$ | | $CH_3$ |
| Cl | $OCH_3$ | H | $-(CH_2)_5-$ | | $CH_3$ |
| Cl | $OCH_3$ | H | $-(CH_2)_6-$ | | $CH_3$ |
| Cl | $OCH_3$ | H | $-(CH_2)_7-$ | | $CH_3$ |
| Cl | $OCH_3$ | H | $-(CH_2)_2-O-(CH_2)_2-$ | | $CH_3$ |
| Cl | $OCH_3$ | H | $-(CH_2)_2-S-(CH_2)_2-$ | | $CH_3$ |
| Cl | $OCH_3$ | H | $-CH_2-CHCH_3-(CH_2)_3-$ | | $CH_3$ |
| Cl | $OCH_3$ | H | $-(CH_2)_2-CHCH_3-(CH_2)_2-$ | | $CH_3$ |
| Cl | $OCH_3$ | H | $-(CH_2)_2-CHC_2H_5-(CH_2)_2-$ | | $CH_3$ |
| Cl | $OCH_3$ | H | $-(CH_2)_2-CHC_3H_7-(CH_2)_2-$ | | $CH_3$ |
| Cl | $OCH_3$ | H | $-(CH_2)_2-CHi-C_3H_7-(CH_2)_2-$ | | $CH_3$ |
| Cl | $OCH_3$ | H | $-(CH_2)_2-CHOCH_3-(CH_2)_2-$ | | $CH_3$ |
| Cl | $OCH_3$ | H | $-(CH_2)_2-CHOC_2H_5-(CH_2)_2-$ | | $CH_3$ |
| Cl | $OCH_3$ | H | $-(CH_2)_2-CHOC_3H_7-(CH_2)_2-$ | | $CH_3$ |
| Cl | $OCH_3$ | H | $-(CH_2)_2-CHi-OC_3H_7-(CH_2)_2-$ | | $CH_3$ |
| Cl | $OCH_3$ | H | $-(CH_2)_2-C(CH_3)_2-(CH_2)_2-$ | | $CH_3$ |
| Cl | $OCH_3$ | H | $-CH_2-(CHCH_3)_2-(CH_2)_2-$ | | $CH_3$ |
| Cl | $OCH_3$ | H | 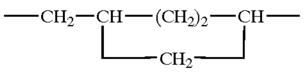 | | $CH_3$ |
| Cl | $OCH_3$ | H | 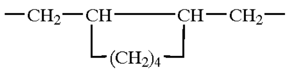 | | $CH_3$ |
| Cl | $OCH_3$ | H | 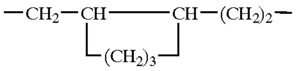 | | $CH_3$ |
| Cl | H | 6-$OCH_3$ | $-(CH_2)_2-$ | | $CH_3$ |
| Cl | H | 6-$OCH_3$ | $-(CH_2)_4-$ | | $CH_3$ |
| Cl | H | 6-$OCH_3$ | $-(CH_2)_5-$ | | $CH_3$ |
| Cl | H | 6-$OCH_3$ | $-(CH_2)_6-$ | | $CH_3$ |
| Cl | H | 6-$OCH_3$ | $-(CH_2)_7-$ | | $CH_3$ |
| Cl | H | 6-$OCH_3$ | $-(CH_2)_2-O-(CH_2)_2-$ | | $CH_3$ |
| Cl | H | 6-$OCH_3$ | $-(CH_2)_2-S-(CH_2)_2-$ | | $CH_3$ |

TABLE 4-continued (Id)

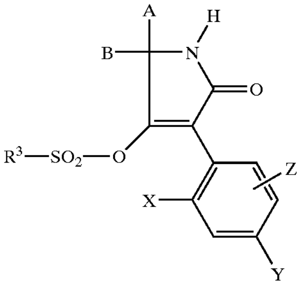

| | Y | Z | A B | R³ |
|---|---|---|---|---|
| Cl | H | 6-OCH$_3$ | $-CH_2-CHCH_3-(CH_2)_3-$ | CH$_3$ |
| Cl | H | 6-OCH$_3$ | $-(CH_2)_2-CHCH_3-(CH_2)_2-$ | CH$_3$ |
| Cl | H | 6-OCH$_3$ | $-(CH_2)_2-CHC_2H_5-(CH_2)_2-$ | CH$_3$ |
| Cl | H | 6-OCH$_3$ | $-(CH_2)_2-CHC_3H_7-(CH_2)_2-$ | CH$_3$ |
| Cl | H | 6-OCH$_3$ | $-(CH_2)_2-CHi-C_3H_7-(CH_2)_2-$ | CH$_3$ |
| Cl | H | 6-OCH$_3$ | $-(CH_2)_2-CHOCH_3-(CH_2)_2-$ | CH$_3$ |
| Cl | H | 6-OCH$_3$ | $-(CH_2)_2-CHOC_2H_5-(CH_2)_2-$ | CH$_3$ |
| Cl | H | 6-OCH$_3$ | $-(CH_2)_2-CHOC_3H_7-(CH_2)_2-$ | CH$_3$ |
| Cl | H | 6-OCH$_3$ | $-(CH_2)_2-CHi-OC_3H_7-(CH_2)_2-$ | CH$_3$ |
| Cl | H | 6-OCH$_3$ | $-(CH_2)_2-C(CH_3)_2-(CH_2)_2-$ | CH$_3$ |
| Cl | H | 6-OCH$_3$ | $-CH_2-(CHCH_3)_2-(CH_2)_2-$ | CH$_3$ |
| Cl | H | 6-OCH$_3$ | 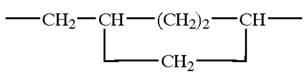 | CH$_3$ |
| Cl | H | 6-OCH$_3$ | 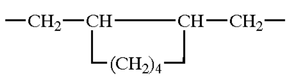 | CH$_3$ |
| Cl | H | 6-OCH$_3$ | 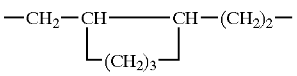 | CH$_3$ |
| OCH$_3$ | Cl | H | $-(CH_2)_2-$ | CH$_3$ |
| OCH$_3$ | Cl | H | $-(CH_2)_4-$ | CH$_3$ |
| OCH$_3$ | Cl | H | $-(CH_2)_5-$ | CH$_3$ |
| OCH$_3$ | Cl | H | $-(CH_2)_6-$ | CH$_3$ |
| OCH$_3$ | Cl | H | $-(CH_2)_7-$ | CH$_3$ |
| OCH$_3$ | Cl | H | $-(CH_2)_2-O-(CH_2)_2-$ | CH$_3$ |

TABLE 4-continued (Id)

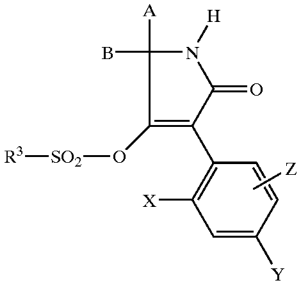

| | Y | Z | A B | R³ |
|---|---|---|---|---|
| OCH$_3$ | Cl | H | $-(CH_2)_2-S-(CH_2)_2-$ | CH$_3$ |
| OCH$_3$ | Cl | H | $-CH_2-CHCH_3-(CH_2)_3-$ | CH$_3$ |
| OCH$_3$ | Cl | H | $-(CH_2)_2-CHCH_3-(CH_2)_2-$ | CH$_3$ |
| OCH$_3$ | Cl | H | $-(CH_2)_2-CHC_2H_5-(CH_2)_2-$ | CH$_3$ |
| OCH$_3$ | Cl | H | $-(CH_2)_2-CHC_3H_7-(CH_2)_2-$ | CH$_3$ |
| OCH$_3$ | Cl | H | $-(CH_2)_2-CHi-C_3H_7-(CH_2)_2-$ | CH$_3$ |
| OCH$_3$ | Cl | H | $-(CH_2)_2-CHOCH_3-(CH_2)_2-$ | CH$_3$ |
| OCH$_3$ | Cl | H | $-(CH_2)_2-CHOC_2H_5-(CH_2)_2-$ | CH$_3$ |
| OCH$_3$ | Cl | H | $-(CH_2)_2-CHOC_3H_7-(CH_2)_2-$ | CH$_3$ |
| OCH$_3$ | Cl | H | $-(CH_2)_2-CHi-OC_3H_7-(CH_2)_2-$ | CH$_3$ |
| OCH$_3$ | Cl | H | $-(CH_2)_2-C(CH_3)_2-(CH_2)_2-$ | CH$_3$ |
| OCH$_3$ | Cl | H | $-CH_2-(CHCH_3)_2-(CH_2)_2-$ | CH$_3$ |
| OCH$_3$ | Cl | H | 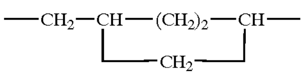 | CH$_3$ |
| OCH$_3$ | Cl | H | 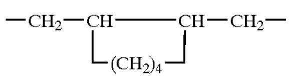 | CH$_3$ |
| OCH$_3$ | Cl | H | 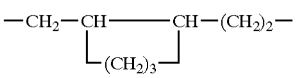 | CH$_3$ |

The following compounds of the formula (Ie) may be mentioned individually in addition to the compounds mentioned in the preparation examples:

TABLE 5

(Ie)

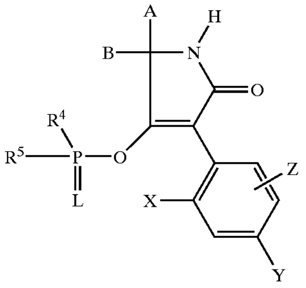

| X | Y | Z | A | B | L | R⁴ | R⁵ |
|---|---|---|---|---|---|---|---|
| Cl | OCH$_3$ | H | CH$_3$ | H | S | CH$_3$ | i-C$_3$H$_7$—S— |
| Cl | OCH$_3$ | H | C$_2$H$_5$ | H | S | CH$_3$ | i-C$_3$H$_7$—S— |
| Cl | OCH$_3$ | H | C$_3$H$_7$ | H | S | CH$_3$ | i-C$_3$H$_7$—S— |
| Cl | OCH$_3$ | H | i-C$_3$H$_7$ | H | S | CH$_3$ | i-C$_3$H$_7$—S— |
| Cl | OCH$_3$ | H | C$_4$H$_9$ | H | S | CH$_3$ | i-C$_3$H$_7$—S— |
| Cl | OCH$_3$ | H | i-C$_4$H$_9$ | H | S | CH$_3$ | i-C$_3$H$_7$—S— |
| Cl | OCH$_3$ | H | s-C$_4$H$_9$ | H | S | CH$_3$ | i-C$_3$H$_7$—S— |

TABLE 5-continued (Ie)

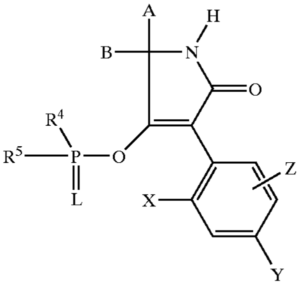

| X | Y | Z | A | B | L | $R^4$ | $R^5$ |
|---|---|---|---|---|---|---|---|
| Cl | $OCH_3$ | H | t-$C_4H_9$ | H | S | $CH_3$ | i-$C_3H_7$—S— |
| Cl | $OCH_3$ | H | $CH_3$ | $CH_3$ | S | $CH_3$ | i-$C_3H_7$—S— |
| Cl | $OCH_3$ | H | $C_2H_5$ | $CH_3$ | S | $CH_3$ | i-$C_3H_7$—S— |
| Cl | $OCH_3$ | H | $C_3H_7$ | $CH_3$ | S | $CH_3$ | i-$C_3H_7$—S— |
| Cl | $OCH_3$ | H | i-$C_3H_7$ | $CH_3$ | S | $CH_3$ | i-$C_3H_7$—S— |
| Cl | $OCH_3$ | H | $C_4H_9$ | $CH_3$ | S | $CH_3$ | i-$C_3H_7$—S— |
| Cl | $OCH_3$ | H | i-$C_4H_9$ | $CH_3$ | S | $CH_3$ | i-$C_3H_7$—S— |
| Cl | $OCH_3$ | H | s-$C_4H_9$ | $CH_3$ | S | $CH_3$ | i-$C_3H_7$—S— |
| Cl | $OCH_3$ | H | t-$C_4H_9$ | $CH_3$ | S | $CH_3$ | i-$C_3H_7$—S— |
| Cl | $OCH_3$ | H | $C_2H_5$ | $C_2H_5$ | S | $CH_3$ | i-$C_3H_7$—S— |
| Cl | $OCH_3$ | H | $C_3H_7$ | $C_3H_7$ | S | $CH_3$ | i-$C_3H_7$—S— |
| Cl | $OCH_3$ | H | 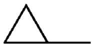 | $CH_3$ | S | $CH_3$ | i-$C_3H_7$—S— |
| Cl | $OCH_3$ | H | 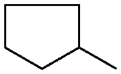 | $CH_3$ | S | $CH_3$ | i-$C_3H_7$—S— |
| Cl | $OCH_3$ | H | 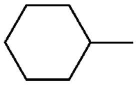 | $CH_3$ | S | $CH_3$ | i-$C_3H_7$—S— |
| Cl | H | 6-$OCH_3$ | $CH_3$ | H | S | $CH_3$ | i-$C_3H_7$—S— |
| Cl | H | 6-$OCH_3$ | $C_2H_5$ | H | S | $CH_3$ | i-$C_3H_7$—S— |
| Cl | H | 6-$OCH_3$ | $C_3H_7$ | H | S | $CH_3$ | i-$C_3H_7$—S— |
| Cl | H | 6-$OCH_3$ | i-$C_3H_7$ | H | S | $CH_3$ | i-$C_3H_7$—S— |
| Cl | H | 6-$OCH_3$ | $C_4H_9$ | H | S | $CH_3$ | i-$C_3H_7$—S— |
| Cl | H | 6-$OCH_3$ | i-$C_4H_9$ | H | S | $CH_3$ | i-$C_3H_7$—S— |
| Cl | H | 6-$OCH_3$ | s-$C_4H_9$ | H | S | $CH_3$ | i-$C_3H_7$—S— |
| Cl | H | 6-$OCH_3$ | t-$C_4H_9$ | H | S | $CH_3$ | i-$C_3H_7$—S— |
| Cl | H | 6-$OCH_3$ | $CH_3$ | $CH_3$ | S | $CH_3$ | i-$C_3H_7$—S— |
| Cl | H | 6-$OCH_3$ | $C_2H_5$ | $CH_3$ | S | $CH_3$ | i-$C_3H_7$—S— |
| Cl | H | 6-$OCH_3$ | $C_3H_7$ | $CH_3$ | S | $CH_3$ | i-$C_3H_7$—S— |
| Cl | H | 6-$OCH_3$ | i-$C_3H_7$ | $CH_3$ | S | $CH_3$ | i-$C_3H_7$—S— |
| Cl | H | 6-$OCH_3$ | $C_4H_9$ | $CH_3$ | S | $CH_3$ | i-$C_3H_7$—S— |
| Cl | H | 6-$OCH_3$ | i-$C_4H_9$ | $CH_3$ | S | $CH_3$ | i-$C_3H_7$—S— |
| Cl | H | 6-$OCH_3$ | s-$C_4H_9$ | $CH_3$ | S | $CH_3$ | i-$C_3H_7$—S— |
| Cl | H | 6-$OCH_3$ | t-$C_4H_9$ | $CH_3$ | S | $CH_3$ | i-$C_3H_7$—S— |
| Cl | H | 6-$OCH_3$ | $C_2H_5$ | $C_2H_5$ | S | $CH_3$ | i-$C_3H_7$—S— |
| Cl | H | 6-$OCH_3$ | $C_3H_7$ | $C_3H_7$ | S | $CH_3$ | i-$C_3H_7$—S— |
| Cl | H | 6-$OCH_3$ | 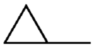 | $CH_3$ | S | $CH_3$ | i-$C_3H_7$—S— |
| Cl | H | 6-$OCH_3$ | 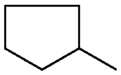 | $CH_3$ | S | $CH_3$ | i-$C_3H_7$—S— |
| Cl | H | 6-$OCH_3$ | 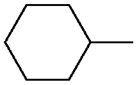 | $CH_3$ | S | $CH_3$ | i-$C_3H_7$—S— |
| $OCH_3$ | Cl | H | $CH_3$ | H | S | $CH_3$ | i-$C_3H_7$—S— |
| $OCH_3$ | Cl | H | $C_2H_5$ | H | S | $CH_3$ | i-$C_3H_7$—S— |
| $OCH_3$ | Cl | H | $C_3H_7$ | H | S | $CH_3$ | i-$C_3H_7$—S— |
| $OCH_3$ | Cl | H | i-$C_3H_7$ | H | S | $CH_3$ | i-$C_3H_7$—S— |
| $OCH_3$ | Cl | H | $C_4H_9$ | H | S | $CH_3$ | i-$C_3H_7$—S— |

TABLE 5-continued (Ie)

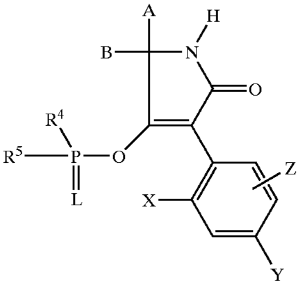

| X | Y | Z | A | B | L | $R^4$ | $R^5$ |
|---|---|---|---|---|---|---|---|
| $OCH_3$ | Cl | H | i-$C_4H_9$ | H | S | $CH_3$ | i-$C_3H_7$—S— |
| $OCH_3$ | Cl | H | s-$C_4H_9$ | H | S | $CH_3$ | i-$C_3H_7$—S— |
| $OCH_3$ | Cl | H | t-$C_4H_9$ | H | S | $CH_3$ | i-$C_3H_7$—S— |
| $OCH_3$ | Cl | H | $CH_3$ | $CH_3$ | S | $CH_3$ | i-$C_3H_7$—S— |
| $OCH_3$ | Cl | H | $C_2H_5$ | $CH_3$ | S | $CH_3$ | i-$C_3H_7$—S— |
| $OCH_3$ | Cl | H | $C_3H_7$ | $CH_3$ | S | $CH_3$ | i-$C_3H_7$—S— |
| $OCH_3$ | Cl | H | i-$C_3H_7$ | $CH_3$ | S | $CH_3$ | i-$C_3H_7$—S— |
| $OCH_3$ | Cl | H | $C_4H_9$ | $CH_3$ | S | $CH_3$ | i-$C_3H_7$—S— |
| $OCH_3$ | Cl | H | i-$C_4H_9$ | $CH_3$ | S | $CH_3$ | i-$C_3H_7$—S— |
| $OCH_3$ | Cl | H | s-$C_4H_9$ | $CH_3$ | S | $CH_3$ | i-$C_3H_7$—S— |
| $OCH_3$ | Cl | H | t-$C_4H_9$ | $CH_3$ | S | $CH_3$ | i-$C_3H_7$—S— |
| $OCH_3$ | Cl | H | $C_2H_5$ | $C_2H_5$ | S | $CH_3$ | i-$C_3H_7$—S— |
| $OCH_3$ | Cl | H | $C_3H_7$ | $C_3H_7$ | S | $CH_3$ | i-$C_3H_7$—S— |
| $OCH_3$ | Cl | H | 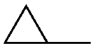 | $CH_3$ | S | $CH_3$ | i-$C_3H_7$—S— |
| $OCH_3$ | Cl | H | 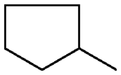 | $CH_3$ | S | $CH_3$ | i-$C_3H_7$—S— |
| $OCH_3$ | Cl | H | 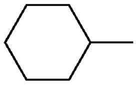 | $CH_3$ | S | $CH_3$ | i-$C_3H_7$—S— |
| Cl | $OCH_3$ | H | $—(CH_2)_2—$ | | S | $CH_3$ | i-$C_3H_7$—S— |
| Cl | $OCH_3$ | H | $—(CH_2)_4—$ | | S | $CH_3$ | i-$C_3H_7$—S— |
| Cl | $OCH_3$ | H | $—(CH_2)_5—$ | | S | $CH_3$ | i-$C_3H_7$—S— |
| Cl | $OCH_3$ | H | $—(CH_2)_6—$ | | S | $CH_3$ | i-$C_3H_7$—S— |
| Cl | $OCH_3$ | H | $—(CH_2)_7—$ | | S | $CH_3$ | i-$C_3H_7$—S— |
| Cl | $OCH_3$ | H | $—(CH_2)_2—O—(CH_2)_2—$ | | S | $CH_3$ | i-$C_3H_7$—S— |
| Cl | $OCH_3$ | H | $—(CH_2)_2—S—(CH_2)_2—$ | | S | $CH_3$ | i-$C_3H_7$—S— |
| Cl | $OCH_3$ | H | $—(CH_2)_2—CHCH_3—(CH_2)_3—$ | | S | $CH_3$ | i-$C_3H_7$—S— |
| Cl | $OCH_3$ | H | $—(CH_2)_2—CHCH_3—(CH_2)_2—$ | | S | $CH_3$ | i-$C_3H_7$—S— |
| Cl | $OCH_3$ | H | $—(CH_2)_2—CHC_2H_5—(CH_2)_2—$ | | S | $CH_3$ | i-$C_3H_7$—S— |
| Cl | $OCH_3$ | H | $—(CH_2)_2—CHC_3H_7—(CH_2)_2—$ | | S | $CH_3$ | i-$C_3H_7$—S— |
| Cl | $OCH_3$ | H | $—(CH_2)_2—$CHi—$C_3H_7—(CH_2)_2—$ | | S | $CH_3$ | i-$C_3H_7$—S— |
| Cl | $OCH_3$ | H | $—(CH_2)_2—CHOCH_3—(CH_2)_2—$ | | S | $CH_3$ | i-$C_3H_7$—S— |
| Cl | $OCH_3$ | H | $—(CH_2)_2—CHOC_2H_5—(CH_2)_2—$ | | S | $CH_3$ | i-$C_3H_7$—S— |
| Cl | $OCH_3$ | H | $—(CH_2)_2—CHOC_3H_7—(CH_2)_2—$ | | S | $CH_3$ | i-$C_3H_7$—S— |
| Cl | $OCH_3$ | H | $—(CH_2)_2—$CHi—$OC_3H_7—(CH_2)_2—$ | | S | $CH_3$ | i-$C_3H_7$—S— |
| Cl | $OCH_3$ | H | $—(CH_2)_2—C(CH_3)_2—(CH_2)_2—$ | | S | $CH_3$ | i-$C_3H_7$—S— |
| Cl | $OCH_3$ | H | $—CH_2—(CHCH_3)_2—(CH_2)_2—$ | | S | $CH_3$ | i-$C_3H_7$—S— |
| Cl | $OCH_3$ | H | 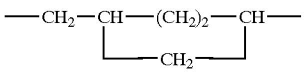 | | S | $CH_3$ | i-$C_3H_7$—S— |
| Cl | $OCH_3$ | H | 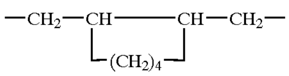 | | S | $CH_3$ | i-$C_3H_7$—S— |
| Cl | $OCH_3$ | H | 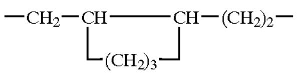 | | S | $CH_3$ | i-$C_3H_7$—S— |
| Cl | H | 6-$OCH_3$ | $—(CH_2)_2—$ | | S | $CH_3$ | i-$C_3H_7$—S— |
| Cl | H | 6-$OCH_3$ | $—(CH_2)_4—$ | | S | $CH_3$ | i-$C_3H_7$—S— |
| Cl | H | 6-$OCH_3$ | $—(CH_2)_5—$ | | S | $CH_3$ | i-$C_3H_7$—S— |

TABLE 5-continued (Ie)

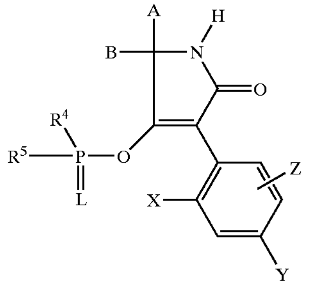

| X | Y | Z | A | B | L | $R^4$ | $R^5$ |
|---|---|---|---|---|---|---|---|
| Cl | H | 6-$OCH_3$ | $-(CH_2)_6-$ | | S | $CH_3$ | i-$C_3H_7$—S— |
| Cl | H | 6-$OCH_3$ | $-(CH_2)_7-$ | | S | $CH_3$ | i-$C_3H_7$—S— |
| Cl | H | 6-$OCH_3$ | $-(CH_2)_2-O-(CH_2)_2-$ | | S | $CH_3$ | i-$C_3H_7$—S— |
| Cl | H | 6-$OCH_3$ | $-(CH_2)_2-S-(CH_2)_2-$ | | S | $CH_3$ | i-$C_3H_7$—S— |
| Cl | H | 6-$OCH_3$ | $-(CH_2)_2-CHCH_3-(CH_2)_3-$ | | S | $CH_3$ | i-$C_3H_7$—S— |
| Cl | H | 6-$OCH_3$ | $-(CH_2)_2-CHCH_3-(CH_2)_2-$ | | S | $CH_3$ | i-$C_3H_7$—S— |
| Cl | H | 6-$OCH_3$ | $-(CH_2)_2-CHC_2H_5-(CH_2)_2-$ | | S | $CH_3$ | i-$C_3H_7$—S— |
| Cl | H | 6-$OCH_3$ | $-(CH_2)_2-CHC_3H_7-(CH_2)_2-$ | | S | $CH_3$ | i-$C_3H_7$—S— |
| Cl | H | 6-$OCH_3$ | $-(CH_2)_2-CHi-C_3H_7-(CH_2)_2-$ | | S | $CH_3$ | i-$C_3H_7$—S— |
| Cl | H | 6-$OCH_3$ | $-(CH_2)_2-CHOCH_3-(CH_2)_2-$ | | S | $CH_3$ | i-$C_3H_7$—S— |
| Cl | H | 6-$OCH_3$ | $-(CH_2)_2-CHOC_2H_5-(CH_2)_2-$ | | S | $CH_3$ | i-$C_3H_7$—S— |
| Cl | H | 6-$OCH_3$ | $-(CH_2)_2-CHOC_3H_7-(CH_2)_2-$ | | S | $CH_3$ | i-$C_3H_7$—S— |
| Cl | H | 6-$OCH_3$ | $-(CH_2)_2-CHi-OC_3H_7-(CH_2)_2-$ | | S | $CH_3$ | i-$C_3H_7$—S— |
| Cl | H | 6-$OCH_3$ | $-(CH_2)_2-C(CH_3)_2-(CH_2)_2-$ | | S | $CH_3$ | i-$C_3H_7$—S— |
| Cl | H | 6-$OCH_3$ | $-CH_2-(CHCH_3)_2-(CH_2)_2-$ | | S | $CH_3$ | i-$C_3H_7$—S— |
| Cl | H | 6-$OCH_3$ | 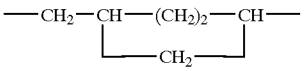 | | S | $CH_3$ | i-$C_3H_7$—S— |
| Cl | H | 6-$OCH_3$ | 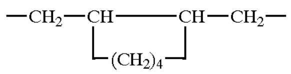 | | S | $CH_3$ | i-$C_3H_7$—S— |
| Cl | H | 6-$OCH_3$ | 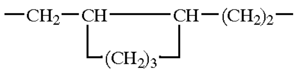 | | S | $CH_3$ | i-$C_3H_7$—S— |
| $OCH_3$ | Cl | H | $-(CH_2)_2-$ | | S | $CH_3$ | i-$C_3H_7$—S— |
| $OCH_3$ | Cl | H | $-(CH_2)_4-$ | | S | $CH_3$ | i-$C_3H_7$—S— |
| $OCH_3$ | Cl | H | $-(CH_2)_5-$ | | S | $CH_3$ | i-$C_3H_7$—S— |
| $OCH_3$ | Cl | H | $-(CH_2)_6-$ | | S | $CH_3$ | i-$C_3H_7$—S— |
| $OCH_3$ | Cl | H | $-(CH_2)_7-$ | | S | $CH_3$ | i-$C_3H_7$—S— |
| $OCH_3$ | Cl | H | $-(CH_2)_2-O-(CH_2)_2-$ | | S | $CH_3$ | i-$C_3H_7$—S— |
| $OCH_3$ | Cl | H | $-(CH_2)_2-S-(CH_2)_2-$ | | S | $CH_3$ | i-$C_3H_7$—S— |
| $OCH_3$ | Cl | H | $-(CH_2)_2-CHCH_3-(CH_2)_3-$ | | S | $CH_3$ | i-$C_3H_7$—S— |
| $OCH_3$ | Cl | H | $-(CH_2)_2-CHCH_3-(CH_2)_2-$ | | S | $CH_3$ | i-$C_3H_7$—S— |
| $OCH_3$ | Cl | H | $-(CH_2)_2-CHC_2H_5-(CH_2)_2-$ | | S | $CH_3$ | i-$C_3H_7$—S— |
| $OCH_3$ | Cl | H | $-(CH_2)_2-CHC_3H_7-(CH_2)_2-$ | | S | $CH_3$ | i-$C_3H_7$—S— |
| $OCH_3$ | Cl | H | $-(CH_2)_2-CHi-C_3H_7-(CH_2)_2-$ | | S | $CH_3$ | i-$C_3H_7$—S— |
| $OCH_3$ | Cl | H | $-(CH_2)_2-CHOCH_3-(CH_2)_2-$ | | S | $CH_3$ | i-$C_3H_7$—S— |
| $OCH_3$ | Cl | H | $-(CH_2)_2-CHOC_2H_5-(CH_2)_2-$ | | S | $CH_3$ | i-$C_3H_7$—S— |
| $OCH_3$ | Cl | H | $-(CH_2)_2-CHOC_3H_7-(CH_2)_2-$ | | S | $CH_3$ | i-$C_3H_7$—S— |
| $OCH_3$ | Cl | H | $-(CH_2)_2-CHi-OC_3H_7-(CH_2)_2-$ | | S | $CH_3$ | i-$C_3H_7$—S— |
| $OCH_3$ | Cl | H | $-(CH_2)_2-C(CH_3)_2-(CH_2)_2-$ | | S | $CH_3$ | i-$C_3H_7$—S— |
| $OCH_3$ | Cl | H | $-CH_2-(CHCH_3)_2-(CH_2)_2-$ | | S | $CH_3$ | i-$C_3H_7$—S— |
| $OCH_3$ | Cl | H | 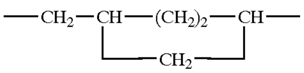 | | S | $CH_3$ | i-$C_3H_7$—S— |
| $OCH_3$ | Cl | H | 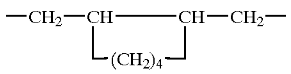 | | S | $CH_3$ | i-$C_3H_7$—S— |
| $OCH_3$ | Cl | H | 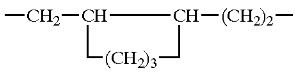 | | S | $CH_3$ | i-$C_3H_7$—S— |

TABLE 5-continued (Ie)

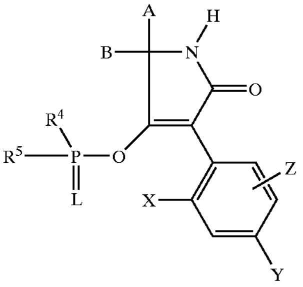

| X | Y | Z | A | B | L | $R^4$ | $R^5$ |
|---|---|---|---|---|---|---|---|
| Cl | $OCH_3$ | H | $CH_3$ | H | S | $C_2H_5$ | i-$C_3H_7$—S— |
| Cl | $OCH_3$ | H | $C_2H_5$ | H | S | $C_2H_5$ | i-$C_3H_7$—S— |
| Cl | $OCH_3$ | H | $C_3H_7$ | H | S | $C_2H_5$ | i-$C_3H_7$—S— |
| Cl | $OCH_3$ | H | i-$C_3H_7$ | H | S | $C_2H_5$ | i-$C_3H_7$—S— |
| Cl | $OCH_3$ | H | $C_4H_9$ | H | S | $C_2H_5$ | i-$C_3H_7$—S— |
| Cl | $OCH_3$ | H | i-$C_4H_9$ | H | S | $C_2H_5$ | i-$C_3H_7$—S— |
| Cl | $OCH_3$ | H | s-$C_4H_9$ | H | S | $C_2H_5$ | i-$C_3H_7$—S— |
| Cl | $OCH_3$ | H | t-$C_4H_9$ | H | S | $C_2H_5$ | i-$C_3H_7$—S— |
| Cl | $OCH_3$ | H | $CH_3$ | $CH_3$ | S | $C_2H_5$ | i-$C_3H_7$—S— |
| Cl | $OCH_3$ | H | $C_2H_5$ | $CH_3$ | S | $C_2H_5$ | i-$C_3H_7$—S— |
| Cl | $OCH_3$ | H | $C_3H_7$ | $CH_3$ | S | $C_2H_5$ | i-$C_3H_7$—S— |
| Cl | $OCH_3$ | H | i-$C_3H_7$ | $CH_3$ | S | $C_2H_5$ | i-$C_3H_7$—S— |
| Cl | $OCH_3$ | H | $C_4H_9$ | $CH_3$ | S | $C_2H_5$ | i-$C_3H_7$—S— |
| Cl | $OCH_3$ | H | i-$C_4H_9$ | $CH_3$ | S | $C_2H_5$ | i-$C_3H_7$—S— |
| Cl | $OCH_3$ | H | s-$C_4H_9$ | $CH_3$ | S | $C_2H_5$ | i-$C_3H_7$—S— |
| Cl | $OCH_3$ | H | t-$C_4H_9$ | $CH_3$ | S | $C_2H_5$ | i-$C_3H_7$—S— |
| Cl | $OCH_3$ | H | $C_2H_5$ | $C_2H_5$ | S | $C_2H_5$ | i-$C_3H_7$—S— |
| Cl | $OCH_3$ | H | $C_3H_7$ | $C_3H_7$ | S | $C_2H_5$ | i-$C_3H_7$—S— |
| Cl | $OCH_3$ | H | 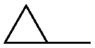 | $CH_3$ | S | $C_2H_5$ | i-$C_3H_7$—S— |
| Cl | $OCH_3$ | H | 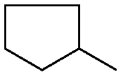 | $CH_3$ | S | $C_2H_5$ | i-$C_3H_7$—S— |
| Cl | $OCH_3$ | H | 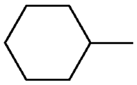 | $CH_3$ | S | $C_2H_5$ | i-$C_3H_7$—S— |
| Cl | H | 6-$OCH_3$ | $CH_3$ | H | S | $C_2H_5$ | i-$C_3H_7$—S— |
| Cl | H | 6-$OCH_3$ | $C_2H_5$ | H | S | $C_2H_5$ | i-$C_3H_7$—S— |
| Cl | H | 6-$OCH_3$ | $C_3H_7$ | H | S | $C_2H_5$ | i-$C_3H_7$—S— |
| Cl | H | 6-$OCH_3$ | i-$C_3H_7$ | H | S | $C_2H_5$ | i-$C_3H_7$—S— |
| Cl | H | 6-$OCH_3$ | $C_4H_9$ | H | S | $C_2H_5$ | i-$C_3H_7$—S— |
| Cl | H | 6-$OCH_3$ | i-$C_4H_9$ | H | S | $C_2H_5$ | i-$C_3H_7$—S— |
| Cl | H | 6-$OCH_3$ | s-$C_4H_9$ | H | S | $C_2H_5$ | i-$C_3H_7$—S— |
| Cl | H | 6-$OCH_3$ | t-$C_4H_9$ | H | S | $C_2H_5$ | i-$C_3H_7$—S— |
| Cl | H | 6-$OCH_3$ | $CH_3$ | $CH_3$ | S | $C_2H_5$ | i-$C_3H_7$—S— |
| Cl | H | 6-$OCH_3$ | $C_2H_5$ | $CH_3$ | S | $C_2H_5$ | i-$C_3H_7$—S— |
| Cl | H | 6-$OCH_3$ | $C_3H_7$ | $CH_3$ | S | $C_2H_5$ | i-$C_3H_7$—S— |
| Cl | H | 6-$OCH_3$ | i-$C_3H_7$ | $CH_3$ | S | $C_2H_5$ | i-$C_3H_7$—S— |
| Cl | H | 6-$OCH_3$ | $C_4H_9$ | $CH_3$ | S | $C_2H_5$ | i-$C_3H_7$—S— |
| Cl | H | 6-$OCH_3$ | i-$C_4H_9$ | $CH_3$ | S | $C_2H_5$ | i-$C_3H_7$—S— |
| Cl | H | 6-$OCH_3$ | s-$C_4H_9$ | $CH_3$ | S | $C_2H_5$ | i-$C_3H_7$—S— |
| Cl | H | 6-$OCH_3$ | t-$C_4H_9$ | $CH_3$ | S | $C_2H_5$ | i-$C_3H_7$—S— |
| Cl | H | 6-$OCH_3$ | $C_2H_5$ | $C_2H_5$ | S | $C_2H_5$ | i-$C_3H_7$—S— |
| Cl | H | 6-$OCH_3$ | $C_3H_7$ | $C_3H_7$ | S | $C_2H_5$ | i-$C_3H_7$—S— |
| Cl | H | 6-$OCH_3$ | 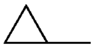 | $CH_3$ | S | $C_2H_5$ | i-$C_3H_7$—S— |
| Cl | H | 6-$OCH_3$ | 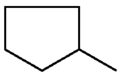 | $CH_3$ | S | $C_2H_5$ | i-$C_3H_7$—S— |

TABLE 5-continued (Ie)

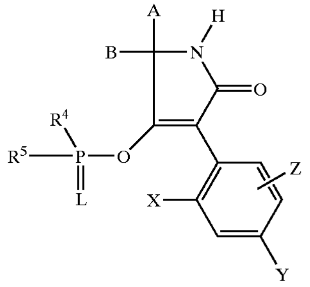

| X | Y | Z | A | B | L | $R^4$ | $R^5$ |
|---|---|---|---|---|---|---|---|
| Cl | H | 6-$OCH_3$ | 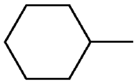 | $CH_3$ | S | $C_2H_5$ | i-$C_3H_7$—S— |
| $OCH_3$ | Cl | H | $CH_3$ | H | S | $C_2H_5$ | i-$C_3H_7$—S— |
| $OCH_3$ | Cl | H | $C_2H_5$ | H | S | $C_2H_5$ | i-$C_3H_7$—S— |
| $OCH_3$ | Cl | H | $C_3H_7$ | H | S | $C_2H_5$ | i-$C_3H_7$—S— |
| $OCH_3$ | Cl | H | i-$C_3H_7$ | H | S | $C_2H_5$ | i-$C_3H_7$—S— |
| $OCH_3$ | Cl | H | $C_4H_9$ | H | S | $C_2H_5$ | i-$C_3H_7$—S— |
| $OCH_3$ | Cl | H | i-$C_4H_9$ | H | S | $C_2H_5$ | i-$C_3H_7$—S— |
| $OCH_3$ | Cl | H | s-$C_4H_9$ | H | S | $C_2H_5$ | i-$C_3H_7$—S— |
| $OCH_3$ | Cl | H | t-$C_4H_9$ | H | S | $C_2H_5$ | i-$C_3H_7$—S— |
| $OCH_3$ | Cl | H | $CH_3$ | $CH_3$ | S | $C_2H_5$ | i-$C_3H_7$—S— |
| $OCH_3$ | Cl | H | $C_2H_5$ | $CH_3$ | S | $C_2H_5$ | i-$C_3H_7$—S— |
| $OCH_3$ | Cl | H | $C_3H_7$ | $CH_3$ | S | $C_2H_5$ | i-$C_3H_7$—S— |
| $OCH_3$ | Cl | H | i-$C_3H_7$ | $CH_3$ | S | $C_2H_5$ | i-$C_3H_7$—S— |
| $OCH_3$ | Cl | H | $C_4H_9$ | $CH_3$ | S | $C_2H_5$ | i-$C_3H_7$—S— |
| $OCH_3$ | Cl | H | i-$C_4H_9$ | $CH_3$ | S | $C_2H_5$ | i-$C_3H_7$—S— |
| $OCH_3$ | Cl | H | s-$C_4H_9$ | $CH_3$ | S | $C_2H_5$ | i-$C_3H_7$—S— |
| $OCH_3$ | Cl | H | t-$C_4H_9$ | $CH_3$ | S | $C_2H_5$ | i-$C_3H_7$—S— |
| $OCH_3$ | Cl | H | $C_2H_5$ | $C_2H_5$ | S | $C_2H_5$ | i-$C_3H_7$—S— |
| $OCH_3$ | Cl | H | $C_3H_7$ | $C_3H_7$ | S | $C_2H_5$ | i-$C_3H_7$—S— |
| $OCH_3$ | Cl | H | 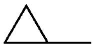 | $CH_3$ | S | $C_2H_5$ | i-$C_3H_7$—S— |
| $OCH_3$ | Cl | H | 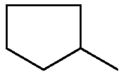 | $CH_3$ | S | $C_2H_5$ | i-$C_3H_7$—S— |
| $OCH_3$ | Cl | H | 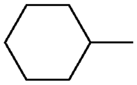 | $CH_3$ | S | $C_2H_5$ | i-$C_3H_7$—S— |
| Cl | $OCH_3$ | H | $-(CH_2)_2-$ | | S | $C_2H_5$ | i-$C_3H_7$—S— |
| Cl | $OCH_3$ | H | $-(CH_2)_4-$ | | S | $C_2H_5$ | i-$C_3H_7$—S— |
| Cl | $OCH_3$ | H | $-(CH_2)_5-$ | | S | $C_2H_5$ | i-$C_3H_7$—S— |
| Cl | $OCH_3$ | H | $-(CH_2)_6-$ | | S | $C_2H_5$ | i-$C_3H_7$—S— |
| Cl | $OCH_3$ | H | $-(CH_2)_7-$ | | S | $C_2H_5$ | i-$C_3H_7$—S— |
| Cl | $OCH_3$ | H | $-(CH_2)_2-O-(CH_2)_2-$ | | S | $C_2H_5$ | i-$C_3H_7$—S— |
| Cl | $OCH_3$ | H | $-(CH_2)_2-S-(CH_2)_2-$ | | S | $C_2H_5$ | i-$C_3H_7$—S— |
| Cl | $OCH_3$ | H | $-(CH_2)_2-CHCH_3-(CH_2)_3-$ | | S | $C_2H_5$ | i-$C_3H_7$—S— |
| Cl | $OCH_3$ | H | $-(CH_2)_2-CHCH_3-(CH_2)_2-$ | | S | $C_2H_5$ | i-$C_3H_7$—S— |
| Cl | $OCH_3$ | H | $-(CH_2)_2-CHC_2H_5-(CH_2)_2-$ | | S | $C_2H_5$ | i-$C_3H_7$—S— |
| Cl | $OCH_3$ | H | $-(CH_2)_2-CHC_3H_7-(CH_2)_2-$ | | S | $C_2H_5$ | i-$C_3H_7$—S— |
| Cl | $OCH_3$ | H | $-(CH_2)_2-$CHi$-C_3H_7-(CH_2)_2-$ | | S | $C_2H_5$ | i-$C_3H_7$—S— |
| Cl | $OCH_3$ | H | $-(CH_2)_2-CHOCH_3-(CH_2)_2-$ | | S | $C_2H_5$ | i-$C_3H_7$—S— |
| Cl | $OCH_3$ | H | $-(CH_2)_2-CHOC_2H_5-(CH_2)_2-$ | | S | $C_2H_5$ | i-$C_3H_7$—S— |
| Cl | $OCH_3$ | H | $-(CH_2)_2-CHOC_3H_7-(CH_2)_2-$ | | S | $C_2H_5$ | i-$C_3H_7$—S— |
| Cl | $OCH_3$ | H | $-(CH_2)_2-$CHi$-OC_3H_7-(CH_2)_2-$ | | S | $C_2H_5$ | i-$C_3H_7$—S— |
| Cl | $OCH_3$ | H | $-(CH_2)_2-C(CH_3)_2-(CH_2)_2-$ | | S | $C_2H_5$ | i-$C_3H_7$—S— |
| Cl | $OCH_3$ | H | $-CH_2-(CHCH_3)_2-(CH_2)_2-$ | | S | $C_2H_5$ | i-$C_3H_7$—S— |
| Cl | $OCH_3$ | H | 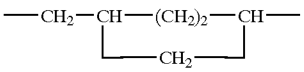 | | S | $C_2H_5$ | i-$C_3H_7$—S— |

TABLE 5-continued (Ie)

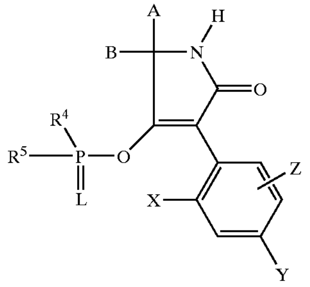

| X | Y | Z | A | B | L | $R^4$ | $R^5$ |
|---|---|---|---|---|---|---|---|
| Cl | $OCH_3$ | H | 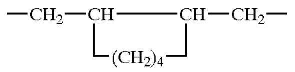 | | S | $C_2H_5$ | i-$C_3H_7$—S— |
| Cl | $OCH_3$ | H | 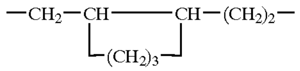 | | S | $C_2H_5$ | i-$C_3H_7$—S— |
| Cl | H | 6-$OCH_3$ | —$(CH_2)_2$— | | S | $C_2H_5$ | i-$C_3H_7$—S— |
| Cl | H | 6-$OCH_3$ | —$(CH_2)_4$— | | S | $C_2H_5$ | i-$C_3H_7$—S— |
| Cl | H | 6-$OCH_3$ | —$(CH_2)_5$— | | S | $C_2H_5$ | i-$C_3H_7$—S— |
| Cl | H | 6-$OCH_3$ | —$(CH_2)_6$— | | S | $C_2H_5$ | i-$C_3H_7$—S— |
| Cl | H | 6-$OCH_3$ | —$(CH_2)_7$— | | S | $C_2H_5$ | i-$C_3H_7$—S— |
| Cl | H | 6-$OCH_3$ | —$(CH_2)_2$—O—$(CH_2)_2$— | | S | $C_2H_5$ | i-$C_3H_7$—S— |
| Cl | H | 6-$OCH_3$ | —$(CH_2)_2$—S—$(CH_2)_2$— | | S | $C_2H_5$ | i-$C_3H_7$—S— |
| Cl | H | 6-$OCH_3$ | —$(CH_2)_2$—$CHCH_3$—$(CH_2)_3$— | | S | $C_2H_5$ | i-$C_3H_7$—S— |
| Cl | H | 6-$OCH_3$ | —$(CH_2)_2$—$CHCH_3$—$(CH_2)_2$— | | S | $C_2H_5$ | i-$C_3H_7$—S— |
| Cl | H | 6-$OCH_3$ | —$(CH_2)_2$—$CHC_2H_5$—$(CH_2)_2$— | | S | $C_2H_5$ | i-$C_3H_7$—S— |
| Cl | H | 6-$OCH_3$ | —$(CH_2)_2$—$CHC_3H_7$—$(CH_2)_2$— | | S | $C_2H_5$ | i-$C_3H_7$—S— |
| Cl | H | 6-$OCH_3$ | —$(CH_2)_2$—CHi—$C_3H_7$—$(CH_2)_2$— | | S | $C_2H_5$ | i-$C_3H_7$—S— |
| Cl | H | 6-$OCH_3$ | —$(CH_2)_2$—$CHOCH_3$—$(CH_2)_2$— | | S | $C_2H_5$ | i-$C_3H_7$—S— |
| Cl | H | 6-$OCH_3$ | —$(CH_2)_2$—$CHOC_2H_5$—$(CH_2)_2$— | | S | $C_2H_5$ | i-$C_3H_7$—S— |
| Cl | H | 6-$OCH_3$ | —$(CH_2)_2$—$CHOC_3H_7$—$(CH_2)_2$— | | S | $C_2H_5$ | i-$C_3H_7$—S— |
| Cl | H | 6-$OCH_3$ | —$(CH_2)_2$—CHi—$OC_3H_7$—$(CH_2)_2$— | | S | $C_2H_5$ | i-$C_3H_7$—S— |
| Cl | H | 6-$OCH_3$ | —$(CH_2)_2$—$C(CH_3)_2$—$(CH_2)_2$— | | S | $C_2H_5$ | i-$C_3H_7$—S— |
| Cl | H | 6-$OCH_3$ | —$CH_2$—$(CHCH_3)_2$—$(CH_2)_2$— | | S | $C_2H_5$ | i-$C_3H_7$—S— |
| Cl | H | 6-$OCH_3$ | 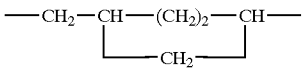 | | S | $C_2H_5$ | i-$C_3H_7$—S— |
| Cl | H | 6-$OCH_3$ | 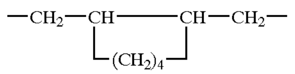 | | S | $C_2H_5$ | i-$C_3H_7$—S— |
| Cl | H | 6-$OCH_3$ | 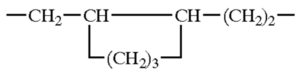 | | S | $C_2H_5$ | i-$C_3H_7$—S— |
| $OCH_3$ | Cl | H | —$(CH_2)_2$— | | S | $C_2H_5$ | i-$C_3H_7$—S— |
| $OCH_3$ | Cl | H | —$(CH_2)_4$— | | S | $C_2H_5$ | i-$C_3H_7$—S— |
| $OCH_3$ | Cl | H | —$(CH_2)_5$— | | S | $C_2H_5$ | i-$C_3H_7$—S— |
| $OCH_3$ | Cl | H | —$(CH_2)_6$— | | S | $C_2H_5$ | i-$C_3H_7$—S— |
| $OCH_3$ | Cl | H | —$(CH_2)_7$— | | S | $C_2H_5$ | i-$C_3H_7$—S— |
| $OCH_3$ | Cl | H | —$(CH_2)_2$—O—$(CH_2)_2$— | | S | $C_2H_5$ | i-$C_3H_7$—S— |
| $OCH_3$ | Cl | H | —$(CH_2)_2$—S—$(CH_2)_2$— | | S | $C_2H_5$ | i-$C_3H_7$—S— |
| $OCH_3$ | Cl | H | —$(CH_2)_2$—$CHCH_3$—$(CH_2)_3$— | | S | $C_2H_5$ | i-$C_3H_7$—S— |
| $OCH_3$ | Cl | H | —$(CH_2)_2$—$CHCH_3$—$(CH_2)_2$— | | S | $C_2H_5$ | i-$C_3H_7$—S— |
| $OCH_3$ | Cl | H | —$(CH_2)_2$—$CHC_2H_5$—$(CH_2)_2$— | | S | $C_2H_5$ | i-$C_3H_7$—S— |
| $OCH_3$ | Cl | H | —$(CH_2)_2$—$CHC_3H_7$—$(CH_2)_2$— | | S | $C_2H_5$ | i-$C_3H_7$—S— |
| $OCH_3$ | Cl | H | —$(CH_2)_2$—CHi—$C_3H_7$—$(CH_2)_2$— | | S | $C_2H_5$ | i-$C_3H_7$—S— |
| $OCH_3$ | Cl | H | —$(CH_2)_2$—$CHOCH_3$—$(CH_2)_2$— | | S | $C_2H_5$ | i-$C_3H_7$—S— |
| $OCH_3$ | Cl | H | —$(CH_2)_2$—$CHOC_2H_5$—$(CH_2)_2$— | | S | $C_2H_5$ | i-$C_3H_7$—S— |
| $OCH_3$ | Cl | H | —$(CH_2)_2$—$CHOC_3H_7$—$(CH_2)_2$— | | S | $C_2H_5$ | i-$C_3H_7$—S— |
| $OCH_3$ | Cl | H | —$(CH_2)_2$—CHi—$OC_3H_7$—$(CH_2)_2$— | | S | $C_2H_5$ | i-$C_3H_7$—S— |
| $OCH_3$ | Cl | H | —$(CH_2)_2$—$C(CH_3)_2$—$(CH_2)_2$— | | S | $C_2H_5$ | i-$C_3H_7$—S— |
| $OCH_3$ | Cl | H | —$CH_2$—$(CHCH_3)_2$—$(CH_2)_2$— | | S | $C_2H_5$ | i-$C_3H_7$—S— |

TABLE 5-continued (Ie)

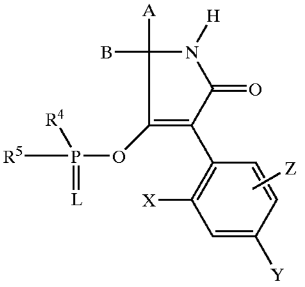

| X | Y | Z | A | B | L | $R^4$ | $R^5$ |
|---|---|---|---|---|---|---|---|
| $OCH_3$ | Cl | H | 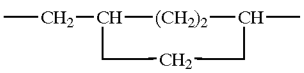 | | S | $C_2H_5$ | i-$C_3H_7$—S— |
| $OCH_3$ | Cl | H | 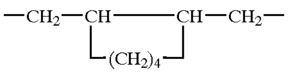 | | S | $C_2H_5$ | i-$C_3H_7$—S— |
| $OCH_3$ | Cl | H | 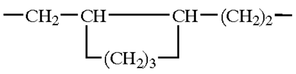 | | S | $C_2H_5$ | i-$C_3H_7$—S— |
| Cl | $OCH_3$ | H | $CH_3$ | H | O | $CH_3$ | i-$C_3H_7$—S— |
| Cl | $OCH_3$ | H | $C_2H_5$ | H | O | $CH_3$ | i-$C_3H_7$—S— |
| Cl | $OCH_3$ | H | $C_3H_7$ | H | O | $CH_3$ | i-$C_3H_7$—S— |
| Cl | $OCH_3$ | H | i-$C_3H_7$ | H | O | $CH_3$ | i-$C_3H_7$—S— |
| Cl | $OCH_3$ | H | $C_4H_9$ | H | O | $CH_3$ | i-$C_3H_7$—S— |
| Cl | $OCH_3$ | H | i-$C_4H_9$ | H | O | $CH_3$ | i-$C_3H_7$—S— |
| Cl | $OCH_3$ | H | s-$C_4H_9$ | H | O | $CH_3$ | i-$C_3H_7$—S— |
| Cl | $OCH_3$ | H | t-$C_4H_9$ | H | O | $CH_3$ | i-$C_3H_7$—S— |
| Cl | $OCH_3$ | H | $CH_3$ | $CH_3$ | O | $CH_3$ | i-$C_3H_7$—S— |
| Cl | $OCH_3$ | H | $C_2H_5$ | $CH_3$ | O | $CH_3$ | i-$C_3H_7$—S— |
| Cl | $OCH_3$ | H | $C_3H_7$ | $CH_3$ | O | $CH_3$ | i-$C_3H_7$—S— |
| Cl | $OCH_3$ | H | i-$C_3H_7$ | $CH_3$ | O | $CH_3$ | i-$C_3H_7$—S— |
| Cl | $OCH_3$ | H | $C_4H_9$ | $CH_3$ | O | $CH_3$ | i-$C_3H_7$—S— |
| Cl | $OCH_3$ | H | i-$C_4H_9$ | $CH_3$ | O | $CH_3$ | i-$C_3H_7$—S— |
| Cl | $OCH_3$ | H | s-$C_4H_9$ | $CH_3$ | O | $CH_3$ | i-$C_3H_7$—S— |
| Cl | $OCH_3$ | H | t-$C_4H_9$ | $CH_3$ | O | $CH_3$ | i-$C_3H_7$—S— |
| Cl | $OCH_3$ | H | $C_2H_5$ | $C_2H_5$ | O | $CH_3$ | i-$C_3H_7$—S— |
| Cl | $OCH_3$ | H | $C_3H_7$ | $C_3H_7$ | O | $CH_3$ | i-$C_3H_7$—S— |
| Cl | $OCH_3$ | H | 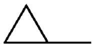 | $CH_3$ | O | $CH_3$ | i-$C_3H_7$—S— |
| Cl | $OCH_3$ | H | 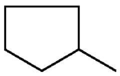 | $CH_3$ | O | $CH_3$ | i-$C_3H_7$—S— |
| Cl | $OCH_3$ | H | 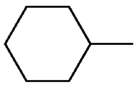 | $CH_3$ | O | $CH_3$ | i-$C_3H_7$—S— |
| Cl | H | 6-$OCH_3$ | $CH_3$ | H | O | $CH_3$ | i-$C_3H_7$—S— |
| Cl | H | 6-$OCH_3$ | $C_2H_5$ | H | O | $CH_3$ | i-$C_3H_7$—S— |
| Cl | H | 6-$OCH_3$ | $C_3H_7$ | H | O | $CH_3$ | i-$C_3H_7$—S— |
| Cl | H | 6-$OCH_3$ | i-$C_3H_7$ | H | O | $CH_3$ | i-$C_3H_7$—S— |
| Cl | H | 6-$OCH_3$ | $C_4H_9$ | H | O | $CH_3$ | i-$C_3H_7$—S— |
| Cl | H | 6-$OCH_3$ | i-$C_4H_9$ | H | O | $CH_3$ | i-$C_3H_7$—S— |
| Cl | H | 6-$OCH_3$ | s-$C_4H_9$ | H | O | $CH_3$ | i-$C_3H_7$—S— |
| Cl | H | 6-$OCH_3$ | t-$C_4H_9$ | H | O | $CH_3$ | i-$C_3H_7$—S— |
| Cl | H | 6-$OCH_3$ | $CH_3$ | $CH_3$ | O | $CH_3$ | i-$C_3H_7$—S— |
| Cl | H | 6-$OCH_3$ | $C_2H_5$ | $CH_3$ | O | $CH_3$ | i-$C_3H_7$—S— |
| Cl | H | 6-$OCH_3$ | $C_3H_7$ | $CH_3$ | O | $CH_3$ | i-$C_3H_7$—S— |
| Cl | H | 6-$OCH_3$ | i-$C_3H_7$ | $CH_3$ | O | $CH_3$ | i-$C_3H_7$—S— |
| Cl | H | 6-$OCH_3$ | $C_4H_9$ | $CH_3$ | O | $CH_3$ | i-$C_3H_7$—S— |
| Cl | H | 6-$OCH_3$ | i-$C_4H_9$ | $CH_3$ | O | $CH_3$ | i-$C_3H_7$—S— |
| Cl | H | 6-$OCH_3$ | s-$C_4H_9$ | $CH_3$ | O | $CH_3$ | i-$C_3H_7$—S— |
| Cl | H | 6-$OCH_3$ | t-$C_4H_9$ | $CH_3$ | O | $CH_3$ | i-$C_3H_7$—S— |

TABLE 5-continued (Ie)

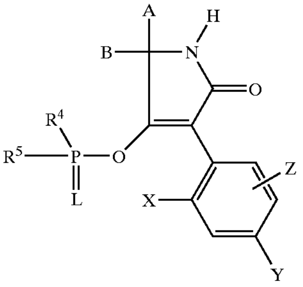

| X | Y | Z | A | B | L | $R^4$ | $R^5$ |
|---|---|---|---|---|---|---|---|
| Cl | H | 6-$OCH_3$ | $C_2H_5$ | $C_2H_5$ | O | $CH_3$ | i-$C_3H_7$—S— |
| Cl | H | 6-$OCH_3$ | $C_3H_7$ | $C_3H_7$ | O | $CH_3$ | i-$C_3H_7$—S— |
| Cl | H | 6-$OCH_3$ | 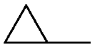 | $CH_3$ | O | $CH_3$ | i-$C_3H_7$—S— |
| Cl | H | 6-$OCH_3$ | 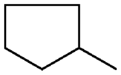 | $CH_3$ | O | $CH_3$ | i-$C_3H_7$—S— |
| Cl | H | 6-$OCH_3$ | 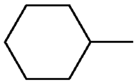 | $CH_3$ | O | $CH_3$ | i-$C_3H_7$—S— |
| $OCH_3$ | Cl | H | $CH_3$ | H | O | $CH_3$ | i-$C_3H_7$—S— |
| $OCH_3$ | Cl | H | $C_2H_5$ | H | O | $CH_3$ | i-$C_3H_7$—S— |
| $OCH_3$ | Cl | H | $C_3H_7$ | H | O | $CH_3$ | i-$C_3H_7$—S— |
| $OCH_3$ | Cl | H | i-$C_3H_7$ | H | O | $CH_3$ | i-$C_3H_7$—S— |
| $OCH_3$ | Cl | H | $C_4H_9$ | H | O | $CH_3$ | i-$C_3H_7$—S— |
| $OCH_3$ | Cl | H | i-$C_4H_9$ | H | O | $CH_3$ | i-$C_3H_7$—S— |
| $OCH_3$ | Cl | H | s-$C_4H_9$ | H | O | $CH_3$ | i-$C_3H_7$—S— |
| $OCH_3$ | Cl | H | t-$C_4H_9$ | H | O | $CH_3$ | i-$C_3H_7$—S— |
| $OCH_3$ | Cl | H | $CH_3$ | $CH_3$ | O | $CH_3$ | i-$C_3H_7$—S— |
| $OCH_3$ | Cl | H | $C_2H_5$ | $CH_3$ | O | $CH_3$ | i-$C_3H_7$—S— |
| $OCH_3$ | Cl | H | $C_3H_7$ | $CH_3$ | O | $CH_3$ | i-$C_3H_7$—S— |
| $OCH_3$ | Cl | H | i-$C_3H_7$ | $CH_3$ | O | $CH_3$ | i-$C_3H_7$—S— |
| $OCH_3$ | Cl | H | $C_4H_9$ | $CH_3$ | O | $CH_3$ | i-$C_3H_7$—S— |
| $OCH_3$ | Cl | H | i-$C_4H_9$ | $CH_3$ | O | $CH_3$ | i-$C_3H_7$—S— |
| $OCH_3$ | Cl | H | s-$C_4H_9$ | $CH_3$ | O | $CH_3$ | i-$C_3H_7$—S— |
| $OCH_3$ | Cl | H | t-$C_4H_9$ | $CH_3$ | O | $CH_3$ | i-$C_3H_7$—S— |
| $OCH_3$ | Cl | H | $C_2H_5$ | $C_2H_5$ | O | $CH_3$ | i-$C_3H_7$—S— |
| $OCH_3$ | Cl | H | $C_3H_7$ | $C_3H_7$ | O | $CH_3$ | i-$C_3H_7$—S— |
| $OCH_3$ | Cl | H | 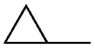 | $CH_3$ | O | $CH_3$ | i-$C_3H_7$—S— |
| $OCH_3$ | Cl | H | 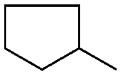 | $CH_3$ | O | $CH_3$ | i-$C_3H_7$—S— |
| $OCH_3$ | Cl | H | 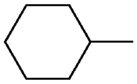 | $CH_3$ | O | $CH_3$ | i-$C_3H_7$—S— |
| Cl | $OCH_3$ | H | —$(CH_2)_2$— | | O | $CH_3$ | i-$C_3H_7$—S— |
| Cl | $OCH_3$ | H | —$(CH_2)_4$— | | O | $CH_3$ | i-$C_3H_7$—S— |
| Cl | $OCH_3$ | H | —$(CH_2)_5$— | | O | $CH_3$ | i-$C_3H_7$—S— |
| Cl | $OCH_3$ | H | —$(CH_2)_6$— | | O | $CH_3$ | i-$C_3H_7$—S— |
| Cl | $OCH_3$ | H | —$(CH_2)_7$— | | O | $CH_3$ | i-$C_3H_7$—S— |
| Cl | $OCH_3$ | H | —$(CH_2)_2$—O—$(CH_2)_2$— | | O | $CH_3$ | i-$C_3H_7$—S— |
| Cl | $OCH_3$ | H | —$(CH_2)_2$—S—$(CH_2)_2$— | | O | $CH_3$ | i-$C_3H_7$—S— |
| Cl | $OCH_3$ | H | —$(CH_2)_2$—$CHCH_3$—$(CH_2)_3$— | | O | $CH_3$ | i-$C_3H_7$—S— |
| Cl | $OCH_3$ | H | —$(CH_2)_2$—$CHCH_3$—$(CH_2)_2$— | | O | $CH_3$ | i-$C_3H_7$—S— |
| Cl | $OCH_3$ | H | —$(CH_2)_2$—$CHC_2H_5$—$(CH_2)_2$— | | O | $CH_3$ | i-$C_3H_7$—S— |
| Cl | $OCH_3$ | H | —$(CH_2)_2$—$CHC_3H_7$—$(CH_2)_2$— | | O | $CH_3$ | i-$C_3H_7$—S— |
| Cl | $OCH_3$ | H | —$(CH_2)_2$—CHi—$C_3H_7$—$(CH_2)_2$— | | O | $CH_3$ | i-$C_3H_7$—S— |
| Cl | $OCH_3$ | H | —$(CH_2)_2$—$CHOCH_3$—$(CH_2)_2$— | | O | $CH_3$ | i-$C_3H_7$—S— |
| Cl | $OCH_3$ | H | —$(CH_2)_2$—$CHOC_2H_5$—$(CH_2)_2$— | | O | $CH_3$ | i-$C_3H_7$—S— |

TABLE 5-continued (Ie)

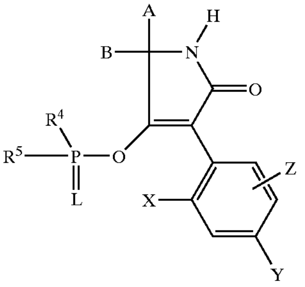

| X | Y | Z | A | B | L | $R^4$ | $R^5$ |
|---|---|---|---|---|---|---|---|
| Cl | $OCH_3$ | H | —$(CH_2)_2$—$CHOC_3H_7$—$(CH_2)_2$— | | O | $CH_3$ | i-$C_3H_7$—S— |
| Cl | $OCH_3$ | H | —$(CH_2)_2$—CHi—$OC_3H_7$—$(CH_2)_2$— | | O | $CH_3$ | i-$C_3H_7$—S— |
| Cl | $OCH_3$ | H | —$(CH_2)_2$—$C(CH_3)_2$—$(CH_2)_2$— | | O | $CH_3$ | i-$C_3H_7$—S— |
| Cl | $OCH_3$ | H | —$CH_2$—$(CHCH_3)_2$—$(CH_2)_2$— | | O | $CH_3$ | i-$C_3H_7$—S— |
| Cl | $OCH_3$ | H | 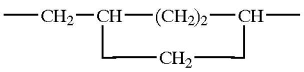 | | O | $CH_3$ | i-$C_3H_7$—S— |
| Cl | $OCH_3$ | H | 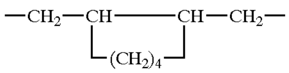 | | O | $CH_3$ | i-$C_3H_7$—S— |
| Cl | $OCH_3$ | H | 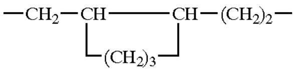 | | O | $CH_3$ | i-$C_3H_7$—S— |
| Cl | H | 6-$OCH_3$ | —$(CH_2)_2$— | | O | $CH_3$ | i-$C_3H_7$—S— |
| Cl | H | 6-$OCH_3$ | —$(CH_2)_4$— | | O | $CH_3$ | i-$C_3H_7$—S— |
| Cl | H | 6-$OCH_3$ | —$(CH_2)_5$— | | O | $CH_3$ | i-$C_3H_7$—S— |
| Cl | H | 6-$OCH_3$ | —$(CH_2)_6$— | | O | $CH_3$ | i-$C_3H_7$—S— |
| Cl | H | 6-$OCH_3$ | —$(CH_2)_7$— | | O | $CH_3$ | i-$C_3H_7$—S— |
| Cl | H | 6-$OCH_3$ | —$(CH_2)_2$—O—$(CH_2)_2$— | | O | $CH_3$ | i-$C_3H_7$—S— |
| Cl | H | 6-$OCH_3$ | —$(CH_2)_2$—S—$(CH_2)_2$— | | O | $CH_3$ | i-$C_3H_7$—S— |
| Cl | H | 6-$OCH_3$ | —$(CH_2)_2$—$CHCH_3$—$(CH_2)_3$— | | O | $CH_3$ | i-$C_3H_7$—S— |
| Cl | H | 6-$OCH_3$ | —$(CH_2)_2$—$CHCH_3$—$(CH_2)_2$— | | O | $CH_3$ | i-$C_3H_7$—S— |
| Cl | H | 6-$OCH_3$ | —$(CH_2)_2$—$CHC_2H_5$—$(CH_2)_2$— | | O | $CH_3$ | i-$C_3H_7$—S— |
| Cl | H | 6-$OCH_3$ | —$(CH_2)_2$—$CHC_3H_7$—$(CH_2)_2$— | | O | $CH_3$ | i-$C_3H_7$—S— |
| Cl | H | 6-$OCH_3$ | —$(CH_2)_2$—CHi—$C_3H_7$—$(CH_2)_2$— | | O | $CH_3$ | i-$C_3H_7$—S— |
| Cl | H | 6-$OCH_3$ | —$(CH_2)_2$—$CHOCH_3$—$(CH_2)_2$— | | O | $CH_3$ | i-$C_3H_7$—S— |
| Cl | H | 6-$OCH_3$ | —$(CH_2)_2$—$CHOC_2H_5$—$(CH_2)_2$— | | O | $CH_3$ | i-$C_3H_7$—S— |
| Cl | H | 6-$OCH_3$ | —$(CH_2)_2$—$CHOC_3H_7$—$(CH_2)_2$— | | O | $CH_3$ | i-$C_3H_7$—S— |
| Cl | H | 6-$OCH_3$ | —$(CH_2)_2$—CHi—$OC_3H_7$—$(CH_2)_2$— | | O | $CH_3$ | i-$C_3H_7$—S— |
| Cl | H | 6-$OCH_3$ | —$(CH_2)_2$—$C(CH_3)_2$—$(CH_2)_2$— | | O | $CH_3$ | i-$C_3H_7$—S— |
| Cl | H | 6-$OCH_3$ | —$CH_2$—$(CHCH_3)_2$—$(CH_2)_2$— | | O | $CH_3$ | i-$C_3H_7$—S— |
| Cl | H | 6-$OCH_3$ | 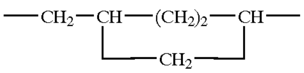 | | O | $CH_3$ | i-$C_3H_7$—S— |
| Cl | H | 6-$OCH_3$ | 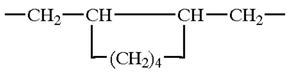 | | O | $CH_3$ | i-$C_3H_7$—S— |
| Cl | H | 6-$OCH_3$ | 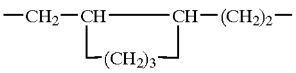 | | O | $CH_3$ | i-$C_3H_7$—S— |
| $OCH_3$ | Cl | H | —$(CH_2)_2$— | | O | $CH_3$ | i-$C_3H_7$—S— |
| $OCH_3$ | Cl | H | —$(CH_2)_4$— | | O | $CH_3$ | i-$C_3H_7$—S— |
| $OCH_3$ | Cl | H | —$(CH_2)_5$— | | O | $CH_3$ | i-$C_3H_7$—S— |
| $OCH_3$ | Cl | H | —$(CH_2)_6$— | | O | $CH_3$ | i-$C_3H_7$—S— |
| $OCH_3$ | Cl | H | —$(CH_2)_7$— | | O | $CH_3$ | i-$C_3H_7$—S— |
| $OCH_3$ | Cl | H | —$(CH_2)_2$—O—$(CH_2)_2$— | | O | $CH_3$ | i-$C_3H_7$—S— |
| $OCH_3$ | Cl | H | —$(CH_2)_2$—S—$(CH_2)_2$— | | O | $CH_3$ | i-$C_3H_7$—S— |
| $OCH_3$ | Cl | H | —$(CH_2)_2$—$CHCH_3$—$(CH_2)_3$— | | O | $CH_3$ | i-$C_3H_7$—S— |
| $OCH_3$ | Cl | H | —$(CH_2)_2$—$CHCH_3$—$(CH_2)_2$— | | O | $CH_3$ | i-$C_3H_7$—S— |
| $OCH_3$ | Cl | H | —$(CH_2)_2$—$CHC_2H_5$—$(CH_2)_2$— | | O | $CH_3$ | i-$C_3H_7$—S— |
| $OCH_3$ | Cl | H | —$(CH_2)_2$—$CHC_3H_7$—$(CH_2)_2$— | | O | $CH_3$ | i-$C_3H_7$—S— |
| $OCH_3$ | Cl | H | —$(CH_2)_2$—CHi—$C_3H_7$—$(CH_2)_2$— | | O | $CH_3$ | i-$C_3H_7$—S— |

TABLE 5-continued (Ie)

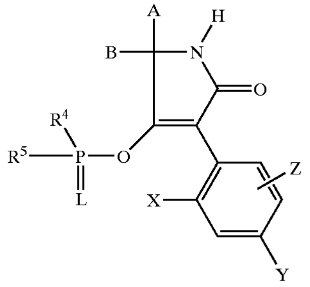

| X | Y | Z | A | B | L | $R^4$ | $R^5$ |
|---|---|---|---|---|---|---|---|
| $OCH_3$ | Cl | H | $—(CH_2)_2—CHOCH_3—(CH_2)_2—$ | | O | $CH_3$ | $i-C_3H_7—S—$ |
| $OCH_3$ | Cl | H | $—(CH_2)_2—CHOC_2H_5—(CH_2)_2—$ | | O | $CH_3$ | $i-C_3H_7—S—$ |
| $OCH_3$ | Cl | H | $—(CH_2)_2—CHOC_3H_7—(CH_2)_2—$ | | O | $CH_3$ | $i-C_3H_7—S—$ |
| $OCH_3$ | Cl | H | $—(CH_2)_2—CHi—OC_3H_7—(CH_2)_2—$ | | O | $CH_3$ | $i-C_3H_7—S—$ |
| $OCH_3$ | Cl | H | $—(CH_2)_2—C(CH_3)_2—(CH_2)_2—$ | | O | $CH_3$ | $i-C_3H_7—S—$ |
| $OCH_3$ | Cl | H | $—CH_2—(CHCH_3)_2—(CH_2)_2—$ | | O | $CH_3$ | $i-C_3H_7—S—$ |
| $OCH_3$ | Cl | H | 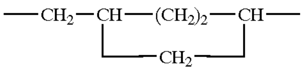 | | O | $CH_3$ | $i-C_3H_7—S—$ |
| $OCH_3$ | Cl | H | 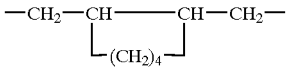 | | O | $CH_3$ | $i-C_3H_7—S—$ |
| $OCH_3$ | Cl | H | 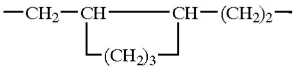 | | O | $CH_3$ | $i-C_3H_7—S—$ |
| Cl | $OCH_3$ | H | $CH_3$ | H | O | $C_2H_5$ | $i-C_3H_7—S—$ |
| Cl | $OCH_3$ | H | $C_2H_5$ | H | O | $C_2H_5$ | $i-C_3H_7—S—$ |
| Cl | $OCH_3$ | H | $C_3H_7$ | H | O | $C_2H_5$ | $i-C_3H_7—S—$ |
| Cl | $OCH_3$ | H | $i-C_3H_7$ | H | O | $C_2H_5$ | $i-C_3H_7—S—$ |
| Cl | $OCH_3$ | H | $C_4H_9$ | H | O | $C_2H_5$ | $i-C_3H_7—S—$ |
| Cl | $OCH_3$ | H | $i-C_4H_9$ | H | O | $C_2H_5$ | $i-C_3H_7—S—$ |
| Cl | $OCH_3$ | H | $s-C_4H_9$ | H | O | $C_2H_5$ | $i-C_3H_7—S—$ |
| Cl | $OCH_3$ | H | $t-C_4H_9$ | H | O | $C_2H_5$ | $i-C_3H_7—S—$ |
| Cl | $OCH_3$ | H | $CH_3$ | $CH_3$ | O | $C_2H_5$ | $i-C_3H_7—S—$ |
| Cl | $OCH_3$ | H | $C_2H_5$ | $CH_3$ | O | $C_2H_5$ | $i-C_3H_7—S—$ |
| Cl | $OCH_3$ | H | $C_3H_7$ | $CH_3$ | O | $C_2H_5$ | $i-C_3H_7—S—$ |
| Cl | $OCH_3$ | H | $i-C_3H_7$ | $CH_3$ | O | $C_2H_5$ | $i-C_3H_7—S—$ |
| Cl | $OCH_3$ | H | $C_4H_9$ | $CH_3$ | O | $C_2H_5$ | $i-C_3H_7—S—$ |
| Cl | $OCH_3$ | H | $i-C_4H_9$ | $CH_3$ | O | $C_2H_5$ | $i-C_3H_7—S—$ |
| Cl | $OCH_3$ | H | $s-C_4H_9$ | $CH_3$ | O | $C_2H_5$ | $i-C_3H_7—S—$ |
| Cl | $OCH_3$ | H | $t-C_4H_9$ | $CH_3$ | O | $C_2H_5$ | $i-C_3H_7—S—$ |
| Cl | $OCH_3$ | H | $C_2H_5$ | $C_2H_5$ | O | $C_2H_5$ | $i-C_3H_7—S—$ |
| Cl | $OCH_3$ | H | $C_3H_7$ | $C_3H_7$ | O | $C_2H_5$ | $i-C_3H_7—S—$ |
| Cl | $OCH_3$ | H | 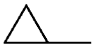 | $CH_3$ | O | $C_2H_5$ | $i-C_3H_7—S—$ |
| Cl | $OCH_3$ | H | 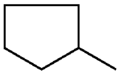 | $CH_3$ | O | $C_2H_5$ | $i-C_3H_7—S—$ |
| Cl | $OCH_3$ | H | 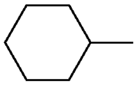 | $CH_3$ | O | $C_2H_5$ | $i-C_3H_7—S—$ |
| Cl | H | $6-OCH_3$ | $CH_3$ | H | O | $C_2H_5$ | $i-C_3H_7—S—$ |
| Cl | H | $6-OCH_3$ | $C_2H_5$ | H | O | $C_2H_5$ | $i-C_3H_7—S—$ |
| Cl | H | $6-OCH_3$ | $C_3H_7$ | H | O | $C_2H_5$ | $i-C_3H_7—S—$ |
| Cl | H | $6-OCH_3$ | $i-C_3H_7$ | H | O | $C_2H_5$ | $i-C_3H_7—S—$ |
| Cl | H | $6-OCH_3$ | $C_4H_9$ | H | O | $C_2H_5$ | $i-C_3H_7—S—$ |
| Cl | H | $6-OCH_3$ | $i-C_4H_9$ | H | O | $C_2H_5$ | $i-C_3H_7—S—$ |
| Cl | H | $6-OCH_3$ | $s-C_4H_9$ | H | O | $C_2H_5$ | $i-C_3H_7—S—$ |
| Cl | H | $6-OCH_3$ | $t-C_4H_9$ | H | O | $C_2H_5$ | $i-C_3H_7—S—$ |
| Cl | H | $6-OCH_3$ | $CH_3$ | $CH_3$ | O | $C_2H_5$ | $i-C_3H_7—S—$ |
| Cl | H | $6-OCH_3$ | $C_2H_5$ | $CH_3$ | O | $C_2H_5$ | $i-C_3H_7—S—$ |

TABLE 5-continued (Ie)

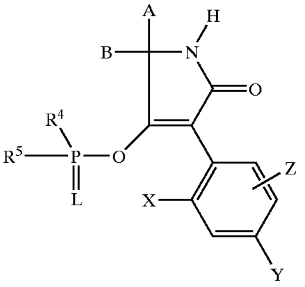

| X | Y | Z | A | B | L | $R^4$ | $R^5$ |
|---|---|---|---|---|---|---|---|
| Cl | H | 6-$OCH_3$ | $C_3H_7$ | $CH_3$ | O | $C_2H_5$ | i-$C_3H_7$—S— |
| Cl | H | 6-$OCH_3$ | i-$C_3H_7$ | $CH_3$ | O | $C_2H_5$ | i-$C_3H_7$—S— |
| Cl | H | 6-$OCH_3$ | $C_4H_9$ | $CH_3$ | O | $C_2H_5$ | i-$C_3H_7$—S— |
| Cl | H | 6-$OCH_3$ | i-$C_4H_9$ | $CH_3$ | O | $C_2H_5$ | i-$C_3H_7$—S— |
| Cl | H | 6-$OCH_3$ | s-$C_4H_9$ | $CH_3$ | O | $C_2H_5$ | i-$C_3H_7$—S— |
| Cl | H | 6-$OCH_3$ | t-$C_4H_9$ | $CH_3$ | O | $C_2H_5$ | i-$C_3H_7$—S— |
| Cl | H | 6-$OCH_3$ | $C_2H_5$ | $C_2H_5$ | O | $C_2H_5$ | i-$C_3H_7$—S— |
| Cl | H | 6-$OCH_3$ | $C_3H_7$ | $C_3H_7$ | O | $C_2H_5$ | i-$C_3H_7$—S— |
| Cl | H | 6-$OCH_3$ | 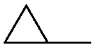 | $CH_3$ | O | $C_2H_5$ | i-$C_3H_7$—S— |
| Cl | H | 6-$OCH_3$ | 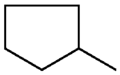 | $CH_3$ | O | $C_2H_5$ | i-$C_3H_7$—S— |
| Cl | H | 6-$OCH_3$ | 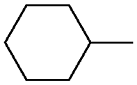 | $CH_3$ | O | $C_2H_5$ | i-$C_3H_7$—S— |
| $OCH_3$ | Cl | H | $CH_3$ | H | O | $C_2H_5$ | i-$C_3H_7$—S— |
| $OCH_3$ | Cl | H | $C_2H_5$ | H | O | $C_2H_5$ | i-$C_3H_7$—S— |
| $OCH_3$ | Cl | H | $C_3H_7$ | H | O | $C_2H_5$ | i-$C_3H_7$—S— |
| $OCH_3$ | Cl | H | i-$C_3H_7$ | H | O | $C_2H_5$ | i-$C_3H_7$—S— |
| $OCH_3$ | Cl | H | $C_4H_9$ | H | O | $C_2H_5$ | i-$C_3H_7$—S— |
| $OCH_3$ | Cl | H | i-$C_4H_9$ | H | O | $C_2H_5$ | i-$C_3H_7$—S— |
| $OCH_3$ | Cl | H | s-$C_4H_9$ | H | O | $C_2H_5$ | i-$C_3H_7$—S— |
| $OCH_3$ | Cl | H | t-$C_4H_9$ | H | O | $C_2H_5$ | i-$C_3H_7$—S— |
| $OCH_3$ | Cl | H | $CH_3$ | $CH_3$ | O | $C_2H_5$ | i-$C_3H_7$—S— |
| $OCH_3$ | Cl | H | $C_2H_5$ | $CH_3$ | O | $C_2H_5$ | i-$C_3H_7$—S— |
| $OCH_3$ | Cl | H | $C_3H_7$ | $CH_3$ | O | $C_2H_5$ | i-$C_3H_7$—S— |
| $OCH_3$ | Cl | H | i-$C_3H_7$ | $CH_3$ | O | $C_2H_5$ | i-$C_3H_7$—S— |
| $OCH_3$ | Cl | H | $C_4H_9$ | $CH_3$ | O | $C_2H_5$ | i-$C_3H_7$—S— |
| $OCH_3$ | Cl | H | i-$C_4H_9$ | $CH_3$ | O | $C_2H_5$ | i-$C_3H_7$—S— |
| $OCH_3$ | Cl | H | s-$C_4H_9$ | $CH_3$ | O | $C_2H_5$ | i-$C_3H_7$—S— |
| $OCH_3$ | Cl | H | t-$C_4H_9$ | $CH_3$ | O | $C_2H_5$ | i-$C_3H_7$—S— |
| $OCH_3$ | Cl | H | $C_2H_5$ | $C_2H_5$ | O | $C_2H_5$ | i-$C_3H_7$—S— |
| $OCH_3$ | Cl | H | $C_3H_7$ | $C_3H_7$ | O | $C_2H_5$ | i-$C_3H_7$—S— |
| $OCH_3$ | Cl | H | 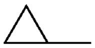 | $CH_3$ | O | $C_2H_5$ | i-$C_3H_7$—S— |
| $OCH_3$ | Cl | H | 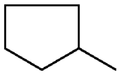 | $CH_3$ | O | $C_2H_5$ | i-$C_3H_7$—S— |
| $OCH_3$ | Cl | H | 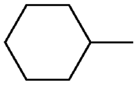 | $CH_3$ | O | $C_2H_5$ | i-$C_3H_7$—S— |
| Cl | $OCH_3$ | H | $—(CH_2)_2—$ | | O | $C_2H_5$ | i-$C_3H_7$—S— |
| Cl | $OCH_3$ | H | $—(CH_2)_4—$ | | O | $C_2H_5$ | i-$C_3H_7$—S— |
| Cl | $OCH_3$ | H | $—(CH_2)_5—$ | | O | $C_2H_5$ | i-$C_3H_7$—S— |
| Cl | $OCH_3$ | H | $—(CH_2)_6—$ | | O | $C_2H_5$ | i-$C_3H_7$—S— |
| Cl | $OCH_3$ | H | $—(CH_2)_7—$ | | O | $C_2H_5$ | i-$C_3H_7$—S— |
| Cl | $OCH_3$ | H | $—(CH_2)_2—O—(CH_2)_2—$ | | O | $C_2H_5$ | i-$C_3H_7$—S— |
| Cl | $OCH_3$ | H | $—(CH_2)_2—S—(CH_2)_2—$ | | O | $C_2H_5$ | i-$C_3H_7$—S— |
| Cl | $OCH_3$ | H | $—(CH_2)_2—CHCH_3—(CH_2)_3—$ | | O | $C_2H_5$ | i-$C_3H_7$—S— |

TABLE 5-continued (Ie)

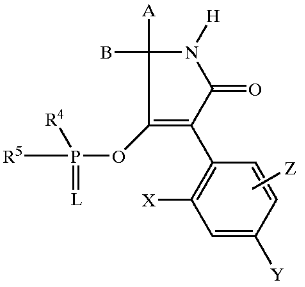

| X | Y | Z | A | B | L | $R^4$ | $R^5$ |
|---|---|---|---|---|---|---|---|
| Cl | $OCH_3$ | H | $—(CH_2)_2—CHCH_3—(CH_2)_2—$ | | O | $C_2H_5$ | $i\text{-}C_3H_7—S—$ |
| Cl | $OCH_3$ | H | $—(CH_2)_2—CHC_2H_5—(CH_2)_2—$ | | O | $C_2H_5$ | $i\text{-}C_3H_7—S—$ |
| Cl | $OCH_3$ | H | $—(CH_2)_2—CHC_3H_7—(CH_2)_2—$ | | O | $C_2H_5$ | $i\text{-}C_3H_7—S—$ |
| Cl | $OCH_3$ | H | $—(CH_2)_2—CHi—C_3H_7—(CH_2)_2—$ | | O | $C_2H_5$ | $i\text{-}C_3H_7—S—$ |
| Cl | $OCH_3$ | H | $—(CH_2)_2—CHOCH_3—(CH_2)_2—$ | | O | $C_2H_5$ | $i\text{-}C_3H_7—S—$ |
| Cl | $OCH_3$ | H | $—(CH_2)_2—CHOC_2H_5—(CH_2)_2—$ | | O | $C_2H_5$ | $i\text{-}C_3H_7—S—$ |
| Cl | $OCH_3$ | H | $—(CH_2)_2—CHOC_3H_7—(CH_2)_2—$ | | O | $C_2H_5$ | $i\text{-}C_3H_7—S—$ |
| Cl | $OCH_3$ | H | $—(CH_2)_2—CHi—OC_3H_7—(CH_2)_2—$ | | O | $C_2H_5$ | $i\text{-}C_3H_7—S—$ |
| Cl | $OCH_3$ | H | $—(CH_2)_2—C(CH_3)_2—(CH_2)_2—$ | | O | $C_2H_5$ | $i\text{-}C_3H_7—S—$ |
| Cl | $OCH_3$ | H | $—CH_2—(CHCH_3)_2—(CH_2)_2—$ | | O | $C_2H_5$ | $i\text{-}C_3H_7—S—$ |
| Cl | $OCH_3$ | H | 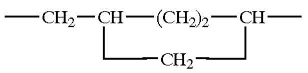 | | O | $C_2H_5$ | $i\text{-}C_3H_7—S—$ |
| Cl | $OCH_3$ | H | 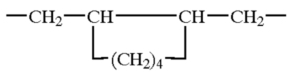 | | O | $C_2H_5$ | $i\text{-}C_3H_7—S—$ |
| Cl | $OCH_3$ | H | 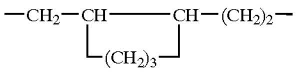 | | O | $C_2H_5$ | $i\text{-}C_3H_7—S—$ |
| Cl | H | $6\text{-}OCH_3$ | $—(CH_2)_2—$ | | O | $C_2H_5$ | $i\text{-}C_3H_7—S—$ |
| Cl | H | $6\text{-}OCH_3$ | $—(CH_2)_4—$ | | O | $C_2H_5$ | $i\text{-}C_3H_7—S—$ |
| Cl | H | $6\text{-}OCH_3$ | $—(CH_2)_5—$ | | O | $C_2H_5$ | $i\text{-}C_3H_7—S—$ |
| Cl | H | $6\text{-}OCH_3$ | $—(CH_2)_6—$ | | O | $C_2H_5$ | $i\text{-}C_3H_7—S—$ |
| Cl | H | $6\text{-}OCH_3$ | $—(CH_2)_7—$ | | O | $C_2H_5$ | $i\text{-}C_3H_7—S—$ |
| Cl | H | $6\text{-}OCH_3$ | $—(CH_2)_2—O—(CH_2)_2—$ | | O | $C_2H_5$ | $i\text{-}C_3H_7—S—$ |
| Cl | H | $6\text{-}OCH_3$ | $—(CH_2)_2—S—(CH_2)_2—$ | | O | $C_2H_5$ | $i\text{-}C_3H_7—S—$ |
| Cl | H | $6\text{-}OCH_3$ | $—(CH_2)_2—CHCH_3—(CH_2)_3—$ | | O | $C_2H_5$ | $i\text{-}C_3H_7—S—$ |
| Cl | H | $6\text{-}OCH_3$ | $—(CH_2)_2—CHCH_3—(CH_2)_2—$ | | O | $C_2H_5$ | $i\text{-}C_3H_7—S—$ |
| Cl | H | $6\text{-}OCH_3$ | $—(CH_2)_2—CHC_2H_5—(CH_2)_2—$ | | O | $C_2H_5$ | $i\text{-}C_3H_7—S—$ |
| Cl | H | $6\text{-}OCH_3$ | $—(CH_2)_2—CHC_3H_7—(CH_2)_2—$ | | O | $C_2H_5$ | $i\text{-}C_3H_7—S—$ |
| Cl | H | $6\text{-}OCH_3$ | $—(CH_2)_2—CHi—C_3H_7—(CH_2)_2—$ | | O | $C_2H_5$ | $i\text{-}C_3H_7—S—$ |
| Cl | H | $6\text{-}OCH_3$ | $—(CH_2)_2—CHOCH_3—(CH_2)_2—$ | | O | $C_2H_5$ | $i\text{-}C_3H_7—S—$ |
| Cl | H | $6\text{-}OCH_3$ | $—(CH_2)_2—CHOC_2H_5—(CH_2)_2—$ | | O | $C_2H_5$ | $i\text{-}C_3H_7—S—$ |
| Cl | H | $6\text{-}OCH_3$ | $—(CH_2)_2—CHOC_3H_7—(CH_2)_2—$ | | O | $C_2H_5$ | $i\text{-}C_3H_7—S—$ |
| Cl | H | $6\text{-}OCH_3$ | $—(CH_2)_2—CHi—OC_3H_7—(CH_2)_2—$ | | O | $C_2H_5$ | $i\text{-}C_3H_7—S—$ |
| Cl | H | $6\text{-}OCH_3$ | $—(CH_2)_2—C(CH_3)_2—(CH_2)_2—$ | | O | $C_2H_5$ | $i\text{-}C_3H_7—S—$ |
| Cl | H | $6\text{-}OCH_3$ | $—CH_2—(CHCH_3)_2—(CH_2)_2—$ | | O | $C_2H_5$ | $i\text{-}C_3H_7—S—$ |
| Cl | H | $6\text{-}OCH_3$ | 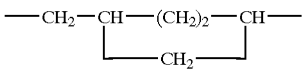 | | O | $C_2H_5$ | $i\text{-}C_3H_7—S—$ |
| Cl | H | $6\text{-}OCH_3$ | 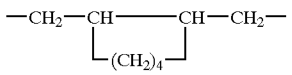 | | O | $C_2H_5$ | $i\text{-}C_3H_7—S—$ |
| Cl | H | $6\text{-}OCH_3$ | 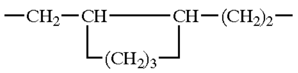 | | O | $C_2H_5$ | $i\text{-}C_3H_7—S—$ |
| $OCH_3$ | Cl | H | $—(CH_2)_2—$ | | O | $C_2H_5$ | $i\text{-}C_3H_7—S—$ |
| $OCH_3$ | Cl | H | $—(CH_2)_4—$ | | O | $C_2H_5$ | $i\text{-}C_3H_7—S—$ |
| $OCH_3$ | Cl | H | $—(CH_2)_5—$ | | O | $C_2H_5$ | $i\text{-}C_3H_7—S—$ |
| $OCH_3$ | Cl | H | $—(CH_2)_6—$ | | O | $C_2H_5$ | $i\text{-}C_3H_7—S—$ |
| $OCH_3$ | Cl | H | $—(CH_2)_7—$ | | O | $C_2H_5$ | $i\text{-}C_3H_7—S—$ |
| $OCH_3$ | Cl | H | $—(CH_2)_2—O—(CH_2)_2—$ | | O | $C_2H_5$ | $i\text{-}C_3H_7—S—$ |

TABLE 5-continued (Ie)

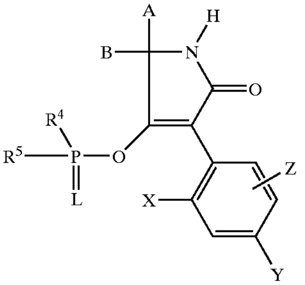

| X | Y | Z | A | B | L | $R^4$ | $R^5$ |
|---|---|---|---|---|---|---|---|
| $OCH_3$ | Cl | H | $—(CH_2)_2—S—(CH_2)_2—$ | | O | $C_2H_5$ | $i\text{-}C_3H_7—S—$ |
| $OCH_3$ | Cl | H | $—(CH_2)_2—CHCH_3—(CH_2)_3—$ | | O | $C_2H_5$ | $i\text{-}C_3H_7—S—$ |
| $OCH_3$ | Cl | H | $—(CH_2)_2—CHCH_3—(CH_2)_2—$ | | O | $C_2H_5$ | $i\text{-}C_3H_7—S—$ |
| $OCH_3$ | Cl | H | $—(CH_2)_2—CHC_2H_5—(CH_2)_2—$ | | O | $C_2H_5$ | $i\text{-}C_3H_7—S—$ |
| $OCH_3$ | Cl | H | $—(CH_2)_2—CHC_3H_7—(CH_2)_2—$ | | O | $C_2H_5$ | $i\text{-}C_3H_7—S—$ |
| $OCH_3$ | Cl | H | $—(CH_2)_2—CHi—C_3H_7—(CH_2)_2—$ | | O | $C_2H_5$ | $i\text{-}C_3H_7—S—$ |
| $OCH_3$ | Cl | H | $—(CH_2)_2—CHOCH_3—(CH_2)_2—$ | | O | $C_2H_5$ | $i\text{-}C_3H_7—S—$ |
| $OCH_3$ | Cl | H | $—(CH_2)_2—CHOC_2H_5—(CH_2)_2—$ | | O | $C_2H_5$ | $i\text{-}C_3H_7—S—$ |
| $OCH_3$ | Cl | H | $—(CH_2)_2—CHOC_3H_7—(CH_2)_2—$ | | O | $C_2H_5$ | $i\text{-}C_3H_7—S—$ |
| $OCH_3$ | Cl | H | $—(CH_2)_2—CHi—OC_3H_7—(CH_2)_2—$ | | O | $C_2H_5$ | $i\text{-}C_3H_7—S—$ |
| $OCH_3$ | Cl | H | $—(CH_2)_2—C(CH_3)_2—(CH_2)_2—$ | | O | $C_2H_5$ | $i\text{-}C_3H_7—S—$ |
| $OCH_3$ | Cl | H | $—CH_2—(CHCH_3)_2—(CH_2)_2—$ | | O | $C_2H_5$ | $i\text{-}C_3H_7—S—$ |
| $OCH_3$ | Cl | H | 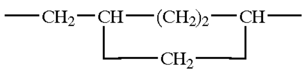 | | O | $C_2H_5$ | $i\text{-}C_3H_7—S—$ |
| $OCH_3$ | Cl | H | 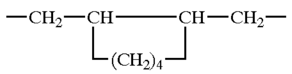 | | O | $C_2H_5$ | $i\text{-}C_3H_7—S—$ |
| $OCH_3$ | Cl | H | 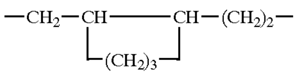 | | O | $C_2H_5$ | $i\text{-}C_3H_7—S—$ |

The following compounds of the formula (If-a) may be mentioned individually in addition to the compounds mentioned in the preparation examples:

TABLE 6a (If-a)

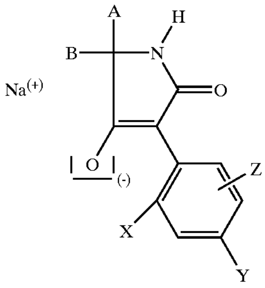

| X | Y | Z | A | B |
|---|---|---|---|---|
| Cl | $OCH_3$ | H | $CH_3$ | H |
| Cl | $OCH_3$ | H | $C_2H_5$ | H |
| Cl | $OCH_3$ | H | $C_3H_7$ | H |
| Cl | $OCH_3$ | H | $i\text{-}C_3H_7$ | H |
| Cl | $OCH_3$ | H | $C_4H_9$ | H |
| Cl | $OCH_3$ | H | $i\text{-}C_4H_9$ | H |
| Cl | $OCH_3$ | H | $s\text{-}C_4H_9$ | H |
| Cl | $OCH_3$ | H | $t\text{-}C_4H_9$ | H |
| Cl | $OCH_3$ | H | $CH_3$ | $CH_3$ |

TABLE 6a-continued (If-a)

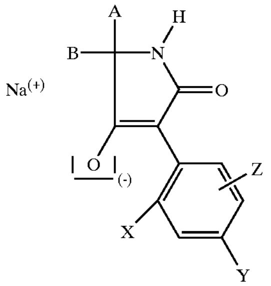

| X | Y | Z | A | B |
|---|---|---|---|---|
| Cl | $OCH_3$ | H | $C_2H_5$ | $CH_3$ |
| Cl | $OCH_3$ | H | $C_3H_7$ | $CH_3$ |
| Cl | $OCH_3$ | H | $i\text{-}C_3H_7$ | $CH_3$ |
| Cl | $OCH_3$ | H | $C_4H_9$ | $CH_3$ |
| Cl | $OCH_3$ | H | $i\text{-}C_4H_9$ | $CH_3$ |
| Cl | $OCH_3$ | H | $s\text{-}C_4H_9$ | $CH_3$ |
| Cl | $OCH_3$ | H | $t\text{-}C_4H_9$ | $CH_3$ |
| Cl | $OCH_3$ | H | $C_2H_5$ | $C_2H_5$ |
| Cl | $OCH_3$ | H | $C_3H_7$ | $C_3H_7$ |
| Cl | $OCH_3$ | H | 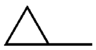 | $CH_3$ |

TABLE 6a-continued (If-a)

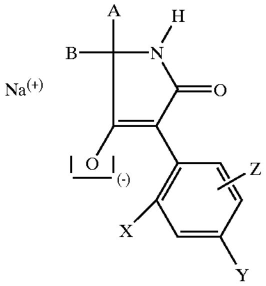

| X | Y | Z | A | B |
|---|---|---|---|---|
| Cl | $OCH_3$ | H | 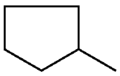 | $CH_3$ |
| Cl | $OCH_3$ | H | 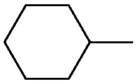 | $CH_3$ |
| Cl | H | 6-$OCH_3$ | $CH_3$ | H |
| Cl | H | 6-$OCH_3$ | $C_2H_5$ | H |
| Cl | H | 6-$OCH_3$ | $C_3H_7$ | H |
| Cl | H | 6-$OCH_3$ | i-$C_3H_7$ | H |
| Cl | H | 6-$OCH_3$ | $C_4H_9$ | H |
| Cl | H | 6-$OCH_3$ | i-$C_4H_9$ | H |
| Cl | H | 6-$OCH_3$ | s-$C_4H_9$ | H |
| Cl | H | 6-$OCH_3$ | t-$C_4H_9$ | H |
| Cl | H | 6-$OCH_3$ | $CH_3$ | $CH_3$ |
| Cl | H | 6-$OCH_3$ | $C_2H_5$ | $CH_3$ |
| Cl | H | 6-$OCH_3$ | $C_3H_7$ | $CH_3$ |
| Cl | H | 6-$OCH_3$ | i-$C_3H_7$ | $CH_3$ |
| Cl | H | 6-$OCH_3$ | $C_4H_9$ | $CH_3$ |
| Cl | H | 6-$OCH_3$ | i-$C_4H_9$ | $CH_3$ |
| Cl | H | 6-$OCH_3$ | s-$C_4H_9$ | $CH_3$ |
| Cl | H | 6-$OCH_3$ | t-$C_4H_9$ | $CH_3$ |
| Cl | H | 6-$OCH_3$ | $C_2H_5$ | $C_2H_5$ |
| Cl | H | 6-$OCH_3$ | $C_3H_7$ | $C_3H_7$ |
| Cl | H | 6-$OCH_3$ | 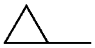 | $CH_3$ |
| Cl | H | 6-$OCH_3$ | 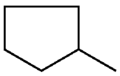 | $CH_3$ |
| Cl | H | 6-$OCH_3$ | 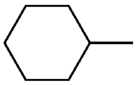 | $CH_3$ |
| $OCH_3$ | Cl | H | $CH_3$ | H |
| $OCH_3$ | Cl | H | $C_2H_5$ | H |
| $OCH_3$ | Cl | H | $C_3H_7$ | H |
| $OCH_3$ | Cl | H | i-$C_3H_7$ | H |
| $OCH_3$ | Cl | H | $C_4H_9$ | H |
| $OCH_3$ | Cl | H | i-$C_4H_9$ | H |
| $OCH_3$ | Cl | H | s-$C_4H_9$ | H |
| $OCH_3$ | Cl | H | t-$C_4H_9$ | H |
| $OCH_3$ | Cl | H | $CH_3$ | $CH_3$ |
| $OCH_3$ | Cl | H | $C_2H_5$ | $CH_3$ |
| $OCH_3$ | Cl | H | $C_3H_7$ | $CH_3$ |
| $OCH_3$ | Cl | H | i-$C_3H_7$ | $CH_3$ |
| $OCH_3$ | Cl | H | $C_4H_9$ | $CH_3$ |
| $OCH_3$ | Cl | H | i-$C_4H_9$ | $CH_3$ |
| $OCH_3$ | Cl | H | s-$C_4H_9$ | $CH_3$ |
| $OCH_3$ | Cl | H | t-$C_4H_9$ | $CH_3$ |
| $OCH_3$ | Cl | H | $C_2H_5$ | $C_2H_5$ |
| $OCH_3$ | Cl | H | $C_3H_7$ | $C_3H_7$ |

TABLE 6a-continued (If-a)

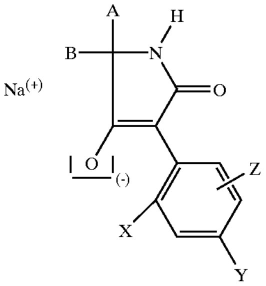

| X | Y | Z | A | B |
|---|---|---|---|---|
| $OCH_3$ | Cl | H | 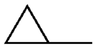 | $CH_3$ |
| $OCH_3$ | Cl | H | 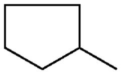 | $CH_3$ |
| $OCH_3$ | Cl | H | 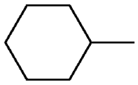 | $CH_3$ |
| Cl | $OCH_3$ | H | $-(CH_2)_2-$ | |
| Cl | $OCH_3$ | H | $-(CH_2)_4-$ | |
| Cl | $OCH_3$ | H | $-(CH_2)_5-$ | |
| Cl | $OCH_3$ | H | $-(CH_2)_6-$ | |
| Cl | $OCH_3$ | H | $-(CH_2)_7-$ | |
| Cl | $OCH_3$ | H | $-(CH_2)_2-O-(CH_2)_2-$ | |
| Cl | $OCH_3$ | H | $-(CH_2)_2-S-(CH_2)_2-$ | |
| Cl | $OCH_3$ | H | $-CH_2-CHCH_3-(CH_2)_3-$ | |
| Cl | $OCH_3$ | H | $-(CH_2)_2-CHCH_3-(CH_2)_2-$ | |
| Cl | $OCH_3$ | H | $-(CH_2)_2-CHC_2H_5-(CH_2)_2-$ | |
| Cl | $OCH_3$ | H | $-(CH_2)_2-CHC_3H_7-(CH_2)_2-$ | |
| Cl | $OCH_3$ | H | $-(CH_2)_2-CHi-C_3H_7-(CH_2)_2-$ | |
| Cl | $OCH_3$ | H | $-(CH_2)_2-CHOCH_3-(CH_2)_2-$ | |
| Cl | $OCH_3$ | H | $-(CH_2)_2-CHOC_2H_5-(CH_2)_2-$ | |
| Cl | $OCH_3$ | H | $-(CH_2)_2-CHOC_3H_7-(CH_2)_2-$ | |
| Cl | $OCH_3$ | H | $-(CH_2)_2-CHi-OC_3H_7-(CH_2)_2-$ | |
| Cl | $OCH_3$ | H | $-(CH_2)_2-C(CH_3)_2-(CH_2)_2-$ | |
| Cl | $OCH_3$ | H | $-CH_2-(CHCH_3)_2-(CH_2)_2-$ | |
| Cl | $OCH_3$ | H | 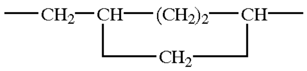 | |
| Cl | $OCH_3$ | H | 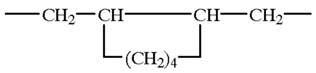 | |
| Cl | $OCH_3$ | H | 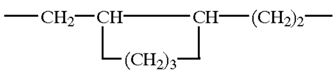 | |
| Cl | H | 6-$OCH_3$ | $-(CH_2)_2-$ | |
| Cl | H | 6-$OCH_3$ | $-(CH_2)_4-$ | |
| Cl | H | 6-$OCH_3$ | $-(CH_2)_5-$ | |
| Cl | H | 6-$OCH_3$ | $-(CH_2)_6-$ | |
| Cl | H | 6-$OCH_3$ | $-(CH_2)_7-$ | |
| Cl | H | 6-$OCH_3$ | $-(CH_2)_2-O-(CH_2)_2-$ | |
| Cl | H | 6-$OCH_3$ | $-(CH_2)_2-S-(CH_2)_2-$ | |
| Cl | H | 6-$OCH_3$ | $-CH_2-CHCH_3-(CH_2)_3-$ | |
| Cl | H | 6-$OCH_3$ | $-(CH_2)_2-CHCH_3-(CH_2)_2-$ | |
| Cl | H | 6-$OCH_3$ | $-(CH_2)_2-CHC_2H_5-(CH_2)_2-$ | |
| Cl | H | 6-$OCH_3$ | $-(CH_2)_2-CHC_3H_7-(CH_2)_2-$ | |
| Cl | H | 6-$OCH_3$ | $-(CH_2)_2-CHi-C_3H_7-(CH_2)_2-$ | |
| Cl | H | 6-$OCH_3$ | $-(CH_2)_2-CHOCH_3-(CH_2)_2-$ | |
| Cl | H | 6-$OCH_3$ | $-(CH_2)_2-CHOC_2H_5-(CH_2)_2-$ | |
| Cl | H | 6-$OCH_3$ | $-(CH_2)_2-CHOC_3H_7-(CH_2)_2-$ | |

TABLE 6a-continued (If-a)

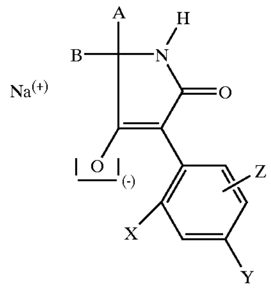

| X | Y | Z | A | B |
|---|---|---|---|---|
| Cl | H | 6-$OCH_3$ | | $-(CH_2)_2-CHi-OC_3H_7-(CH_2)_2-$ |
| Cl | H | 6-$OCH_3$ | | $-(CH_2)_2-C(CH_3)_2-(CH_2)_2-$ |
| Cl | H | 6-$OCH_3$ | | $-CH_2-(CHCH_3)_2-(CH_2)_2-$ |
| Cl | H | 6-$OCH_3$ | | 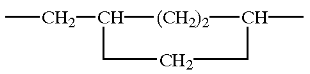 |
| Cl | H | 6-$OCH_3$ | | 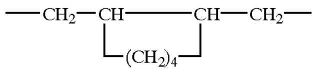 |
| Cl | H | 6-$OCH_3$ | | 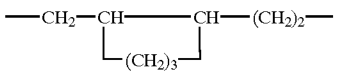 |
| $OCH_3$ | Cl | H | | $-(CH_2)_2-$ |
| $OCH_3$ | Cl | H | | $-(CH_2)_4-$ |
| $OCH_3$ | Cl | H | | $-(CH_2)_5-$ |
| $OCH_3$ | Cl | H | | $-(CH_2)_6-$ |
| $OCH_3$ | Cl | H | | $-(CH_2)_7-$ |
| $OCH_3$ | Cl | H | | $-(CH_2)_2-O-(CH_2)_2-$ |
| $OCH_3$ | Cl | H | | $-(CH_2)_2-S-(CH_2)_2-$ |
| $OCH_3$ | Cl | H | | $-CH_2-CHCH_3-(CH_2)_3-$ |
| $OCH_3$ | Cl | H | | $-(CH_2)_2-CHCH_3-(CH_2)_2-$ |
| $OCH_3$ | Cl | H | | $-(CH_2)_2-CHC_2H_5-(CH_2)_2-$ |
| $OCH_3$ | Cl | H | | $-(CH_2)_2-CHC_3H_7-(CH_2)_2-$ |
| $OCH_3$ | Cl | H | | $-(CH_2)_2-CHi-C_3H_7-(CH_2)_2-$ |
| $OCH_3$ | Cl | H | | $-(CH_2)_2-CHOCH_3-(CH_2)_2-$ |
| $OCH_3$ | Cl | H | | $-(CH_2)_2-CHOC_2H_5-(CH_2)_2-$ |
| $OCH_3$ | Cl | H | | $-(CH_2)_2-CHOC_3H_7-(CH_2)_2-$ |
| $OCH_3$ | Cl | H | | $-(CH_2)_2-CHi-OC_3H_7-(CH_2)_2-$ |
| $OCH_3$ | Cl | H | | $-(CH_2)_2-C(CH_3)_2-(CH_2)_2-$ |
| $OCH_3$ | Cl | H | | $-CH_2-(CHCH_3)_2-(CH_2)_2-$ |
| $OCH_3$ | Cl | H | | 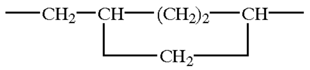 |
| $OCH_3$ | Cl | H | | 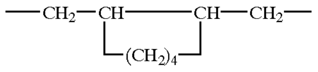 |
| $OCH_3$ | Cl | H | | 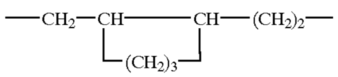 |

The following compounds of the formula (If-b) may be mentioned individually in addition to the compounds mentioned in the preparation examples:

TABLE 6b (If-b)

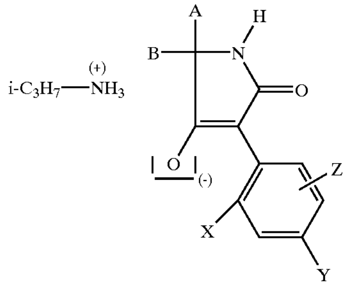

| X | Y | Z | A | B |
|---|---|---|---|---|
| Cl | $OCH_3$ | H | $CH_3$ | H |
| Cl | $OCH_3$ | H | $C_2H_5$ | H |
| Cl | $OCH_3$ | H | $C_3H_7$ | H |
| Cl | $OCH_3$ | H | i-$C_3H_7$ | H |
| Cl | $OCH_3$ | H | $C_4H_9$ | H |
| Cl | $OCH_3$ | H | i-$C_4H_9$ | H |
| Cl | $OCH_3$ | H | s-$C_4H_9$ | H |
| Cl | $OCH_3$ | H | t-$C_4H_9$ | H |
| Cl | $OCH_3$ | H | $CH_3$ | $CH_3$ |
| Cl | $OCH_3$ | H | $C_2H_5$ | $CH_3$ |
| Cl | $OCH_3$ | H | $C_3H_7$ | $CH_3$ |
| Cl | $OCH_3$ | H | i-$C_3H_7$ | $CH_3$ |
| Cl | $OCH_3$ | H | $C_4H_9$ | $CH_3$ |
| Cl | $OCH_3$ | H | i-$C_4H_9$ | $CH_3$ |
| Cl | $OCH_3$ | H | s-$C_4H_9$ | $CH_3$ |
| Cl | $OCH_3$ | H | t-$C_4H_9$ | $CH_3$ |
| Cl | $OCH_3$ | H | $C_2H_5$ | $C_2H_5$ |
| Cl | $OCH_3$ | H | $C_3H_7$ | $C_3H_7$ |
| Cl | $OCH_3$ | H | 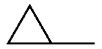 | $CH_3$ |
| Cl | $OCH_3$ | H | 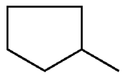 | $CH_3$ |
| Cl | $OCH_3$ | H | 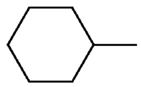 | $CH_3$ |
| Cl | H | 6-$OCH_3$ | $CH_3$ | H |
| Cl | H | 6-$OCH_3$ | $C_2H_5$ | H |
| Cl | H | 6-$OCH_3$ | $C_3H_7$ | H |
| Cl | H | 6-$OCH_3$ | i-$C_3H_7$ | H |
| Cl | H | 6-$OCH_3$ | $C_4H_9$ | H |
| Cl | H | 6-$OCH_3$ | i-$C_4H_9$ | H |
| Cl | H | 6-$OCH_3$ | s-$C_4H_9$ | H |
| Cl | H | 6-$OCH_3$ | t-$C_4H_9$ | H |
| Cl | H | 6-$OCH_3$ | $CH_3$ | $CH_3$ |
| Cl | H | 6-$OCH_3$ | $C_2H_5$ | $CH_3$ |
| Cl | H | 6-$OCH_3$ | $C_3H_7$ | $CH_3$ |
| Cl | H | 6-$OCH_3$ | i-$C_3H_7$ | $CH_3$ |
| Cl | H | 6-$OCH_3$ | $C_4H_9$ | $CH_3$ |
| Cl | H | 6-$OCH_3$ | i-$C_4H_9$ | $CH_3$ |
| Cl | H | 6-$OCH_3$ | s-$C_4H_9$ | $CH_3$ |
| Cl | H | 6-$OCH_3$ | t-$C_4H_9$ | $CH_3$ |
| Cl | H | 6-$OCH_3$ | $C_2H_5$ | $C_2H_5$ |
| Cl | H | 6-$OCH_3$ | $C_3H_7$ | $C_3H_7$ |
| Cl | H | 6-$OCH_3$ | 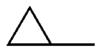 | $CH_3$ |
| Cl | H | 6-$OCH_3$ | 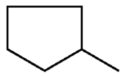 | $CH_3$ |

TABLE 6b-continued (If-b)

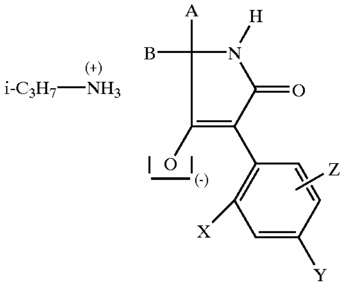

| X | Y | Z | A | B |
|---|---|---|---|---|
| Cl | H | 6-$OCH_3$ | 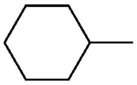 | $CH_3$ |
| $OCH_3$ | Cl | H | $CH_3$ | H |
| $OCH_3$ | Cl | H | $C_2H_5$ | H |
| $OCH_3$ | Cl | H | $C_3H_7$ | H |
| $OCH_3$ | Cl | H | i-$C_3H_7$ | H |
| $OCH_3$ | Cl | H | $C_4H_9$ | H |
| $OCH_3$ | Cl | H | i-$C_4H_9$ | H |
| $OCH_3$ | Cl | H | s-$C_4H_9$ | H |
| $OCH_3$ | Cl | H | t-$C_4H_9$ | H |
| $OCH_3$ | Cl | H | $CH_3$ | $CH_3$ |
| $OCH_3$ | Cl | H | $C_2H_5$ | $CH_3$ |
| $OCH_3$ | Cl | H | $C_3H_7$ | $CH_3$ |
| $OCH_3$ | Cl | H | i-$C_3H_7$ | $CH_3$ |
| $OCH_3$ | Cl | H | $C_4H_9$ | $CH_3$ |
| $OCH_3$ | Cl | H | i-$C_4H_9$ | $CH_3$ |
| $OCH_3$ | Cl | H | s-$C_4H_9$ | $CH_3$ |
| $OCH_3$ | Cl | H | t-$C_4H_9$ | $CH_3$ |
| $OCH_3$ | Cl | H | $C_2H_5$ | $C_2H_5$ |
| $OCH_3$ | Cl | H | $C_3H_7$ | $C_3H_7$ |
| $OCH_3$ | Cl | H | 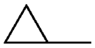 | $CH_3$ |
| $OCH_3$ | Cl | H | 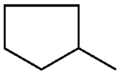 | $CH_3$ |
| $OCH_3$ | Cl | H | 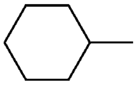 | $CH_3$ |
| Cl | $OCH_3$ | H | $-(CH_2)_2-$ | |
| Cl | $OCH_3$ | H | $-(CH_2)_4-$ | |
| Cl | $OCH_3$ | H | $-(CH_2)_5-$ | |
| Cl | $OCH_3$ | H | $-(CH_2)_6-$ | |
| Cl | $OCH_3$ | H | $-(CH_2)_7-$ | |
| Cl | $OCH_3$ | H | $-(CH_2)_2-O-(CH_2)_2-$ | |
| Cl | $OCH_3$ | H | $-(CH_2)_2-S-(CH_2)_2-$ | |
| Cl | $OCH_3$ | H | $-CH_2-CHCH_3-(CH_2)_3-$ | |
| Cl | $OCH_3$ | H | $-(CH_2)_2-CHCH_3-(CH_2)_2-$ | |
| Cl | $OCH_3$ | H | $-(CH_2)_2-CHC_2H_5-(CH_2)_2-$ | |
| Cl | $OCH_3$ | H | $-(CH_2)_2-CHC_3H_7-(CH_2)_2-$ | |
| Cl | $OCH_3$ | H | $-(CH_2)_2-CHi-C_3H_7-(CH_2)_2-$ | |
| Cl | $OCH_3$ | H | $-(CH_2)_2-CHOCH_3-(CH_2)_2-$ | |
| Cl | $OCH_3$ | H | $-(CH_2)_2-CHOC_2H_5-(CH_2)_2-$ | |
| Cl | $OCH_3$ | H | $-(CH_2)_2-CHOC_3H_7-(CH_2)_2-$ | |
| Cl | $OCH_3$ | H | $-(CH_2)_2-CHi-OC_3H_7-(CH_2)_2-$ | |
| Cl | $OCH_3$ | H | $-(CH_2)_2-C(CH_3)_2-(CH_2)_2-$ | |
| Cl | $OCH_3$ | H | $-CH_2-(CHCH_3)_2-(CH_2)_2-$ | |
| Cl | $OCH_3$ | H | 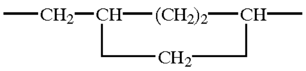 | |

TABLE 6b-continued (If-b)

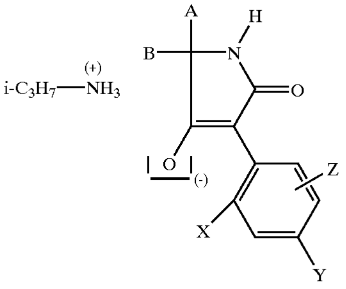

| X | Y | Z | A | B |
|---|---|---|---|---|
| Cl | $OCH_3$ | H | 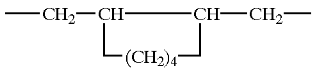 | |
| Cl | $OCH_3$ | H | 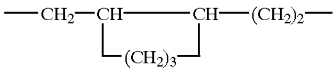 | |
| Cl | H | 6-$OCH_3$ | $-(CH_2)_2-$ | |
| Cl | H | 6-$OCH_3$ | $-(CH_2)_4-$ | |
| Cl | H | 6-$OCH_3$ | $-(CH_2)_5-$ | |
| Cl | H | 6-$OCH_3$ | $-(CH_2)_6-$ | |
| Cl | H | 6-$OCH_3$ | $-(CH_2)_7-$ | |
| Cl | H | 6-$OCH_3$ | $-(CH_2)_2-O-(CH_2)_2-$ | |
| Cl | H | 6-$OCH_3$ | $-(CH_2)_2-S-(CH_2)_2-$ | |
| Cl | H | 6-$OCH_3$ | $-CH_2-CHCH_3-(CH_2)_3-$ | |
| Cl | H | 6-$OCH_3$ | $-(CH_2)_2-CHCH_3-(CH_2)_2-$ | |
| Cl | H | 6-$OCH_3$ | $-(CH_2)_2-CHC_2H_5-(CH_2)_2-$ | |
| Cl | H | 6-$OCH_3$ | $-(CH_2)_2-CHC_3H_7-(CH_2)_2-$ | |
| Cl | H | 6-$OCH_3$ | $-(CH_2)_2-CHi-C_3H_7-(CH_2)_2-$ | |
| Cl | H | 6-$OCH_3$ | $-(CH_2)_2-CHOCH_3-(CH_2)_2-$ | |
| Cl | H | 6-$OCH_3$ | $-(CH_2)_2-CHOC_2H_5-(CH_2)_2-$ | |
| Cl | H | 6-$OCH_3$ | $-(CH_2)_2-CHOC_3H_7-(CH_2)_2-$ | |
| Cl | H | 6-$OCH_3$ | $-(CH_2)_2-CHi-OC_3H_7-(CH_2)_2-$ | |
| Cl | H | 6-$OCH_3$ | $-(CH_2)_2-C(CH_3)_2-(CH_2)_2-$ | |
| Cl | H | 6-$OCH_3$ | $-CH_2-(CHCH_3)_2-(CH_2)_2-$ | |
| Cl | H | 6-$OCH_3$ | 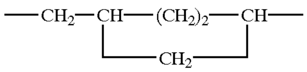 | |
| Cl | H | 6-$OCH_3$ | 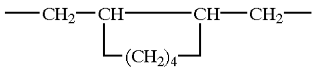 | |
| Cl | H | 6-$OCH_3$ | 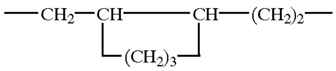 | |
| $OCH_3$ | Cl | H | $-(CH_2)_2-$ | |
| $OCH_3$ | Cl | H | $-(CH_2)_4-$ | |
| $OCH_3$ | Cl | H | $-(CH_2)_5-$ | |
| $OCH_3$ | Cl | H | $-(CH_2)_6-$ | |
| $OCH_3$ | Cl | H | $-(CH_2)_7-$ | |
| $OCH_3$ | Cl | H | $-(CH_2)_2-O-(CH_2)_2-$ | |
| $OCH_3$ | Cl | H | $-(CH_2)_2-S-(CH_2)_2-$ | |
| $OCH_3$ | Cl | H | $-CH_2-CHCH_3-(CH_2)_3-$ | |
| $OCH_3$ | Cl | H | $-(CH_2)_2-CHCH_3-(CH_2)_2-$ | |
| $OCH_3$ | Cl | H | $-(CH_2)_2-CHC_2H_5-(CH_2)_2-$ | |
| $OCH_3$ | Cl | H | $-(CH_2)_2-CHC_3H_7-(CH_2)_2-$ | |
| $OCH_3$ | Cl | H | $-(CH_2)_2-CHi-C_3H_7-(CH_2)_2-$ | |
| $OCH_3$ | Cl | H | $-(CH_2)_2-CHOCH_3-(CH_2)_2-$ | |
| $OCH_3$ | Cl | H | $-(CH_2)_2-CHOC_2H_5-(CH_2)_2-$ | |
| $OCH_3$ | Cl | H | $-(CH_2)_2-CHOC_3H_7-(CH_2)_2-$ | |
| $OCH_3$ | Cl | H | $-(CH_2)_2-CHi-OC_3H_7-(CH_2)_2-$ | |
| $OCH_3$ | Cl | H | $-(CH_2)_2-C(CH_3)_2-(CH_2)_2-$ | |
| $OCH_3$ | Cl | H | $-CH_2-(CHCH_3)_2-(CH_2)_2-$ | |

TABLE 6b-continued (If-b)

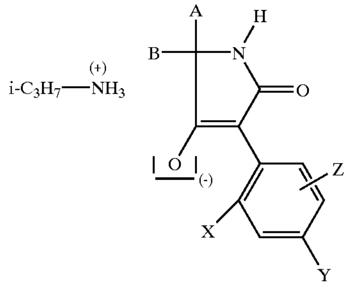

| X | Y | Z | A | B |
|---|---|---|---|---|
| $OCH_3$ | Cl | H | 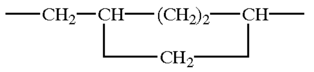 | |
| $OCH_3$ | Cl | H | 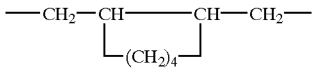 | |
| $OCH_3$ | Cl | H | 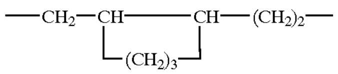 | |

The following compounds of the formula (Ig-a) may be mentioned individually in addition to the compounds mentioned in the preparation examples:

TABLE 7a (Ig-a)

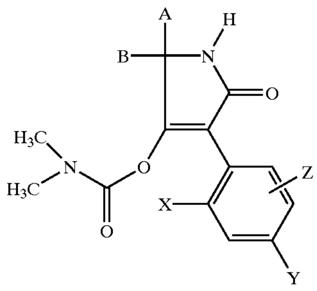

| X | Y | Z | A | B |
|---|---|---|---|---|
| Cl | $OCH_3$ | H | $CH_3$ | H |
| Cl | $OCH_3$ | H | $C_2H_5$ | H |
| Cl | $OCH_3$ | H | $C_3H_7$ | H |
| Cl | $OCH_3$ | H | $i-C_3H_7$ | H |
| Cl | $OCH_3$ | H | $C_4H_9$ | H |
| Cl | $OCH_3$ | H | $i-C_4H_9$ | H |
| Cl | $OCH_3$ | H | $s-C_4H_9$ | H |
| Cl | $OCH_3$ | H | $t-C_4H_9$ | H |
| Cl | $OCH_3$ | H | $CH_3$ | $CH_3$ |
| Cl | $OCH_3$ | H | $C_2H_5$ | $CH_3$ |
| Cl | $OCH_3$ | H | $C_3H_7$ | $CH_3$ |
| Cl | $OCH_3$ | H | $i-C_3H_7$ | $CH_3$ |
| Cl | $OCH_3$ | H | $C_4H_9$ | $CH_3$ |
| Cl | $OCH_3$ | H | $i-C_4H_9$ | $CH_3$ |
| Cl | $OCH_3$ | H | $s-C_4H_9$ | $CH_3$ |
| Cl | $OCH_3$ | H | $t-C_4H_9$ | $CH_3$ |
| Cl | $OCH_3$ | H | $C_2H_5$ | $C_2H_5$ |
| Cl | $OCH_3$ | H | $C_3H_7$ | $C_3H_7$ |
| Cl | $OCH_3$ | H | 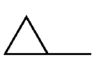 | $CH_3$ |

TABLE 7a-continued (Ig-a)

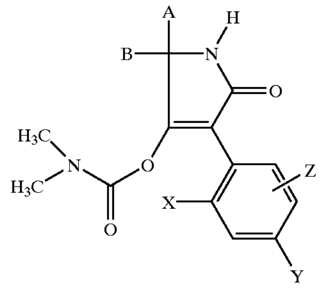

| X | Y | Z | A | B |
|---|---|---|---|---|
| Cl | $OCH_3$ | H | 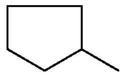 | $CH_3$ |
| Cl | $OCH_3$ | H | 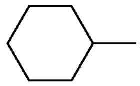 | $CH_3$ |
| Cl | H | $6-OCH_3$ | $CH_3$ | H |
| Cl | H | $6-OCH_3$ | $C_2H_5$ | H |
| Cl | H | $6-OCH_3$ | $C_3H_7$ | H |
| Cl | H | $6-OCH_3$ | $i-C_3H_7$ | H |
| Cl | H | $6-OCH_3$ | $C_4H_9$ | H |
| Cl | H | $6-OCH_3$ | $i-C_4H_9$ | H |
| Cl | H | $6-OCH_3$ | $s-C_4H_9$ | H |
| Cl | H | $6-OCH_3$ | $t-C_4H_9$ | H |
| Cl | H | $6-OCH_3$ | $CH_3$ | $CH_3$ |
| Cl | H | $6-OCH_3$ | $C_2H_5$ | $CH_3$ |
| Cl | H | $6-OCH_3$ | $C_3H_7$ | $CH_3$ |
| Cl | H | $6-OCH_3$ | $i-C_3H_7$ | $CH_3$ |
| Cl | H | $6-OCH_3$ | $C_4H_9$ | $CH_3$ |
| Cl | H | $6-OCH_3$ | $i-C_4H_9$ | $CH_3$ |
| Cl | H | $6-OCH_3$ | $s-C_4H_9$ | $CH_3$ |
| Cl | H | $6-OCH_3$ | $t-C_4H_9$ | $CH_3$ |
| Cl | H | $6-OCH_3$ | $C_2H_5$ | $C_2H_5$ |
| Cl | H | $6-OCH_3$ | $C_3H_7$ | $C_3H_7$ |
| Cl | H | $6-OCH_3$ | 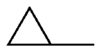 | $CH_3$ |
| Cl | H | $6-OCH_3$ | 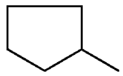 | $CH_3$ |
| Cl | H | $6-OCH_3$ | 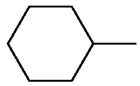 | $CH_3$ |
| $OCH_3$ | Cl | H | $CH_3$ | H |
| $OCH_3$ | Cl | H | $C_2H_5$ | H |
| $OCH_3$ | Cl | H | $C_3H_7$ | H |
| $OCH_3$ | Cl | H | $i-C_3H_7$ | H |
| $OCH_3$ | Cl | H | $C_4H_9$ | H |
| $OCH_3$ | Cl | H | $i-C_4H_9$ | H |
| $OCH_3$ | Cl | H | $s-C_4H_9$ | H |
| $OCH_3$ | Cl | H | $t-C_4H_9$ | H |
| $OCH_3$ | Cl | H | $CH_3$ | $CH_3$ |
| $OCH_3$ | Cl | H | $C_2H_5$ | $CH_3$ |
| $OCH_3$ | Cl | H | $C_3H_7$ | $CH_3$ |
| $OCH_3$ | Cl | H | $i-C_3H_7$ | $CH_3$ |
| $OCH_3$ | Cl | H | $C_4H_9$ | $CH_3$ |
| $OCH_3$ | Cl | H | $i-C_4H_9$ | $CH_3$ |
| $OCH_3$ | Cl | H | $s-C_4H_9$ | $CH_3$ |
| $OCH_3$ | Cl | H | $t-C_4H_9$ | $CH_3$ |
| $OCH_3$ | Cl | H | $C_2H_5$ | $C_2H_5$ |
| $OCH_3$ | Cl | H | $C_3H_7$ | $C_3H_7$ |

TABLE 7a-continued (Ig-a)

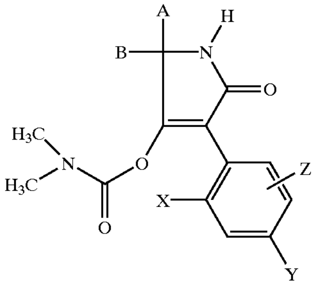

| X | Y | Z | A | B |
|---|---|---|---|---|
| $OCH_3$ | Cl | H | 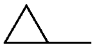 | $CH_3$ |
| $OCH_3$ | Cl | H | 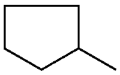 | $CH_3$ |
| $OCH_3$ | Cl | H | 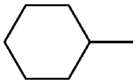 | $CH_3$ |
| Cl | $OCH_3$ | H | $-(CH_2)_2-$ | |
| Cl | $OCH_3$ | H | $-(CH_2)_4-$ | |
| Cl | $OCH_3$ | H | $-(CH_2)_5-$ | |
| Cl | $OCH_3$ | H | $-(CH_2)_6-$ | |
| Cl | $OCH_3$ | H | $-(CH_2)_7-$ | |
| Cl | $OCH_3$ | H | $-(CH_2)_2-O-(CH_2)_2-$ | |
| Cl | $OCH_3$ | H | $-(CH_2)_2-S-(CH_2)_2-$ | |
| Cl | $OCH_3$ | H | $-CH_2-CHCH_3-(CH_2)_3-$ | |
| Cl | $OCH_3$ | H | $-(CH_2)_2-CHCH_3-(CH_2)_2-$ | |
| Cl | $OCH_3$ | H | $-(CH_2)_2-CHC_2H_5-(CH_2)_2-$ | |
| Cl | $OCH_3$ | H | $-(CH_2)_2-CHC_3H_7-(CH_2)_2-$ | |
| Cl | $OCH_3$ | H | $-(CH_2)_2-CHi-C_3H_7-(CH_2)_2-$ | |
| Cl | $OCH_3$ | H | $-(CH_2)_2-CHOCH_3-(CH_2)_2-$ | |
| Cl | $OCH_3$ | H | $-(CH_2)_2-CHOC_2H_5-(CH_2)_2-$ | |
| Cl | $OCH_3$ | H | $-(CH_2)_2-CHOC_3H_7-(CH_2)_2-$ | |
| Cl | $OCH_3$ | H | $-(CH_2)_2-CHi-OC_3H_7-(CH_2)_2-$ | |
| Cl | $OCH_3$ | H | $-(CH_2)_2-C(CH_3)_2-(CH_2)_2-$ | |
| Cl | $OCH_3$ | H | $-CH_2-(CHCH_3)_2-(CH_2)_2-$ | |
| Cl | $OCH_3$ | H | 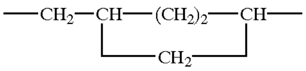 | |
| Cl | $OCH_3$ | H | 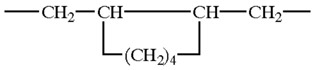 | |
| Cl | $OCH_3$ | H | 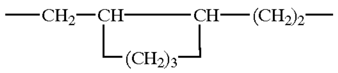 | |
| Cl | H | 6-$OCH_3$ | $-(CH_2)_2-$ | |
| Cl | H | 6-$OCH_3$ | $-(CH_2)_4-$ | |
| Cl | H | 6-$OCH_3$ | $-(CH_2)_5-$ | |
| Cl | H | 6-$OCH_3$ | $-(CH_2)_6-$ | |
| Cl | H | 6-$OCH_3$ | $-(CH_2)_7-$ | |
| Cl | H | 6-$OCH_3$ | $-(CH_2)_2-O-(CH_2)_2-$ | |
| Cl | H | 6-$OCH_3$ | $-(CH_2)_2-S-(CH_2)_2-$ | |
| Cl | H | 6-$OCH_3$ | $-CH_2-CHCH_3-(CH_2)_3-$ | |
| Cl | H | 6-$OCH_3$ | $-(CH_2)_2-CHCH_3-(CH_2)_2-$ | |
| Cl | H | 6-$OCH_3$ | $-(CH_2)_2-CHC_2H_5-(CH_2)_2-$ | |
| Cl | H | 6-$OCH_3$ | $-(CH_2)_2-CHC_3H_7-(CH_2)_2-$ | |
| Cl | H | 6-$OCH_3$ | $-(CH_2)_2-CHi-C_3H_7-(CH_2)_2-$ | |
| Cl | H | 6-$OCH_3$ | $-(CH_2)_2-CHOCH_3-(CH_2)_2-$ | |
| Cl | H | 6-$OCH_3$ | $-(CH_2)_2-CHOC_2H_5-(CH_2)_2-$ | |
| Cl | H | 6-$OCH_3$ | $-(CH_2)_2-CHOC_3H_7-(CH_2)_2-$ | |
| Cl | H | 6-$OCH_3$ | $-(CH_2)_2-CHi-OC_3H_7-(CH_2)_2-$ | |

TABLE 7a-continued (Ig-a)

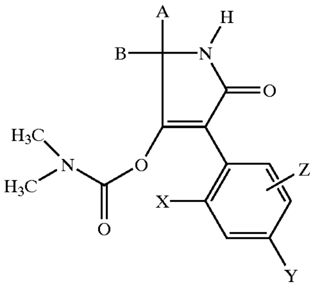

| X | Y | Z | A | B |
|---|---|---|---|---|
| Cl | H | 6-$OCH_3$ | $-(CH_2)_2-C(CH_3)_2-(CH_2)_2-$ | |
| Cl | H | 6-$OCH_3$ | $-CH_2-(CHCH_3)_2-(CH_2)_2-$ | |
| Cl | H | 6-$OCH_3$ | 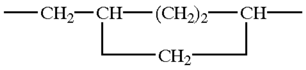 | |
| Cl | H | 6-$OCH_3$ | 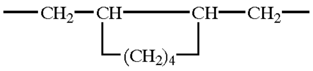 | |
| Cl | H | 6-$OCH_3$ | 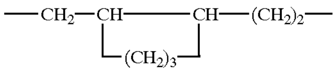 | |
| $OCH_3$ | Cl | H | $-(CH_2)_2-$ | |
| $OCH_3$ | Cl | H | $-(CH_2)_4-$ | |
| $OCH_3$ | Cl | H | $-(CH_2)_5-$ | |
| $OCH_3$ | Cl | H | $-(CH_2)_6-$ | |
| $OCH_3$ | Cl | H | $-(CH_2)_7-$ | |
| $OCH_3$ | Cl | H | $-(CH_2)_2-O-(CH_2)_2-$ | |
| $OCH_3$ | Cl | H | $-(CH_2)_2-S-(CH_2)_2-$ | |
| $OCH_3$ | Cl | H | $-CH_2-CHCH_3-(CH_2)_3-$ | |
| $OCH_3$ | Cl | H | $-(CH_2)_2-CHCH_3-(CH_2)_2-$ | |
| $OCH_3$ | Cl | H | $-(CH_2)_2-CHC_2H_5-(CH_2)_2-$ | |
| $OCH_3$ | Cl | H | $-(CH_2)_2-CHC_3H_7-(CH_2)_2-$ | |
| $OCH_3$ | Cl | H | $-(CH_2)_2-CHi-C_3H_7-(CH_2)_2-$ | |
| $OCH_3$ | Cl | H | $-(CH_2)_2-CHOCH_3-(CH_2)_2-$ | |
| $OCH_3$ | Cl | H | $-(CH_2)_2-CHOC_2H_5-(CH_2)_2-$ | |
| $OCH_3$ | Cl | H | $-(CH_2)_2-CHOC_3H_7-(CH_2)_2-$ | |
| $OCH_3$ | Cl | H | $-(CH_2)_2-CHi-OC_3H_7-(CH_2)_2-$ | |
| $OCH_3$ | Cl | H | $-(CH_2)_2-C(CH_3)_2-(CH_2)_2-$ | |
| $OCH_3$ | Cl | H | $-CH_2-(CHCH_3)_2-(CH_2)_2-$ | |
| $OCH_3$ | Cl | H | 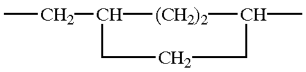 | |
| $OCH_3$ | Cl | H | 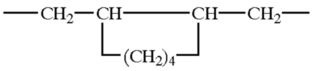 | |
| $OCH_3$ | Cl | H | 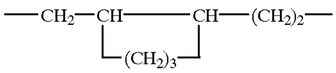 | |

The following compounds of the formula (Ig-b) may be mentioned individually in addition to the compounds mentioned in the preparation examples:

TABLE 7b (Ig-b)

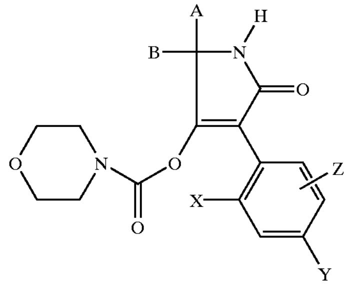

| X | Y | Z | A | B |
|---|---|---|---|---|
| Cl | $OCH_3$ | H | $CH_3$ | H |
| Cl | $OCH_3$ | H | $C_2H_5$ | H |
| Cl | $OCH_3$ | H | $C_3H_7$ | H |
| Cl | $OCH_3$ | H | i-$C_3H_7$ | H |
| Cl | $OCH_3$ | H | $C_4H_9$ | H |
| Cl | $OCH_3$ | H | i-$C_4H_9$ | H |
| Cl | $OCH_3$ | H | s-$C_4H_9$ | H |
| Cl | $OCH_3$ | H | t-$C_4H_9$ | H |
| Cl | $OCH_3$ | H | $CH_3$ | $CH_3$ |
| Cl | $OCH_3$ | H | $C_2H_5$ | $CH_3$ |
| Cl | $OCH_3$ | H | $C_3H_7$ | $CH_3$ |
| Cl | $OCH_3$ | H | i-$C_3H_7$ | $CH_3$ |
| Cl | $OCH_3$ | H | $C_4H_9$ | $CH_3$ |
| Cl | $OCH_3$ | H | i-$C_4H_9$ | $CH_3$ |
| Cl | $OCH_3$ | H | s-$C_4H_9$ | $CH_3$ |
| Cl | $OCH_3$ | H | t-$C_4H_9$ | $CH_3$ |
| Cl | $OCH_3$ | H | $C_2H_5$ | $C_2H_5$ |
| Cl | $OCH_3$ | H | $C_3H_7$ | $C_3H_7$ |
| Cl | $OCH_3$ | H | 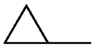 | $CH_3$ |
| Cl | $OCH_3$ | H | 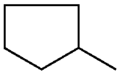 | $CH_3$ |
| Cl | $OCH_3$ | H | 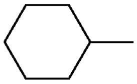 | $CH_3$ |
| Cl | H | 6-$OCH_3$ | $CH_3$ | H |
| Cl | H | 6-$OCH_3$ | $C_2H_5$ | H |
| Cl | H | 6-$OCH_3$ | $C_3H_7$ | H |
| Cl | H | 6-$OCH_3$ | i-$C_3H_7$ | H |
| Cl | H | 6-$OCH_3$ | $C_4H_9$ | H |
| Cl | H | 6-$OCH_3$ | i-$C_4H_9$ | H |
| Cl | H | 6-$OCH_3$ | s-$C_4H_9$ | H |
| Cl | H | 6-$OCH_3$ | t-$C_4H_9$ | H |
| Cl | H | 6-$OCH_3$ | $CH_3$ | $CH_3$ |
| Cl | H | 6-$OCH_3$ | $C_2H_5$ | $CH_3$ |
| Cl | H | 6-$OCH_3$ | $C_3H_7$ | $CH_3$ |
| Cl | H | 6-$OCH_3$ | i-$C_3H_7$ | $CH_3$ |
| Cl | H | 6-$OCH_3$ | $C_4H_9$ | $CH_3$ |
| Cl | H | 6-$OCH_3$ | i-$C_4H_9$ | $CH_3$ |
| Cl | H | 6-$OCH_3$ | s-$C_4H_9$ | $CH_3$ |
| Cl | H | 6-$OCH_3$ | t-$C_4H_9$ | $CH_3$ |
| Cl | H | 6-$OCH_3$ | $C_2H_5$ | $C_2H_5$ |
| Cl | H | 6-$OCH_3$ | $C_3H_7$ | $C_3H_7$ |
| Cl | H | 6-$OCH_3$ | 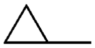 | $CH_3$ |
| Cl | H | 6-$OCH_3$ | 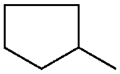 | $CH_3$ |

TABLE 7b-continued (Ig-b)

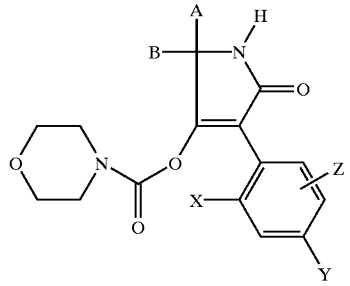

| X | Y | Z | A | B |
|---|---|---|---|---|
| Cl | H | 6-$OCH_3$ | 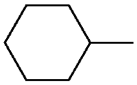 | $CH_3$ |
| $OCH_3$ | Cl | H | $CH_3$ | H |
| $OCH_3$ | Cl | H | $C_2H_5$ | H |
| $OCH_3$ | Cl | H | $C_3H_7$ | H |
| $OCH_3$ | Cl | H | i-$C_3H_7$ | H |
| $OCH_3$ | Cl | H | $C_4H_9$ | H |
| $OCH_3$ | Cl | H | i-$C_4H_9$ | H |
| $OCH_3$ | Cl | H | s-$C_4H_9$ | H |
| $OCH_3$ | Cl | H | t-$C_4H_9$ | H |
| $OCH_3$ | Cl | H | $CH_3$ | $CH_3$ |
| $OCH_3$ | Cl | H | $C_2H_5$ | $CH_3$ |
| $OCH_3$ | Cl | H | $C_3H_7$ | $CH_3$ |
| $OCH_3$ | Cl | H | i-$C_3H_7$ | $CH_3$ |
| $OCH_3$ | Cl | H | $C_4H_9$ | $CH_3$ |
| $OCH_3$ | Cl | H | i-$C_4H_9$ | $CH_3$ |
| $OCH_3$ | Cl | H | s-$C_4H_9$ | $CH_3$ |
| $OCH_3$ | Cl | H | t-$C_4H_9$ | $CH_3$ |
| $OCH_3$ | Cl | H | $C_2H_5$ | $C_2H_5$ |
| $OCH_3$ | Cl | H | $C_3H_7$ | $C_3H_7$ |
| $OCH_3$ | Cl | H | 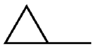 | $CH_3$ |
| $OCH_3$ | Cl | H | 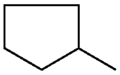 | $CH_3$ |
| $OCH_3$ | Cl | H | 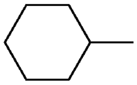 | $CH_3$ |
| Cl | $OCH_3$ | H | $-(CH_2)_2-$ | |
| Cl | $OCH_3$ | H | $-(CH_2)_4-$ | |
| Cl | $OCH_3$ | H | $-(CH_2)_5-$ | |
| Cl | $OCH_3$ | H | $-(CH_2)_6-$ | |
| Cl | $OCH_3$ | H | $-(CH_2)_7-$ | |
| Cl | $OCH_3$ | H | $-(CH_2)_2-O-(CH_2)_2-$ | |
| Cl | $OCH_3$ | H | $-(CH_2)_2-S-(CH_2)_2-$ | |
| Cl | $OCH_3$ | H | $-CH_2-CHCH_3-(CH_2)_3-$ | |
| Cl | $OCH_3$ | H | $-(CH_2)_2-CHCH_3-(CH_2)_2-$ | |
| Cl | $OCH_3$ | H | $-(CH_2)_2-CHC_2H_5-(CH_2)_2-$ | |
| Cl | $OCH_3$ | H | $-(CH_2)_2-CHC_3H_7-(CH_2)_2-$ | |
| Cl | $OCH_3$ | H | $-(CH_2)_2-CHi-C_3H_7-(CH_2)_2-$ | |
| Cl | $OCH_3$ | H | $-(CH_2)_2-CHOCH_3-(CH_2)_2-$ | |
| Cl | $OCH_3$ | H | $-(CH_2)_2-CHOC_2H_5-(CH_2)_2-$ | |
| Cl | $OCH_3$ | H | $-(CH_2)_2-CHOC_3H_7-(CH_2)_2-$ | |
| Cl | $OCH_3$ | H | $-(CH_2)_2-CHi-OC_3H_7-(CH_2)_2-$ | |
| Cl | $OCH_3$ | H | $-(CH_2)_2-C(CH_3)_2-(CH_2)_2-$ | |
| Cl | $OCH_3$ | H | $-CH_2-(CHCH_3)_2-(CH_2)_2-$ | |
| Cl | $OCH_3$ | H | 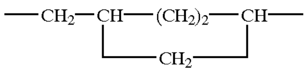 | |

TABLE 7b-continued (Ig-b)

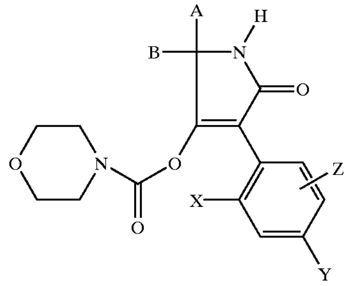

| X | Y | Z | A | B |
|---|---|---|---|---|
| Cl | $OCH_3$ | H | | 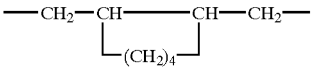 |
| Cl | $OCH_3$ | H | | 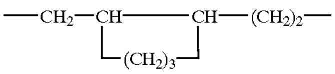 |
| Cl | H | 6-$OCH_3$ | | $-(CH_2)_2-$ |
| Cl | H | 6-$OCH_3$ | | $-(CH_2)_4-$ |
| Cl | H | 6-$OCH_3$ | | $-(CH_2)_5-$ |
| Cl | H | 6-$OCH_3$ | | $-(CH_2)_6-$ |
| Cl | H | 6-$OCH_3$ | | $-(CH_2)_7-$ |
| Cl | H | 6-$OCH_3$ | | $-(CH_2)_2-O-(CH_2)_2-$ |
| Cl | H | 6-$OCH_3$ | | $-(CH_2)_2-S-(CH_2)_2-$ |
| Cl | H | 6-$OCH_3$ | | $-CH_2-CHCH_3-(CH_2)_3-$ |
| Cl | H | 6-$OCH_3$ | | $-(CH_2)_2-CHCH_3-(CH_2)_2-$ |
| Cl | H | 6-$OCH_3$ | | $-(CH_2)_2-CHC_2H_5-(CH_2)_2-$ |
| Cl | H | 6-$OCH_3$ | | $-(CH_2)_2-CHC_3H_7-(CH_2)_2-$ |
| Cl | H | 6-$OCH_3$ | | $-(CH_2)_2-CHi-C_3H_7-(CH_2)_2-$ |
| Cl | H | 6-$OCH_3$ | | $-(CH_2)_2-CHOCH_3-(CH_2)_2-$ |
| Cl | H | 6-$OCH_3$ | | $-(CH_2)_2-CHOC_2H_5-(CH_2)_2-$ |
| Cl | H | 6-$OCH_3$ | | $-(CH_2)_2-CHOC_3H_7-(CH_2)_2-$ |
| Cl | H | 6-$OCH_3$ | | $-(CH_2)_2-CHi-OC_3H_7-(CH_2)_2-$ |
| Cl | H | 6-$OCH_3$ | | $-(CH_2)_2-C(CH_3)_2-(CH_2)_2-$ |
| Cl | H | 6-$OCH_3$ | | $-CH_2-(CHCH_3)_2-(CH_2)_2-$ |
| Cl | H | 6-$OCH_3$ | | 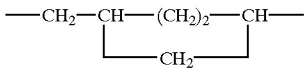 |
| Cl | H | 6-$OCH_3$ | | 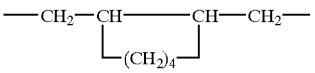 |
| Cl | H | 6-$OCH_3$ | | 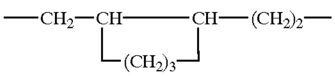 |
| $OCH_3$ | Cl | H | | $-(CH_2)_2-$ |
| $OCH_3$ | Cl | H | | $-(CH_2)_4-$ |
| $OCH_3$ | Cl | H | | $-(CH_2)_5-$ |
| $OCH_3$ | Cl | H | | $-(CH_2)_6-$ |
| $OCH_3$ | Cl | H | | $-(CH_2)_7-$ |
| $OCH_3$ | Cl | H | | $-(CH_2)_2-O-(CH_2)_2-$ |
| $OCH_3$ | Cl | H | | $-(CH_2)_2-S-(CH_2)_2-$ |
| $OCH_3$ | Cl | H | | $-CH_2-CHCH_3-(CH_2)_3-$ |
| $OCH_3$ | Cl | H | | $-(CH_2)_2-CHCH_3-(CH_2)_2-$ |
| $OCH_3$ | Cl | H | | $-(CH_2)_2-CHC_2H_5-(CH_2)_2-$ |
| $OCH_3$ | Cl | H | | $-(CH_2)_2-CHC_3H_7-(CH_2)_2-$ |
| $OCH_3$ | Cl | H | | $-(CH_2)_2-CHi-C_3H_7-(CH_2)_2-$ |
| $OCH_3$ | Cl | H | | $-(CH_2)_2-CHOCH_3-(CH_2)_2-$ |
| $OCH_3$ | Cl | H | | $-(CH_2)_2-CHOC_2H_5-(CH_2)_2-$ |
| $OCH_3$ | Cl | H | | $-(CH_2)_2-CHOC_3H_7-(CH_2)_2-$ |
| $OCH_3$ | Cl | H | | $-(CH_2)_2-CHi-OC_3H_7-(CH_2)_2-$ |
| $OCH_3$ | Cl | H | | $-(CH_2)_2-C(CH_3)_2-(CH_2)_2-$ |
| $OCH_3$ | Cl | H | | $-CH_2-(CHCH_3)_2-(CH_2)_2-$ |

TABLE 7b-continued (Ig-b)

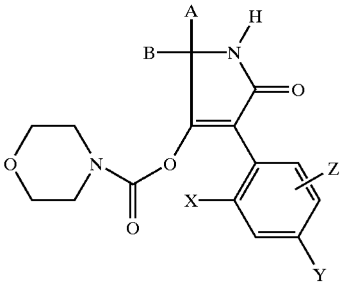

| X | Y | Z | A | B |
|---|---|---|---|---|
| $OCH_3$ | Cl | H | | 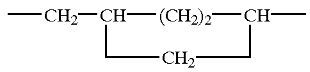 |
| $OCH_3$ | Cl | H | | 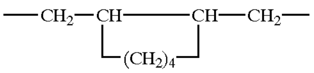 |
| $OCH_3$ | Cl | H | | 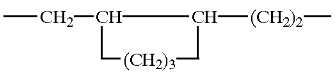 |

If, in accordance with process ($A_\alpha$), ethyl N-(2-chloro-4-methoxyphenylacetyl)-1-amino-4-ethyl-cyclohexanecarboxylate is used as starting substance, the course of the process according to the invention can be represented by the following equation:

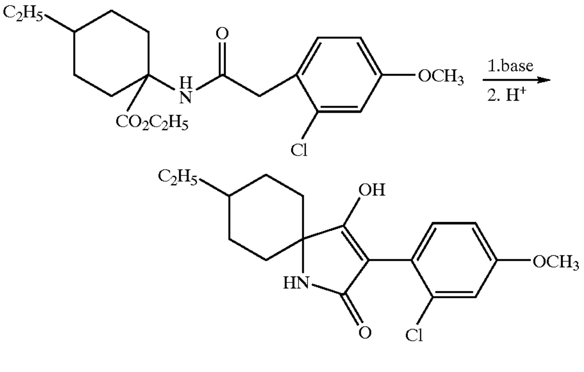

If, in accordance with process ($A_\beta$), methyl N-(2-chloro-4-fluorophenylacetyl)-2-amino-2,3-dimethyl-butyrate is used as starting substance, the course of the process according to the invention can be represented by the following equation:

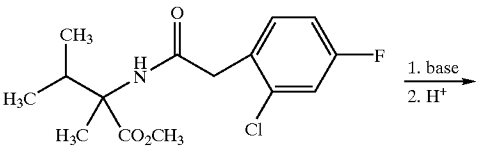

-continued

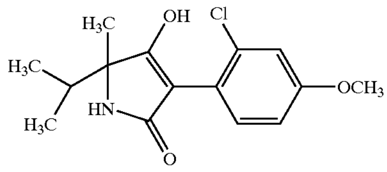

If, in accordance with process ($B_\alpha$), 3-(2-chloro-6-methoxyphenyl-5,5-dimethyl-pyrrolidine-2,4-dione and pivaloyl chloride are used as starting substances, the course of the process according to the invention can be represented by the following equation:

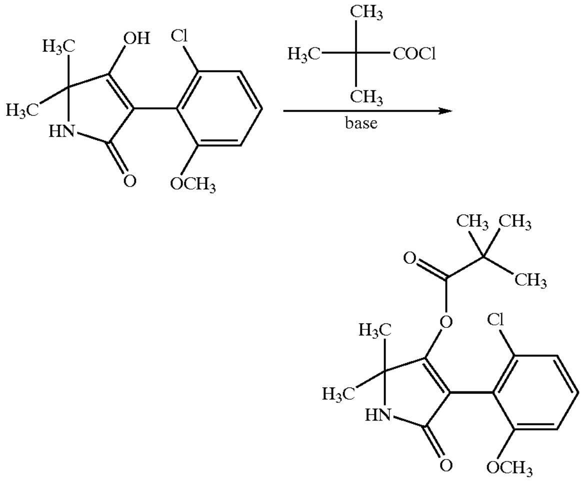

If, in accordance with process ($B_\beta$), 3-(2-bromo-6-methoxyphenyl)-5-isopropyl-5-methyl-pyrrolidine-2,4-dione and acetic anhydride are used as starting compounds, the course of the process according to the invention can be represented by the following equation:

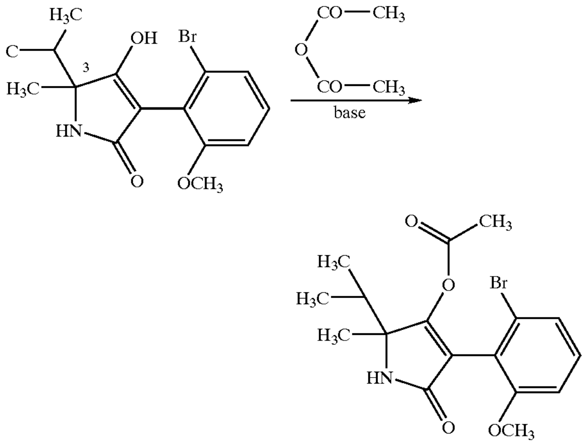

If, in accordance with process (C), 3-(2-methoxy-2-chlorophenyl)-5,5-diethyl-pyrrolidine-2,4-dione and ethoxyethyl chloroformate are used as starting compounds, the course of the process according to the invention can be represented by the following equation:

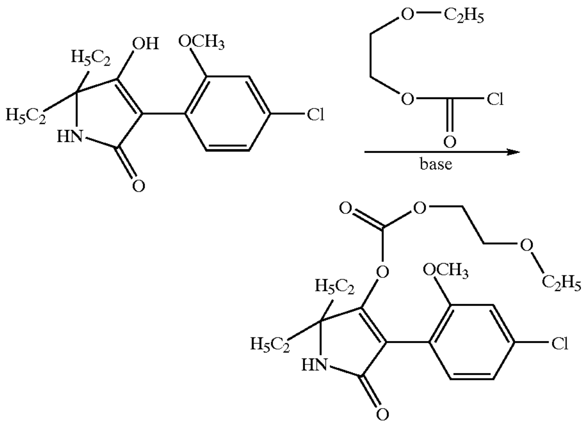

If, in accordance with process ($D_\alpha$), 3-(2-chloro-4-methoxyphenyl)-5,5-pentamethylene-pyrrolidine-2,4-dione and methyl chloromonothioformate are used as starting materials, the course of the reaction can be represented as follows:

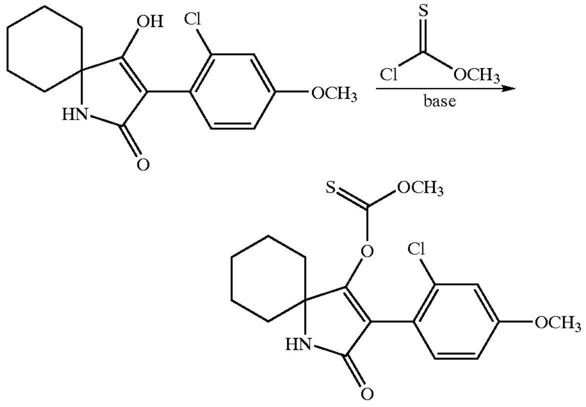

If, in accordance with process ($D_\beta$), 3-(2-bromo-4-ethoxyphenyl)-5,5-ethylmercaptoethyl-pyrrolidine-2,4-dione, carbon disulfide and methyl iodide are used as starting components, the course of the reaction can be represented as follows:

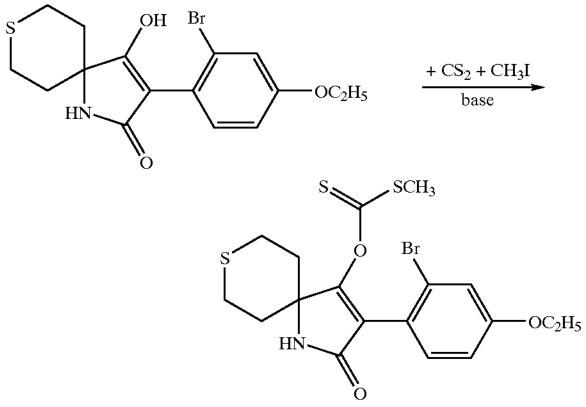

If, in accordance with process (E), 3-(2-chloro-4-isopropoxy-phenyl)-5,5-(2-methyl)-pentamethylenepyrrolidine-2,4-dione and methanesulfonyl chloride are used as starting materials, the course of the reaction can be represented by the following equation:

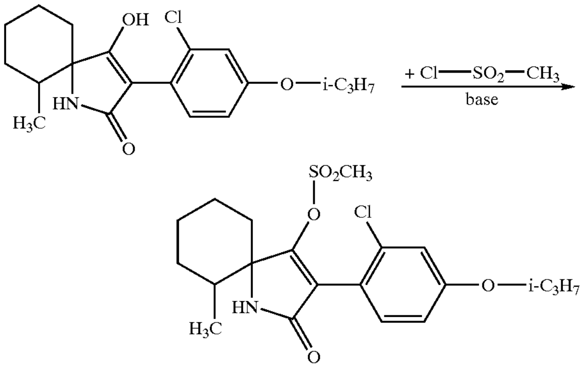

If, in accordance with process (F), 3-(2-methoxy-4-chlorophenyl)-5-isobutyl-5-methyl-pyrrolidine-2,4-dione and 2,2,2-trifluoroethyl methanechlorothiophosphate are used as starting materials, the course of the reaction can be represented by the following equation:

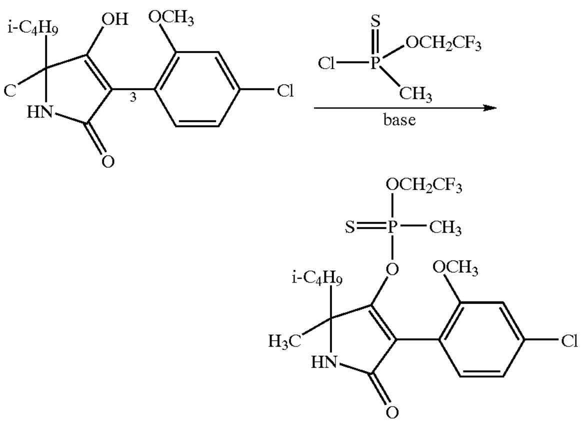

If, in accordance with process (G), 3-(2,4-dimethoxyphenyl)-5-cyclopropyl-5-methyl-pyrrolidine-2,4-dione and NaOH are used as components, the course of the process according to the invention can be represented by the following equation:

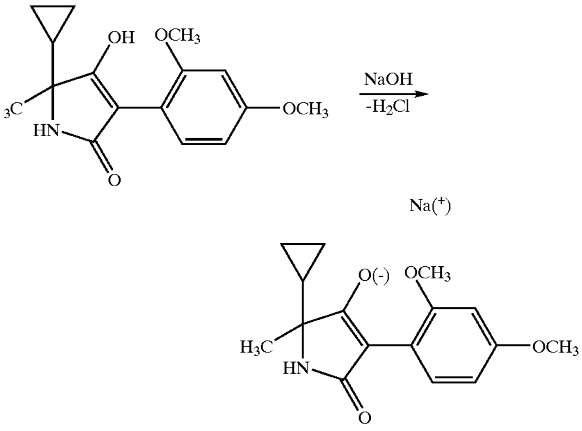

If, in accordance with process ($H_\alpha$), 3-(2-chloro-4-ethoxyphenyl)-5,5-hexamethylene-pyrrolidine-2,4-dione and ethyl isocyanate are used as starting materials, the course of the reaction can be represented by the following equation:

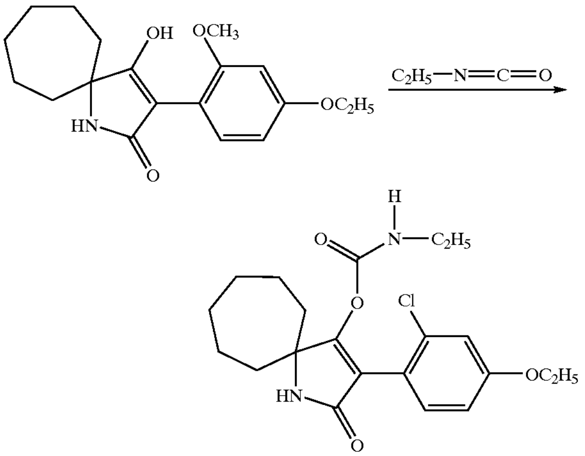

If, in accordance with process ($H_\beta$), 3-(2-methoxy-4-chlorophenyl)-5-methyl-pyrrolidine-2,4-dione and dimethylcarbamoyl chloride are used as starting materials, the course of the reaction can be represented by the following equation:

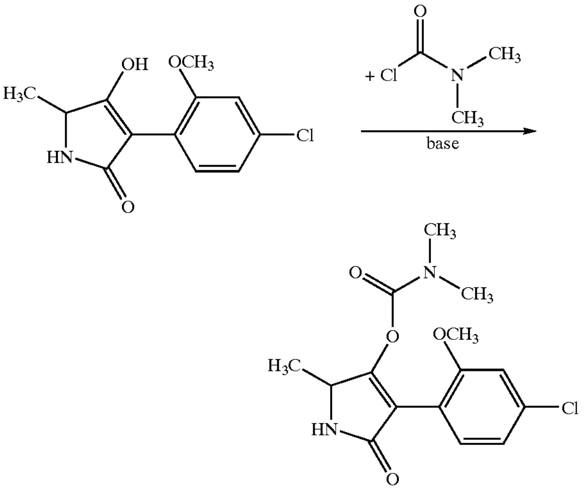

The compounds of the formula (II)

(II)

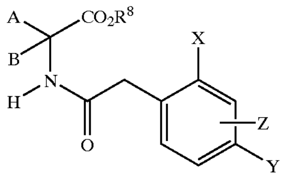

in which

A, B, X, Y, Z and $R^8$ have the abovementioned meanings, which are required as starting substances in processes (A) according to the invention, are new.

Acyl-amino acid esters of the formula (II) are obtained, for example, when amino acid derivatives of the formula (XIV)

(XIV)

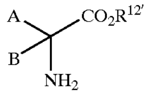

in which $R^{12'}$ represents hydrogen (XIVa) or allyl (XIVb) and

A and B have the abovementioned meanings are acylated with phenylacetyl halides of the formula (XV)

(XV)

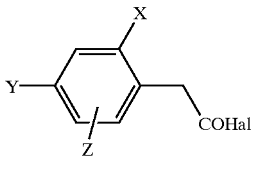

in which

X, Y and Z have the abovementioned meanings and

Hal represents chlorine or bromine, (Chem. Reviews 52, 237–416 (1953); Bhattacharya, Indian J. Chem. 6, 341–5, 1968) and, if $R^{12'}$=hydrogen, the resulting acylamine acids of the formula (IIa)

(IIa)

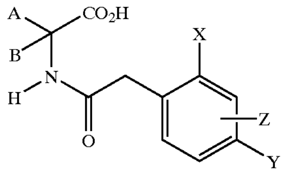

in which

A, B, X, Y and Z have the abovementioned meanings are esterified (Chem. Ind. (London) 1568 (1968)).

The substituted cyclic aminocarboxylic acids of the formula (XIVa) are generally obtainable by a Bucherer-Bergs reaction or by Strecker synthesis and are obtained in each case in various isomeric forms. Under the conditions of a Bucherer-Bergs reaction, for example, the result of predominantly those isomers (for simplicity's sake term β hereinafter) in which the radicals R and the carboxyl group are in the equatorial position, while the conditions of Strecker synthesis give predominantly those isomers (for simplicity's sake termed α hereinafter) in which the amino group and the radicals R are in the equatorial position.

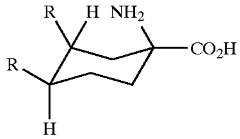

Bucherer-Bergs synthesis
(β isomers)

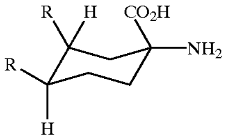

Strecker synthesis
(α isomers)

(L. Munday,. J. Chem. Soc. 4372 (1961); J. T. Eward, C. Jitrangeri, Can. J. Chem. 53, 3339 (1975).

Moreover, the starting substances of the formula (II)

II

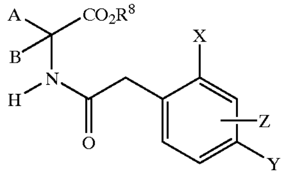

in which

A, B, X, Y, Z and $R^8$ have the abovementioned meanings, which are used in the above processes (A) can be prepared when aminonitrile of the formula (XVI)

(XVI)

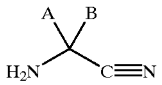

in which

A and B have the abovementioned meanings are reacted with phenylacetyl halides of the formula (XV)

(XV)

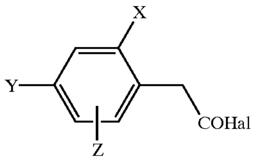

in which

X, Y and Z have the abovementioned meanings and

Hal represents chlorine or bromine to give compounds of the formula (XVII)

(XVII)

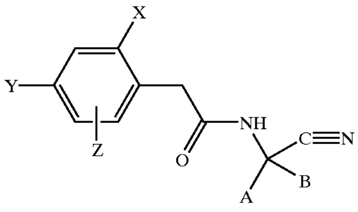

in which

A, B, X, Y and Z have the abovementioned meanings, and these compounds are subsequently subjected to alcoholysis in the presence of sulfuric acid.

The compounds of the formula (XVII) are also new.

In addition to the intermediates mentioned in the preparation examples, the following compounds of the formula (II) may be mentioned by way of example, but not by way of limitation:

N-(2-chloro-4-methoxyphenylacetyl)-alanine methyl ester

N-(2-chloro-4-methoxyphenylacetyl)-leucine methyl ester

N-(2-chloro-4-methoxyphenylacetyl)-isoleucine methyl ester

N-(2-chloro-4-methoxyphenylacetyl)-valine methyl ester methyl N-(2-chloro-4-methoxyphenylacetyl)-aminoisobutyrate methyl N-(2-chloro-4-methoxyphenylacetyl)-2-ethyl-2-aminobutyrate methyl N-(2-chloro-4-methoxyphenylacetyl)-2-methyl-2-aminovalerate methyl N-(2-chloro-4-methoxyphenylacetyl)-2,3-dimethyl-2-aminovalerate methyl N-(2-chloro-4-methoxyphenylacetyl)-1-amino-cyclopentanecarboxylate methyl N-(2-chloro-4-methoxyphenylacetyl)-1-amino-cyclohexanecarboxylate methyl N-(2-chloro-4-methoxyphenylacetyl)-1-amino-cycloheptanecarboxylate methyl N-(2-chloro-4-methoxyphenylacetyl)-1-amino-cyclooctanecarboxylate N-(4-chloro-2-methoxyphenylacetyl)-alanine methyl ester N-(4-chloro-2-methoxyphenylacetyl)-leucine methyl ester N-(4-chloro-2-methoxyphenylacetyl)-isoleucine methyl ester N-(4-chloro-2-methoxyphenylacetyl)-valine methyl ester methyl N-(4-chloro-2-methoxyphenylacetyl)-aminoisobutyrate methyl N-(4-chloro-2-methoxyphenylacetyl)-2-ethyl-2-aminobutyrate methyl N-(4-chloro-2-methoxyphenylacetyl)-2-methyl-2-aminovalerate methyl N-(4-chloro-2-methoxyphenylacetyl)-2,3-dimethyl-2-aminovalerate methyl N-(4-chloro-2-methoxyphenylacetyl)-1-amino-cyclopentanecarboxylate methyl N-(4-chloro-2-methoxyphenylacetyl)-1-amino-cyclohexanecarboxylate methyl N-(4-chloro-2-methoxyphenylacetyl)-1-amino-cycloheptanecarboxylate methyl N-(4-chloro-2-methoxyphenylacetyl)-1-amino-cyclooctanecarboxylate N-(2-chloro-6-methoxyphenylacetyl)-alanine methyl ester N-(2-chloro-6-methoxyphenylacetyl)-leucine methyl ester N-(2-chloro-6-methoxyphenylacetyl)-isoleucine methyl ester N-(2-chloro-6-methoxyphenylacetyl)-valine methyl ester methyl N-(2-chloro-6-methoxyphenylacetyl)-aminoisobutyrate methyl N-(2-chloro-6-methoxyphenylacetyl)-2-ethyl-2-aminobutyrate methyl N-(2-chloro-6-methoxyphenylacetyl)-2-methyl-2-aminovalerate methyl N-(2-chloro-6-methoxyphenylacetyl)-2,3-dimethyl-2-aminovalerate methyl N-(2-chloro-6-methoxyphenylacetyl)-1-amino-cyclopentanecarboxylate methyl N-(2-chloro-6-methoxyphenylacetyl)-1-amino-cyclohexanecarboxylate methyl N-(2-chloro-6-methoxyphenylacetyl)-1-amino-cycloheptanecarboxylate methyl N-(2-chloro-6-methoxyphenylacetyl)-1-amino-cyclooctanecarboxylate methyl N-(2-chloro-4-methoxy-phenylacetyl)-1-amino-2-methyl-cyclohexanecarboxylate methyl N-(2-chloro-4-methoxy-phenylacetyl)-1-amino-3-methyl-cyclohexanecarboxylate methyl N-(2-chloro-4-methoxy-phenylacetyl)-1-amino-4-methyl-cyclohexanecarboxylate methyl N-(2-chloro-4-methoxy-phenylacetyl)-1-amino-3,4-dimethyl-cyclohexanecarboxylate methyl N-(2-chloro-4-methoxy-phenylacetyl)-1-amino-4-ethyl-cyclohexanecarboxylate methyl N-(2-chloro-4-methoxy-phenylacetyl)-1-amino-4-isopropyl-cyclohexanecarboxylate methyl N-(2-chloro-4-methoxy-phenylacetyl)-1-amino-4-tert-butyl-cyclohexanecarboxylate methyl N-(2-chloro-4-methoxy-phenylacetyl)-1-amino-4-methoxy-cyclohexanecarboxylate methyl N-(2-chloro-6-methoxy-phenylacetyl)-1-amino-2-methyl-cyclohexanecarboxylate methyl N-(2-chloro-6-methoxy-phenylacetyl)-1-amino-3-methyl-cyclohexanecarboxylate methyl N-(2-chloro-6-methoxy-phenylacetyl)-1-amino-4-methyl-cyclohexanecarboxylate methyl N-(2-chloro-6-methoxy-phenylacetyl)-1-amino-3,4dimethyl-cyclohexanecarboxylate methyl N-(2-chloro-6-methoxy-phenylacetyl)-1-amino-4-ethyl-cyclohexanecarboxylate methyl N-(2-chloro-6-methoxy-phenylacetyl)-1-amino-4-isopropyl-cyclohexanecarboxylate methyl N-(2-chloro-6-methoxy-phenylacetyl)-1-amino-4-tert-butyl-cyclohexanecarboxylate methyl N-(2-chloro-6-methoxy-phenylacetyl)-1-amino-4-methoxy-cyclohexanecarboxylate methyl N-(4-chloro-2-methoxy-phenylacetyl)-1-amino-2-methyl-cyclohexanecarboxylate methyl N-(4-chloro-2-methoxy-phenylacetyl)-1-amino-3-methyl-cyclohexanecarboxylate methyl N-(4-chloro-2-methoxy-phenylacetyl)-1-amino-4-methyl-cyclohexanecarboxylate methyl N-(4-chloro-2-methoxy-phenylacetyl)-1-amino-3,4-dimethyl-cyclohexanecarboxylate methyl N-(4-chloro-2-methoxy-phenylacetyl)-1-amino-4-ethyl-cyclohexanecarboxylate methyl N-(4-chloro-2-methoxy-phenylacetyl)-1-amino-4-isopropyl-cyclohexanecarboxylate methyl N-(4-chloro-2-methoxy-phenylacetyl)-1-amino-4-tert-butyl-cyclohexanecarboxylate methyl N-(4-chloro-2-methoxy-phenylacetyl)-1-amino-4-methoxy-cyclohexanecarboxylate.

In addition to the intermediates mentioned in the preparation examples, the following compounds of the formula (IIa) may be mentioned by way of example, but not by way of limitation:

N-(2-chloro-4-methoxyphenylacetyl)-alanine

N-(2-chloro-4-methoxyphenylacetyl)-leucine

N-(2-chloro-4-methoxyphenylacetyl)-isoleucine

N-(2-chloro-4-methoxyphenylacetyl)-valine

N-(2-chloro-4-methoxyphenylacetyl)-aminoisobutyric acid

N-(2-chloro-4-methoxyphenylacetyl)-2-ethyl-2-aminobutyric acid

N-(2-chloro-4-methoxyphenylacetyl)-2-methyl-2-aminovaleric acid

N-(2-chloro-4-methoxyphenylacetyl)-2,3-dimethyl-2-aminovaleric acid

N-(2-chloro-4-methoxyphenylacetyl)-1-amino-cyclopentanecarboxylic acid

N-(2-chloro-4-methoxyphenylacetyl)-1-amino-cyclohexanecarboxylic acid

N-(2-chloro-4-methoxyphenylacetyl)-1-amino-cycloheptanecarboxylic acid

N-(2-chloro-4-methoxyphenylacetyl)-1-amino-cyclooctanecarboxylic acid

N-(4-chloro-2-methoxyphenylacetyl)-alanine

N-(4-chloro-2-methoxyphenylacetyl)-leucine

N-(4-chloro-2-methoxyphenylacetyl)-isoleucine

N-(4-chloro-2-methoxyphenylacetyl)-valine

N-(4-chloro-2-methoxyphenylacetyl)-aminoisobutyric acid

N-(4-chloro-2-methoxyphenylacetyl)-2-ethyl-2-aminobutyric acid

N-(4-chloro-2-methoxyphenylacetyl)-2-methyl-2-aminovaleric acid

N-(4-chloro-2-methoxyphenylacetyl)-2,3-dimethyl-2-aminovaleric acid

N-(4-chloro-2-methoxyphenylacetyl)-1-amino-cyclopentanecarboxylic acid

N-(4-chloro-2-methoxyphenylacetyl)-1-amino-cyclohexanecarboxylic acid
N-(4-chloro-2-methoxyphenylacetyl)-1-amino-cycloheptanecarboxylic acid
N-(4-chloro-2-methoxyphenylacetyl)-1-amino-cyclooctanecarboxylic acid
N-(2-chloro-6-methoxyphenylacetyl)-alanine
N-(2-chloro-6-methoxyphenylacetyl)-leucine
N-(2-chloro-6-methoxyphenylacetyl)-isoleucine
N-(2-chloro-6-methoxyphenylacetyl)-valine
N-(2-chloro-6-methoxyphenylacetyl)-aminoisobutyric acid
N-(2-chloro-6-methoxyphenylacetyl)-2-ethyl-2-aminobutyric acid
N-(2-chloro-6-methoxyphenylacetyl)-2-methyl-2-aminovaleric acid
N-(2-chloro-6-methoxyphenylacetyl)-2,3-dimethyl-2-aminovaleric acid
N-(2-chloro-6-methoxyphenylacetyl)-1-amino-cyclopentanecarboxylic acid
N-(2-chloro-6-methoxyphenylacetyl)-1-amino-cyclohexanecarboxylic acid
N-(2-chloro-6-methoxyphenylacetyl)-1-amino-cycloheptanecarboxylic acid
N-(2-chloro-6-methoxyphenylacetyl)-1-amino-cyclooctanecarboxylic acid
N-(2-chloro-4-methoxyphenylacetyl)-1-amino-2-methyl-cyclohexanecarboxylic acid
N-(2-chloro-4-methoxyphenylacetyl)-1-amino-3-methyl-cyclohexanecarboxylic acid
N-(2-chloro-4-methoxyphenylacetyl)-1-amino-4-methyl-cyclohexanecarboxylic acid
N-(2-chloro-4-methoxyphenylacetyl)-1-amino-3,4-dimethyl-cyclohexanecarboxylic acid
N-(2-chloro-4-methoxyphenylacetyl)-1-amino-4-ethyl-cyclohexanecarboxylic acid
N-(2-chloro-4-methoxyphenylacetyl)-1-amino-4-isopropyl-cyclohexanecarboxylic acid
N-(2-chloro-4-methoxyphenylacetyl)-1-amino-4-tert-butyl-cyclohexanecarboxylic acid
N-(2-chloro-4-methoxyphenylacetyl)-1-amino-4-methoxy-cyclohexanecarboxylic acid
N-(4-chloro-2-methoxyphenylacetyl)-1-amino-2-methyl-cyclohexanecarboxylic acid
N-(4-chloro-2-methoxyphenylacetyl)-1-amino-3-methyl-cyclohexanecarboxylic acid
N-(4-chloro-2-methoxyphenylacetyl)-1-amino-4-methyl-cyclohexanecarboxylic acid
N-(4-chloro-2-methoxyphenylacetyl)-1-amino-3,4-dimethyl-cyclohexanecarboxylic acid
N-(4-chloro-2-methoxyphenylacetyl)-1-amino-4-ethyl-cyclohexanecarboxylic acid
N-(4-chloro-2-methoxyphenylacetyl)-1-amino-4-isopropyl-cyclohexanecarboxylic acid
N-(4-chloro-2-methoxyphenylacetyl)-1-amino-4-tert-butyl-cyclohexanecarboxylic acid
N-(4-chloro-2-methoxyphenylacetyl)-1-amino-4-methoxy-cyclohexanecarboxylic acid
N-(2-chloro-6-methoxyphenylacetyl)-1-amino-2-methyl-cyclohexanecarboxylic acid
N-(2-chloro-6-methoxyphenylacetyl)-1-amino-3-methyl-cyclohexanecarboxylic acid
N-(2-chloro-6-methoxyphenylacetyl)-1-amino-4-methyl-cyclohexanecarboxylic acid
N-(2-chloro-6-methoxyphenylacetyl)-1-amino-3,4-dimethyl-cyclohexanecarboxylic acid
N-(2-chloro-6-methoxyphenylacetyl)-1-amino-4-ethyl-cyclohexanecarboxylic acid
N-(2-chloro-6-methoxyphenylacetyl)-1-amino-4-isopropyl-cyclohexanecarboxylic acid
N-(2-chloro-6-methoxyphenylacetyl)-1-amino-4-tert-butyl-cyclohexanecarboxylic acid
N-(2-chloro-6-methoxyphenylacetyl)-1-amino-4-methoxy-cyclohexanecarboxylic acid Compounds of the formula (IIa) can be obtained, for example, from the phenylacetyl halides of the formula (XV) and amino acids of the formula (XIVa) by the method of Schotten-Baumann (organikum [Laboratory Practical Organic Chemistry], 9th Edition, 446 (1970) VEB Deutscher Verlag der Wissenschaften, Berlin).

The phenylacetyl halides of the formula (XV)

(XV)

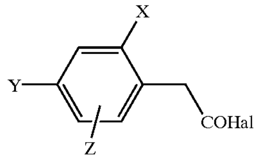

in which

X, Y and Z have the abovementioned meanings and

Hal represents bromine or chlorine are new with the exception of the compound 2-chloro-4-methoxyphenylacetyl chloride (cf. J. Polym. Sci., Part A, Polym. Chem. 30, 997 (1992), FR-2 054 532).

The new phenylacetyl halides of the formula (XV) are obtained when phenylacetic acids of the formula (XVIII)

(XVIII)

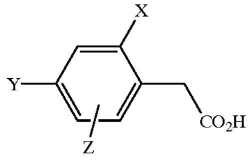

in which

X, Y and Z have the abovementioned meanings, are reacted with halogenating agents, such as, for example, phosgene, phosphorus trichloride, phosphorus pentachloride, phosphorus tribromide or phosphorus pentabromide or thionyl chloride, if appropriate in the presence of an inert diluent, such as hydrocarbons or halogenated hydrocarbons, at temperatures between −30° C. and 150° C., preferably between −20° C. and 100° C.

Some of the phenylacetic acids of the formula (XVIII) are Known and/or can be prepared for example by the following equation:

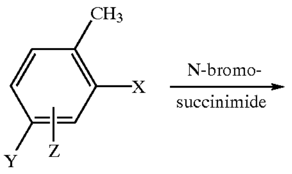

(XIX)

-continued

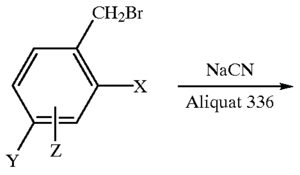

(XX)

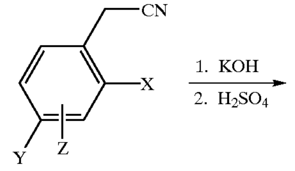

(XXI)

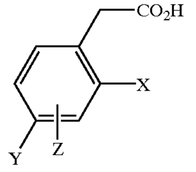

(XVIII)

X, Y and Z in formulae (XIX), (XX), (XXI) and (XVIII) have the abovementioned meanings.

The toluenes of the formula (XIX) are generally known compounds of organic chemistry.

The acid halides of the formula (III), carboxylic anhydrides of the formula (IV), chloroformic esters or chloroformic thioesters of the formula (V), chloramonothioformic esters or chlorodithioformic esters of the formula (VI), alkyl halides of the formula (VII), sulfonyl chlorides of the formula (VIII), phosphorus compounds of the formula (IX) and metal hydroxides or amines of the formulae (X) and (XI) as well as isocyanates, isothiocyanates or carbamoyl chlorides of the formula (XIII), which are furthermore required as starting substances for carrying out processes (B), (C), (D), (E), (F) (G) and (H) according to the invention are generally known compounds of organic or inorganic chemistry.

Process (A) is characterized in that compounds of the formula (II) in which A, B, X, Y, Z and $R^8$ have the abovementioned meanings are subjected to an intramolecular condensation reaction in the presence of bases.

Diluents which can be employed in process (A) according to the invention are all inert organic solvents. The following can preferably be used: hydrocarbons, such as toluene and xylene, furthermore ethers, such as dibutyl ether, tetrahydrofuran, dioxane, glycol dimethyl ether and diglycol dimethyl ether, furthermore polar solvents, such as dimethyl sulfoxide, sulfolane, dimethylformamide and N-methylpyrrolidone, and also alcohols, such as methanol, ethanol, propanol, isopropanol, butanol, iso-butanol and tert-butanol.

Bases (deprotonating agents) which can be employed when carrying out process (A) according to the invention are all customary proton acceptors. The following can preferably be used: the oxides, hydroxides and carbonates of alkali metals and alkaline earth metals, such as sodium hydroxide, potassium hydroxide, magnesium oxide, calcium oxide, sodium carbonate, potassium carbonate and calcium carbonate, all of which can also be employed in the presence of phase transfer catalysts such as, for example, triethylbenzylammonium chloride, tetrabutylammonium bromide, Adogen 464 (=methyltrialkyl($C_8$–$C_{10}$)ammonium chloride) or TDA 1 (=tris-(methoxyethoxyethyl)amine). Alkali metals such as sodium or potassium can furthermore be used. Moreover, alkali metal amides, alkali metal hydrides, alkaline earth metal amides and alkaline earth metal hydrides, such as sodium amide, sodium hydride and calcium hydride, and, moreover, also alkali metal alcoholates, such as sodium methylate, sodium ethylate and potassium tert-butylate, can be employed.

When carrying out process (A) according to the invention, the reaction temperatures can be varied within a substantial range. In general, the process is carried out at temperatures between 0° C. and 250° C., preferably between 50° C. and 150° C.

Process (A) is generally carried out under atmospheric pressure.

When carrying out processes ($A_\alpha$) and ($A_\beta$) according to the invention, the reactants of the formulae (II) and (IIa) and the deprotonating bases are generally employed in approximately twice the equimolar amounts. However, it is also possible to use one or the other component in a larger excess (up to 3 mol).

Process ($B_\alpha$) is characterized in that compounds of the formula (Ia) are reacted with carboxylic halides of the formula (III).

If the acid halides are used, then diluents which can be employed in process ($B_\alpha$) according to the invention are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, moreover carboxylic esters, such as ethyl acetate, and also strongly polar solvents, such as dimethyl sulfoxide and sulfolane. If the acid halide is sufficiently stable to hydrolysis, the reaction can also be carried out in the presence of water.

If the corresponding carboxylic halides are used, then suitable acid-binding agents in the reaction in accordance with process ($B_\alpha$) according to the invention are all customary acid acceptors. The following can preferably be used: tertiary amines, such as triethylamine, pyridine, diazabicyclooctane (DABCO), diazabicycloundecane (DBU), diazabicyclononene (DBN), Hünig base and N,N-dimethylaniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

If carboxylic acid halides are used, the reaction temperatures in process ($B_\alpha$) according to the invention can be varied within a substantial range. In general, the process is carried out at temperatures between −20° C. and +150° C., preferably between 0° C. and 100° C.

When carrying out process ($B_\alpha$) according to the invention, the starting substances of the formula (Ia) and the carboxylic acid halide of the formula (III) are generally used in approximately equivalent amounts. However, it is also possible to employ the carboxylic acid halide in a larger excess (up to 5 mol). Working-up is carried out by customary methods.

Process ($B_\beta$) is characterized in that compounds of the formula (Ia) are reacted with carboxylic anhydrides of the formula (IV).

If, in process ($B_\beta$) according to the invention, carboxylic anhydrides are used as reactants of the formula (IV), then the diluents which can be used are preferably those which are also preferred when acid halides are used. Besides, an excess of a carboxylic anhydride may also simultaneously act as the diluent.

When using carboxylic anhydrides, the reaction temperatures in process ($B_\beta$) according to the invention can be varied within a substantial range. In general, the process is carried out at temperatures between −20° C. and +150° C., preferably between 0° C. and 100° C.

When carrying out the process according to the invention, the starting substances of the formula (Ia) and the carboxylic anhydride of the formula (IV) are generally used in approximately equivalent amounts. However, it is also possible to employ the carboxylic anhydride in a larger excess (up to 5 mol). Working-up is carried out by customary methods.

In general, a procedure is followed in which diluent and excess of carboxylic anhydride as well as the carboxylic acid which forms are removed by distillation or by washing with an organic solvent or water.

Process (C) is characterized in that compounds of the formula (Ia) are reacted with chloroformic esters or chloroformic thioesters of the formula (V).

If the corresponding chloroformic esters or chloroformic thioesters are used, then suitable acid-binding agents in the reaction in accordance with process (C) according to the invention are all customary acid acceptors. The following can preferably be used: tertiary amines, such as triethylamine, pyridine, (DABCO), (DBU), (DBA), Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

When using the chloroformic esters or chloroformic thioesters, then diluents which can be employed in process (C) according to the invention are all solvents which are inert to these compounds. The following can preferably be used: hydrocarbons, such as benzine, benzene, toluene, xylene and tetralin, furthermore halogenohydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, moreover carboxylic esters, such as ethyl acetate, and also strongly polar solvents, such as dimethyl sulfoxide and sulfolane.

When using the chloroformic esters or chloroformic thioesters as carboxylic acid derivatives of the formula (V), the reaction temperatures when carrying out process (C) according to the invention can be varied within a substantial range. If the process is carried out in the presence of a diluent and of an acid-binding agent, then the reaction temperatures are generally between −20° C. and +100° C., preferably between 0° C. and 50° C.

Process (C) according to the invention is generally carried out under atmospheric pressure.

When carrying out process (C) according to the invention, the starting substances of the formula (Ia) and the corresponding chloroformic ester or chloroformic thioester of the formula (V) are generally used in approximately equivalent amounts. However, it is also possible to employ one or the other component in a larger excess (up to 2 mol). Working-up is then carried out by customary methods. In general, a procedure is followed in which the salts which have precipitated are removed and the reaction mixture which remains is concentrated by stripping of the diluent.

In preparation process ($D_\alpha$), approximately 1 mol of chloromonothioformic ester or chlorodithioformic ester of the formula (VI) is reacted per mole of starting compound of the formula (Ia) at 0 to 120° C., preferably at 20 to 60° C.

Suitable diluents which are optionally added are all inert polar organic solvents, such as ethers, amides, sulfones, sulfoxides, but also halogenalkenes.

Dimethyl sulfoxide, tetrahydrofuran dimethylformamide or methylene chloride are preferably employed.

If, in a preferred embodiment, the enolate salt of the compound (Ia) is synthesized by adding strong deprotonating agents, such as, for example, sodium hydride or potassium tertiary-butylate, a further addition of acid-binding agents can be dispensed with.

If acid-binding agents are employed, then customary inorganic or organic bases are suitable, and sodium hydroxide, sodium carbonate, potassium carbonate, pyridine and triethylamine may be mentioned by way of example.

The reaction can be carried out under atmospheric pressure or under elevated pressure, it is preferably carried out under atmospheric pressure. Working-up is carried out by customary methods.

In preparation process ($D_\beta$), an equimolar amount or an excess of carbon disulfide is added per mole of starting compound of the formula (Ia). This process is preferably carried out at temperatures from 0 to 50° C. and, in particular, at 20 to 30° C.

It is frequently expedient first to prepare the corresponding salt from the compound of the formula (Ia) by adding a deprotonating agent (such as, for example, potassium tertiary-butylate or sodium hydride). The compound (Ia) is reacted with carbon disulfide until the formation of the intermediate is complete, for example after stirring for several hours at room temperature.

The product is further reacted with the alkyl halide of the formula (VII) at, preferably, 0 to 70° C. and, in particular, 20 to 50° C. At least an equimolar amount of alkyl halide is employed.

The process is carried out under atmospheric pressure or under elevated pressure, preferably under atmospheric pressure.

Again, working-up is carried out by customary methods.

In preparation process (E), approximately 1 mol of sulfonyl chloride (VIII) is reacted per mole of starting compound of the formula (Ia) at −20 to 150° C., preferably 20 to 70° C.

Suitable diluents which are optionally added are all inert polar organic solvents such as ethers, amides, nitriles, sulfones, sulfoxides or halogenated hydrocarbons such as methylene chloride.

Dimethyl sulfoxide, tetrahydrofuran, dimethylformamide, dimethyl sulfide or methylenechloride are preferably employed.

If, in a preferred embodiment, the enolate salt of the compound (Ia) is synthesized by adding strong deprotonating agents, such as, for example, sodium hydride or potassium tertiary-butylate, a further addition of acid-binding agents can be dispensed with.

If acid-binding agents are employed, then customary inorganic or organic bases are suitable, and sodium hydroxide, sodium carbonate, potassium carbonate, pyridine and triethylamine may be mentioned by way of example.

The reaction can be carried out under atmospheric pressure or under elevated pressure, it is preferably carried out under atmospheric pressure. Working-up is carried out by customary methods.

To obtain compounds of the structure (Ie) in preparation process (F), 1 to 2, preferably 1 to 1.3, mol of the phosphorus compound of the formula (IX) are reacted per mole of compound of the formula (Ia) at temperatures between −40° C. and 150° C., preferably between −10 and 110° C.

Suitable diluents which are optionally added are all inert polar organic solvents such as ethers, amides, nitrites, alcohols, sulfides, sulfones, sulfoxides and the like.

Acetonitrile, dimethyl sulfoxide, tetrahydrofuran, dimethylformamide or methylene chloride are preferably employed.

Suitable acid-binding agents which are optionally added are customary inorganic or organic bases, such as hydroxides, carbonates or amines. Sodium hydroxide, sodium carbonate, potassium carbonate, pyridine and triethylamine may be mentioned by way of example.

The reaction can be carried out under atmospheric pressure or under elevated pressure, it is preferably carried out under atmospheric pressure. Working-up is carried out by customary methods of organic chemistry. The end products obtained are preferably purified by crystallization, chromatography or by so-called "incipient distillation", i.e. removal of the volatile components in vacuo.

Process (G) is characterized in that compounds of the formula (Ia) are reacted with metal compounds (X) or amines (XI).

Diluents which can be employed in the process according to the invention are preferably ethers, such as tetrahydrofuran, dioxane or diethyl ether, or else alcohols, such as methanol, ethanol or isopropanol, but also water. Process (G) according to the invention is generally carried out under atmospheric pressure. The reaction temperatures are generally between −20° C. and 100° C., preferably between 0° C. and 50° C.

In preparation process ($H_\alpha$), approximately 1 mol of isocyanate of the formula (XII) is reacted per mole of starting compound of the formula (Ia) at 0 to 100° C., preferably 20 to 50° C.

Suitable diluents which are optionally added are all inert organic solvents, such as ethers, amides, nitriles, sulfones or sulfoxides.

If appropriate, catalysts may be added to accelerate the reaction. Catalysts which can very advantageously be employed are organotin compounds such as, for example dibutyltin dilaurate. The process is preferably carried out under atmospheric pressure.

In preparation process ($H_\beta$), approximately 1 mol of carbamoyl chloride of the formula (XIII) is reacted per mole of starting compound of the formula (Ia) at 0 to 150° C., preferably 20 to 70° C.

Suitable diluents which are optionally added are all inert polar organic solvents, such as ethers, amides, sulfones, sulfoxides or halogenated hydrocarbons.

Dimethyl sulfoxide, tetrahydrofuran, dimethylformamide or methylene chloride are preferably employed.

If, in a preferred embodiment, the enolate salt of the compound (Ia) is synthesized by adding strong deprotonating agents (such as, for example, sodium hydride or potassium tertiary-butylate), a further addition of acid-binding agents can be dispensed with.

If acid-binding agents are employed, then suitable substances are customary inorganic or organic bases, and sodium hydroxide, sodium carbonate, potassium carbonate, triethylamine or pyridine may be mentioned by way of example.

The reaction can be carried out under atmospheric pressure or under elevated pressure, it is preferably carried out under atmospheric pressure. Working-up is carried out by customary methods.

The active compounds are suitable for combating animal pests, preferably anthropods and nematodes particularly insects and arachnids encountered in agriculture, in forests, in the protection of stored products and of materials, and in the hygiene sector. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and Scutigera spec.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria.*

From the order of the Dermaptera, for example, *Forficula auricularia.*

From the order of the Isoptera, for example, *Reticulitermes* spp.

From the order of the Anoplura, for example, *Phylloxera vastatrix, Pemphigus* spp., *Pediculus humanus corporis, Haenatopinus* spp. and *Linsgnathus* spp.

From the order of the Mallophaga, for example, *Trichodectes* spp. and *Damalinea* spp.

From the order of the Thysanoptera, for example, *Hercinothrips femoralis* and *Thrips tabaci.*

From the order of the *Heteroptera*, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae, Myzus* spp., *Phorodon humuli, Rhopalosiphunm padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Spodoptera exigua, Mamestra brassicae, Panolis flammea, Prodenia litura, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermastes* spp., *Trgoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha; Amphimallon solstitialis* and *Costelytra zealandica.*

From the order of the Hymenoptera, for exaxmple, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Droscphila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae* and *Tipula paludosa.*

From the order of the Siphonaptera, for example, *Xenopsylla cheopis* and *Ceratophyllus* spp.

From the order of the Arachnida, for example, *Scorpio maurus* and *Latrodectus mactans.*

From the order of the Acarina, for example, *Acarus siro, Argas* spp., *Ornithodoros* spp., *Dexmanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp. and *Tetranychus* spp.

The active compounds according to the invention are distinguished by powerful insecticidal and acaricidal activity.

They can be employed particularly successfully for combating plant-injurious insects, such as, for example, against the larvae of the mustard beetle (*Phaedon cochleariae*), against the larvae of the green rice leafhopper (*Nephotettix cincticeps*) or against diamond-back moth caterpillars (*Plutella maculipennis*).

The compounds according to the invention also show a good activity against *Venturia inaequalis.*

The active compounds can be converted into the customary formulations, such as solutions, emlusions, wettable powders, suspensions, powders, dusts, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is, liquid solvents and/or solid carriers, optionally with the use of surface-active agents, that is, emulsifying agents and/or dispersing agents, and/or foam-forming agents.

In the case of the use of water as an extender, organic solvents can, for example, also be used as auxiliary solvents. As liquid solvents, there are suitable in the main: aromatics, such as xylene, toluene or alkyl-naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example mineral oil fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulfoxide, as well as water.

As solid carriers there are suitable:

for example ammonium salts and ground natural minerals, such as kaolins, clays, talc, chalk, quartz, attapulgite, montmorillonite or diatomaceous earth, and ground synthetic minerals, such as highly-disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulfonates, allyl sulfates, arylsulfonates as well as albumen hydrolysis products; as dispersing agents there are suitable: for example ligninsulfite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compound according to the invention can be present in its commercially available formulations and in the use forms, prepared from these formulations, as a mixture with other active compounds, such as insecticides, attractants, sterilants, acaricides, nematicides, fungicides, growth-regulating substances or herbicides. The insecticides include, for example, phosphates, carbamates, carboxylates, chlorinated hydrocarbons, phenylureas, substances produced by microorganisms, or the like.

The following compounds may be mentioned:

acrinathrin, alphmethrin, betacyfluthrin, bifenthrin, brofenprox, cis-Resmethrin, clocythrin, cycloprothrin, cyfluthrin, cyhalothrin, cyperxethrin, deltamethrin, esfenvalerate, ethofenprox, fenpropathrin, fenvalerate, flucythrinate, fluvalinate, lambda-cyhalothrin, permethrin, pyresmethrin, pyrethrum, silafluofen, tralomethrin, zetamethrin, alanycarb, bendiocarb, benfuracarb, bufencarb, butocarboxim, carbaryl, cartap, ethiofencarb, fenobucarb, fenoxycarb, isoprocarb, methiocarb, methomyl, metolcarb, oxamyl, pirimicarb, promecarb, propoxur, terbam, thiodicarb, thiofanox, trimethacarb, XMC, xylylcarb, acephate, azinphos A, azinphos M, bromophos A, cadusafos, carbophenothion, chlorfenvinphos, chlormephos, chlorpyrifos, chlorpyrifos M, cyanophos, demeton M, demeton-S-methyl, demeton S, diazinon, dichlorvos, dicliphos, dichlofenthion, dicrotophos, dimethoate, dimethylvinphos, dioxathion, disulfoton, edifenphos, ethion, etrinrhos, fenitrothion, fenthion, fonophos formothion, heptenophos, iprobenfos, isazophos, isoxathion, phorate, nalathion, mecarbam, nevinphos, nesulfenphos, methacrifos, methamidophos, naled, onethoate, oxydemethon M, oxydeprofos, parathion A, parathion M, phenthoate, phorate, phosalone, phosmet, phosphamidon, phoxim, pirimiphos A, pirimiphos M, propaphos, prothiophos, prothoate, pyraclophos, pyridaphention, quinaiphos, salithion, sebufos, sulfotep, sulprofos, tetrachlorvinphos, temephos, thicmethon, thionazin, trichlorfon, triazophos, vamidothion, buprofezin, chlorfluazuron, diflubenzuron, flucycloxuron, flufenoxuro, hexaflumarn, pyriproxifen, tebufenozide, teflubenzuron, triflumuron, imidacloprid, nitenpyram, abamectin, amitraz, avermectin, azadirachtin, bensultap, *Bacillus thuringiensis*, cyromazine, diafenthiuron, emamectin, ethofenprox, fenpyrad, fipronil, flufenprox, lufenuron, metaldehyde, milbemectin, pymetrozine, tebufenpyrad, triazuron, aldicarb, bendiocarb, benfuracarb, carbofuran, carbosulfan, chloret oxyos, cloethocarb, disulfoton, ethoprophos, etrinphos, fenamiphos, fipronil, fonofos, fosthiazate, furathiocarb, HCH, isazophos, isofenphos, methiocarb, monocrotophos, nitenpyram, oxamyl, phorate, phoxim, prothiofos, pyrachlofos, sebufos, silafluofen, tebupirimiphos, tefluthrin, terbufos, thiodicarb, thiafenox, azocyclotin, butylpyridaben, clofentezine, cyhexatin, diafenthiuron, diethion, emamectin, fenazaquin, fenbutatin, oxide, fenothiocaxb, fenpropathrin, fenpyrad, fenpyroxite, fluazinam, fluazuron, flucycloxuron, flufenoxuron, fluvalinate, fubfenprox, hexythiazox, ivermectin, methidathion, tonocrotophos, moxidectin, naled, phosalone, profenofos, pyraclofos, pyridaben, pyrimidifen, tebufenpyrad, thuringiensin, triarathene, the compound of the formula

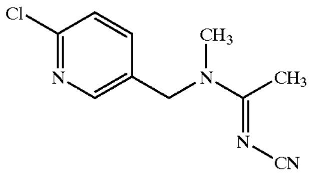

and the compound of the formula

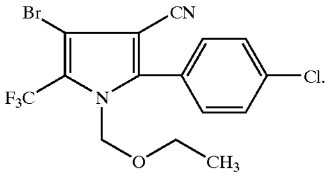

The active, compound according to the invention can furthermore be present in its commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide ranges. The active compound concentration of the use forms can be from 0.0000001 to 95% by weight of active compound, preferably between 0.0001 and 1% by weight.

Application is effected in the customary manner adapted to suit the use forms.

When used against hygiene pests and stored-product pests, the active compound is distinguished by an outstanding residual action on wood and clay and by a good stability to alkali on limed surfaces.

Preparation and use of the active compound according to the invention can be seen from the examples which follow.

PREPARATION EXAMPLES

Example (Ia-1)

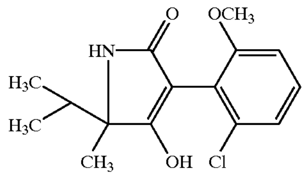

23.8 g (0.073 mol) of methyl N-(2-chloro-6-methoxyphenylacetyl)-2-amino-2,3-dimethyl-butyrate, dissolved in 150 ml of absolute toluene, are added dropwise to a suspension of 18.06 g (0.16 mol) of potassium tert-butylate in 50 ml of absolute tetrahydrofuran at the boil, and the mixture was heated at reflux temperature for 1.5 hours. After the reaction mixture has cooled to room temperature, 230 ml of water are added, the aqueous phase is separated off, the toluene phase is reextracted using 110 ml of water, and the combined aqueous phases are acidified at 15–20° C. using approximately 25 ml of concentrated hydrochloric acid. The product is filtered off with suction and dried. 20.2 g (93% of theory) of 3-(2-chloro-6-methoxyphenyl)-5-isopropyl-5-methyl-pyrrolidine-2,4-dione of m.p. 172–174° C. are obtained.

Example (Ia-2)

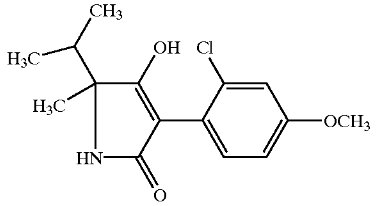

71.4 g (0.226 mol) of methyl N-(2-chloro-4-fluorophenylacetyl)-2-amino-2,3-dimethyl-butyrate, dissolved in 450 ml of absolute toluene, are added dropwise to a suspension of 56 g (0.498 mol) of potassium tert-butylate in 150 ml of absolute tetrahydrofuran at the boil, and stirring is continued for 90 minutes at reflux temperature. After the reaction mixture has cooled to room temperature, 700 ml of water are added, the organic phase is separated off and washed again using 340 ml of water. The combined aqueous phases are acidified at 15–20° C. using approximately 80 ml of concentrated hydrochloric acid, and the product is filtered off with suction. After drying, 57.1 g (85% of theory) of 3-(2-chloro-4-methoxyphenyl)-5-isopropyl-5-methyl-pyrrolidine-2,4-dione of m.p. 130–140° C. are obtained.

$^1$H NMR (300 MHz, $d_6$-DMSO): 0.78, 0.94 (2d, 6H, 5-CH—($CH_3)_2$)); 1.3 (s, 3H, 5-$CH_3$; 1.93 (m, 1H, 5-CH ($CH_3)_2$); 3.77 (s, 3H, $OCH_3$); 6.8, 6.9 (dd, 1H, Ar 5-H); 7.03 (d, 1H, Ar 3-H); 7.11 (d, 1H, Ar 6-H); 7.46 (br, 1H, NH); 10.77 (B, 1H, OH).

The end products of the formula (Ia) listed in Table 8 below are obtained analogously to Exmaple (Ia-1) and in accordance with the general information in the description.

TABLE 8

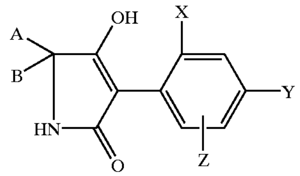

| Ex. No. | X | Y | Z | A | B | Isomer | m.p. ° C. |
|---|---|---|---|---|---|---|---|
| Ia-3 | $OCH_3$ | Cl | H | $i\text{-}C_3H_7$ | $CH_3$ | — | 204–206 |
| Ia-4 | Cl | $OCH_3$ | H | $-(CH_2)_2-CH(CH_3)-(CH_2)_2-$ | | β | >220 |
| Ia-5 | Cl | $OCH_3$ | H | $-(CH_2)_3-CH(CH_3)-CH_2-$ | | β | >220 |
| Ia-6 | Cl | $OCH_3$ | H | $-(CH_2)_5-$ | | — | 116 |
| Ia-7 | Cl | $OCH_3$ | H | $CH_3$ | $CH_3$ | — | 132 |
| Ia-8 | $OCH_3$ | Cl | H | $-(CH_2)_2-CH(CH_3)-(CH_2)_2-$ | | β | 212 |
| Ia-9 | Cl | H | 6-$OCH_3$ | $-(CH_2)_2-CH(CH_3)-(CH_2)_2-$ | | β | 196 |

Example (Ib-1)

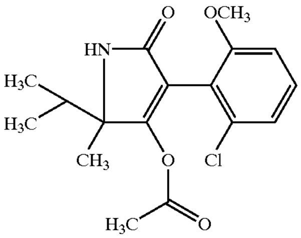

4.43 g (0.015 mol) of 3-(2-chloro-6-methoxyphenyl)-5-isopropyl-5-methyl-pyrrolidine-2,4-dione are introduced into 70 ml of absolute dichloromethane, 2.1 ml of triethylamine are added. 1.13 ml of acetyl chloride in 5 ml of absolute dichloromethane are added at 0 to 10° C., and stirring of the batch is continued at room temperature. The end of the reaction is determined by thin-layer chromatography. The batch is then washed twice using in each case 100 ml of 0.5 N sodium hydroxide solution, the organic phase is dried over magnesium sulfate, and the solvent is stripped off in vacuo.

4.62 g (91% of theory) of 3-(2-chloro-6-methoxyphenyl)-5-isopropyl-5-methyl-4-acetoxy-Δ3-pyrrolidine-2-one of melting point 70–72° C. are obtained.

The end products of the formula (Ib) listed in Table 9 below are obtained analogously to Example (Ib-1) and in accordance with the general information in the description of the processes according to the invention:

TABLE 9

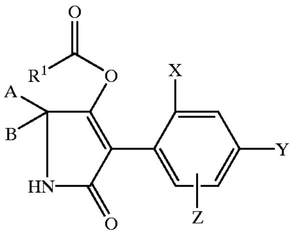

| Ex. No. | X | Y | Z | A | B | $R^1$ | Isomer | m.p. ° C. |
|---|---|---|---|---|---|---|---|---|
| Ib-2 | Cl | $OCH_3$ | H | $i\text{-}C_3H_7$ | $CH_3$ | $CH_3$ | — | 138 |
| Ib-3 | Cl | $OCH_3$ | H | $i\text{-}C_3H_7$ | $CH_3$ | $t\text{-}C_3H_7$ | — | 113 |
| Ib-4 | $OCH_3$ | Cl | H | $i\text{-}C_3H_7$ | $CH_3$ | $CH_3$ | — | 122–123 |
| Ib-5 | $OCH_3$ | Cl | H | $i\text{-}C_3H_7$ | $CH_3$ | $t\text{-}C_3H_7$ | — | 182 |

TABLE 9-continued

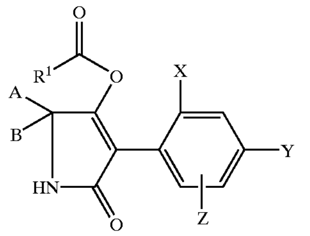

| Ex. No. | X | Y | Z | A | B | $R^1$ | Isomer | m.p. ° C. |
|---|---|---|---|---|---|---|---|---|
| Ib-6 | Cl | $OCH_3$ | H | $-(CH_2)_2-CH-(CH_2)_2-$<br>$CH_3$ | | $CH_3$ | β | >220 |
| Ib-7 | Cl | $OCH_3$ | H | $-(CH_2)_2-CH-(CH_2)_2-$<br>$CH_3$ | | $i-C_3H_7$ | β | >220 |
| Ib-8 | Cl | $OCH_3$ | H | $-(CH_2)_3-CH-CH_2-$<br>$CH_3$ | | $CH_3$ | β | >220 |
| Ib-9 | Cl | $OCH_3$ | H | $-(CH_2)_3-CH-CH_2-$<br>$CH_3$ | | $i-C_3H_7$ | β | 207 |
| Ib-10 | $OCH_3$ | Cl | H | $-(CH_2)_2-CH-(CH_2)_2-$<br>$CH_3$ | | $i-C_3H_7$ | β | 211 |
| Ib-11 | Cl | H | $6-OCH_3$ | $-(CH_2)_2-CH-(CH_2)_2-$<br>$CH_3$ | | $i-C_3H_7$ | β | >220 |

Example (Ic-1)

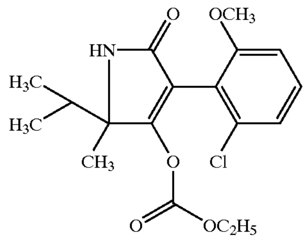

4.43 g (0.015 mol) of 3-(2-chloro-6-methoxyphenyl)-5-isopropyl-5-methyl-pyrrolidine-2,4-dione are introduced into 70 ml of absolute dichloromethane, and 2.1 ml of triethylamine are added. 1.5 ml of ethyl chloroformate in 5 ml of absolute dichloromethane are added at 0 to 10° C., and stirring of the batch is continued at room temperature. The end of the reaction is determined by thin-layer chromatography. The mixture is then washed twice using in each case 100 ml of 0.5 N sodium hydroxide solution, the organic phase is dried aver magnesium sulfate, and the solvent is stripped off in vacuo.

2.68 g (48% of theory) of O-ethyl O-[3-(2-chloro-6-methoxyphenyl)]-5-isopropyl-5-methyl-Δ3-pyrrolidine-2-on-4-yl carbonate of melting point 104–106° C. are obtained.

The end products of the formula (Ic) listed in Table 10 below are obtained analogously to Example (Ic-1) and in accordance with the general information in the description of the processes according to the invention:

TABLE 10

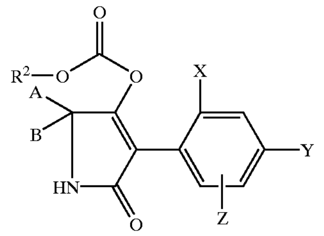

| Ex. No. | X | Y | Z | A | B | $R^1$ | Isomer | m.p. ° C. |
|---|---|---|---|---|---|---|---|---|
| Ic-2 | Cl | $OCH_3$ | H | $i-C_3H_7$ | $CH_3$ | $C_2H_5$ | — | 58–66 |
| Ic-3 | $OCH_3$ | Cl | H | $i-C_3H_7$ | $CH_3$ | $C_2H_5$ | — | 120 |
| Ic-4 | Cl | $OCH_3$ | H | $-(CH_2)_2-\underset{CH_3}{\underset{\mid}{CH}}-(CH_2)_2-$ | | $C_2H_5$ | β | >220 |
| Ic-5 | Cl | $OCH_3$ | H | $-(CH_2)_2-\underset{CH_3}{\underset{\mid}{CH}}-(CH_2)_2-$ | | $n-C_4H_9$ | β | >220 |
| Ic-6 | Cl | $OCH_3$ | H | $-(CH_2)_3-\underset{CH_3}{\underset{\mid}{CH}}-CH_2-$ | | $C_2H_5$ | β | 182 |
| Ic-7 | Cl | $OCH_3$ | H | $-(CH_2)_3-\underset{CH_3}{\underset{\mid}{CH}}-CH_2-$ | | $n-C_4H_9$ | β | 174 |
| Ic-8 | $OCH_3$ | Cl | H | $-(CH_2)_2-\underset{CH_3}{\underset{\mid}{CH}}-(CH_2)_2-$ | | $C_2H_5$ | β | 201 |
| Ic-9 | Cl | H | 6-$OCH_3$ | $-(CH_2)_2-\underset{CH_3}{\underset{\mid}{CH}}-(CH_2)_2-$ | | $C_2H_5$ | β | >220 |

Preparation of the Starting Compounds:

Example (II-1)

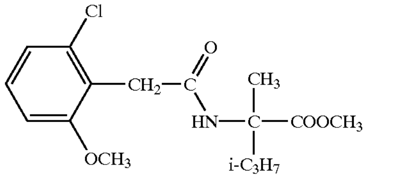

29.9 g (0.101 mol) of 2-(2-chloro-6-methoxyphenyl)-N-[1-cyano-2-(3-methyl)-butyl]-acetamide dissolved in 200 ml of dichloromethane are added dropwise with stirring and ice-cooling to 47 g (0.481 mol) of concentrated sulfuric acid, the temperature of the reaction mixture rising to 30° C. to 40° C., and, after the addition has ended, the mixture is stirred for a further 2 hours at 30° C. to 40° C., until the dichloromethane phase of the reaction mixture has turned colorless. 66 ml of absolute methanol are subsequently added, also dropwise and with ice-cooling, during which process the temperature of the reaction mixture again rises to 40° C. The mixture is subsequently stirred for 6 hours at 40° C. to 70° C. For working-up, the reaction mixture is poured into 460 g of ice, with stirring, and extracted with dichloromethane, the combined organic phases are washed with aqueous sodium hydrogen carbonate solution until acid-free and dried over magnesium sulfate, and the solvent is removed in vacuo.

23.8 g (72% of theory) of 2-(2-chloro-6-methoxyphenyl)-N-[1-methoxycarbonyl-2-(3-methyl)-butyl]-acetamide of melting point 76–78° C. are obtained.

Example (II-2)

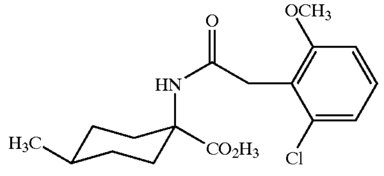

32.7 ml of triethylamine are added to 24.28 g (0.117 mol) of methyl 1-amino-4-methyl-cyclohexanecarboxylate hydrochloride in 220 ml of absolute tetrahydrofuran, and 25.6 g (0.117 mol) of 2-chloro-6-methoxy-phenylacetyl chloride in 25 ml of absolute tetrahydrofuran are added dropwise at 0 to 10° C. After the reaction bas ended, the precipitate is filtered off with suction, the filtrate is concentrated, the residue is taken up in methylene chloride, the mixture is washed with dilute hydrochloric acid and dried, and the solvent is evaporated in vacuo. After recrystallization from MTB ether/n-hexane, 30.3 g (73% of theory) of methyl cis-N-(2-chloro-6-methoxyphenylacetyl)-4-methyl-1-aminocyclohexanecarboxylate of m.p. 159° C. were obtained.

The products of the formula (II) listed in Table 11 below are obtained analogously to compounds II-1 and II-2 and in accordance with the general information on the processes cesses according to the invention.

TABLE 11

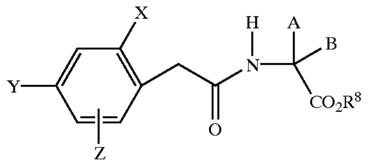

(II)

| Ex. No. | X | Y | Z | A | B | $R^4$ | Isomer | m.p. ° C. |
|---|---|---|---|---|---|---|---|---|
| II-3 | $OCH_3$ | Cl | H | $-(CH_2)_2-CH(CH_3)-(CH_2)_2-$ | | $CH_2$ | β | 131 |
| II-4 | $OCH_3$ | Cl | H | i-$C_3H_7$ | $CH_3$ | $CH_3$ | — | 75–76 |
| II-5 | Cl | $OCH_3$ | H | $-(CH_2)_2-CH(CH_3)-(CH_2)_2-$ | | $CH_3$ | β | 133 |
| II-6 | Cl | $OCH_3$ | H | $-(CH_2)_3-CH(CH_3)-CH_2-$ | | $CH_3$ | β | 125 |
| II-6 | Cl | $OCH_3$ | H | $CH_3$ | $CH_3$ | $CH_3$ | — | oil |
| II-8 | Cl | $OCH_3$ | H | $-(CH_2)_3-$ | | $CH_3$ | — | 106 |

Example (XVII-1)

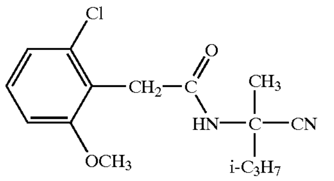

32.9 g (0.15 mol) of 2-chloro-6-methoxyphenylacetyl chloride in 50 ml of absolute tetrahydrofuran are added dropwise with stirring at 0° C. to 10° C. to 16.8 g (0.15 mol) of 2-amino-2-methyl-isovaleronitrile and 22.4 ml (0.16 mol) of triethylamine in 250 ml of absolute tetrahydrofuran, and, after the addition has ended, the mixture is stirred at roan temperature until starting product is no longer detectable in the thin-layer chromatogram. For working-up, the reaction mixture is added to a stirred mixture of 600 ml of ice-water and 200 ml of 1N hydrochloric acid, this mixture is extracted 3 times using dichloromethane, the organic phases are washed using sodium hydrogencarbonate solution, the organic phase is dried over magnesium sulfate, and the solvent is removed in vacuo.

29.9 g (67% of theory) of 2-(2-chloro-6-methoxyphenyl)-N-[2-cyano-2-(3-methyl)-butyl]-acetamide of melting point 104–106° C. are obtained.

Example (XVII-2)

2-(4-Chloro-2-methoxyphenyl)-N-[2-cyano-2-(3-methyl)-butyl]-acetamide of melting point 110–111° C. is obtained analogously.

Example (XVII-3)

2-(2-Chloro-4-fluorophenyl)-N-[2-cyano-2-(3-methyl)-butyl]-acetamide of melting point 109–111° C. is obtained analogously.

Example (XX-1)

2-Chloro-6-methoxybenzyl bromide 442 g of 2-chloro-6-methoxytoluene are dissolved in 2420 ml of carbon tetrachloride and, together with 516 g of N-bromosuccinimide, heated at reflux for 2 h while 5.8 g of AIBN are added. The solid is filtered off and washed with a small amount of carbon tetrachloride, the filtrate is concentrated, and the residue which remains is fractionated. 483 g of colorless oil are obtained (b.p. 100° C./1.4 mbar, m.p. 44–47° C.).

| | |
|---|---|
| $^1H$ NMR ($CDCl_3$): | 7.24 (t, 1H); 7.03 (dd, 1H); 6.83 (dd, 1H); 4.76 (s, 2H); 3.93 (s, 3H). |

Example (XX-2)

4-Chloro-2-methoxybenzyl bromide 303 g of 4-chloro-2-methoxytoluene are dissolved in 1665 ml of carbon tetrachloride and, together with 355 g of N-bromosuccinimide, heated at reflux for 2 h while 4.0 g of AIBN are added. The solid is filtered off and washed with a small amount of carbon tetrachloride, the filtrate is concentrated, and the residue which remains is fractionated. 307 g of colorless oil are obtained (b.p. 103° C./1.5 mbar, m.p. 42–45° C.).

| | |
|---|---|
| $^1H$ NMR ($CDCl_3$): | 7.29 (d, 1H); 6.95 (dd, 1H); 6.93 (dd, 1H); 4.95 (s, 2H); 3.93 (s, 3H). |

Example (XX-3)

2-Chloro-4-methoxybenzyl bromide 186 g of 2-chloro-4-3methoxytoluene are dissolved in 1000 ml of carbon tetrachloride and, together with 212 g of N-bromosuccinimide, heated at reflux for 2 h while 2.4 g of AIBN are added. The solid is filtered off and washed with a small amount of carbon tetrachloride, the filtrate is concentrated, and the residue which remains is fractionated. 252 g of orange oil are obtained (Purity 82%).

| | |
|---|---|
| $^1H$ NMR ($CDCl_3$): | 7.40 (d, 1H); 7.23 (dd, 1H); 6.85 (dd, 1H); 4.43 (s, 2H); 3.88 (s, 3H). |

General Protocol for Preparation of the Compounds of the Formula (XXI):

1.3 mol of sodium cyanide are introduced into 65 ml of water, and 1.7 g of phase transfer catalyst-Aliquat 336 are added. The mixture is heated to 70° C., and 1 mol of a benzyl bromide derivative of the formula (XX) dissolved in 200 ml of toluene is added dropwise in the course of 30 minutes. The mixture is heated at 70° C. for 3 to 6 hours. When the reaction mixture has cooled down, it is poured into 600 ml of toluene/600 ml of water, and the organic phase is separated off and washed repeatedly using water. It is dried and concentrated, and the residue is distilled.

Example (XXI-1)

(2-Chloro-6-methoxyphenyl)acetonitrile 483 g of 2-chloro-6-methoxybenzyl bromide in 410 ml of toluene are reacted with 131 g of sodium cyanide in 132 ml of water and 3.28 g of Aliquat 336. 325 g of colorless oil are obtained (b.p. 103° C./0.08 mbar).

| | |
|---|---|
| $^1H$ NMR ($CDCl_3$): | 7.25 (t, 1H); 7.03 (dd, 1H); 6.82 (dd, 1H); 3.89 (s, 3H); 3.83 (s, 2H). |

Example (XXI-2)

(4-Chloro-2-methoxyphenyl)acetonitrile 269 g of 4-chloro-2-methoxybenzyl bromide in 214 ml of toluene are reacted with 68.2 g of sodium cyanide in 69 ml of water and 1.8 g of Aliquat 336. 141 g of colorless oil are obtained (b.p. 107° C./0.08 mbar).

| | |
|---|---|
| $^1H$ NMR ($CDCl_3$): | 7.30 (d, 1H); 6.98 (dd, 1H); 6.90 (d, 1H); 3.89 (s, 3H); 3.66 (s, 2H). |

Example (XXI-3)

(2-Chloro-4-methoxyphenyl)acetonitrile 212 g (purity 82%) of 2-chloro-4-methoxybenzyl bromide in 900 ml of dichloromethane are reacted in the course of 4 h at 40° C. with 176 g of potassium cyanide in 675 ml of water and 15.5 g of tetrabutylammonium hydrogen sulfate. After working-up, 157 g of brownish oil are obtained (purity 79%).

| | |
|---|---|
| $^1H$ NMR ($CDCl_3$): | 7.33 (d, 1H); 7.19 (dd, 1H); 6.91 (d, 1H); 3.87 (s, 3H); 3.67 (s, 2H). |

General Protocol for the Preparation of the Compounds of the Formula (XVIII):

2 mol of potassium hydroxide are dissolved in 400 ml of ethylene glycol, and 1 mol of arylacetonitrile of the formula (XXI) is added. The mixture is heated for 5 hours at 100° C., then cooled to room temperature and diluted with 800 ml of water. The solution is acidified to approximately pH 1 using 20% sulfuric acid. The acid is filtered off with suction, and the product is washed with water and dried.

Example (XVIII-1)

(2-Chloro-6-methoxyphenyl)acetic acid 325 g of 2-chloro-6-methoxyphenylacetonitrile are reacted with 171 g of potassium hydroxide in 690 ml of ethylene glycol. 331 g of solid are obtained (m.p. 164–165° C.).

| | |
|---|---|
| $^1H$ NMR ($CDCl_3$): | 7.19 (t, 1H); 7.00 (dd, 1H); 6.80 (dd, 1H); 3.90 (s, 2H); 3.83 (s, 3H). |

Example (XVIII-2)

(4-Chloro-2-methoxyphenyl)acetic acid 141 g of 4-chloro-2-methoxyphenylacetonitrile are reacted with 83.2 g of potassium hydroxide in 280 ml of ethylene glycol. 148 g of solid are obtained (m.p.: 100° C.).

| | |
|---|---|
| $^1H$ NMR ($CDCl_3$): | 8.40–8.90 (m br, 1H); 7.10 (d, 1H); 6.86 (dd, 1H); 6.89 (d, 1H); 3.80 (s, 3H); 3.60 (s, 2H). |

Example (XVIII-3)

(2-Chloro-4-methoxyphenyl)acetic acid 657 g (purity 75%) of 2-chloro-4-methoxyphenylacetonitrile are reacted with 303 g of potassium hydroxide in 1308 ml of ethylene glycol. 430 g of solid are obtained (m.p.: 83–86° C.).

| | |
|---|---|
| $^1H$ NMR ($CDCl_3$): | 8.10–8.60 (m br, 1H); 7.32 (d, 1H); 7.16 (dd, 1H); 6.89 (d, 1H); 3.87 (s, 3H); 3.53 (s, 2H). |

Example (XV-1)

(2-Chloro-4-methoxyphenyl)acetyl chloride 160 g of 2-chloro-4-methoxyphenylacetic acid are suspended in 210 ml of toluene, and the suspension is stirred together with 96 ml of thionyl chloride at 80° C. until the evolution of gas has ceased. The volatile components are stripped off, and the residue is distilled. 90 g of an orange oil are obtained (thin-film evaporator 170° C., 0.08 mbar).

| | |
|---|---|
| $^{1}H$ NMR ($CDCl_3$): | 7.29 (d, 1H); 7.14 (dd, 1H); 6.91 (d, 1H); 4.05 (s, 2H); 3.90 (s, 3H). |

Example (XV-2)

(2-Chloro-6-methoxyphenyl)acetyl chloride of b.p. 106° C./1.1 mbar is obtained analogously to Example (XV-1).

Example (XV-3)

(4-Chloro-2-methoxyphenyl)acetyl chloride of b.p. 111° C./1.1 mbar is obtained analogously to Example (XV-1).

The compounds listed below were employed as comparison substances in the use examples which follow:

(A)

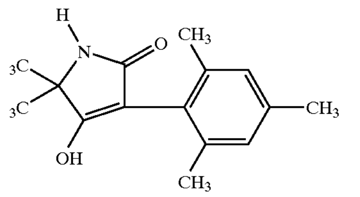

(B)

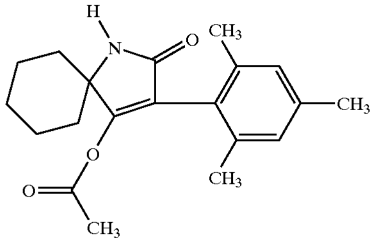

(C)

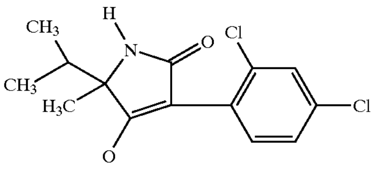

(D)

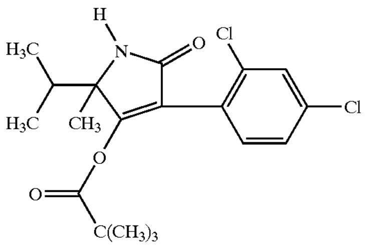

-continued (E)

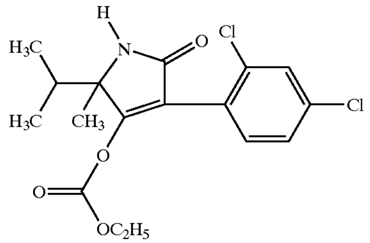

all disclosed in EP 0 456 063.

Example A

*Plutella* Test

| | |
|---|---|
| Solvent: | 7 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Cabbage leaves (*Brassica olearacea*) are treated by being dipped into the preparation of active compound of the desired concentration and are infested with caterpillars of the diamond-back moth (*Plutella maculipennis*) while the leaves are still moist.

After the specified periods of time, the destruction in % is determined. 100% means that all the caterpillars have been killed; 0% means that none of the caterpillars have been killed.

In this test, a destruction rate of at least 90% was caused, after 7 days, for example by the compounds of Preparation Examples Ia-1, Ia-2 and Ib-2 at an exemplary concentration of active compound of 0.001%, while the compounds (A) and (B), which are known from the prior art, caused a destruction rate of only 10%.

Example B

*Tetranychus* Test (OP Resistant)

| | |
|---|---|
| Solvent: | 3 parts by weight of dimethylformamide |
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with emulsifier-containing water to the desired concentration.

Bean plants (*Phaseolus vulgaris*) which are severely infested with all development stages of the greenhouse red spider mite (*Tetranychus urticae*) are sprayed with a preparation of active compound of the desired concentration.

After the specified periods of time, the destruction in % is determined. 100% means that all the spider mites have been killed; 0% means that none of the spider mites have been killed.

In this test, a destruction rate of at least 80% was caused, after 7 days, for example by the compounds of Preparation Examples Ib-3 and Ic-2 at an exemplary concentration of active compound of 0.00016%, while the compounds (D) and (E), which are known from the prior art, caused no destruction.

What is claimed is:

1. A 1-H-3-aryl-pyrrolidine-2,4-dione of the formula (I)

(I)

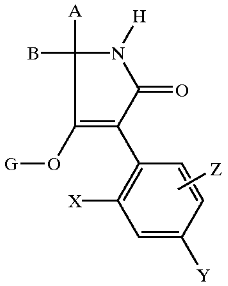

in which

A, B and the carbon atom to which they are bonded represent a saturated or unsaturated C6-spirocycle which is optionally monsubstituted or polysubstituted by $C_1$–$C_6$-alkyl, $C_3$–$C_8$-cycloalkyl, $C_1$–$C_3$-halogenoalkyl, $C_1$–$C_8$-alkoxy, $C_1$–$C_6$-thioalkyl, fluorine, chlorine or phenyl, or A, B and the carbon atom to which they are bonded represent a C6-spirocycle which is substituted by an alkylenediyl group which together with the carbon atom to which it is bonded forms a further five- to seven-membered spirocycle, or A, B and the carbon atom to which they are bonded represent a C6-spirocycle in which two adjacent substituents together represent a saturated or unsaturated five- or six-membered cycle which is substituted by C1–$C_3$-alkyl, C1–C3-alkoxy, fluorine, chlorine or bromine, X represents halogen or $C_1$–$C_4$-alkoxy, Y represents hydrogen, halogen or $C_1$–$C_4$-alkoxy, Z represents hydrogen or $C_1$–$C_4$-alkoxy, wherein at least one of X or Y is halogen; one of X, Y or Z is $C_1$–$C_4$ alkoxy; and one of Y or Z is hydrogen;

with the proviso that X and Y or X and Z do not simultaneously represent halogen, G represents hydrogen.

2. The 1-H-3-aryl-pyrrolidine-2,4-dione of the formula (I) as claimed in claim 1, in which A, B and the carbon atom to which they are bonded represent a saturated or unsaturated C6-spirocycle which is optionally monosubstituted or polysubstituted by methyl, ethyl, propyl, isopropyl, butyl, iso-butyl, sec-butyl, tert-butyl, cyclohexyl, trifluoromethyl, methoxy, ethoxy, propoxy, iso-propoxy, butoxy, iso-butoxy, sec-butoxy, tert-butoxy, methylthio, ethylthio, fluorine, chlorine or phenyl, or A, B and the carbon atom to which they are bonded represent a C6-spirocycle which is substituted by an alkylenediyl group together with the carbon atom to which it is bonded forms a further five- to seven-membered spirocycle, or A, B and the carbon atom to which they are bonded represent a C6-spirocycle in which two substituents together represent a saturated or unsaturated five- or six-membered cycle, X represents fluorine, chlorine, bromine, methoxy, ethoxy, propoxy or isopropoxy, Y represents hydrogen, fluorine, chlorine, bromine, methoxy, ethoxy, propoxy or iso-propoxy, Z represents hydrogen, methoxy, ethoxy, propoxy or iso-propoxy, wherein at least one of X or Y is fluorine, chlorine or bromine, one X, Y or Z is methoxy, ethoxy, propoxy or iso-propoxy; and one of Y or Z is hydrogen;

with the proviso that X and Y or X and Z do not simultaneously represent halogen, G represents hydrogen.

3. A pesticide composition for combating pests selected from the group consisting of arthropods, nematodes, insects and arachnids, which comprises at least one 1-H-3-aryl-pyrrolidine-2,4-dione derivative of the formula (I) as claimed in claim 1 and a pesticidally effective carrier.

4. A method of combating pests selected from the group consisting of arthropods, nematodes, insects and arachnids, wherein a pesticidally effective amount of 1-H-3-aryl-pyrrolidine-2,4-dione derivatives of the formula (I) as claimed in claim 5 are administered to said pests.

5. The 1-H-3-aryl-pyrrolidine-2,4-dione of the formula (I) as claimed in claim 1, wherein A, B and the carbon atom to which they are bonded represent a saturated, unsubstituted C6-spirocycle.

6. The 1-H-3-aryl-pyrrolidine-2,4-dione of the formula (I) as claimed in claim 1, wherein A, B and the carbon atom to which they are bonded represent a saturated $C_6$-spirocycle which is substituted with one or more $C_1$–$C_6$-alkyl or $C_1$–$C_8$-alkoxy.

7. The 1-H-3-aryl-pyrrolidine-2,4-dione of the formula (I) as claimed in claim 6, wherein X and Y are fluorine, chlorine or bromine and Z is in the 6-position and is methoxy.

8. The 1-H-3-aryl-pyrrolidine-2,4-dione of the formula (I) as claimed in claim 6, wherein A, B and the carbon atom to which they are bonded represent a saturated $C_6$-spirocycle which is substituted with one methyl, X and Y are chlorine and Z is in the 6-position and is methoxy.

* * * * *